US008357523B2

(12) United States Patent
Postlethwaite et al.

(10) Patent No.: US 8,357,523 B2
(45) Date of Patent: Jan. 22, 2013

(54) BETA-GLUCOSIDASE VARIANT ENZYMES AND RELATED POLYNUCLEOTIDES

(75) Inventors: Sally Rhiannon Postlethwaite, Redwood City, CA (US); Louis Clark, San Francisco, CA (US); Catherine M. Cho, Redwood City, CA (US)

(73) Assignee: Codexis, Inc., Redwood City, CA (US)

( * ) Notice: Subject to any disclaimer, the term of this patent is extended or adjusted under 35 U.S.C. 154(b) by 259 days.

(21) Appl. No.: 12/816,989

(22) Filed: Jun. 16, 2010

(65) Prior Publication Data

US 2010/0317059 A1 Dec. 16, 2010

Related U.S. Application Data

(60) Provisional application No. 61/187,565, filed on Jun. 16, 2009, provisional application No. 61/218,020, filed on Jun. 17, 2009.

(51) Int. Cl.
*C12N 9/26* (2006.01)

(52) U.S. Cl. ........................................................ 435/201

(58) Field of Classification Search ........................ None
See application file for complete search history.

(56) References Cited

U.S. PATENT DOCUMENTS

2007/0292930 A1 12/2007 Shu et al.

FOREIGN PATENT DOCUMENTS

WO 99/09834 A2 3/1999

OTHER PUBLICATIONS

UnitProt Accession No. B4R8X0, Sep. 2008.*

Luo et al., BMC Genomics 9:386, 2008, 17 pages.*

Barnett, C.C., et al., "Cloning and amplification of the gene encoding an extracellular β-glucosidase from *Trichoderma reesei*: Evidence for improved rates of saccharification of cellulosic substrates," Biotechnology, 9:562-567, 1991.

Clarke, A. J., et al., "β-Glucosidases, β-Glucanases, and Xylanses. Their Mechanism of Catalysis," β-Glucosidases: Biochemistry and Molecular Biology, Chapter 3, pp. 27-41, 1993.

Dekker, R.F.H., ""Kinetic, Inhibition, and Stability Properties of aCommercial β-D-Glucosidase (Cellobiase) Preparation from *Aspergillus niger* and Its Suitability in the Hydrolysis of Lignocellulose,"" Biotechnology and Bioengineering, vol. XXVIII, pp. 1438-1442, 1986.

Esen, A., "β-Glucosidases. Overview," β-Glucosidases:Biochemistry and Molecular Biology, Chapter 1, pp. 1-14, 1993.

Faure, D., "The Family-3 Glycoside Hydrolases: from Housekeeping Functions to Host-Microbe Interactions," Applied and Environmental Microbiology, 68(4):1485-1490, 2002.

Faure, D., et al. "Growth of *Azospirillum irakense* KBC1 on the Aryl β-Glucoside Salicin Requires either salA or salB," Journal of Bacteriology, 181(10):3003-3009, 1999.

Faure, D., et al., ""The celA Gene, Encoding a Glycosyl Hydrolase Family 3 β-Glucosidase in *Azospirillum irakense*, Is Requiredfor Optimal Growth on Cellobiosides,"" Applied and Environmental Microbiology, 67(5):2380-2383, 2001.

Feng, H.-Y., et al., "Converting β-Glycosidase into a β-Transglycosidase by Directed Evolution," The Journal of Biological Chemistry, 280(44):37088-37097, 2005.

Gong, C.-S., et al., ""Cellobiase from *Trichoderma viride*:Purification, Properties, Kinetics, and Mechanism,"" Biotechnology and Bioengineering, vol. XIX, pp. 959-981, 1977.

Hansson, T., et al., "Enhanced Transglucosylation/Hydrolysis Ratio of Mutants of *Purococcus furiosus* β-Glucosidase: Effects of Donor Concentration, Water Content, and Temperature on Activity and Selectivity in Hexanol," Biotechnology and Bioengineering, 75(6):656-665, 2001.

Hansson, T., et al., ""Improved Oligosaccharide Synthesis byProtein Engineering of β-Glucosidase CelB from Hyperthermophilic *Pyrococcus furiosus*,"" Biotechnology and Bioengineering, 73(3):203-210, 2001.

Harnpicharnchai, P., et al., "A thermotolerant β-glucosidase isolated from an endophytic fungi, *Periconia* sp., with a possible use for biomass conversion to sugars," Protein Expression and Purification, 67:61-69, 2009.

Hong, J., et al., "Cloning and functional expression of thermostable β-glucosidase gene from *Thermoascus aurantiacus*," App. Microbiol. Biotechnol., 73:1331-1339, 2007.

Inohara-Ochiai, M., et al., "An active-site mutation causes enhanced reactivity and altered regiospecificity of transglucosylation catalyzed by the *Bacillus* sp. SAM1606 α-glucosidase," Journal of Bioscience and Bioengineering, 89(5):431-437, 2000.

Korotkova, O. G., et al., "Isolation and Properties of Fungal β-Glucosidases," Biochemistry (Moscow), 74 (5):569-577, 2009.

Oh, S.-W., et al., "Modulation of Hydrolysis and Transglycosylation Activity of *Thermus* Maltogenic Amylase by Combinatorial Saturation Mutagenesis," J. Microbiol. Biotechnol., 18(8):1401-1407, 2008.

Skory, C. D., et al., "Cloning and Characterization of a Gene Encoding a Cell-Bound, Extracellular β-Glucosidase in the Yeast *Candida wickerhamii*," Applied and Environmental Microbiology, 61(2):518-525, 1995.

Spilliaert, R., et al., "Cloning and sequencing of a *Rhodothermus marinus* gene, bglA, coding for a thermostable β-glucanase and its expression in *Escherichia coli*," Eur. J. Biochem., 224:923-930, 1994.

Takashima, S., et al., "Molecular Cloning and Expression of the Novel Fungal β-Glucosidase Genes from *Humicola grisea* and *Trichoderma reesei*," J. Biochem., 125:728-736, 1999.

Watanabe, T., et al., "Purificication and properties of *Aspergillus niger* β-glucosidase," Eur. J. Biochem., 209:651-659, 1992.

Woodward, J., "Fungal and other β-D-glucosidases—their properties and applications," Enzyme Microb. Technol., 4:73-79, 1982.

Yao, Q., et al., "Heterologous expression and site-directed mutagenesis of endoglucanase CelA from *Clostridium thermocellum*," Biotechnol. Lett., 29:1243-1247, 2007.

* cited by examiner

*Primary Examiner* — David J Steadman
(74) *Attorney, Agent, or Firm* — Codexis, Inc.

(57) ABSTRACT

The invention provides variants of the *Azospirillum irakense* CelA β-glucosidase that have improve β-glucosidase activity, particularly improved thermoactivity, compared to the wild type enzyme. The invention further provides related polynucleotides, vectors, host cell, and methods for making and using the variants.

32 Claims, 18 Drawing Sheets

```
ATG AAG ACG AAG TGG CTA ATA TCA GTC ATA ATC CTA TTT GTT TTC
-72                                                     -28
ATT TTT CCT CAA AAT CTA GTT TTT GCT GGT ACT AGT AGT ACG GCA
-27                                -1+1                  18
ATC GCA CAG GAA GGA GCA GCT CCG GCC GCT ATA TTA CAT CCA GAG
19                                                       63
AAA TGG CCT CGA CCT GCG ACA CAA CGA CTT ATT GAC CCG GCA GTT
64                                                      108
GAA AAA AGA GTT GAT GCT CTG TTA AAA CAG TTA TCT GTT GAA GAA
109                                                     153
AAA GTA GGG CAA GTT ATA CAG GGT GAT ATT GGG ACA ATT ACA CCA
154                                                     198
GAA GAC CTG CGC AAA TAT CCA CTA GGT TCT ATT TTA GCC GGA GGA
199                                                     243
AAC AGC GGC CCG AAT GGA GAT GAT CGT GCT CCT CCA AAG GAG TGG
244                                                     288
CTT GAT CTA GCT GAT GCT TTT TAC CGT GTA AGT TTA GAA AAA CGG
289                                                     333
CCA GGC CAT ACC CCG ATA CCA GTG CTT TTT GGC ATT GAT GCA GTT
334                                                     378
CAT GGA CAT GGC AAT ATC GGG TCT GCG ACA ATT TTC CCT CAC AAT
379                                                     423
ATT GCA CTT GGA GCA ACC CAT GAT CCA GAA CTT CTA CGA AGA ATT
424                                                     468
GGT GAG GTA ACA GCT GTT GAA ATG GCT GCT ACG GGA ATT GAT TGG
469                                                     513
ACA TTT GCG CCT GCA CTG TCT GTT GTG AGA GAT GAT CGA TGG GGA
514                                                     558
CGA ACA TAT GAA GGC TTC TCA GAA GAT CCA GAA ATT GTA GCT GCG
559                                                     603
TAT TCA GCA GCA ATT GTG GAA GGC GTA CAG GGT AAA TTT GGT TCT
604                                                     648
AAG GAT TTT ATG GCG CCG GGT CGC ATT GTA GCG TCA GCA AAG CAC
649                                                     693
TTC TTA GCT GAT GGT GGA ACA GAT CAA GGA CGC GAT CAG GGA GAT
694                                                     738
GCA CGC ATT TCA GAA GAC GAA CTA ATT CGC ATT CAT AAT GCT GGA
739                                                     783
TAC CCT CCT GCG ATT GAC GCA GGA GTG CTG ACA GTA ATG GCT TCT
784                                                     828
TTT TCA TCC TGG CAG GGG ATT AAA CAC CAT GGC CAT AAA CAA CTT
829                                                     873
TTA ACA GAT GTA TTA AAA GGA CAA ATG GGG TTT AAT GGA TTT ATT
874                                                     918
```

FIGURE 1A

GTG GGG GAT TGG AAT GCT CAT GAC CAA GTA CCG GGC TGT ACT AAA
919 963
TTT AAT TGT CCA ACA TCT CTT ATT GCG GGT TTA GAT ATG TAT ATG
964 1008
GCC GCC GAT TCC TGG AAG CAG CTG TAC GAA AAC ACC TTA GCA CAA
1009 1053
GTG AAA GAT GGT ACT ATT CCT ATG GCA CGT CTA GAT GAT GCC GTA
1054 1098
AGA CGA ATC TTG CGA GTC AAG GTG TTG GCT GGC TTA TTC GAG AAA
1099 1143
CCT GCG CCA AAA GAT CGT CCG GGG TTA CCA GGC CTT GAA ACA CTA
1144 1188
GGA TCA CCT GAA CAT AGA GCC GTA GGC CGT GAA GCT GTT CGA AAA
1189 1233
AGC CTA GTT CTT CTT AAA AAT GAT AAA GGT ACC CTT CCA CTG TCA
1234 1278
CCA AAG GCT AGA GTA TTA GTT GCA GGT GAC GGA GCA GAT AAT ATT
1279 1323
GGC AAA CAG TCG GGG GGC TGG ACG ATT AGT TGG CAA GGA ACT GGA
1324 1368
AAC CGT AAC GAT GAA TTT CCG GGT GCT ACA TCC ATT TTA GGT GGG
1369 1413
ATT CGA GAC GCT GTA GCT GAT GCA GGA GGG TCC GTA GAA TTT GAT
1414 1458
GTA GCG GGT CAG TAT AAA ACA AAA CCT GAT GTA GCT ATT GTT GTT
1459 1503
TTT GGC GAA GAA CCT TAT GCT GAG TTT CAG GGA GAT GTG GAG ACA
1504 1548
CTG GAA TAT CAA CCA GAT CAA AAA CAA GAT CTT GCT CTA CTC AAG
1549 1593
AAA CTG AAA GAT CAG GGA ATA CCT GTT GTT GCT GTT TTC CTT TCT
1594 1638
GGA CGA CCG ATG TGG GTT AAT CCT GAA CTT AAT GCC AGC GAT GCT
1639 1683
TTC GTT GCA GCA TGG CTT CCT GGC ACA GAA GGT GGC GGT GTG GCG
1684 1728
GAT GTA TTG TTT ACA GAC AAA GCG GGA AAA GTA CAA CAT GAT TTT
1729 1773

FIGURE 1A (CONTINUED)

GCA GGA AAA TTG TCA TAT AGT TGG CCG CGT ACG GCA GCC CAG ACA
1774 1818
ACA GTT AAC CGT GGT GAT GCA GAT TAT AAT CCG TTA TTT GCG TAT
1819 1863
GGT TAC GGT TTA ACG TAC AAA GAT AAA TCG AAA GTG GGC ACT CTA
1864 1908
CCT GAA GAA AGT GGA GTA CCG GCT GAA GCG CGA CAG AAT GCA GGG
1909 1953
ATT TAT TTT CGC GCA GGG GCG CTG AGA TTA CCA GGA AGG TTT CTG
1954 1998
TGA
2001

(SEQ ID NO: 1)

FIGURE 1A (CONTINUED)

```
MKTKWLISVIILFVFIFPQNLVFAGTSSTAIAQEGAAPAAILHPEKWPRPA
-24             -10         -1+1   5                 27
TQRLIDPAVEKRVDALLKQLSVEEKVGQVIQGDIGTITPEDLRKYPLGSIL
28                                                 78
AGGNSGPNGDDRAPPKEWLDLADAFYRVSLEKRPGHTPIPVLFGIDAVHGH
79                                                129
GNIGSATIFPHNIALGATHDPELLRRIGEVTAVEMAATGIDWTFAPALSVV
130                                               180
RDDRWGRTYEGFSEDPEIVAAYSAAIVEGVQGKFGSKDFMAPGRIVASAKH
181                                               231
FLADGGTDQGRDQGDARISEDELIRIHNAGYPPAIDAGVLTVMASFSSWQG
232                                               282
IKHHGHKQLLTDVLKGQMGFNGFIVGDWNAHDQVPGCTKFNCPTSLIAGLD
283                                               333
MYMAADSWKQLYENTLAQVKDGTIPMARLDDAVRRILRVKVLAGLFEKPAP
334                                                384
KDRPGLPGLETLGSPEHRAVGREAVRKSLVLLKNDKGTLPLSPKARVLVAG
385                                               435
DGADNIGKQSGGWTISWQGTGNRNDEFPGATSILGGIRDAVADAGGSVEFD
436                                               486
VAGQYKTKPDVAIVVFGEEPYAEFQGDVETLEYQPDQKQDLALLKKLKDQG
487                                               537
IPVVAVFLSGRPMWVNPELNASDAFVAAWLPGTEGGGVADVLFTDKAGKVQ
538                                                588
HDFAGKLSYSWPRTAAQTTVNRGDADYNPLFAYGYGLTYKDKSKVGTLPEE
589                                                639
SGVPAEARQNAGIYFRAGALRLPGRFL
640                        666
```

(SEQ ID NO: 2)

FIGURE 1B

```
AGT ACG GCA ATC GCA CAG GAA GGA GCA GCT CCG GCC GCT ATA TTA
1                                                        45
CAT CCA GAG AAA TGG CCT CGA CCT GCG ACA CAA CGA CTT ATT GAC
46                                                       90
CCG GCA GTT GAA AAA AGA GTT GAT GCT CTG TTA AAA CAG TTA TCT
91                                                      135
GTT GAA GAA AAA GTA GGG CAA GTT ATA CAG GGT GAT ATT GGG ACA
136                                                     180
ATT ACA CCA GAA GAC CTG CGC AAA TAT CCA CTA GGT TCT ATT TTA
181                                                     225
GCC GGA GGA AAC AGC GGC CCG AAT GGA GAT GAT CGT GCT CCT CCA
226                                                     270
AAG GAG TGG CTT GAT CTA GCT GAT GCT TTT TAC CGT GTA AGT TTA
271                                                     315
GAA AAA CGG CCA GGC CAT ACC CCG ATA CCA GTG CTT TTT GGC ATT
316                                                     360
GAT GCA GTT CAT GGA CAT GGC AAT ATC GGG TCT GCG ACA ATT TTC
361                                                     405
CCT CAC AAT ATT GCA CTT GGA GCA ACC CAT GAT CCA GAA CTT CTA
406                                                     450
CGA AGA ATT GGT GAG GTA ACA GCT GTT GAA ATG GCT GCT ACG GGA
451                                                     495
ATT GAT TGG ACA TTT GCG CCT GCA CTG TCT GTT GTG AGA GAT GAT
496                                                     540
CGA TGG GGA CGA ACA TAT GAA GGC TTC TCA GAA GAT CCA GAA ATT
541                                                     585
GTA GCT GCG TAT TCA GCA GCA ATT GTG GAA GGC GTA CAG GGT AAA
586                                                     630
TTT GGT TCT AAG GAT TTT ATG GCG CCG GGT CGC ATT GTA GCG TCA
621                                                     675
GCA AAG CAC TTC TTA GCT GAT GGT GGA ACA GAT CAA GGA CGC GAT
666                                                     720
CAG GGA GAT GCA CGC ATT TCA GAA GAC GAA CTA ATT CGC ATT CAT
711                                                     765
AAT GCT GGA TAC CCT CCT GCG ATT GAC GCA GGA GTG CTG ACA GTA
756                                                     810
ATG GCT TCT TTT TCA TCC TGG CAG GGG ATT AAA CAC CAT GGC CAT
801                                                     855
AAA CAA CTT TTA ACA GAT GTA TTA AAA GGA CAA ATG GGG TTT AAT
846                                                     900
```

FIGURE 2A

GGA TTT ATT GTG GGG GAT TGG AAT GCT CAT GAC CAA GTA CCG GGC
891 945
TGT ACT AAA TTT AAT TGT CCA ACA TCT CTT ATT GCG GGT TTA GAT
936 990
ATG TAT ATG GCC GCC GAT TCC TGG AAG CAG CTG TAC GAA AAC ACC
981 1035
TTA GCA CAA GTG AAA GAT GGT ACT ATT CCT ATG GCA CGT CTA GAT
1026 1080
GAT GCC GTA AGA CGA ATC TTG CGA GTC AAG GTG TTG GCT GGC TTA
1071 1125
TTC GAG AAA CCT GCG CCA AAA GAT CGT CCG GGG TTA CCA GGC CTT
1116 1170
GAA ACA CTA GGA TCA CCT GAA CAT AGA GCC GTA GGC CGT GAA GCT
1161 1215
GTT CGA AAA AGC CTA GTT CTT CTT AAA AAT GAT AAA GGT ACC CTT
1206 1260
CCA CTG TCA CCA AAG GCT AGA GTA TTA GTT GCA GGT GAC GGA GCA
1251 1305
GAT AAT ATT GGC AAA CAG TCG GGG GGC TGG ACG ATT AGT TGG CAA
1296 1350
GGA ACT GGA AAC CGT AAC GAT GAA TTT CCG GGT GCT ACA TCC ATT
1341 1395
TTA GGT GGG ATT CGA GAC GCT GTA GCT GAT GCA GGA GGG TCC GTA
1386 1440
GAA TTT GAT GTA GCG GGT CAG TAT AAA ACA AAA CCT GAT GTA GCT
1431 1485
ATT GTT GTT TTT GGC GAA GAA CCT TAT GCT GAG TTT CAG GGA GAT
1476 1530
GTG GAG ACA CTG GAA TAT CAA CCA GAT CAA AAA CAA GAT CTT GCT
1521 1575
CTA CTC AAG AAA CTG AAA GAT CAG GGA ATA CCT GTT GTT GCT GTT
1566 1620
TTC CTT TCT GGA CGA CCG ATG TGG GTT AAT CCT GAA CTT AAT GCC
1611 1665
AGC GAT GCT TTC GTT GCA GCA TGG CTT CCT GGC ACA GAA GGT GGC
1656 1710
GGT GTG GCG GAT GTA TTG TTT ACA GAC AAA GCG GGA AAA GTA CAA
1701 1755

FIGURE 2A (CONTINUED)

CAT GAT TTT GCA GGA AAA TTG TCA TAT AGT TGG CCG CGT ACG GCA
1746 1800
GCC CAG ACA ACA GTT AAC CGT GGT GAT GCA GAT TAT AAT CCG TTA
1791 1845
TTT GCG TAT GGT TAC GGT TTA ACG TAC AAA GAT AAA TCG AAA GTG
1836 1890
GGC ACT CTA CCT GAA GAA AGT GGA GTA CCG GCT GAA GCG CGA CAG
1881 1935
AAT GCA GGG ATT TAT TTT CGC GCA GGG GCG CTG AGA TTA CCA GGA
1926 1980
AGG TTT CTG TGA
1981 1992

(SEQ ID NO: 3)

FIGURE 2A (CONTINUED)

```
STAIAQEGAAPAAILHPEKWPRPATQRLIDPAVEKRVDALLKQLSVEEKVG
1                                                 51
QVIQGDIGTITPEDLRKYPLGSILAGGNSGPNGDDRAPPKEWLDLADAFYR
52                                               102
VSLEKRPGHTPIPVLFGIDAVHGHGNIGSATIFPHNIALGATHDPELLRRI
103                                              153
GEVTAVEMAATGIDWTFAPALSVVRDDRWGRTYEGFSEDPEIVAAYSAAIV
154                                              204
EGVQGKFGSKDFMAPGRIVASAKHFLADGGTDQGRDQGDARISEDELIRIH
205                                              255
NAGYPPAIDAGVLTVMASFSSWQGIKHHGHKQLLTDVLKGQMGFNGFIVGD
256                                              306
WNAHDQVPGCTKFNCPTSLIAGLDMYMAADSWKQLYENTLAQVKDGTIPMA
307                                              357
RLDDAVRRILRVKVLAGLFEKPAPKDRPGLPGLETLGSPEHRAVGREAVRK
358                                              408
SLVLLKNDKGTLPLSPKARVLVAGDGADNIGKQSGGWTISWQGTGNRNDEF
409                                              459
PGATSILGGIRDAVADAGGSVEFDVAGQYKTKPDVAIVVFGEEPYAEFQGD
460                                              510
VETLEYQPDQKQDLALLKKLKDQGIPVVAVFLSGRPMWVNPELNASDAFVA
511                                              561
AWLPGTEGGGVADVLFTDKAGKVQHDFAGKLSYSWPRTAAQTTVNRGDADY
562                                              612
NPLFAYGYGLTYKDKSKVGTLPEESGVPAEARQNAGIYFRAGALRLPGRFL
613                                              633
```

(SEQ ID NO: 4)

FIGURE 2B

STAIAQEGAAPAAILHPEKWPRPATQRLIDPAVEKRVDALLKQLSVEEKVG
1 51
QVIQGDIGTITPEDLRKYPLGSILAGGNSGPNGDDRAPPKEWLDLADAFYR
52 102
VSLEKRPGHTPIPVLFGIDAVHGHGNIGSATIFPHNIALGATRDPELLRRI
103 153
GEVTAVEMAATGIDWTFAPALSVVRDDRWGRTYEGFSEDPEIVAAYSAAIV
154 204
EGVQGKFGSKDFMAPGRIVASAKHFLADGGTDQGRDQGDARISEDELIRIH
205 255
NAGYPPAIDAGVLTVMASFSSWQGIKHHGHKQLLTDVLKGQMGFNGFIVGD
256 306
WNAHDQVPGCTKFNCPTSLIAGLDMYMAADSWKQLYENTLAQVKDGTIPMA
307 357
RLDDAVRRILRVKVLAGLFEKPAPKDRPGLPGLETLGSPEHRAVGREAVRK
358 408
SLVLLKNDKGTLPLSPKARVLVAGDGADNIGKQSGGWTISWQGTGNRNDEF
409 459
PGATSILGGIRDAVADAGGSVEFDVAGQYKTKPDVAIVVFGEEPYAEFQGD
460 510
VETLEYQPDQKQDLALLKKLKDQGIPVVAVFLSGRPMWVNPELNASDAFVA
511 561
AWLPGTEGGGVADVLFTDKAGKVQHDFAGKLSYSWPRTAAQTTVNRGDADY
562 612
NPLFAYGYGLTYKDKSKVGTLPEESGVPAEARQNAGIYFRAGALRLPGRFL
613 663

(SEQ ID NO: 5)

FIGURE 3

```
STAIAQEGAAPAAILHPEKWPRPATQRLIDPAVEKRVDALLKQLSVEEKVG
1                                                 51
QVIQGDIGTITPEDLRKYPLGSILAGGDSGPNGDDRAPPKEWLDLADAFYR
52                                               102
VSLEKRPGHTPIPVLFGIDAVHGHGNIGSATIFPHNIALGMTRDPELLRRI
103                                              153
GEVTAEEMAATGIDWTFAPALSVVRDDRWGRTYEGFSEDPEIVASYSAAIV
154                                              204
EGVQGKYGSKDFMAPGRIVASAKHFLADGGTDQGRDQGDARISEDELIRIH
205                                              255
NAGYPPAIDAGVLTVMASFSSWQGIKHHGHKQLLTDVLKGQMGFNGFIVGD
256                                              306
WNAHDQVPGCTKFNCPTSLIAGLDMYMAADSWKQLYENTLAQVKDGTIPMA
307                                              357
RLDDAVRRILRVKVLAGLFEKPAPKDRPGLPGLETLGSPEHRAVGREAVRK
358                                              408
SLVLLKNDKGTLPLSPKARVLVAGDGADNIGKQSGGWTISWQGTGNRNDEF
409                                              459
PGATSILGGIRDAVADAGGSVEFDVAGQYKTKPDVAIVVFGEEPYAEFQGD
460                                              510
VETLEYQPDQKQDLALLKKLKDQGIPVVAVFLSGRPMWVNPELNASDAFVA
511                                              561
AWLPGTEGGGVADVLFTDKAGKVQHDFAGKLSYSWPRTAAQTTVNRGDADY
562                                              612
NPLFAYGYGLTYKDKSKVGTLPEESGVPAEARQNAGIYFRAGALRLPGRFL
613                                              663
```

(SEQ ID NO: 6)

FIGURE 4

```
SAAIAQEGAAPAAMLHPEKWPRPATQRLIDPAVEKRVDALLKQLSVEEKVG
1                                                 51
QVIQGDIGTITPEDLRKYPLGSILAGGDSGPNGDDRAPPKEWLDLADAFYR
52                                               102
VSLEKRPGHTPIPVLFGIDAVHGHGNIGSATIFPHNIALGMTRDPELLRRI
103                                              153
GEVTAEEMAATGIDWTFAPALSVVRDDRWGRTYEGFSEDPEIVASYSAAIV
154                                              204
EGVQGKYGSKDFMAPGRAVACAKHFLADGGTDQGRDQGDARISEDELIRIH
205                                              255
NAGYPPAIDAGVLTVMASFSSWQGIKHHGHKQLLTDVLKGQMGFNGFIVGD
256                                              306
WNAHDQVPGCTKFNCPTSLIAGLDMYMAADSWKQLYENTLAQVKDGTIPMA
307                                              357
RLDDAVRRILRVKVLAGLFEKPAPKDRPGLPGLETLGSPEHRAVGREAVRK
358                                              408
SLVLLKNDKGTLPLSPKARVLVAGDGADNIGKQSGGWTISWQGTGNRNDEF
409                                              459
PGATSILGGIRDAVADAGGSVEFDVAGQYKTKPDVAIVVFGEEPYAEFRGD
460                                              510
VETLEYQPDQKQDLTLLKKLKDQGIPVVAVFLSGRPMWVNPELNASDAFVA
511                                              561
AWLPGTEGGGVADVLFTDKAGKVQHDFAGKLSYSWPRTAAQTTVNRGDADY
562                                              612
NPLFAYGYGLTYKDKSKVGTLPEESGVPAEARQN
613                             646
```

(SEQ ID NO: 7)

FIGURE 5

SEQUENCE LISTING

```
<160> NUMBER OF SEQ ID NOS: 13

<210> SEQ ID NO 1
<211> LENGTH: 2073
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(2073)
<220> FEATURE:
<221> NAME/KEY: sig_peptide
<222> LOCATION: (1)..(72)

<400> SEQUENCE: 1

atg aag acg aag tgg cta ata tca gtc ata atc cta ttt gtt ttc att       48
Met Lys Thr Lys Trp Leu Ile Ser Val Ile Ile Leu Phe Val Phe Ile
1               5                   10                  15

ttt cct caa aat cta gtt ttt gct ggt act agt agt acg gca atc gca       96
Phe Pro Gln Asn Leu Val Phe Ala Gly Thr Ser Ser Thr Ala Ile Ala
            20                  25                  30

cag gaa gga gca gct ccg gcc gct ata tta cat cca gag aaa tgg cct      144
Gln Glu Gly Ala Ala Pro Ala Ala Ile Leu His Pro Glu Lys Trp Pro
        35                  40                  45

cga cct gcg aca caa cga ctt att gac ccg gca gtt gaa aaa aga gtt      192
Arg Pro Ala Thr Gln Arg Leu Ile Asp Pro Ala Val Glu Lys Arg Val
```

```
    50                  55                  60

gat gct ctg tta aaa cag tta tct gtt gaa gaa aaa gta ggg caa gtt       240
Asp Ala Leu Leu Lys Gln Leu Ser Val Glu Glu Lys Val Gly Gln Val
65                  70                  75                  80

ata cag ggt gat att ggg aca att aca cca gaa gac ctg cgc aaa tat       288
Ile Gln Gly Asp Ile Gly Thr Ile Thr Pro Glu Asp Leu Arg Lys Tyr
                85                  90                  95

cca cta ggt tct att tta gcc gga gga aac agc ggc ccg aat gga gat       336
Pro Leu Gly Ser Ile Leu Ala Gly Gly Asn Ser Gly Pro Asn Gly Asp
            100                 105                 110

gat cgt gct cct cca aag gag tgg ctt gat cta gct gat gct ttt tac       384
Asp Arg Ala Pro Pro Lys Glu Trp Leu Asp Leu Ala Asp Ala Phe Tyr
        115                 120                 125

cgt gta agt tta gaa aaa cgg cca ggc cat acc ccg ata cca gtg ctt       432
Arg Val Ser Leu Glu Lys Arg Pro Gly His Thr Pro Ile Pro Val Leu
    130                 135                 140

ttt ggc att gat gca gtt cat gga cat ggc aat atc ggg tct gcg aca       480
Phe Gly Ile Asp Ala Val His Gly His Gly Asn Ile Gly Ser Ala Thr
145                 150                 155                 160

att ttc cct cac aat att gca ctt gga gca acc cat gat cca gaa ctt       528
Ile Phe Pro His Asn Ile Ala Leu Gly Ala Thr His Asp Pro Glu Leu
                165                 170                 175

cta cga aga att ggt gag gta aca gct gtt gaa atg gct gct acg gga       576
Leu Arg Arg Ile Gly Glu Val Thr Ala Val Glu Met Ala Ala Thr Gly
            180                 185                 190

att gat tgg aca ttt gcg cct gca ctg tct gtt gtg aga gat gat cga       624
Ile Asp Trp Thr Phe Ala Pro Ala Leu Ser Val Val Arg Asp Asp Arg
        195                 200                 205

tgg gga cga aca tat gaa ggc ttc tca gaa gat cca gaa att gta gct       672
Trp Gly Arg Thr Tyr Glu Gly Phe Ser Glu Asp Pro Glu Ile Val Ala
    210                 215                 220

gcg tat tca gca gca att gtg gaa ggc gta cag ggt aaa ttt ggt tct       720
Ala Tyr Ser Ala Ala Ile Val Glu Gly Val Gln Gly Lys Phe Gly Ser
225                 230                 235                 240

aag gat ttt atg gcg ccg ggt cgc att gta gcg tca gca aag cac ttc       768
Lys Asp Phe Met Ala Pro Gly Arg Ile Val Ala Ser Ala Lys His Phe
                245                 250                 255

tta gct gat ggt gga aca gat caa gga cgc gat cag gga gat gca cgc       816
Leu Ala Asp Gly Gly Thr Asp Gln Gly Arg Asp Gln Gly Asp Ala Arg
            260                 265                 270

att tca gaa gac gaa cta att cgc att cat aat gct gga tac cct cct       864
Ile Ser Glu Asp Glu Leu Ile Arg Ile His Asn Ala Gly Tyr Pro Pro
        275                 280                 285

gcg att gac gca gga gtg ctg aca gta atg gct tct ttt tca tcc tgg       912
Ala Ile Asp Ala Gly Val Leu Thr Val Met Ala Ser Phe Ser Ser Trp
    290                 295                 300

cag ggg att aaa cac cat ggc cat aaa caa ctt tta aca gat gta tta       960
Gln Gly Ile Lys His His Gly His Lys Gln Leu Leu Thr Asp Val Leu
305                 310                 315                 320

aaa gga caa atg ggg ttt aat gga ttt att gtg ggg gat tgg aat gct      1008
Lys Gly Gln Met Gly Phe Asn Gly Phe Ile Val Gly Asp Trp Asn Ala
                325                 330                 335

cat gac caa gta ccg ggc tgt act aaa ttt aat tgt cca aca tct ctt      1056
His Asp Gln Val Pro Gly Cys Thr Lys Phe Asn Cys Pro Thr Ser Leu
            340                 345                 350

att gcg ggt tta gat atg tat atg gcc gcc gat tcc tgg aag cag ctg      1104
Ile Ala Gly Leu Asp Met Tyr Met Ala Ala Asp Ser Trp Lys Gln Leu
        355                 360                 365

tac gaa aac acc tta gca caa gtg aaa gat ggt act att cct atg gca      1152
Tyr Glu Asn Thr Leu Ala Gln Val Lys Asp Gly Thr Ile Pro Met Ala
```

-continued

```
    370                 375                 380

cgt cta gat gat gcc gta aga cga atc ttg cga gtc aag gtg ttg gct      1200
Arg Leu Asp Asp Ala Val Arg Arg Ile Leu Arg Val Lys Val Leu Ala
385                 390                 395                 400

ggc tta ttc gag aaa cct gcg cca aaa gat cgt ccg ggg tta cca ggc      1248
Gly Leu Phe Glu Lys Pro Ala Pro Lys Asp Arg Pro Gly Leu Pro Gly
                405                 410                 415

ctt gaa aca cta gga tca cct gaa cat aga gcc gta ggc cgt gaa gct      1296
Leu Glu Thr Leu Gly Ser Pro Glu His Arg Ala Val Gly Arg Glu Ala
            420                 425                 430

gtt cga aaa agc cta gtt ctt ctt aaa aat gat aaa ggt acc ctt cca      1344
Val Arg Lys Ser Leu Val Leu Leu Lys Asn Asp Lys Gly Thr Leu Pro
        435                 440                 445

ctg tca cca aag gct aga gta tta gtt gca ggt gac gga gca gat aat      1392
Leu Ser Pro Lys Ala Arg Val Leu Val Ala Gly Asp Gly Ala Asp Asn
    450                 455                 460

att ggc aaa cag tcg ggg ggc tgg acg att agt tgg caa gga act gga      1440
Ile Gly Lys Gln Ser Gly Gly Trp Thr Ile Ser Trp Gln Gly Thr Gly
465                 470                 475                 480

aac cgt aac gat gaa ttt ccg ggt gct aca tcc att tta ggt ggg att      1488
Asn Arg Asn Asp Glu Phe Pro Gly Ala Thr Ser Ile Leu Gly Gly Ile
                485                 490                 495

cga gac gct gta gct gat gca gga ggg tcc gta gaa ttt gat gta gcg      1536
Arg Asp Ala Val Ala Asp Ala Gly Gly Ser Val Glu Phe Asp Val Ala
            500                 505                 510

ggt cag tat aaa aca aaa cct gat gta gct att gtt gtt ttt ggc gaa      1584
Gly Gln Tyr Lys Thr Lys Pro Asp Val Ala Ile Val Val Phe Gly Glu
        515                 520                 525

gaa cct tat gct gag ttt cag gga gat gtg gag aca ctg gaa tat caa      1632
Glu Pro Tyr Ala Glu Phe Gln Gly Asp Val Glu Thr Leu Glu Tyr Gln
    530                 535                 540

cca gat caa aaa caa gat ctt gct cta ctc aag aaa ctg aaa gat cag      1680
Pro Asp Gln Lys Gln Asp Leu Ala Leu Leu Lys Lys Leu Lys Asp Gln
545                 550                 555                 560

gga ata cct gtt gtt gct gtt ttc ctt tct gga cga ccg atg tgg gtt      1728
Gly Ile Pro Val Val Ala Val Phe Leu Ser Gly Arg Pro Met Trp Val
                565                 570                 575

aat cct gaa ctt aat gcc agc gat gct ttc gtt gca gca tgg ctt cct      1776
Asn Pro Glu Leu Asn Ala Ser Asp Ala Phe Val Ala Ala Trp Leu Pro
            580                 585                 590

ggc aca gaa ggt ggc ggt gtg gcg gat gta ttg ttt aca gac aaa gcg      1824
Gly Thr Glu Gly Gly Gly Val Ala Asp Val Leu Phe Thr Asp Lys Ala
        595                 600                 605

gga aaa gta caa cat gat ttt gca gga aaa ttg tca tat agt tgg ccg      1872
Gly Lys Val Gln His Asp Phe Ala Gly Lys Leu Ser Tyr Ser Trp Pro
    610                 615                 620

cgt acg gca gcc cag aca aca gtt aac cgt ggt gat gca gat tat aat      1920
Arg Thr Ala Ala Gln Thr Thr Val Asn Arg Gly Asp Ala Asp Tyr Asn
625                 630                 635                 640

ccg tta ttt gcg tat ggt tac ggt tta acg tac aaa gat aaa tcg aaa      1968
Pro Leu Phe Ala Tyr Gly Tyr Gly Leu Thr Tyr Lys Asp Lys Ser Lys
                645                 650                 655

gtg ggc act cta cct gaa gaa agt gga gta ccg gct gaa gcg cga cag      2016
Val Gly Thr Leu Pro Glu Glu Ser Gly Val Pro Ala Glu Ala Arg Gln
            660                 665                 670

aat gca ggg att tat ttt cgc gca ggg gcg ctg aga tta cca gga agg      2064
Asn Ala Gly Ile Tyr Phe Arg Ala Gly Ala Leu Arg Leu Pro Gly Arg
        675                 680                 685

ttt ctg tga                                                          2073
Phe Leu
```

690

<210> SEQ ID NO 2
<211> LENGTH: 690
<212> TYPE: PRT
<213> ORGANISM: Artificial Sequence
<220> FEATURE:
<223> OTHER INFORMATION: Synthetic Construct

<400> SEQUENCE: 2

```
Met Lys Thr Lys Trp Leu Ile Ser Val Ile Ile Leu Phe Val Phe Ile
1               5                   10                  15

Phe Pro Gln Asn Leu Val Phe Ala Gly Thr Ser Ser Thr Ala Ile Ala
            20                  25                  30

Gln Glu Gly Ala Ala Pro Ala Ala Ile Leu His Pro Glu Lys Trp Pro
        35                  40                  45

Arg Pro Ala Thr Gln Arg Leu Ile Asp Pro Ala Val Glu Lys Arg Val
    50                  55                  60

Asp Ala Leu Leu Lys Gln Leu Ser Val Glu Glu Lys Val Gly Gln Val
65                  70                  75                  80

Ile Gln Gly Asp Ile Gly Thr Ile Thr Pro Glu Asp Leu Arg Lys Tyr
                85                  90                  95

Pro Leu Gly Ser Ile Leu Ala Gly Gly Asn Ser Gly Pro Asn Gly Asp
            100                 105                 110

Asp Arg Ala Pro Pro Lys Glu Trp Leu Asp Leu Ala Asp Ala Phe Tyr
        115                 120                 125

Arg Val Ser Leu Glu Lys Arg Pro Gly His Thr Pro Ile Pro Val Leu
    130                 135                 140

Phe Gly Ile Asp Ala Val His Gly His Gly Asn Ile Gly Ser Ala Thr
145                 150                 155                 160

Ile Phe Pro His Asn Ile Ala Leu Gly Ala Thr His Asp Pro Glu Leu
                165                 170                 175

Leu Arg Arg Ile Gly Glu Val Thr Ala Val Glu Met Ala Ala Thr Gly
            180                 185                 190

Ile Asp Trp Thr Phe Ala Pro Ala Leu Ser Val Val Arg Asp Asp Arg
        195                 200                 205

Trp Gly Arg Thr Tyr Glu Gly Phe Ser Glu Asp Pro Glu Ile Val Ala
    210                 215                 220

Ala Tyr Ser Ala Ala Ile Val Glu Gly Val Gln Gly Lys Phe Gly Ser
225                 230                 235                 240

Lys Asp Phe Met Ala Pro Gly Arg Ile Val Ala Ser Ala Lys His Phe
                245                 250                 255

Leu Ala Asp Gly Gly Thr Asp Gln Gly Arg Asp Gln Gly Asp Ala Arg
            260                 265                 270

Ile Ser Glu Asp Glu Leu Ile Arg Ile His Asn Ala Gly Tyr Pro Pro
        275                 280                 285

Ala Ile Asp Ala Gly Val Leu Thr Val Met Ala Ser Phe Ser Ser Trp
    290                 295                 300

Gln Gly Ile Lys His His Gly His Lys Gln Leu Leu Thr Asp Val Leu
305                 310                 315                 320

Lys Gly Gln Met Gly Phe Asn Gly Phe Ile Val Gly Asp Trp Asn Ala
                325                 330                 335

His Asp Gln Val Pro Gly Cys Thr Lys Phe Asn Cys Pro Thr Ser Leu
            340                 345                 350

Ile Ala Gly Leu Asp Met Tyr Met Ala Ala Asp Ser Trp Lys Gln Leu
        355                 360                 365
```

```
Tyr Glu Asn Thr Leu Ala Gln Val Lys Asp Gly Thr Ile Pro Met Ala
    370                 375                 380

Arg Leu Asp Asp Ala Val Arg Arg Ile Leu Arg Val Lys Val Leu Ala
385                 390                 395                 400

Gly Leu Phe Glu Lys Pro Ala Pro Lys Asp Arg Pro Gly Leu Pro Gly
                405                 410                 415

Leu Glu Thr Leu Gly Ser Pro Glu His Arg Ala Val Gly Arg Glu Ala
            420                 425                 430

Val Arg Lys Ser Leu Val Leu Leu Lys Asn Asp Lys Gly Thr Leu Pro
        435                 440                 445

Leu Ser Pro Lys Ala Arg Val Leu Val Ala Gly Asp Gly Ala Asp Asn
    450                 455                 460

Ile Gly Lys Gln Ser Gly Gly Trp Thr Ile Ser Trp Gln Gly Thr Gly
465                 470                 475                 480

Asn Arg Asn Asp Glu Phe Pro Gly Ala Thr Ser Ile Leu Gly Gly Ile
                485                 490                 495

Arg Asp Ala Val Ala Asp Ala Gly Gly Ser Val Glu Phe Asp Val Ala
            500                 505                 510

Gly Gln Tyr Lys Thr Lys Pro Asp Val Ala Ile Val Val Phe Gly Glu
        515                 520                 525

Glu Pro Tyr Ala Glu Phe Gln Gly Asp Val Glu Thr Leu Glu Tyr Gln
    530                 535                 540

Pro Asp Gln Lys Gln Asp Leu Ala Leu Leu Lys Lys Leu Lys Asp Gln
545                 550                 555                 560

Gly Ile Pro Val Val Ala Val Phe Leu Ser Gly Arg Pro Met Trp Val
                565                 570                 575

Asn Pro Glu Leu Asn Ala Ser Asp Ala Phe Val Ala Ala Trp Leu Pro
            580                 585                 590

Gly Thr Glu Gly Gly Gly Val Ala Asp Val Leu Phe Thr Asp Lys Ala
        595                 600                 605

Gly Lys Val Gln His Asp Phe Ala Gly Lys Leu Ser Tyr Ser Trp Pro
    610                 615                 620

Arg Thr Ala Ala Gln Thr Thr Val Asn Arg Gly Asp Ala Asp Tyr Asn
625                 630                 635                 640

Pro Leu Phe Ala Tyr Gly Tyr Gly Leu Thr Tyr Lys Asp Lys Ser Lys
                645                 650                 655

Val Gly Thr Leu Pro Glu Glu Ser Gly Val Pro Ala Glu Ala Arg Gln
            660                 665                 670

Asn Ala Gly Ile Tyr Phe Arg Ala Gly Ala Leu Arg Leu Pro Gly Arg
        675                 680                 685

Phe Leu
    690


<210> SEQ ID NO 3
<211> LENGTH: 1992
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(1992)

<400> SEQUENCE: 3

agt acg gca atc gca cag gaa gga gca gct ccg gcc gct ata tta cat       48
Ser Thr Ala Ile Ala Gln Glu Gly Ala Ala Pro Ala Ala Ile Leu His
1               5                   10                  15
```

-continued

```
cca gag aaa tgg cct cga cct gcg aca caa cga ctt att gac ccg gca       96
Pro Glu Lys Trp Pro Arg Pro Ala Thr Gln Arg Leu Ile Asp Pro Ala
            20                  25                  30

gtt gaa aaa aga gtt gat gct ctg tta aaa cag tta tct gtt gaa gaa      144
Val Glu Lys Arg Val Asp Ala Leu Leu Lys Gln Leu Ser Val Glu Glu
        35                  40                  45

aaa gta ggg caa gtt ata cag ggt gat att ggg aca att aca cca gaa      192
Lys Val Gly Gln Val Ile Gln Gly Asp Ile Gly Thr Ile Thr Pro Glu
    50                  55                  60

gac ctg cgc aaa tat cca cta ggt tct att tta gcc gga gga aac agc      240
Asp Leu Arg Lys Tyr Pro Leu Gly Ser Ile Leu Ala Gly Gly Asn Ser
65                  70                  75                  80

ggc ccg aat gga gat gat cgt gct cct cca aag gag tgg ctt gat cta      288
Gly Pro Asn Gly Asp Asp Arg Ala Pro Pro Lys Glu Trp Leu Asp Leu
                85                  90                  95

gct gat gct ttt tac cgt gta agt tta gaa aaa cgg cca ggc cat acc      336
Ala Asp Ala Phe Tyr Arg Val Ser Leu Glu Lys Arg Pro Gly His Thr
            100                 105                 110

ccg ata cca gtg ctt ttt ggc att gat gca gtt cat gga cat ggc aat      384
Pro Ile Pro Val Leu Phe Gly Ile Asp Ala Val His Gly His Gly Asn
        115                 120                 125

atc ggg tct gcg aca att ttc cct cac aat att gca ctt gga gca acc      432
Ile Gly Ser Ala Thr Ile Phe Pro His Asn Ile Ala Leu Gly Ala Thr
    130                 135                 140

cat gat cca gaa ctt cta cga aga att ggt gag gta aca gct gtt gaa      480
His Asp Pro Glu Leu Leu Arg Arg Ile Gly Glu Val Thr Ala Val Glu
145                 150                 155                 160

atg gct gct acg gga att gat tgg aca ttt gcg cct gca ctg tct gtt      528
Met Ala Ala Thr Gly Ile Asp Trp Thr Phe Ala Pro Ala Leu Ser Val
                165                 170                 175

gtg aga gat gat cga tgg gga cga aca tat gaa ggc ttc tca gaa gat      576
Val Arg Asp Asp Arg Trp Gly Arg Thr Tyr Glu Gly Phe Ser Glu Asp
            180                 185                 190

cca gaa att gta gct gcg tat tca gca gca att gtg gaa ggc gta cag      624
Pro Glu Ile Val Ala Ala Tyr Ser Ala Ala Ile Val Glu Gly Val Gln
        195                 200                 205

ggt aaa ttt ggt tct aag gat ttt atg gcg ccg ggt cgc att gta gcg      672
Gly Lys Phe Gly Ser Lys Asp Phe Met Ala Pro Gly Arg Ile Val Ala
    210                 215                 220

tca gca aag cac ttc tta gct gat ggt gga aca gat caa gga cgc gat      720
Ser Ala Lys His Phe Leu Ala Asp Gly Gly Thr Asp Gln Gly Arg Asp
225                 230                 235                 240

cag gga gat gca cgc att tca gaa gac gaa cta att cgc att cat aat      768
Gln Gly Asp Ala Arg Ile Ser Glu Asp Glu Leu Ile Arg Ile His Asn
                245                 250                 255

gct gga tac cct cct gcg att gac gca gga gtg ctg aca gta atg gct      816
Ala Gly Tyr Pro Pro Ala Ile Asp Ala Gly Val Leu Thr Val Met Ala
            260                 265                 270

tct ttt tca tcc tgg cag ggg att aaa cac cat ggc cat aaa caa ctt      864
Ser Phe Ser Ser Trp Gln Gly Ile Lys His His Gly His Lys Gln Leu
        275                 280                 285

tta aca gat gta tta aaa gga caa atg ggg ttt aat gga ttt att gtg      912
Leu Thr Asp Val Leu Lys Gly Gln Met Gly Phe Asn Gly Phe Ile Val
    290                 295                 300

ggg gat tgg aat gct cat gac caa gta ccg ggc tgt act aaa ttt aat      960
Gly Asp Trp Asn Ala His Asp Gln Val Pro Gly Cys Thr Lys Phe Asn
305                 310                 315                 320

tgt cca aca tct ctt att gcg ggt tta gat atg tat atg gcc gcc gat     1008
Cys Pro Thr Ser Leu Ile Ala Gly Leu Asp Met Tyr Met Ala Ala Asp
                325                 330                 335
```

```
tcc tgg aag cag ctg tac gaa aac acc tta gca caa gtg aaa gat ggt      1056
Ser Trp Lys Gln Leu Tyr Glu Asn Thr Leu Ala Gln Val Lys Asp Gly
            340                 345                 350

act att cct atg gca cgt cta gat gat gcc gta aga cga atc ttg cga      1104
Thr Ile Pro Met Ala Arg Leu Asp Asp Ala Val Arg Arg Ile Leu Arg
        355                 360                 365

gtc aag gtg ttg gct ggc tta ttc gag aaa cct gcg cca aaa gat cgt      1152
Val Lys Val Leu Ala Gly Leu Phe Glu Lys Pro Ala Pro Lys Asp Arg
    370                 375                 380

ccg ggg tta cca ggc ctt gaa aca cta gga tca cct gaa cat aga gcc      1200
Pro Gly Leu Pro Gly Leu Glu Thr Leu Gly Ser Pro Glu His Arg Ala
385                 390                 395                 400

gta ggc cgt gaa gct gtt cga aaa agc cta gtt ctt ctt aaa aat gat      1248
Val Gly Arg Glu Ala Val Arg Lys Ser Leu Val Leu Leu Lys Asn Asp
                405                 410                 415

aaa ggt acc ctt cca ctg tca cca aag gct aga gta tta gtt gca ggt      1296
Lys Gly Thr Leu Pro Leu Ser Pro Lys Ala Arg Val Leu Val Ala Gly
            420                 425                 430

gac gga gca gat aat att ggc aaa cag tcg ggg ggc tgg acg att agt      1344
Asp Gly Ala Asp Asn Ile Gly Lys Gln Ser Gly Gly Trp Thr Ile Ser
        435                 440                 445

tgg caa gga act gga aac cgt aac gat gaa ttt ccg ggt gct aca tcc      1392
Trp Gln Gly Thr Gly Asn Arg Asn Asp Glu Phe Pro Gly Ala Thr Ser
    450                 455                 460

att tta ggt ggg att cga gac gct gta gct gat gca gga ggg tcc gta      1440
Ile Leu Gly Gly Ile Arg Asp Ala Val Ala Asp Ala Gly Gly Ser Val
465                 470                 475                 480

gaa ttt gat gta gcg ggt cag tat aaa aca aaa cct gat gta gct att      1488
Glu Phe Asp Val Ala Gly Gln Tyr Lys Thr Lys Pro Asp Val Ala Ile
                485                 490                 495

gtt gtt ttt ggc gaa gaa cct tat gct gag ttt cag gga gat gtg gag      1536
Val Val Phe Gly Glu Glu Pro Tyr Ala Glu Phe Gln Gly Asp Val Glu
            500                 505                 510

aca ctg gaa tat caa cca gat caa aaa caa gat ctt gct cta ctc aag      1584
Thr Leu Glu Tyr Gln Pro Asp Gln Lys Gln Asp Leu Ala Leu Leu Lys
        515                 520                 525

aaa ctg aaa gat cag gga ata cct gtt gtt gct gtt ttc ctt tct gga      1632
Lys Leu Lys Asp Gln Gly Ile Pro Val Val Ala Val Phe Leu Ser Gly
    530                 535                 540

cga ccg atg tgg gtt aat cct gaa ctt aat gcc agc gat gct ttc gtt      1680
Arg Pro Met Trp Val Asn Pro Glu Leu Asn Ala Ser Asp Ala Phe Val
545                 550                 555                 560

gca gca tgg ctt cct ggc aca gaa ggt ggc ggt gtg gcg gat gta ttg      1728
Ala Ala Trp Leu Pro Gly Thr Glu Gly Gly Gly Val Ala Asp Val Leu
                565                 570                 575

ttt aca gac aaa gcg gga aaa gta caa cat gat ttt gca gga aaa ttg      1776
Phe Thr Asp Lys Ala Gly Lys Val Gln His Asp Phe Ala Gly Lys Leu
            580                 585                 590

tca tat agt tgg ccg cgt acg gca gcc cag aca aca gtt aac cgt ggt      1824
Ser Tyr Ser Trp Pro Arg Thr Ala Ala Gln Thr Thr Val Asn Arg Gly
        595                 600                 605

gat gca gat tat aat ccg tta ttt gcg tat ggt tac ggt tta acg tac      1872
Asp Ala Asp Tyr Asn Pro Leu Phe Ala Tyr Gly Tyr Gly Leu Thr Tyr
    610                 615                 620

aaa gat aaa tcg aaa gtg ggc act cta cct gaa gaa agt gga gta ccg      1920
Lys Asp Lys Ser Lys Val Gly Thr Leu Pro Glu Glu Ser Gly Val Pro
625                 630                 635                 640

gct gaa gcg cga cag aat gca ggg att tat ttt cgc gca ggg gcg ctg      1968
Ala Glu Ala Arg Gln Asn Ala Gly Ile Tyr Phe Arg Ala Gly Ala Leu
                645                 650                 655
```

```
aga tta cca gga agg ttt ctg tga                                      1992
Arg Leu Pro Gly Arg Phe Leu
            660


<210> SEQ ID NO 4
<211> LENGTH: 663
<212> TYPE: PRT
<213> ORGANISM: Artificial Sequence
<220> FEATURE:
<223> OTHER INFORMATION: Synthetic Construct

<400> SEQUENCE: 4

Ser Thr Ala Ile Ala Gln Glu Gly Ala Ala Pro Ala Ala Ile Leu His
1               5                   10                  15

Pro Glu Lys Trp Pro Arg Pro Ala Thr Gln Arg Leu Ile Asp Pro Ala
            20                  25                  30

Val Glu Lys Arg Val Asp Ala Leu Leu Lys Gln Leu Ser Val Glu Glu
        35                  40                  45

Lys Val Gly Gln Val Ile Gln Gly Asp Ile Gly Thr Ile Thr Pro Glu
    50                  55                  60

Asp Leu Arg Lys Tyr Pro Leu Gly Ser Ile Leu Ala Gly Gly Asn Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Gly Asn
        115                 120                 125

Ile Gly Ser Ala Thr Ile Phe Pro His Asn Ile Ala Leu Gly Ala Thr
    130                 135                 140

His Asp Pro Glu Leu Leu Arg Arg Ile Gly Glu Val Thr Ala Val Glu
145                 150                 155                 160

Met Ala Ala Thr Gly Ile Asp Trp Thr Phe Ala Pro Ala Leu Ser Val
                165                 170                 175

Val Arg Asp Asp Arg Trp Gly Arg Thr Tyr Glu Gly Phe Ser Glu Asp
            180                 185                 190

Pro Glu Ile Val Ala Ala Tyr Ser Ala Ala Ile Val Glu Gly Val Gln
        195                 200                 205

Gly Lys Phe Gly Ser Lys Asp Phe Met Ala Pro Gly Arg Ile Val Ala
    210                 215                 220

Ser Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Ala
            260                 265                 270

Ser Phe Ser Ser Trp Gln Gly Ile Lys His His Gly His Lys Gln Leu
        275                 280                 285

Leu Thr Asp Val Leu Lys Gly Gln Met Gly Phe Asn Gly Phe Ile Val
    290                 295                 300

Gly Asp Trp Asn Ala His Asp Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350
```

Thr Ile Pro Met Ala Arg Leu Asp Asp Ala Val Arg Arg Ile Leu Arg
355 360 365

Val Lys Val Leu Ala Gly Leu Phe Glu Lys Pro Ala Pro Lys Asp Arg
370 375 380

Pro Gly Leu Pro Gly Leu Glu Thr Leu Gly Ser Pro Glu His Arg Ala
385 390 395 400

Val Gly Arg Glu Ala Val Arg Lys Ser Leu Val Leu Leu Lys Asn Asp
405 410 415

Lys Gly Thr Leu Pro Leu Ser Pro Lys Ala Arg Val Leu Val Ala Gly
420 425 430

Asp Gly Ala Asp Asn Ile Gly Lys Gln Ser Gly Gly Trp Thr Ile Ser
435 440 445

Trp Gln Gly Thr Gly Asn Arg Asn Asp Glu Phe Pro Gly Ala Thr Ser
450 455 460

Ile Leu Gly Gly Ile Arg Asp Ala Val Ala Asp Ala Gly Gly Ser Val
465 470 475 480

Glu Phe Asp Val Ala Gly Gln Tyr Lys Thr Lys Pro Asp Val Ala Ile
485 490 495

Val Val Phe Gly Glu Glu Pro Tyr Ala Glu Phe Gln Gly Asp Val Glu
500 505 510

Thr Leu Glu Tyr Gln Pro Asp Gln Lys Gln Asp Leu Ala Leu Leu Lys
515 520 525

Lys Leu Lys Asp Gln Gly Ile Pro Val Val Ala Val Phe Leu Ser Gly
530 535 540

Arg Pro Met Trp Val Asn Pro Glu Leu Asn Ala Ser Asp Ala Phe Val
545 550 555 560

Ala Ala Trp Leu Pro Gly Thr Glu Gly Gly Gly Val Ala Asp Val Leu
565 570 575

Phe Thr Asp Lys Ala Gly Lys Val Gln His Asp Phe Ala Gly Lys Leu
580 585 590

Ser Tyr Ser Trp Pro Arg Thr Ala Ala Gln Thr Thr Val Asn Arg Gly
595 600 605

Asp Ala Asp Tyr Asn Pro Leu Phe Ala Tyr Gly Tyr Gly Leu Thr Tyr
610 615 620

Lys Asp Lys Ser Lys Val Gly Thr Leu Pro Glu Glu Ser Gly Val Pro
625 630 635 640

Ala Glu Ala Arg Gln Asn Ala Gly Ile Tyr Phe Arg Ala Gly Ala Leu
645 650 655

Arg Leu Pro Gly Arg Phe Leu
660

<210> SEQ ID NO 5
<211> LENGTH: 663
<212> TYPE: PRT
<213> ORGANISM: Artificial Sequence
<220> FEATURE:
<223> OTHER INFORMATION: Synthetic Sequence

<400> SEQUENCE: 5

Ser Thr Ala Ile Ala Gln Glu Gly Ala Ala Pro Ala Ala Ile Leu His
1 5 10 15

Pro Glu Lys Trp Pro Arg Pro Ala Thr Gln Arg Leu Ile Asp Pro Ala
20 25 30

Val Glu Lys Arg Val Asp Ala Leu Leu Lys Gln Leu Ser Val Glu Glu
35 40 45

-continued

```
Lys Val Gly Gln Val Ile Gln Gly Asp Ile Gly Thr Ile Thr Pro Glu
    50                  55                  60

Asp Leu Arg Lys Tyr Pro Leu Gly Ser Ile Leu Ala Gly Gly Asn Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Gly Asn
        115                 120                 125

Ile Gly Ser Ala Thr Ile Phe Pro His Asn Ile Ala Leu Gly Ala Thr
    130                 135                 140

Arg Asp Pro Glu Leu Leu Arg Arg Ile Gly Glu Val Thr Ala Val Glu
145                 150                 155                 160

Met Ala Ala Thr Gly Ile Asp Trp Thr Phe Ala Pro Ala Leu Ser Val
                165                 170                 175

Val Arg Asp Asp Arg Trp Gly Arg Thr Tyr Glu Gly Phe Ser Glu Asp
            180                 185                 190

Pro Glu Ile Val Ala Ala Tyr Ser Ala Ala Ile Val Glu Gly Val Gln
        195                 200                 205

Gly Lys Phe Gly Ser Lys Asp Phe Met Ala Pro Gly Arg Ile Val Ala
    210                 215                 220

Ser Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Ala
            260                 265                 270

Ser Phe Ser Ser Trp Gln Gly Ile Lys His His Gly His Lys Gln Leu
        275                 280                 285

Leu Thr Asp Val Leu Lys Gly Gln Met Gly Phe Asn Gly Phe Ile Val
    290                 295                 300

Gly Asp Trp Asn Ala His Asp Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350

Thr Ile Pro Met Ala Arg Leu Asp Asp Ala Val Arg Arg Ile Leu Arg
        355                 360                 365

Val Lys Val Leu Ala Gly Leu Phe Glu Lys Pro Ala Pro Lys Asp Arg
    370                 375                 380

Pro Gly Leu Pro Gly Leu Glu Thr Leu Gly Ser Pro Glu His Arg Ala
385                 390                 395                 400

Val Gly Arg Glu Ala Val Arg Lys Ser Leu Val Leu Leu Lys Asn Asp
                405                 410                 415

Lys Gly Thr Leu Pro Leu Ser Pro Lys Ala Arg Val Leu Val Ala Gly
            420                 425                 430

Asp Gly Ala Asp Asn Ile Gly Lys Gln Ser Gly Gly Trp Thr Ile Ser
        435                 440                 445

Trp Gln Gly Thr Gly Asn Arg Asn Asp Glu Phe Pro Gly Ala Thr Ser
    450                 455                 460

Ile Leu Gly Gly Ile Arg Asp Ala Val Ala Asp Ala Gly Gly Ser Val
465                 470                 475                 480
```

```
Glu Phe Asp Val Ala Gly Gln Tyr Lys Thr Lys Pro Asp Val Ala Ile
                485                 490                 495

Val Val Phe Gly Glu Glu Pro Tyr Ala Glu Phe Gln Gly Asp Val Glu
            500                 505                 510

Thr Leu Glu Tyr Gln Pro Asp Gln Lys Gln Asp Leu Ala Leu Leu Lys
        515                 520                 525

Lys Leu Lys Asp Gln Gly Ile Pro Val Val Ala Val Phe Leu Ser Gly
    530                 535                 540

Arg Pro Met Trp Val Asn Pro Glu Leu Asn Ala Ser Asp Ala Phe Val
545                 550                 555                 560

Ala Ala Trp Leu Pro Gly Thr Glu Gly Gly Gly Val Ala Asp Val Leu
                565                 570                 575

Phe Thr Asp Lys Ala Gly Lys Val Gln His Asp Phe Ala Gly Lys Leu
            580                 585                 590

Ser Tyr Ser Trp Pro Arg Thr Ala Ala Gln Thr Thr Val Asn Arg Gly
        595                 600                 605

Asp Ala Asp Tyr Asn Pro Leu Phe Ala Tyr Gly Tyr Gly Leu Thr Tyr
    610                 615                 620

Lys Asp Lys Ser Lys Val Gly Thr Leu Pro Glu Glu Ser Gly Val Pro
625                 630                 635                 640

Ala Glu Ala Arg Gln Asn Ala Gly Ile Tyr Phe Arg Ala Gly Ala Leu
                645                 650                 655

Arg Leu Pro Gly Arg Phe Leu
            660


<210> SEQ ID NO 6
<211> LENGTH: 663
<212> TYPE: PRT
<213> ORGANISM: Artificial Sequence
<220> FEATURE:
<223> OTHER INFORMATION: Synthetic Sequence

<400> SEQUENCE: 6

Ser Thr Ala Ile Ala Gln Glu Gly Ala Ala Pro Ala Ala Ile Leu His
1               5                   10                  15

Pro Glu Lys Trp Pro Arg Pro Ala Thr Gln Arg Leu Ile Asp Pro Ala
            20                  25                  30

Val Glu Lys Arg Val Asp Ala Leu Leu Lys Gln Leu Ser Val Glu Glu
        35                  40                  45

Lys Val Gly Gln Val Ile Gln Gly Asp Ile Gly Thr Ile Thr Pro Glu
    50                  55                  60

Asp Leu Arg Lys Tyr Pro Leu Gly Ser Ile Leu Ala Gly Gly Asp Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Gly Asn
        115                 120                 125

Ile Gly Ser Ala Thr Ile Phe Pro His Asn Ile Ala Leu Gly Met Thr
    130                 135                 140

Arg Asp Pro Glu Leu Leu Arg Arg Ile Gly Glu Val Thr Ala Glu Glu
145                 150                 155                 160

Met Ala Ala Thr Gly Ile Asp Trp Thr Phe Ala Pro Ala Leu Ser Val
                165                 170                 175
```

-continued

```
Val Arg Asp Asp Arg Trp Gly Arg Thr Tyr Glu Gly Phe Ser Glu Asp
            180                 185                 190

Pro Glu Ile Val Ala Ser Tyr Ser Ala Ala Ile Val Glu Gly Val Gln
        195                 200                 205

Gly Lys Tyr Gly Ser Lys Asp Phe Met Ala Pro Gly Arg Ile Val Ala
    210                 215                 220

Ser Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Ala
            260                 265                 270

Ser Phe Ser Ser Trp Gln Gly Ile Lys His His Gly His Lys Gln Leu
        275                 280                 285

Leu Thr Asp Val Leu Lys Gly Gln Met Gly Phe Asn Gly Phe Ile Val
    290                 295                 300

Gly Asp Trp Asn Ala His Asp Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350

Thr Ile Pro Met Ala Arg Leu Asp Asp Ala Val Arg Arg Ile Leu Arg
        355                 360                 365

Val Lys Val Leu Ala Gly Leu Phe Glu Lys Pro Ala Pro Lys Asp Arg
    370                 375                 380

Pro Gly Leu Pro Gly Leu Glu Thr Leu Gly Ser Pro Glu His Arg Ala
385                 390                 395                 400

Val Gly Arg Glu Ala Val Arg Lys Ser Leu Val Leu Leu Lys Asn Asp
                405                 410                 415

Lys Gly Thr Leu Pro Leu Ser Pro Lys Ala Arg Val Leu Val Ala Gly
            420                 425                 430

Asp Gly Ala Asp Asn Ile Gly Lys Gln Ser Gly Gly Trp Thr Ile Ser
        435                 440                 445

Trp Gln Gly Thr Gly Asn Arg Asn Asp Glu Phe Pro Gly Ala Thr Ser
    450                 455                 460

Ile Leu Gly Gly Ile Arg Asp Ala Val Ala Asp Ala Gly Gly Ser Val
465                 470                 475                 480

Glu Phe Asp Val Ala Gly Gln Tyr Lys Thr Lys Pro Asp Val Ala Ile
                485                 490                 495

Val Val Phe Gly Glu Glu Pro Tyr Ala Glu Phe Gln Gly Asp Val Glu
            500                 505                 510

Thr Leu Glu Tyr Gln Pro Asp Gln Lys Gln Asp Leu Ala Leu Leu Lys
        515                 520                 525

Lys Leu Lys Asp Gln Gly Ile Pro Val Val Ala Val Phe Leu Ser Gly
    530                 535                 540

Arg Pro Met Trp Val Asn Pro Glu Leu Asn Ala Ser Asp Ala Phe Val
545                 550                 555                 560

Ala Ala Trp Leu Pro Gly Thr Glu Gly Gly Gly Val Ala Asp Val Leu
                565                 570                 575

Phe Thr Asp Lys Ala Gly Lys Val Gln His Asp Phe Ala Gly Lys Leu
            580                 585                 590

Ser Tyr Ser Trp Pro Arg Thr Ala Ala Gln Thr Thr Val Asn Arg Gly
        595                 600                 605
```

Asp Ala Asp Tyr Asn Pro Leu Phe Ala Tyr Gly Tyr Gly Leu Thr Tyr
610 615 620

Lys Asp Lys Ser Lys Val Gly Thr Leu Pro Glu Glu Ser Gly Val Pro
625 630 635 640

Ala Glu Ala Arg Gln Asn Ala Gly Ile Tyr Phe Arg Ala Gly Ala Leu
645 650 655

Arg Leu Pro Gly Arg Phe Leu
660

<210> SEQ ID NO 7
<211> LENGTH: 646
<212> TYPE: PRT
<213> ORGANISM: Artificial Sequence
<220> FEATURE:
<223> OTHER INFORMATION: Synthetic Sequence

<400> SEQUENCE: 7

Ser Ala Ala Ile Ala Gln Glu Gly Ala Ala Pro Ala Ala Met Leu His
1 5 10 15

Pro Glu Lys Trp Pro Arg Pro Ala Thr Gln Arg Leu Ile Asp Pro Ala
20 25 30

Val Glu Lys Arg Val Asp Ala Leu Leu Lys Gln Leu Ser Val Glu Glu
35 40 45

Lys Val Gly Gln Val Ile Gln Gly Asp Ile Gly Thr Ile Thr Pro Glu
50 55 60

Asp Leu Arg Lys Tyr Pro Leu Gly Ser Ile Leu Ala Gly Gly Asp Ser
65 70 75 80

Gly Pro Asn Gly Asp Asp Arg Ala Pro Pro Lys Glu Trp Leu Asp Leu
85 90 95

Ala Asp Ala Phe Tyr Arg Val Ser Leu Glu Lys Arg Pro Gly His Thr
100 105 110

Pro Ile Pro Val Leu Phe Gly Ile Asp Ala Val His Gly His Gly Asn
115 120 125

Ile Gly Ser Ala Thr Ile Phe Pro His Asn Ile Ala Leu Gly Met Thr
130 135 140

Arg Asp Pro Glu Leu Leu Arg Arg Ile Gly Glu Val Thr Ala Glu Glu
145 150 155 160

Met Ala Ala Thr Gly Ile Asp Trp Thr Phe Ala Pro Ala Leu Ser Val
165 170 175

Val Arg Asp Asp Arg Trp Gly Arg Thr Tyr Glu Gly Phe Ser Glu Asp
180 185 190

Pro Glu Ile Val Ala Ser Tyr Ser Ala Ala Ile Val Glu Gly Val Gln
195 200 205

Gly Lys Tyr Gly Ser Lys Asp Phe Met Ala Pro Gly Arg Ala Val Ala
210 215 220

Cys Ala Lys His Phe Leu Ala Asp Gly Gly Thr Asp Gln Gly Arg Asp
225 230 235 240

Gln Gly Asp Ala Arg Ile Ser Glu Asp Glu Leu Ile Arg Ile His Asn
245 250 255

Ala Gly Tyr Pro Pro Ala Ile Asp Ala Gly Val Leu Thr Val Met Ala
260 265 270

Ser Phe Ser Ser Trp Gln Gly Ile Lys His His Gly His Lys Gln Leu
275 280 285

Leu Thr Asp Val Leu Lys Gly Gln Met Gly Phe Asn Gly Phe Ile Val
290 295 300

Gly Asp Trp Asn Ala His Asp Gln Val Pro Gly Cys Thr Lys Phe Asn
305 310 315 320

Cys Pro Thr Ser Leu Ile Ala Gly Leu Asp Met Tyr Met Ala Ala Asp
325 330 335

Ser Trp Lys Gln Leu Tyr Glu Asn Thr Leu Ala Gln Val Lys Asp Gly
340 345 350

Thr Ile Pro Met Ala Arg Leu Asp Asp Ala Val Arg Arg Ile Leu Arg
355 360 365

Val Lys Val Leu Ala Gly Leu Phe Glu Lys Pro Ala Pro Lys Asp Arg
370 375 380

Pro Gly Leu Pro Gly Leu Glu Thr Leu Gly Ser Pro Glu His Arg Ala
385 390 395 400

Val Gly Arg Glu Ala Val Arg Lys Ser Leu Val Leu Leu Lys Asn Asp
405 410 415

Lys Gly Thr Leu Pro Leu Ser Pro Lys Ala Arg Val Leu Val Ala Gly
420 425 430

Asp Gly Ala Asp Asn Ile Gly Lys Gln Ser Gly Gly Trp Thr Ile Ser
435 440 445

Trp Gln Gly Thr Gly Asn Arg Asn Asp Glu Phe Pro Gly Ala Thr Ser
450 455 460

Ile Leu Gly Gly Ile Arg Asp Ala Val Ala Asp Ala Gly Gly Ser Val
465 470 475 480

Glu Phe Asp Val Ala Gly Gln Tyr Lys Thr Lys Pro Asp Val Ala Ile
485 490 495

Val Val Phe Gly Glu Glu Pro Tyr Ala Glu Phe Arg Gly Asp Val Glu
500 505 510

Thr Leu Glu Tyr Gln Pro Asp Gln Lys Gln Asp Leu Thr Leu Leu Lys
515 520 525

Lys Leu Lys Asp Gln Gly Ile Pro Val Val Ala Val Phe Leu Ser Gly
530 535 540

Arg Pro Met Trp Val Asn Pro Glu Leu Asn Ala Ser Asp Ala Phe Val
545 550 555 560

Ala Ala Trp Leu Pro Gly Thr Glu Gly Gly Gly Val Ala Asp Val Leu
565 570 575

Phe Thr Asp Lys Ala Gly Lys Val Gln His Asp Phe Ala Gly Lys Leu
580 585 590

Ser Tyr Ser Trp Pro Arg Thr Ala Ala Gln Thr Thr Val Asn Arg Gly
595 600 605

Asp Ala Asp Tyr Asn Pro Leu Phe Ala Tyr Gly Tyr Gly Leu Thr Tyr
610 615 620

Lys Asp Lys Ser Lys Val Gly Thr Leu Pro Glu Glu Ser Gly Val Pro
625 630 635 640

Ala Glu Ala Arg Gln Asn
645

<210> SEQ ID NO 8
<211> LENGTH: 1941
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(1941)

<400> SEQUENCE: 8 agt gcg gca atc aca cag gaa gga gca gct ccg gcc gct atg tta cat 48

-continued

```
Ser Ala Ala Ile Thr Gln Glu Gly Ala Ala Pro Ala Ala Met Leu His
1               5                   10                  15

cca gag aaa tgg cct cga cct gcg aca caa cga ctt att gac ccg gca       96
Pro Glu Lys Trp Pro Arg Pro Ala Thr Gln Arg Leu Ile Asp Pro Ala
            20                  25                  30

gtt gaa aaa aga gtt gat gct ctg tta aaa cag tta tct gtt gaa gaa      144
Val Glu Lys Arg Val Asp Ala Leu Leu Lys Gln Leu Ser Val Glu Glu
        35                  40                  45

aaa gta ggg caa gtt ata cag ggt gat att ggg aca att aca cca gaa      192
Lys Val Gly Gln Val Ile Gln Gly Asp Ile Gly Thr Ile Thr Pro Glu
    50                  55                  60

gac ctg cgc aaa tat cca cta ggt tct att tta gcc gga gga gat agc      240
Asp Leu Arg Lys Tyr Pro Leu Gly Ser Ile Leu Ala Gly Gly Asp Ser
65                  70                  75                  80

ggc ccg aat gga gat gat cgt gct cct cca aag gag tgg ctt gat cta      288
Gly Pro Asn Gly Asp Asp Arg Ala Pro Pro Lys Glu Trp Leu Asp Leu
                85                  90                  95

gct gat gct ttt tac cgt gta agt tta gaa aaa cgg cca ggc cat acc      336
Ala Asp Ala Phe Tyr Arg Val Ser Leu Glu Lys Arg Pro Gly His Thr
            100                 105                 110

ccg ata cca gtg ctt ttt ggc att gat gca gtt cat gga cat aac aat      384
Pro Ile Pro Val Leu Phe Gly Ile Asp Ala Val His Gly His Asn Asn
        115                 120                 125

atc ggg tct gcg aca att ttc cct cac aat att gca ctt gga atg acc      432
Ile Gly Ser Ala Thr Ile Phe Pro His Asn Ile Ala Leu Gly Met Thr
    130                 135                 140

cgt gat cca gaa ctt cta cga aga att ggt gag gta aca gct gaa gaa      480
Arg Asp Pro Glu Leu Leu Arg Arg Ile Gly Glu Val Thr Ala Glu Glu
145                 150                 155                 160

atg gct gcc acg gga att gat tgg aca ttt gcg cct gca ctg tct gtt      528
Met Ala Ala Thr Gly Ile Asp Trp Thr Phe Ala Pro Ala Leu Ser Val
                165                 170                 175

gtg aga gat gat cga tgg gga cga acg tat gaa ggc ttc tca gaa gat      576
Val Arg Asp Asp Arg Trp Gly Arg Thr Tyr Glu Gly Phe Ser Glu Asp
            180                 185                 190

cca gaa att gta gct tct tat tca gca gca att gtg gaa ggc ttt cag      624
Pro Glu Ile Val Ala Ser Tyr Ser Ala Ala Ile Val Glu Gly Phe Gln
        195                 200                 205

ggt aaa tat ggt tct aag gat ttt atg gcg ccg ggt cgc gcg gta gcg      672
Gly Lys Tyr Gly Ser Lys Asp Phe Met Ala Pro Gly Arg Ala Val Ala
    210                 215                 220

tgc gca aag cac ttc tta gct gat ggt gga aca gat caa gga cgc gat      720
Cys Ala Lys His Phe Leu Ala Asp Gly Gly Thr Asp Gln Gly Arg Asp
225                 230                 235                 240

cag gga gat gca cgc att tca gaa gac gaa cta att cgc att cat aat      768
Gln Gly Asp Ala Arg Ile Ser Glu Asp Glu Leu Ile Arg Ile His Asn
                245                 250                 255

gct gga tac cct cct gcg att gac gca gga gtg ctg aca gta atg gct      816
Ala Gly Tyr Pro Pro Ala Ile Asp Ala Gly Val Leu Thr Val Met Ala
            260                 265                 270

tct ttt tca tcc tgg cag ggg att aaa cac cat ggc cat aaa caa ctt      864
Ser Phe Ser Ser Trp Gln Gly Ile Lys His His Gly His Lys Gln Leu
        275                 280                 285

tta aca gat gta tta aaa gga caa atg ggg ttt aat gga ttt att gtg      912
Leu Thr Asp Val Leu Lys Gly Gln Met Gly Phe Asn Gly Phe Ile Val
    290                 295                 300

ggg gat tgg aat gct cat gac caa gta ccg ggc tgt act aaa ttt aat      960
Gly Asp Trp Asn Ala His Asp Gln Val Pro Gly Cys Thr Lys Phe Asn
305                 310                 315                 320

tgt cca aca tct ctt att gcg ggt tta gat atg tat atg gcc gcc gat     1008
```

-continued

```
Cys Pro Thr Ser Leu Ile Ala Gly Leu Asp Met Tyr Met Ala Ala Asp
                325                 330                 335

tcc tgg aag cag ctg tac gaa aac acc tta gca caa gtg aaa gat ggt      1056
Ser Trp Lys Gln Leu Tyr Glu Asn Thr Leu Ala Gln Val Lys Asp Gly
            340                 345                 350

act att cct atg gca cgt cta gat gat gcc gta aga cga atc ttg cga      1104
Thr Ile Pro Met Ala Arg Leu Asp Asp Ala Val Arg Arg Ile Leu Arg
        355                 360                 365

gtc aag gtg ttg gct ggc tta ttc gag aaa cct gcg cca aaa gat cgt      1152
Val Lys Val Leu Ala Gly Leu Phe Glu Lys Pro Ala Pro Lys Asp Arg
    370                 375                 380

ccg ggg tta cca ggc ctt gaa aca cta gga tca cct gaa cat aga gcc      1200
Pro Gly Leu Pro Gly Leu Glu Thr Leu Gly Ser Pro Glu His Arg Ala
385                 390                 395                 400

gta ggc cgt gaa gct gtt cga aaa agc cta gtt ctt ctt aaa aat gat      1248
Val Gly Arg Glu Ala Val Arg Lys Ser Leu Val Leu Leu Lys Asn Asp
                405                 410                 415

aaa ggt acc ctt cca ctg tca cca aag gct aga gta tta gtt gca ggt      1296
Lys Gly Thr Leu Pro Leu Ser Pro Lys Ala Arg Val Leu Val Ala Gly
            420                 425                 430

gac gga gca gat aat att ggc aaa cag tcg ggg ggc tgg acg att agt      1344
Asp Gly Ala Asp Asn Ile Gly Lys Gln Ser Gly Gly Trp Thr Ile Ser
        435                 440                 445

tgg caa gga act gga aac cgt aac gat gaa ttt ccg ggt gct aca tcc      1392
Trp Gln Gly Thr Gly Asn Arg Asn Asp Glu Phe Pro Gly Ala Thr Ser
    450                 455                 460

att tta ggt ggg att cga gac gct gta gct gat gca gga ggg tcc gta      1440
Ile Leu Gly Gly Ile Arg Asp Ala Val Ala Asp Ala Gly Gly Ser Val
465                 470                 475                 480

gaa ttt gat gta gcg ggt cag tat aaa aca aaa cct gat gta gct att      1488
Glu Phe Asp Val Ala Gly Gln Tyr Lys Thr Lys Pro Asp Val Ala Ile
                485                 490                 495

gtt gtt ttt ggc gaa gaa cct tat gct gag ttt cgt gga gat gtg gag      1536
Val Val Phe Gly Glu Glu Pro Tyr Ala Glu Phe Arg Gly Asp Val Glu
            500                 505                 510

aca ctg gaa tat caa cca gat caa aaa caa gat ctt acc cta ctc aag      1584
Thr Leu Glu Tyr Gln Pro Asp Gln Lys Gln Asp Leu Thr Leu Leu Lys
        515                 520                 525

aaa ctg aaa gat cag gga ata cct gtt gtt gct gtt ttc ctt tct gga      1632
Lys Leu Lys Asp Gln Gly Ile Pro Val Val Ala Val Phe Leu Ser Gly
    530                 535                 540

cga ccg atg tgg gtt aat cct gaa ctt aat gcc agc gat gct ttc gtt      1680
Arg Pro Met Trp Val Asn Pro Glu Leu Asn Ala Ser Asp Ala Phe Val
545                 550                 555                 560

gca gca tgg ctt cct ggc aca gaa ggt ggc ggt gtg gcg gat gta ttg      1728
Ala Ala Trp Leu Pro Gly Thr Glu Gly Gly Gly Val Ala Asp Val Leu
                565                 570                 575

ttt aca gac aaa gcg gga aaa gta caa cat gat ttt gca gga aaa ttg      1776
Phe Thr Asp Lys Ala Gly Lys Val Gln His Asp Phe Ala Gly Lys Leu
            580                 585                 590

tca tat agt tgg ccg cgt acg gca gcc cag aca aca gtt aac cgt ggt      1824
Ser Tyr Ser Trp Pro Arg Thr Ala Ala Gln Thr Thr Val Asn Arg Gly
        595                 600                 605

gat gca gat tat aat ccg tta ttt gcg tat ggt tac ggt tta acg tac      1872
Asp Ala Asp Tyr Asn Pro Leu Phe Ala Tyr Gly Tyr Gly Leu Thr Tyr
    610                 615                 620

aaa gat aaa tcg aaa gtg ggc act cta cct gaa gaa agt gga gta ccg      1920
Lys Asp Lys Ser Lys Val Gly Thr Leu Pro Glu Glu Ser Gly Val Pro
625                 630                 635                 640

gct gaa gcg cga cag aat tga                                          1941
```

Ala Glu Ala Arg Gln Asn
645

<210> SEQ ID NO 9
<211> LENGTH: 646
<212> TYPE: PRT
<213> ORGANISM: Artificial Sequence
<220> FEATURE:
<223> OTHER INFORMATION: Synthetic Construct

<400> SEQUENCE: 9

Ser Ala Ala Ile Thr Gln Glu Gly Ala Ala Pro Ala Ala Met Leu His
1 5 10 15

Pro Glu Lys Trp Pro Arg Pro Ala Thr Gln Arg Leu Ile Asp Pro Ala
20 25 30

Val Glu Lys Arg Val Asp Ala Leu Leu Lys Gln Leu Ser Val Glu Glu
35 40 45

Lys Val Gly Gln Val Ile Gln Gly Asp Ile Gly Thr Ile Thr Pro Glu
50 55 60

Asp Leu Arg Lys Tyr Pro Leu Gly Ser Ile Leu Ala Gly Gly Asp Ser
65 70 75 80

Gly Pro Asn Gly Asp Asp Arg Ala Pro Pro Lys Glu Trp Leu Asp Leu
85 90 95

Ala Asp Ala Phe Tyr Arg Val Ser Leu Glu Lys Arg Pro Gly His Thr
100 105 110

Pro Ile Pro Val Leu Phe Gly Ile Asp Ala Val His Gly His Asn Asn
115 120 125

Ile Gly Ser Ala Thr Ile Phe Pro His Asn Ile Ala Leu Gly Met Thr
130 135 140

Arg Asp Pro Glu Leu Leu Arg Arg Ile Gly Glu Val Thr Ala Glu Glu
145 150 155 160

Met Ala Ala Thr Gly Ile Asp Trp Thr Phe Ala Pro Ala Leu Ser Val
165 170 175

Val Arg Asp Asp Arg Trp Gly Arg Thr Tyr Glu Gly Phe Ser Glu Asp
180 185 190

Pro Glu Ile Val Ala Ser Tyr Ser Ala Ala Ile Val Glu Gly Phe Gln
195 200 205

Gly Lys Tyr Gly Ser Lys Asp Phe Met Ala Pro Gly Arg Ala Val Ala
210 215 220

Cys Ala Lys His Phe Leu Ala Asp Gly Gly Thr Asp Gln Gly Arg Asp
225 230 235 240

Gln Gly Asp Ala Arg Ile Ser Glu Asp Glu Leu Ile Arg Ile His Asn
245 250 255

Ala Gly Tyr Pro Pro Ala Ile Asp Ala Gly Val Leu Thr Val Met Ala
260 265 270

Ser Phe Ser Ser Trp Gln Gly Ile Lys His His Gly His Lys Gln Leu
275 280 285

Leu Thr Asp Val Leu Lys Gly Gln Met Gly Phe Asn Gly Phe Ile Val
290 295 300

Gly Asp Trp Asn Ala His Asp Gln Val Pro Gly Cys Thr Lys Phe Asn
305 310 315 320

Cys Pro Thr Ser Leu Ile Ala Gly Leu Asp Met Tyr Met Ala Ala Asp
325 330 335

Ser Trp Lys Gln Leu Tyr Glu Asn Thr Leu Ala Gln Val Lys Asp Gly
340 345 350

Thr Ile Pro Met Ala Arg Leu Asp Asp Ala Val Arg Arg Ile Leu Arg

```
        355                 360                 365

Val Lys Val Leu Ala Gly Leu Phe Glu Lys Pro Ala Pro Lys Asp Arg
    370                 375                 380

Pro Gly Leu Pro Gly Leu Glu Thr Leu Gly Ser Pro Glu His Arg Ala
385                 390                 395                 400

Val Gly Arg Glu Ala Val Arg Lys Ser Leu Val Leu Leu Lys Asn Asp
                405                 410                 415

Lys Gly Thr Leu Pro Leu Ser Pro Lys Ala Arg Val Leu Val Ala Gly
            420                 425                 430

Asp Gly Ala Asp Asn Ile Gly Lys Gln Ser Gly Gly Trp Thr Ile Ser
        435                 440                 445

Trp Gln Gly Thr Gly Asn Arg Asn Asp Glu Phe Pro Gly Ala Thr Ser
    450                 455                 460

Ile Leu Gly Gly Ile Arg Asp Ala Val Ala Asp Ala Gly Gly Ser Val
465                 470                 475                 480

Glu Phe Asp Val Ala Gly Gln Tyr Lys Thr Lys Pro Asp Val Ala Ile
                485                 490                 495

Val Val Phe Gly Glu Glu Pro Tyr Ala Glu Phe Arg Gly Asp Val Glu
            500                 505                 510

Thr Leu Glu Tyr Gln Pro Asp Gln Lys Gln Asp Leu Thr Leu Leu Lys
        515                 520                 525

Lys Leu Lys Asp Gln Gly Ile Pro Val Val Ala Val Phe Leu Ser Gly
    530                 535                 540

Arg Pro Met Trp Val Asn Pro Glu Leu Asn Ala Ser Asp Ala Phe Val
545                 550                 555                 560

Ala Ala Trp Leu Pro Gly Thr Glu Gly Gly Gly Val Ala Asp Val Leu
                565                 570                 575

Phe Thr Asp Lys Ala Gly Lys Val Gln His Asp Phe Ala Gly Lys Leu
            580                 585                 590

Ser Tyr Ser Trp Pro Arg Thr Ala Ala Gln Thr Thr Val Asn Arg Gly
        595                 600                 605

Asp Ala Asp Tyr Asn Pro Leu Phe Ala Tyr Gly Tyr Gly Leu Thr Tyr
    610                 615                 620

Lys Asp Lys Ser Lys Val Gly Thr Leu Pro Glu Glu Ser Gly Val Pro
625                 630                 635                 640

Ala Glu Ala Arg Gln Asn
                645


<210> SEQ ID NO 10
<211> LENGTH: 1941
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(1941)

<400> SEQUENCE: 10

agt gcg cga att aca cag gaa gga gca gct ccg gcc gct atg tta cat       48
Ser Ala Arg Ile Thr Gln Glu Gly Ala Ala Pro Ala Ala Met Leu His
1               5                   10                  15

cca gag aaa tgg cct cga cct gcg aca caa cga ctt att gac ccg gca       96
Pro Glu Lys Trp Pro Arg Pro Ala Thr Gln Arg Leu Ile Asp Pro Ala
            20                  25                  30

gtt gaa aaa aga gtt gat gct ctg tta aaa cag tta tct gtt gaa gaa      144
Val Glu Lys Arg Val Asp Ala Leu Leu Lys Gln Leu Ser Val Glu Glu
        35                  40                  45
```

```
aaa gta ggg caa gtt ata cag ggt gat att ggg aca att aca cca gaa      192
Lys Val Gly Gln Val Ile Gln Gly Asp Ile Gly Thr Ile Thr Pro Glu
    50                  55                  60

gac ctg cgc aaa tat cca cta ggt gct att tta gcc gga gga gat agc      240
Asp Leu Arg Lys Tyr Pro Leu Gly Ala Ile Leu Ala Gly Gly Asp Ser
65                  70                  75                  80

ggc ccg aat gga gat gat cgt gct cct cca aag gag tgg ctt gat cta      288
Gly Pro Asn Gly Asp Asp Arg Ala Pro Pro Lys Glu Trp Leu Asp Leu
                85                  90                  95

gct gat gct ttt tac cgt gta agt tta gaa aaa cgg cca ggc cat acc      336
Ala Asp Ala Phe Tyr Arg Val Ser Leu Glu Lys Arg Pro Gly His Thr
            100                 105                 110

ccg ata cca gtg ctt ttt ggc att gat gca gtt cat gga cat aac aat      384
Pro Ile Pro Val Leu Phe Gly Ile Asp Ala Val His Gly His Asn Asn
        115                 120                 125

atc ggg tct gcg aca att ttc cct cac aat att gca ctt gga atg acc      432
Ile Gly Ser Ala Thr Ile Phe Pro His Asn Ile Ala Leu Gly Met Thr
    130                 135                 140

cgt gat cca gaa ctt cta cga aga att ggt gag gta aca gct gaa gaa      480
Arg Asp Pro Glu Leu Leu Arg Arg Ile Gly Glu Val Thr Ala Glu Glu
145                 150                 155                 160

atg gct gcc acg gga att gat tgg aca ttt gcg cct gca ctg tct gtt      528
Met Ala Ala Thr Gly Ile Asp Trp Thr Phe Ala Pro Ala Leu Ser Val
                165                 170                 175

ccg aga gat gat cga tgg gga cga acg tat gaa ggc ttc tca gaa gat      576
Pro Arg Asp Asp Arg Trp Gly Arg Thr Tyr Glu Gly Phe Ser Glu Asp
            180                 185                 190

cca gaa att gta gct tct tat tca gca gca tat gtg gaa ggc ttt cag      624
Pro Glu Ile Val Ala Ser Tyr Ser Ala Ala Tyr Val Glu Gly Phe Gln
        195                 200                 205

ggt aaa tat ggt tct aag gat ttt atg gcg ccg ggt cgc gcg gta gcg      672
Gly Lys Tyr Gly Ser Lys Asp Phe Met Ala Pro Gly Arg Ala Val Ala
    210                 215                 220

tgc gca aag cac ttc tta gct gat ggt gga aca gat caa gga cgc gat      720
Cys Ala Lys His Phe Leu Ala Asp Gly Gly Thr Asp Gln Gly Arg Asp
225                 230                 235                 240

cag gga gat gca cgc att tca gaa gac gaa cta att cgc att cat aat      768
Gln Gly Asp Ala Arg Ile Ser Glu Asp Glu Leu Ile Arg Ile His Asn
                245                 250                 255

gct gga tac cct cct gcg att gac gca gga gtg ctg aca gta atg gct      816
Ala Gly Tyr Pro Pro Ala Ile Asp Ala Gly Val Leu Thr Val Met Ala
            260                 265                 270

tct ttt tca tcc tgg cag ggg att aaa cac cat ggc cat aaa caa ctt      864
Ser Phe Ser Ser Trp Gln Gly Ile Lys His His Gly His Lys Gln Leu
        275                 280                 285

tta aca gat gta tta aaa gga caa atg ggg ttt aat gga ttt att gtg      912
Leu Thr Asp Val Leu Lys Gly Gln Met Gly Phe Asn Gly Phe Ile Val
    290                 295                 300

ggg gat tgg aat gct cat gac caa gta ccg ggc tgt act aaa ttt aat      960
Gly Asp Trp Asn Ala His Asp Gln Val Pro Gly Cys Thr Lys Phe Asn
305                 310                 315                 320

tgt cca aca tct ctt att gcg ggt tta gat atg tat atg gcc gcc gat     1008
Cys Pro Thr Ser Leu Ile Ala Gly Leu Asp Met Tyr Met Ala Ala Asp
                325                 330                 335

tcc tgg aag cag ctg tac gaa aac acc tta gca caa gtg aaa gat ggt     1056
Ser Trp Lys Gln Leu Tyr Glu Asn Thr Leu Ala Gln Val Lys Asp Gly
            340                 345                 350

act att cct atg gca cgt cta gat gat gcc gta aga cga atc ttg cga     1104
Thr Ile Pro Met Ala Arg Leu Asp Asp Ala Val Arg Arg Ile Leu Arg
        355                 360                 365
```

-continued gtc aag gtg ttg gct ggc tta ttc gag aaa cct gcg cca aaa gat cgt     1152
Val Lys Val Leu Ala Gly Leu Phe Glu Lys Pro Ala Pro Lys Asp Arg
    370                 375                 380 ccg ggg tta cca ggc ctt gaa aca cta gga tca cct gaa cat aga gcc     1200
Pro Gly Leu Pro Gly Leu Glu Thr Leu Gly Ser Pro Glu His Arg Ala
385                 390                 395                 400 gta ggc cgt gaa gct gtt cga aaa agc cta gtt ctt ctt aaa aat gat     1248
Val Gly Arg Glu Ala Val Arg Lys Ser Leu Val Leu Leu Lys Asn Asp
                405                 410                 415 aaa ggt acc ctt cca ctg tca cca aag gct aga gta tta gtt gca ggt     1296
Lys Gly Thr Leu Pro Leu Ser Pro Lys Ala Arg Val Leu Val Ala Gly
            420                 425                 430 gac gga gca gat aat att ggc aaa cag tcg ggg ggc tgg acg att agt     1344
Asp Gly Ala Asp Asn Ile Gly Lys Gln Ser Gly Gly Trp Thr Ile Ser
        435                 440                 445 tgg caa gga act gga aac cgt aac gat gaa ttt ccg ggt gct aca tcc     1392
Trp Gln Gly Thr Gly Asn Arg Asn Asp Glu Phe Pro Gly Ala Thr Ser
    450                 455                 460 att tta ggt ggg att cga gac gct gta gct gat gca gga ggg tcc gta     1440
Ile Leu Gly Gly Ile Arg Asp Ala Val Ala Asp Ala Gly Gly Ser Val
465                 470                 475                 480 gaa ttt gat gta gcg ggt cag tat aaa aca aaa cct gat gta gct att     1488
Glu Phe Asp Val Ala Gly Gln Tyr Lys Thr Lys Pro Asp Val Ala Ile
                485                 490                 495 gtt gtt ttt ggc gaa gaa cct tat gct gag ttt cgt gga gat gtg gag     1536
Val Val Phe Gly Glu Glu Pro Tyr Ala Glu Phe Arg Gly Asp Val Glu
            500                 505                 510 aca ctg gaa tat caa cca gat caa aaa caa gat ctt acc cta ctc aag     1584
Thr Leu Glu Tyr Gln Pro Asp Gln Lys Gln Asp Leu Thr Leu Leu Lys
        515                 520                 525 aaa ctg aaa gat cag gga ata cct gtt gtt gct gtt ttc ctt tct gga     1632
Lys Leu Lys Asp Gln Gly Ile Pro Val Val Ala Val Phe Leu Ser Gly
    530                 535                 540 cga ccg atg tgg gtt aat cct gaa ctt aat gcc agc gat gct ttc gtt     1680
Arg Pro Met Trp Val Asn Pro Glu Leu Asn Ala Ser Asp Ala Phe Val
545                 550                 555                 560 gca gca tgg ctt cct ggc aca gaa ggt ggc ggt gtg gcg gat gta ttg     1728
Ala Ala Trp Leu Pro Gly Thr Glu Gly Gly Gly Val Ala Asp Val Leu
                565                 570                 575 ttt aca gac aaa gcg gga aaa gta caa cat gat ttt gca gga aaa ttg     1776
Phe Thr Asp Lys Ala Gly Lys Val Gln His Asp Phe Ala Gly Lys Leu
            580                 585                 590 tca tat agt tgg ccg cgt acg gca gcc cag aca aca gtt aac cgt ggt     1824
Ser Tyr Ser Trp Pro Arg Thr Ala Ala Gln Thr Thr Val Asn Arg Gly
        595                 600                 605 gat gca gat tat aat ccg tta ttt gcg tat ggt tac ggt tta acg tac     1872
Asp Ala Asp Tyr Asn Pro Leu Phe Ala Tyr Gly Tyr Gly Leu Thr Tyr
    610                 615                 620 aaa gat aaa tcg aaa gtg ggc act cta cct gaa gaa agt gga gta ccg     1920
Lys Asp Lys Ser Lys Val Gly Thr Leu Pro Glu Glu Ser Gly Val Pro
625                 630                 635                 640 gct gaa gcg cga cag aat tga                                         1941
Ala Glu Ala Arg Gln Asn
                645

<210> SEQ ID NO 11
<211> LENGTH: 646
<212> TYPE: PRT
<213> ORGANISM: Artificial Sequence
<220> FEATURE:
<223> OTHER INFORMATION: Synthetic Construct

<400> SEQUENCE: 11

```
Ser Ala Arg Ile Thr Gln Glu Gly Ala Ala Pro Ala Ala Met Leu His
1               5                   10                  15

Pro Glu Lys Trp Pro Arg Pro Ala Thr Gln Arg Leu Ile Asp Pro Ala
            20                  25                  30

Val Glu Lys Arg Val Asp Ala Leu Leu Lys Gln Leu Ser Val Glu Glu
        35                  40                  45

Lys Val Gly Gln Val Ile Gln Gly Asp Ile Gly Thr Ile Thr Pro Glu
    50                  55                  60

Asp Leu Arg Lys Tyr Pro Leu Gly Ala Ile Leu Ala Gly Gly Asp Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Asn Asn
        115                 120                 125

Ile Gly Ser Ala Thr Ile Phe Pro His Asn Ile Ala Leu Gly Met Thr
    130                 135                 140

Arg Asp Pro Glu Leu Leu Arg Arg Ile Gly Glu Val Thr Ala Glu Glu
145                 150                 155                 160

Met Ala Ala Thr Gly Ile Asp Trp Thr Phe Ala Pro Ala Leu Ser Val
                165                 170                 175

Pro Arg Asp Asp Arg Trp Gly Arg Thr Tyr Glu Gly Phe Ser Glu Asp
            180                 185                 190

Pro Glu Ile Val Ala Ser Tyr Ser Ala Ala Tyr Val Glu Gly Phe Gln
        195                 200                 205

Gly Lys Tyr Gly Ser Lys Asp Phe Met Ala Pro Gly Arg Ala Val Ala
    210                 215                 220

Cys Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Ala
            260                 265                 270

Ser Phe Ser Ser Trp Gln Gly Ile Lys His His Gly His Lys Gln Leu
        275                 280                 285

Leu Thr Asp Val Leu Lys Gly Gln Met Gly Phe Asn Gly Phe Ile Val
    290                 295                 300

Gly Asp Trp Asn Ala His Asp Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350

Thr Ile Pro Met Ala Arg Leu Asp Asp Ala Val Arg Arg Ile Leu Arg
        355                 360                 365

Val Lys Val Leu Ala Gly Leu Phe Glu Lys Pro Ala Pro Lys Asp Arg
    370                 375                 380

Pro Gly Leu Pro Gly Leu Glu Thr Leu Gly Ser Pro Glu His Arg Ala
385                 390                 395                 400

Val Gly Arg Glu Ala Val Arg Lys Ser Leu Val Leu Leu Lys Asn Asp
                405                 410                 415
```

```
Lys Gly Thr Leu Pro Leu Ser Pro Lys Ala Arg Val Leu Val Ala Gly
            420                 425                 430

Asp Gly Ala Asp Asn Ile Gly Lys Gln Ser Gly Gly Trp Thr Ile Ser
        435                 440                 445

Trp Gln Gly Thr Gly Asn Arg Asn Asp Glu Phe Pro Gly Ala Thr Ser
    450                 455                 460

Ile Leu Gly Gly Ile Arg Asp Ala Val Ala Asp Ala Gly Gly Ser Val
465                 470                 475                 480

Glu Phe Asp Val Ala Gly Gln Tyr Lys Thr Lys Pro Asp Val Ala Ile
                485                 490                 495

Val Val Phe Gly Glu Glu Pro Tyr Ala Glu Phe Arg Gly Asp Val Glu
            500                 505                 510

Thr Leu Glu Tyr Gln Pro Asp Gln Lys Gln Asp Leu Thr Leu Leu Lys
        515                 520                 525

Lys Leu Lys Asp Gln Gly Ile Pro Val Val Ala Val Phe Leu Ser Gly
    530                 535                 540

Arg Pro Met Trp Val Asn Pro Glu Leu Asn Ala Ser Asp Ala Phe Val
545                 550                 555                 560

Ala Ala Trp Leu Pro Gly Thr Glu Gly Gly Gly Val Ala Asp Val Leu
                565                 570                 575

Phe Thr Asp Lys Ala Gly Lys Val Gln His Asp Phe Ala Gly Lys Leu
            580                 585                 590

Ser Tyr Ser Trp Pro Arg Thr Ala Ala Gln Thr Thr Val Asn Arg Gly
        595                 600                 605

Asp Ala Asp Tyr Asn Pro Leu Phe Ala Tyr Gly Tyr Gly Leu Thr Tyr
    610                 615                 620

Lys Asp Lys Ser Lys Val Gly Thr Leu Pro Glu Glu Ser Gly Val Pro
625                 630                 635                 640

Ala Glu Ala Arg Gln Asn
                645


<210> SEQ ID NO 12
<211> LENGTH: 1941
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(1941)

<400> SEQUENCE: 12

agt gcg cga att aca cag gaa gga gca gct ccg gcc gct atg tta cat       48
Ser Ala Arg Ile Thr Gln Glu Gly Ala Ala Pro Ala Ala Met Leu His
1               5                   10                  15

cca gag aaa tgg cct cga cct gcg aca caa cga ctt att gac ccg gca       96
Pro Glu Lys Trp Pro Arg Pro Ala Thr Gln Arg Leu Ile Asp Pro Ala
            20                  25                  30

gtt gaa aaa aga gtt gat gct ctg tta aaa cag tta tct gtt gaa gaa      144
Val Glu Lys Arg Val Asp Ala Leu Leu Lys Gln Leu Ser Val Glu Glu
        35                  40                  45

aaa gta ggg caa gtt ata cag ggt gat att ggg aca att aca cca gaa      192
Lys Val Gly Gln Val Ile Gln Gly Asp Ile Gly Thr Ile Thr Pro Glu
    50                  55                  60

gac ctg cgc aaa tat cca cta ggt gct att tta gcc gga gga gat agc      240
Asp Leu Arg Lys Tyr Pro Leu Gly Ala Ile Leu Ala Gly Gly Asp Ser
65                  70                  75                  80

ggc ccg aat gga gat gat cgt gct cct cca aag gag tgg ctt gat cta      288
```

-continued

```
Gly Pro Asn Gly Asp Asp Arg Ala Pro Pro Lys Glu Trp Leu Asp Leu
                85                  90                  95

gct gat gct ttt tac cgt gta agt tta gaa aaa cgg cca ggc cat acc      336
Ala Asp Ala Phe Tyr Arg Val Ser Leu Glu Lys Arg Pro Gly His Thr
            100                 105                 110

ccg ata cca gtg ctt ttt ggc att gat gca gtt cat gga cat aac aat      384
Pro Ile Pro Val Leu Phe Gly Ile Asp Ala Val His Gly His Asn Asn
        115                 120                 125

atc ggg tct gcg aca att ttc cct cac aat att gca ctt gga atg acc      432
Ile Gly Ser Ala Thr Ile Phe Pro His Asn Ile Ala Leu Gly Met Thr
    130                 135                 140

cgt gat cca gaa ctt cta cga aga att ggt gag gta aca gct gaa gaa      480
Arg Asp Pro Glu Leu Leu Arg Arg Ile Gly Glu Val Thr Ala Glu Glu
145                 150                 155                 160

atg gct gcc acg gga att gat tgg aat ttt gcg cct gca ctg tct gtt      528
Met Ala Ala Thr Gly Ile Asp Trp Asn Phe Ala Pro Ala Leu Ser Val
                165                 170                 175

ccg aga gat gat cga tgg gga cga acg tat gaa ggc ttc tca gaa gac      576
Pro Arg Asp Asp Arg Trp Gly Arg Thr Tyr Glu Gly Phe Ser Glu Asp
            180                 185                 190

cca gaa att gta gct tct tat tca gca cct tat gtg gaa ggc ttt cag      624
Pro Glu Ile Val Ala Ser Tyr Ser Ala Pro Tyr Val Glu Gly Phe Gln
        195                 200                 205

ggt aaa tat ggt tct aag gat ttt atg gcg ccg ggt cgc gcg gta gcg      672
Gly Lys Tyr Gly Ser Lys Asp Phe Met Ala Pro Gly Arg Ala Val Ala
    210                 215                 220

tgc gca aag cac ttc tta gct gat ggt gga aca gat caa gga cgc gat      720
Cys Ala Lys His Phe Leu Ala Asp Gly Gly Thr Asp Gln Gly Arg Asp
225                 230                 235                 240

cag gga gat gca cgc att tca gaa gac gaa cta att cgc att cat aat      768
Gln Gly Asp Ala Arg Ile Ser Glu Asp Glu Leu Ile Arg Ile His Asn
                245                 250                 255

gct gga tac cct cct gcg att gac gca gga gtg ctt aca gta atg tta      816
Ala Gly Tyr Pro Pro Ala Ile Asp Ala Gly Val Leu Thr Val Met Leu
            260                 265                 270

tct ttt tca tct tgg cag ggg att aaa cac cat ggc cat aaa cgt ctt      864
Ser Phe Ser Ser Trp Gln Gly Ile Lys His His Gly His Lys Arg Leu
        275                 280                 285

tta aca gat gta tta aaa gga caa atg ggg ttt aat gga ttt att gtg      912
Leu Thr Asp Val Leu Lys Gly Gln Met Gly Phe Asn Gly Phe Ile Val
    290                 295                 300

gga gat tgg aat gct cat ggt caa gta ccg ggc tgt act aaa ttt aat      960
Gly Asp Trp Asn Ala His Gly Gln Val Pro Gly Cys Thr Lys Phe Asn
305                 310                 315                 320

tgt cca aca tct ctt att gcg ggt tta gat atg tat atg gcc gcc gat     1008
Cys Pro Thr Ser Leu Ile Ala Gly Leu Asp Met Tyr Met Ala Ala Asp
                325                 330                 335

tcc tgg aag cag ctg tac gaa aac acc tta gca caa gtg aaa gat ggt     1056
Ser Trp Lys Gln Leu Tyr Glu Asn Thr Leu Ala Gln Val Lys Asp Gly
            340                 345                 350

act att cct atg gca cgt cta gat gat gcc gta aga cga atc ttg cga     1104
Thr Ile Pro Met Ala Arg Leu Asp Asp Ala Val Arg Arg Ile Leu Arg
        355                 360                 365

gtc aag gtg ttg gct ggc tta ttc gag aaa cct gcg cca aaa gat cgt     1152
Val Lys Val Leu Ala Gly Leu Phe Glu Lys Pro Ala Pro Lys Asp Arg
    370                 375                 380

ccg ggg tta cca ggc ctt gaa aca cta gga tca cct gaa cat aga gcc     1200
Pro Gly Leu Pro Gly Leu Glu Thr Leu Gly Ser Pro Glu His Arg Ala
385                 390                 395                 400

gta ggc cgt gaa gct gtt cga aaa agc cta gtt ctt ctt aaa aat gat     1248
```

```
Val Gly Arg Glu Ala Val Arg Lys Ser Leu Val Leu Leu Lys Asn Asp
                405                 410                 415

aaa ggt acc ctt cca ctg tca cca aag gct aga gta tta gtt gca ggt     1296
Lys Gly Thr Leu Pro Leu Ser Pro Lys Ala Arg Val Leu Val Ala Gly
            420                 425                 430

gac gga gca gat aat att ggc aaa cag tcg ggg ggc tgg acg att agt     1344
Asp Gly Ala Asp Asn Ile Gly Lys Gln Ser Gly Gly Trp Thr Ile Ser
        435                 440                 445

tgg caa gga act gga aac cgt aac gat gaa ttt ccg ggt gct aca tcc     1392
Trp Gln Gly Thr Gly Asn Arg Asn Asp Glu Phe Pro Gly Ala Thr Ser
    450                 455                 460

att tta ggt ggg att cga gac gct gta gct gat gca gga ggg tcc gta     1440
Ile Leu Gly Gly Ile Arg Asp Ala Val Ala Asp Ala Gly Gly Ser Val
465                 470                 475                 480

gaa ttt gat gta gcg ggt cag tat aaa aca aaa cct gat gta gct att     1488
Glu Phe Asp Val Ala Gly Gln Tyr Lys Thr Lys Pro Asp Val Ala Ile
                485                 490                 495

gtt gtt ttt ggc gaa gaa cct tat gct gag ttt cgt gga gat gtg ggg     1536
Val Val Phe Gly Glu Glu Pro Tyr Ala Glu Phe Arg Gly Asp Val Gly
            500                 505                 510

aca ctg gaa tat caa cca gat caa aaa caa gat ctt acc cta ctc aag     1584
Thr Leu Glu Tyr Gln Pro Asp Gln Lys Gln Asp Leu Thr Leu Leu Lys
        515                 520                 525

aaa ctg aaa gat cag gga ata cct gtt gtt gct gtt ttc ctt tct gga     1632
Lys Leu Lys Asp Gln Gly Ile Pro Val Val Ala Val Phe Leu Ser Gly
    530                 535                 540

cga ccg atg tgg gtt aat cct gaa ctt aat gcc agc gat gct ttc gtt     1680
Arg Pro Met Trp Val Asn Pro Glu Leu Asn Ala Ser Asp Ala Phe Val
545                 550                 555                 560

gca gca tgg ctt cct ggc aca gaa ggt ggc ggt gtg gcg gat gta ttg     1728
Ala Ala Trp Leu Pro Gly Thr Glu Gly Gly Gly Val Ala Asp Val Leu
                565                 570                 575

ttt aca gac aaa gcg gga aaa gta caa cat gat ttt gca gga aaa ttg     1776
Phe Thr Asp Lys Ala Gly Lys Val Gln His Asp Phe Ala Gly Lys Leu
            580                 585                 590

tca tat agt tgg ccg cgt acg gca gcc cag aca aca gtt aac cgt ggt     1824
Ser Tyr Ser Trp Pro Arg Thr Ala Ala Gln Thr Thr Val Asn Arg Gly
        595                 600                 605

gat gca gat tat aat ccg tta ttt gcg tat ggt tac ggt tta acg tac     1872
Asp Ala Asp Tyr Asn Pro Leu Phe Ala Tyr Gly Tyr Gly Leu Thr Tyr
    610                 615                 620

aaa gat aaa tcg aaa gtg ggc act cta cct gaa gaa agt gga gta ccg     1920
Lys Asp Lys Ser Lys Val Gly Thr Leu Pro Glu Glu Ser Gly Val Pro
625                 630                 635                 640

gct gaa gcg cga cag aat tga                                         1941
Ala Glu Ala Arg Gln Asn
                645


<210> SEQ ID NO 13
<211> LENGTH: 646
<212> TYPE: PRT
<213> ORGANISM: Artificial Sequence
<220> FEATURE:
<223> OTHER INFORMATION: Synthetic Construct

<400> SEQUENCE: 13

Ser Ala Arg Ile Thr Gln Glu Gly Ala Ala Pro Ala Ala Met Leu His
1               5                   10                  15

Pro Glu Lys Trp Pro Arg Pro Ala Thr Gln Arg Leu Ile Asp Pro Ala
            20                  25                  30

Val Glu Lys Arg Val Asp Ala Leu Leu Lys Gln Leu Ser Val Glu Glu
```

-continued

```
        35                  40                  45

Lys Val Gly Gln Val Ile Gln Gly Asp Ile Gly Thr Ile Thr Pro Glu
    50                  55                  60

Asp Leu Arg Lys Tyr Pro Leu Gly Ala Ile Leu Ala Gly Gly Asp Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Asn Asn
        115                 120                 125

Ile Gly Ser Ala Thr Ile Phe Pro His Asn Ile Ala Leu Gly Met Thr
    130                 135                 140

Arg Asp Pro Glu Leu Leu Arg Arg Ile Gly Glu Val Thr Ala Glu Glu
145                 150                 155                 160

Met Ala Ala Thr Gly Ile Asp Trp Asn Phe Ala Pro Ala Leu Ser Val
                165                 170                 175

Pro Arg Asp Asp Arg Trp Gly Arg Thr Tyr Glu Gly Phe Ser Glu Asp
            180                 185                 190

Pro Glu Ile Val Ala Ser Tyr Ser Ala Pro Tyr Val Glu Gly Phe Gln
        195                 200                 205

Gly Lys Tyr Gly Ser Lys Asp Phe Met Ala Pro Gly Arg Ala Val Ala
    210                 215                 220

Cys Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Leu
            260                 265                 270

Ser Phe Ser Ser Trp Gln Gly Ile Lys His His Gly His Lys Arg Leu
        275                 280                 285

Leu Thr Asp Val Leu Lys Gly Gln Met Gly Phe Asn Gly Phe Ile Val
    290                 295                 300

Gly Asp Trp Asn Ala His Gly Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350

Thr Ile Pro Met Ala Arg Leu Asp Asp Ala Val Arg Arg Ile Leu Arg
        355                 360                 365

Val Lys Val Leu Ala Gly Leu Phe Glu Lys Pro Ala Pro Lys Asp Arg
    370                 375                 380

Pro Gly Leu Pro Gly Leu Glu Thr Leu Gly Ser Pro Glu His Arg Ala
385                 390                 395                 400

Val Gly Arg Glu Ala Val Arg Lys Ser Leu Val Leu Leu Lys Asn Asp
                405                 410                 415

Lys Gly Thr Leu Pro Leu Ser Pro Lys Ala Arg Val Leu Val Ala Gly
            420                 425                 430

Asp Gly Ala Asp Asn Ile Gly Lys Gln Ser Gly Gly Trp Thr Ile Ser
        435                 440                 445

Trp Gln Gly Thr Gly Asn Arg Asn Asp Glu Phe Pro Gly Ala Thr Ser
    450                 455                 460
```

-continued

```
Ile Leu Gly Gly Ile Arg Asp Ala Val Ala Asp Ala Gly Gly Ser Val
465                 470                 475                 480

Glu Phe Asp Val Ala Gly Gln Tyr Lys Thr Lys Pro Asp Val Ala Ile
                485                 490                 495

Val Val Phe Gly Glu Glu Pro Tyr Ala Glu Phe Arg Gly Asp Val Gly
            500                 505                 510

Thr Leu Glu Tyr Gln Pro Asp Gln Lys Gln Asp Leu Thr Leu Leu Lys
        515                 520                 525

Lys Leu Lys Asp Gln Gly Ile Pro Val Val Ala Val Phe Leu Ser Gly
    530                 535                 540

Arg Pro Met Trp Val Asn Pro Glu Leu Asn Ala Ser Asp Ala Phe Val
545                 550                 555                 560

Ala Ala Trp Leu Pro Gly Thr Glu Gly Gly Gly Val Ala Asp Val Leu
                565                 570                 575

Phe Thr Asp Lys Ala Gly Lys Val Gln His Asp Phe Ala Gly Lys Leu
            580                 585                 590

Ser Tyr Ser Trp Pro Arg Thr Ala Ala Gln Thr Thr Val Asn Arg Gly
        595                 600                 605

Asp Ala Asp Tyr Asn Pro Leu Phe Ala Tyr Gly Tyr Gly Leu Thr Tyr
    610                 615                 620

Lys Asp Lys Ser Lys Val Gly Thr Leu Pro Glu Glu Ser Gly Val Pro
625                 630                 635                 640

Ala Glu Ala Arg Gln Asn
                645
```

BETA-GLUCOSIDASE VARIANT ENZYMES AND RELATED POLYNUCLEOTIDES

This application claims the benefit of provisional applications U.S. Ser. No. 61/187,565, filed Jun. 16, 2009, and U.S. Ser. No. 61/218,020, filed Jun. 17, 2009, pursuant 35 U.S.C. §119(e), both of which are incorporated by reference in their entireties.

FIELD OF THE INVENTION

The present invention relates, inter alia, to novel β-glucosidase polypeptide variants having altered properties relative to *Azospirillum irakense* β-glucosidase (CelA), the polynucleotides that encode the variants, methods of producing the variants, enzyme compositions comprising the variants, and methods for using the variants in industrial applications.

REFERENCE TO SEQUENCE LISTING

The "Sequence Listing" submitted electronically concurrently herewith pursuant 37 C.F.R. §1.821 in a computer readable form (CRF) via EFS-Web as file name CX3-016US1_ST25.txt is incorporated herein by reference. The electronic copy of the Sequence Listing was created on Jun. 16, 2010, and the size on disk is 93 Kbytes.

BACKGROUND OF THE INVENTION

Cellulosic biomass is a significant renewable resource for the generation of sugars. Fermentation of these sugars can yield numerous end-products such as fuels and chemicals that are currently derived from petroleum. While the fermentation of sugars to fuels such as ethanol is relatively straightforward, the hydrolytic conversion of cellulosic biomass to fermentable sugars such as glucose is difficult because of the crystalline structure of cellulose and its close association with lignin. Ladisch, et al., *Enzyme Microb. Technol.* 5:82 (1983). Pretreatment, by means including but not limited to, mechanical and solvent means, increases the susceptibility of cellulose to hydrolysis. Pretreatment may be followed by the enzymatic conversion of cellulose to glucose, cellobiose, cello-oligosaccharides and the like using enzymes that specialize in breaking down the β-1-4 glycosidic bonds of cellulose. These enzymes are collectively referred to as "cellulases".

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "BG"). Endoglucanases randomly attack the interior parts and mainly the amorphous regions of cellulose, mostly yielding glucose, cellobiose, and cellotriose. Exoglucanases incrementally shorten the glucan molecules by binding to the glucan ends and releasing mainly cellobiose units from the ends of the cellulose polymer. β-glucosidases split the cellobiose, a water-soluble β-1,4-linked dimer of glucose, into two units of glucose.

There are several types of microorganisms that produce cellulases. These include fungi, actinomycetes, and bacteria. Cellulases from strains of the filamentous fungi *Trichoderma* sp. and *Chrysosporium* sp. have been particularly productive in hydrolyzing cellulose. *Trichoderma* sp. and other strains typically produce all three types of cellulases described above (e.g., a whole cellulase system). However, one of the major drawbacks of *Trichoderma* cellulases and other cellulases obtained from filamentous fungi is the low level of β-glucosidase activity, and this low level of activity leads to incomplete conversion of cellobiose to glucose in the cellulose hydrolysis process. Additionally, cellobiose and glucose have been reported to be inhibitors of the cellulase enzyme system; for example it is known that cellobiase is inhibited by glucose. Ait, N., et al., *J. Gen. Microbiol.* 128:569-577 (1982). Poor glucose yields, whether due to deficiencies in the inherent activities of certain cellulase activities or due to the effect of end product inhibition, are impediments to commercially viable processes for producing sugars and end-products (e.g., alcohols) from biomass.

In order to maximize the hydrolysis of cellulosic substrates it would be highly desirable to develop new cellulases and particularly new β-glucosidase enzymes that could facilitate the implementation of these commercial processes.

SUMMARY OF THE INVENTION

In one embodiment, the present invention provides a β-glucosidase polypeptide variant comprising:

(a) an amino acid sequence that is at least about 56% identical to wild type *Azospirillum irakense* β-glucosidase (SEQ ID NO: 4) and having at least one substitution or deletion of an amino acid residue at a position selected from the group consisting of T2, A3, I4, A5, Q6, E7, G8, A9, A10, P11, A12, A13, I14, L15, P17, E18, K19, W20, P21, P23, A24, T25, Q26, I29, D30, E34, K35, A39, L41, K42, Q43, L44, E47, V46, G51, Q52, V53, G56, G59, T60, I61, E64, L66, R67, K68, P70, S73, N79, N83, G84, D85, R87, A88, P89, K91, E92, A97, A98, L105, K107, P109, G110, H111, T112, P113, I114, F118, I120, G127, N128, I134, F135, L141, A143, T144, H145, D146, P147, E148, L150, R151, R152, I153, G154, E155, A158, V159, M161, A162, A163, G165, I166, W168, T169, A173, V177, D180, G188, S190, I195, A197, A198, A201, A202, I203, V204, E205, G206, V207, F211, G212, S213, K214, D215, F216, M217, A218, P219, G220, I222, S225, A226, F229, G233, D236, Q237, G238, D243, R245, I246, S247, E248, E250, R253, N256, A257, D264, A272, F274, Q278, I280, H282, H285, Q287, G295, M297, G298, F299, N300, V304, D311, Q312, P314, G315, F319, N320, T323, S324, I326, M331, A335, K339, Q340, Y342, E343, T345, A347, V349, K350, V351, T353, I354, M356, A357, R358, D360, A362, I366, V369, V371, L372, A373, E377, K378, P379, P381, K382, D383, G386, L387, L390, S395, P396, A400, G402, R403, K408, K417, S423, A426, D433, Q418, T419, R425, A426, D436, G439, K440, G444, T452, G453, R455, D456, E458, A460, G461, T463, G467, R470, A474, D475, A476, G478, S479, E481, F482, V484, A485, Q487, Y488, T490, K491, A495, R501, E502, F507, Q508, V511, E512, L514, Q517, P518, D519, Q520, Q522, L524, A525, K528, K529, K531, D532, Q533, G534, 1535, A539, W548, P551, L553, S556, D557, A562, W563, L564, T567, G570, A573, V575, F577, K580, K583, Q585, A589, H586, G590, L592, Y594, S595, P597, T599, A600, A601, T603, T604, D609, D611, N613, A617, T623, Y624, K625, K627, K629, L633, P634, E635, E636, S637, G638, V639, P640, A641, E642, A643, R644, Q645, N646, A647, G648, I649, Y650, F651, R652, A653, G654, A655, L656, R657, L658, P659, G660, R661, F662, and L663, wherein amino acid position is determined by optimal alignment with SEQ ID NO: 4, or a C-terminally truncated variant thereof; and (b) an amino acid sequence encoded by a nucleic acid that hybridizes under stringent conditions over substantially the entire length of a nucleic acid corresponding to a sequence selected from the group consisting of (i) a polynucleotide sequence that is complementary to a polynucleotide that encodes a polypeptide having the amino acid sequence of SEQ ID NO: 4; and (ii) a polynucleotide that is complementary to a polynucleotide that encodes a C-terminally truncated variant of SEQ ID NO:4, wherein the encoded polypeptide has one or more substitutions or deletions at a position selected from the group consisting of T2, A3, I4, A5, Q6, E7, G8, A9, A10, P11, A12, A13, I14, L15, P17, E18, K19, W20, P21, P23, A24, T25, Q26, I29, D30, E34, K35, A39, L41, K42, Q43, L44, E47, V46, G51, Q52, V53, G56, G59, T60, I61, E64, L66, R67, K68, P70, S73, N79, N83, G84, D85, R87, A88, P89, K91, E92, A97, A98, L105, K107, P109, G110, H111, T112, P113, I114, F118, I120, G127, N128, I134, F135, L141, A143, T144, H145, D146, P147, E148, L150, R151, R152, I153, G154, E155, A158, V159, M161, A162, A163, G165, I166, W168, T169, A173, V177, D180, G188, S190, I195, A197, A198, A201, A202, I203, V204, E205, G206, V207, F211, G212, S213, K214, D215, F216, M217, A218, P219, G220, I222, S225, A226, F229, G233, D236, Q237, G238, D243, R245, I246, S247, E248, E250, R253, N256, A257, D264, A272, F274, Q278, I280, H282, H285, Q287, G295, M297, G298, F299, N300, V304, D311, Q312, P314, G315, F319, N320, T323, S324, I326, M331, A335, K339, Q340, Y342, E343, T345, A347, V349, K350, V351, T353, I354, M356, A357, R358, D360, A362, I366, V369, V371, L372, A373, E377, K378, P379, P381, K382, D383, G386, L387, L390, S395, P396, A400, G402, R403, K408, K417, S423, A426, D433, Q418, T419, R425, A426, D436, G439, K440, G444, T452, G453, R455, D456, E458, A460, G461, T463, G467, R470, A474, D475, A476, G478, S479, E481, F482, V484, A485, Q487, Y488, T490, K491, A495, R501, E502, F507, Q508, V511, E512, L514, Q517, P518, D519, Q520, Q522, L524, A525, K528, K529, K531, D532, Q533, G534, 1535, A539, W548, P551, L553, S556, D557, A562, W563, L564, T567, G570, A573, V575, F577, K580, K583, Q585, A589, H586, G590, L592, Y594, S595, P597, T599, A600, A601, T603, T604, D609, D611, N613, A617, T623, Y624, K625, K627, K629, L633, P634, E635, E636, S637, G638, V639, P640, A641, E642, A643, R644, Q645, N646, A647, G648, I649, Y650, F651, R652, A653, G654, A655, L656, R657, L658, P659, G660, R661, F662, and L663, wherein amino acid position is determined by optimal alignment with SEQ ID NO: 4.

In another embodiment, the present invention provides β-glucosidase polypeptide variant having at least one substitution selected from the group consisting of T2A, A3L/N/P/R/G, 14P/Q/R/S/T, A5L/N/T/Y, Q6A/D/G/N/P/S/T, E7A/G/H/L/P, G8A/C/D/P/Q/R/S/Y, A9E/G/I/K/T, A10G/N/P/S, P11A/E/L/R/S, A12E/F/N/R/S/Y/-, A13P/V, I14H/L/M/N/R/T/K, L15I/S, P17R, E18F/G/N/R, K19R, W20T, P21I/S, P23L, A24V, T25P, Q26P/R, A24V, T25A, 129V, D30E, E34D/K, K35E/P/Q/R, A39V, L41F, K42R, Q43P, L44S, E47K, V46F, G51P, Q52P, V53T, G56P, G59E/R/S, T60H/Y, I61V, E64S, L66Q, R67C/H, K68E, P70S, S73A, N79D, N83H, G84A/E/Q, D85N, R87D, A88T, P89S, K91Q, E92D/G/S/V, A97G/T, A99E/K/R/S, L105Y, K107R, P109D/N, G110S, H111D, T112A/I/N, P113A/K/S/V, I114T/V, F118S/L, I120V, G127A/N/S, N128H/K, I134F/N, F135L, L141I, A143IM/Q/T, T144S, H145R, D146C/S, P147I/K/L/T/W/R, E148D/G/K, L150M, R151P/W, R152S, I153T, G154V, E155A/D/K/M/P/Q/W/G, A158T, V159E/I/L/A/Q/R/M161T/V, A162S/T/V, A163T, G165E, I166T/V, W168R, T169N, A173S/C, V177P, D180C, G188D, S190Y, I195L, A197D/M/N, A198C/E/L/M/N/Q/S/T/W/D, A201P/S/G, A202F/K/L/N/P/T/Y/S, 1203F/H/Y, V204I, E205X (where "X" refers to any amino acid residue), G206S, V207A/E/F/I/L/Y, F211C/V/Y/W/Q, G212C/R/V/T, S213C/H/P/V, K214P/Y, D215K/L/N/S/G, F216L, M217L/T/V, A218K/P, P219C/E/I/L/M/T/Q/V, G220S/V, I222A/C/G/I/S/V, S225C/F/N/S/T, A226G, F229I, G233P, D236G/Y, Q237R, G238R, D243G, R245K, I246C/V, S247P, E248K, E250G, R253K/Q, N256L/V, A257P/R, D264G, A272V/L, F274A/K/Q/S/T/Y/N, Q278N/R, I280V, H282N/D, H285D/N, Q287E/L/R, D291G, G295A/Q, M297I, G298R, F299S, N300D, V304L, A309G, D311E/G, Q312L, P314L/S, G315E, F319V, N320E/K/Q/S, T323A/D/G, S324V, I326S, M331L, A335P, K339E/R, Q340R, Y342C, E343A/G, T345S, A347G/K/M/V, V349A, K350F/L/T/Y/E/R, D351E, T353M/N/V/S/Y, I354T, M356K/Q/T, A357E/S/T, R358H, D360G, A362S, I366T, V369A, V371D/E/L/M/Y, L372S/W, A373T, E377D, K378R, P379G/V/Y, P381S, K382R, D383N/G, G386C/E/L/W, L387R, L390I/P, S395G/Q/K, P396N/S, A400K/T, G402S, R403S, K408I, K417R/S, S423D/N, A426S, D433G, Q418D, T419V, R425H, A426Q/S, D436N, G439P, K440N, G444P, T452A, G453R, R455K/P/S/T, D457H/E, E458N/D, A460S, G461K, T463P, G467K/Q, R470K, A474Q, D475K/S/E, A476K, G478P, S479A/H/V, E481G, F482Y, V484D, A485P/K, Q487D/K/N/R/L, Y488N, T490I, K491R, A495T, R501Q, E502G/K/N, F507G/S, Q508R/E, V511L, E512G, L514Q, Q517L, P518Q, D519G/N/K, Q520N/T/G/K, Q522K/R, L524W, A525K/S/T/M/G, K528R, K529R/E, K531E/R, D532G/R, Q533H/L, G534E, I535V/M, A539T/V, W548L, P551R, L553M, S556T, D557G, A562P, W563P, L564P, T567A, G570P, L372S, A573S/V, V575A, F577L, K580N/T, K583N/R/Q, Q585R, H586Y, A589R, G590P, L592F, Y594H/F, S595G, P597A, T599A, A600V, A601V, T603A/F/Y, T604P, D609E, D611C/E, N613D, A617D/P/V, T623S, Y624H, K625Q, K627R, K629C/R, L633D, P634S, E635D/-, E636D/G/-, S637-, G638-, V639-, P640-, A641-, E642A/-, A643P/-, R644-, Q645/-, N646K/-, Q645-, N646-A647-, G648-, I649T/-, Y650-, F651-, R652L/-, A653-, G654-, A655T/-, L656-, R657-, L658-, P659-, G660-, R661-, F662L/-, and L663P/Q/-, wherein amino acid position is determined by optimal alignment with SEQ ID NO: 4.

The present invention further provides β-glucosidase polypeptide variants that exhibit improved thermoactivity as well as improved low pH tolerance as compared to the wild-type *Azospirillum irakense* β-glucosidase.

In certain embodiments, the present invention provides β-glucosidase polypeptide variants that exhibit good tolerance to glucose.

In further embodiments, the present invention provides a polynucleotide encoding the β-glucosidase polypeptide variants of the present invention, vectors containing the polynucleotides, and host cells transformed with the vectors of the present invention.

In a still further embodiment, the present invention provides a method of producing a β-glucosidase polypeptide variant of the present invention, said method comprising culturing a host cell transformed with a β-glucosidase polynucleotide of the present invention under conditions suitable for the expression of the β-glucosidase polypeptide variant.

In another embodiment, the present invention provides compositions containing a β-glucosidase polypeptide of the present invention and another cellulase enzyme.

In other embodiments, the present invention provides methods of using the β-glucosidase polypeptide variants of the present invention. These methods include a method of converting an optionally pretreated biomass substrate to a fermentable sugar, the method comprising contacting a β-glucosidase polypeptide variant of the present invention with the biomass substrate under conditions suitable for the production of the fermentable sugar, and optionally further contacting the fermentable sugar with a fermentable microorganism to produce an alcohol.

BRIEF DESCRIPTION OF THE FIGURES

FIG. 1A depicts a polynucleotide sequence encoding *Azospirillum irakense* β-glucosidase (CelA) (SEQ ID NO: 1). The polynucleotide sequence has been codon optimized for expression in both *Bacillus megaterium* and *Escherichia coli* and includes a polynucleotide sequence encoding the *Bacillus megaterium* penicillin G acylase signal peptide sequence (nucleotides −72 to −1). Nucleotides +1 through +9 encode part of the *Bacillus megaterium* penicillin G acylase cleavage site and an engineered SpeI restriction site. Nucleotides +10 through +2001 encode the wildtype *Azospirillum irakense* β-glucosidase CelA.

FIG. 1B depicts the amino acid (SEQ ID NO: 2) encoded by the polynucleotide sequence of FIG. 1A and comprises the sequence encoding wildtype *Azospirillum irakense* β-glucosidase (CelA). The amino acid sequence includes the *Bacillus megaterium* penicillin G acylase signal peptide (amino acid residues −24 to −1). The amino acid sequence corresponding to the *Bacillus megaterium* penicillin G acylase signal peptide is underlined. Cleavage of the signal peptide from the mature CelA occurs between residues −1 and +1. The amino acid residues at positions 2 and 3, threonine and serine, respectively, are encoded by nucleotides that correspond to an engineered SpeI restriction site. Amino acid residues 4 through 666 encode the wildtype *Azospirillum irakense* β-glucosidase (CelA).

FIG. 2A depicts a codon-optimized (for expression in both *B. megaterium* and *E. coli*) polynucleotide sequence encoding the mature form of the catalytic domain of wildtype *A. irakense* β-glucosidase (CelA) (SEQ ID NO: 3).

FIG. 2B depicts the amino acid sequence encoding the mature form of the catalytic domain of wildtype *A. irakense* β-glucosidase (CelA) (SEQ ID NO: 4).

FIG. 3 depicts the amino acid sequence encoding an improved β-glucosidase polypeptide variant of the present invention, [H145R] CelA (SEQ ID NO: 5).

FIG. 4 depicts the amino acid sequence encoding an improved β-glucosidase polypeptide variant of the present invention, [N79D+A143M+H145R+V159E+A198S+F211Y] CelA (SEQ ID NO: 6).

FIG. 5 depicts the amino acid sequence encoding an improved β-glucosidase polypeptide variant of the present invention, [T2A+I14M+N79D+A143M+H145R+V159E+A198S+F211Y+I222A+S225C+Q508R+A525T] CelA-des [A647-L663] (SEQ ID NO: 7).

DETAILED DESCRIPTION OF THE INVENTION

Definitions

Figure 6:
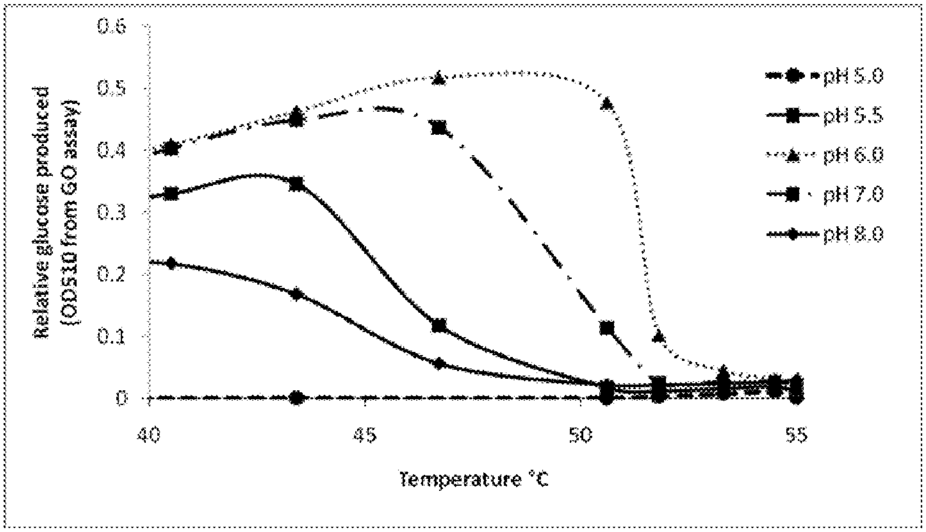
FIG. 6 provides the activity profile for wildtype *Azospirillum irakense* CelA at temperatures 40° C.-55° C. and at pH 5.0-8.0 using cellobiose (10 g/L) as a substrate. The experimental procedures is described in Example 6.

As used herein, the following terms are intended to have the following meanings.

The term "cellulase" refers to a category of enzymes capable of hydrolyzing cellulose (β-1,4-glucan or β-D-glucosidic linkages) to shorter oligosaccharides, cellobiose and/or glucose. 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "BG") are cellulase enzymes.

The term "β-glucosidase" or "cellobiase" used interchangeably herein means a β-D-glucoside glucohydrolase which catalyzes the hydrolysis of a sugar dimer, including but not limited to cellobiose with the release of a corresponding sugar monomer. In one embodiment, a β-glucosidase is a β-glucosidase glucohydrolase of the classification E.C. 3.2.1.21 which catalyzes the hydrolysis of cellobiose to glucose. Some of the β-glucosidases have the ability to also hydrolyze β-D-galactosides, β-L-arabinosides and/or β-D-fucosides and further some β-glucosidases can act on α-1,4-substrates such as starch. β-glucosidase activity may be measured by methods well known in the art (e.g., HPLC). Illustrative assays are described in Examples 5 and 7 using either p-nitrophenyl-β-D-glucopyranoside (pNPG) or cellobiose as a substrate.

The term "β-glucosidase polypeptide" refers herein to a polypeptide having β-glucosidase activity.

The term "β-glucosidase polynucleotide" refers to a polynucleotide encoding a polypeptide having β-glucosidase activity.

"Cellulolytic activity" encompasses exoglucanase activity (CBH), endoglucanase (EG) activity and/or β-glucosidase activity.

The term "exoglucanase", "exo-cellobiohydrolase" or "CBH" refers to a group of cellulase enzymes classified as E.C. 3.2.1.91. These enzymes hydrolyze cellobiose from the reducing or non-reducing end of cellulose.

The term "endoglucanase" or "EG" refers to a group of cellulase enzymes classified as E.C. 3.2.1.4. These enzymes hydrolyze internal β-1,4 glucosidic bonds of cellulose.

As used herein, the term "isolated" refers to a nucleic acid, polynucleotide, polypeptide, protein, or other component that is partially or completely separated from components with which it is normally associated (other proteins, nucleic acids, cells, synthetic reagents, etc.).

The term "wildtype" as applied to a polypeptide (protein) or polynucleotide means a polypeptide (protein) or polynucleotide expressed by a naturally occurring microorganism such as bacteria or filamentous fungus found in nature.

A "variant" as used herein means an β-glucosidase polypeptide or polynucleotide encoding a β-glucosidase comprising one or more modifications relative to wildtype *Azospirillum irankense* β-glucosidase (CelA) or the wildtype polynucleotide such as substitutions, insertions, deletions and/or truncations of one or more specific amino acid residues or of one or more specific nucleotides or codons in the polypeptide or polynucleotide.

A "reference β-glucosidase sequence" refers to a defined sequence used as a basis for a sequence comparison. A reference β-glucosidase sequence may be a subset of a larger sequence. Generally a reference sequence is at least 25 amino acid residues in length, at least 50 residues in length, at least 100 residues in length, at least 150 residues in length at least 200 residues in length, at least 300 residues in length, at least 350 residues in length or the full length of the polypeptide. For instance, a reference sequence based on SEQ ID NO: 4 having at the residue corresponding to E64a valine, refers to a reference sequence in which the corresponding residue at E64 in SEQ ID NO: 4 has been changed to a valine.

A nucleic acid (such as a polynucleotide) or a polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An "improved property" refers to a β-glucosidase polypeptide that exhibits an improvement in any property as compared to the wildtype *Azospirillum irakense* β-glucosidase (CelA) (SEQ ID NO: 4). Improved properties may include increased protein expression, thermostability, thermoactivity, pH activity, pH stability, product specificity, increased activity, increased specific activity, substrate specificity, increased resistance to substrate or end-product inhibition, altered temperature profile, and chemical stability.

The term "improved thermoactivity" issued herein to refer to a variant that displays greater catalytic activity and/or greater thermostability relative to a reference enzyme, such as the wildtype *Azospirillum irakense* β-glucosidase. Greater catalytic activity is demonstrated by a greater rate of hydrolysis and concomitant shorter period of time required and/or lower enzyme concentration required for hydrolysis as compared to the reference (e.g, the wildtype *Azospirillum irakense* β-glucosidase enzyme), where the hydrolysis reaction is carried out at a temperature higher than the temperature optimum of the reference enzyme (e.g., the wildtype *Azospirillum irakense* β-glucosidase enzyme). The term "improved thermoactivity" also refers to a variant having improved thermostability relative to the wildtype *Azospirillum irakense* β-glucosidase. Alternatively a variant with a reduced thermoactivity will catalyze a hydrolysis reaction at a temperature lower than the temperature optimum of the reference enzyme (i.e., wildtype *Azospirillum irakense* β-glucosidase) as defined by the temperature dependent activity profile of the reference enzyme (i.e., wildtype *Azospirillum irakense* β-glucosidase).

The term "improved thermostability" as used herein means a variant enzyme displays greater "residual activity" relative to a reference enzyme, e.g., the wildtype enzyme. Residual activity is determined by exposing the enzyme to stress conditions of elevated temperature for a period of time and then determining the β-glucosidase activity. The β-glucosidase activity of the enzyme exposed to stress conditions ("a") is compared to that of a control in which the enzyme is not exposed to the stress conditions ("b"), and residual activity is equal to the ratio a/b. Exemplary conditions for determining thermostability are provided in Examples 9 and 13. In one embodiment the enzymes are exposed to stress conditions of 50° C. at pH 5.5 or 55° C. at pH 5.0 or 55° C. at pH 5.5, or 65° C. at pH 5.0 for about 1 hour, and assayed at 30° C., pH 7, for about 0.1 hour.

The terms "percent identity," "% identity," "percent identical," and "% identical" are used interchangeably herein to refer to the percent amino acid sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art. See e.g., Dayhoff et al. (1978), "A model of evolutionary change in proteins"; "Atlas of Protein Sequence and Structure," Vol. 5, Suppl. 3 (Ed. M. O. Dayhoff), pp. 345-352, *Natl. Biomed. Res. Round*., Washington, D.C.; and Henikoff et al. (1992) *Proc. Natl. Acad. Sci. USA*, 89:10915-10919, both of which are incorporated herein by reference. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul, et al. (1997) *Nucleic Acids Res.,* 25:3389-3402 (incorporated herein by reference), and made available to the public at the National Center for Biotechnology Information Website. Optimal alignments, including multiple alignments can be prepared using readily available programs such as PSI-BLAST, which is described by Altschul, et al. (1997) *Nucleic Acids Res.,* 25:3389-3402 and which is incorporated herein by reference.

"Corresponding to", "reference to" "or relative to" when used in the context of the numbering of a given amino acid or polynucleotide sequence refers to the numbering of the residues of a specified reference sequence when the given amino acid or polynucleotide sequence is compared to the reference sequence.

The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen (1993) "Laboratory Techniques in biochemistry and Molecular Biology-Hybridization with Nucleic Acid Probes," Part I, Chapter 2 (Elsevier, New York), which is incorporated herein by reference.

For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

In describing the various variants of the present invention, the nomenclature described below is adapted for ease of reference. In all cases the accepted IUPAC single letter or triple letter amino acid abbreviations are employed. For amino acid substitutions the following nomenclature is used: Original amino acid, position, substituted amino acid. Accordingly the substitution of serine with glycine at position 34 is designated "Ser34Gly" or "S34G". A deletion is represented by "-". Thus, for example, "Ser34-" or "S34-" refers to a deletion at position 34. A truncation is designated by "des". For example, "CelA-des[A647-L663]" or "des[A647-L663] refers to a carboxy (C)-terminal truncation of the amino acid residues from the alanine at position 647 to the leucine at position 663 The designation "des[L663]" refers to a deletion/truncation of the terminal leucine at position 663 of SEQ ID NO: 4. *Azospirillum irakense* CelA variants of the present invention having a combination of substitutions and/or a truncation may be designated by identifying both the mutations and the truncation. For example, the variant, T2A+I14M+N79D+A143M+H145R+V159E+A198S+V207F+F211Y+I222A+S225C+Q508R+A525T CelA des[A647-L663] (which may also be referred to as T2A+I14M+N79D+A143M+H145R+V159E+A198S+V207F+F211Y+I222A+S225C+Q508R+A525T-des[A647-L663]) is a variant of the wildtype CelA (SEQ ID NO: 4) that has the combination of substitutions indicated, and in addition, is C-terminally truncated from positions A647 to L663.

The term "culturing" or "cultivation" refers to growing a population of microbial cells under suitable conditions in a liquid or solid medium. In some embodiments, culturing refers to fermentative bioconversion of a cellulosic substrate to an end-product.

The term "contacting" refers to the placing of a respective enzyme in sufficiently close proximity to a respective substrate to enable the enzyme to convert the substrate to a product. Those skilled in the art will recognize that mixing solution of the enzyme with the respective substrate will effect contacting.

As used herein the term "transformed" or "transformation" used in reference to a cell means a cell has a non-native nucleic acid sequence integrated into its genome or as an episomal plasmid that is maintained through multiple generations.

The term "introduced" in the context of inserting a nucleic acid sequence into a cell means transfected, transduced or transformed (collectively "transformed") and wherein the nucleic acid is incorporated into the genome of the cell.

β-Glucosidase Polypeptide Variants

The present invention provides novel enzymes that are variants of the catalytic domain of *Azospirillum irakense* β-glucosidase (CelA). The β-glucosidase of *Azospirillum irakense* belongs to glycosyl hydrolase family 3 (GHF3) and preferentially hydrolyzes cellobiose, releasing glucose units from the C3, C4, and C5 oligosaccharides. Faure, et al., *App. Env. Microbiol.* (May 2001) 67(5):2380-2383. β-glucosidase polypeptide variants of the present invention are variants of CelA that exhibit β-glucosidase activity. The present invention further includes β-glucosidase polypeptide variants that exhibit greater β-glucosidase activity as compared to wild-type *Azospirillum irakense* β-glucosidase (CelA). Also included are β-glucosidase polypeptide variants that exhibit greater stability under conditions relevant to commercial saccharification processes. In particular, variants of the present invention exhibit improved thermoactivity as compared to the wildtype *Azospirillum irakense* β-glucosidase. β-glucosidase polypeptide variants of the present invention also exhibit greater low pH tolerance as compared to the wildtype

*Azospirillum irakense* β-glucosidase. These variants exhibit greater β-glucosidase activity as compared to the wildtype *Azospirillum irakense* glucosidase at a pH that is typically greater than 4.5 and less than 6.0, and more typically in the range of 5.0-5.5 inclusive, at a temperature of 50° C. or 55° C. or 60° C. or 65° C.

More specifically, the present invention provides a β-glucosidase polypeptide variant (e.g., an isolated and/or recombinant variant) comprising an amino acid sequence that is at least about 56% identical to wildtype *Azospirillum irakense* glucosidase (CelA) (SEQ ID NO: 4) (FIG. 2B) and that has at least one substitution or deletion of an amino acid residue at a position selected from the group consisting of T2, A3, I4, A5, Q6, E7, G8, A9, A10, P11, A12, A13, I14, L15, P17, E18, K19, W20, P21, P23, A24, T25, Q26, I29, D30, E34, K35, A39, L41, K42, Q43, L44, E47, V46, G51, Q52, V53, G56, G59, T60, I61, E64, L66, R67, K68, P70, S73, N79, N83, G84, D85, R87, A88, P89, K91, E92, A97, A98, L105, K107, P109, G110, H111, T112, P113, I114, F118, I120, G127, N128, I134, F135, L141, A143, T144, H145, D146, P147, E148, L150, R151, R152, I153, G154, E155, A158, V159, M161, A162, A163, G165, I166, W168, T169, A173, V177, D180, G188, S190, I195, A197, A198, A201, A202, I203, V204, E205, G206, V207, F211, G212, S213, K214, D215, F216, M217, A218, P219, G220, I222, S225, A226, F229, G233, D236, Q237, G238, D243, R245, 1246, S247, E248, E250, R253, N256, A257, D264, A272, F274, Q278, I280, H282, H285, Q287, G295, M297, G298, F299, N300, V304, D311, Q312, P314, G315, F319, N320, T323, S324, I326, M331, A335, K339, Q340, Y342, E343, T345, A347, V349, K350, V351, T353, I354, M356, A357, R358, D360, A362, I366, V369, V371, L372, A373, E377, K378, P379, P381, K382, D383, G386, L387, L390, S395, P396, A400, G402, R403, K408, K417, S423, A426, D433, Q418, T419, R425, A426, D436, G439, K440, G444, T452, G453, R455, D456, E458, A460, G461, T463, G467, R470, A474, D475, A476, G478, S479, E481, F482, V484, A485, Q487, Y488, T490, K491, A495, R501, E502, F507, Q508, V511, E512, L514, Q517, P518, D519, Q520, Q522, L524, A525, K528, K529, K531, D532, Q533, G534, I535, A539, W548, P551, L553, S556, D557, A562, W563, L564, T567, G570, A573, V575, F577, K580, K583, Q585, A589, H586, G590, L592, Y594, S595, P597, T599, A600, A601, T603, T604, D609, D611, N613, A617, T623, Y624, K625, K627, K629, L633, P634, E635, E636, S637, G638, V639, P640, A641, E642, A643, R644, Q645, N646, A647, G648, I649, Y650, F651, R652, A653, G654, A655, L656, R657, L658, P659, G660, R661, F662, and L663 (wherein amino acid position is determined by optimal alignment with SEQ ID NO: 4) or a C-terminally truncated variant thereof. The amino acid sequence encoding the mature form of wildtype *Azospirillum irakense* β-glucosidase is shown in FIG. 2B (SEQ ID NO: 4). As explained above, variants of the present invention exhibit improved thermoactivity as compared to the wildtype *Azospirillum irakense* β-glucosidase. Typically, β-glucosidase variants of the present invention exhibit improved thermoactivity and low pH tolerance relative to wildtype *Azospirillum irakense* β-glucosidase at 55° C. and pH 5.5. In some embodiments, variants of the present invention exhibit improved thermoactivity and low pH tolerance relative to wildtype *Azospirillum irakense* β-glucosidase at 55° C. and pH 5.0 or at 65° C. and pH 5.0. Relative thermoactivity can be readily determined using the methods described in Example 7. Illustrative examples of variants having improved thermoactivity relative to the wildtype *Azospirillum irakense* β-glucosidase are provided in Examples 8-13.

In some embodiments, variants of the present invention exhibit increased thermostability as compared to wildtype *Azospirillum irakense* β-glucosidase under conditions of, for example, 55° C. and pH 5.5 or 55° C. and pH 5.0 or 65° C. and pH 5.0 for a time period in the range of 10 minutes, 1 hour, 4 hours, 5, hours or 48 hours using the methods described in Examples 9 and 13.

In some embodiments, variants of the present invention exhibit good tolerance to glucose. Glucose tolerance can be determined using the method described in Example 16 where an indication of the level of glucose tolerance is the IC50 for glucose. The IC50 for glucose is the glucose concentration at which activity is 50% of the activity under the same conditions with no glucose present. In certain embodiments, variants of the present invention exhibit an IC50 for glucose of at least about 60 g/L, at least about 70 g/L, at least about 80 g/L, at least about 90 g/L, or at least about 100 g/L under conditions of 55° C. and a pH of 5.

β-glucosidase polypeptides encompassed by the invention include those having an amino acid sequence that is at least about 57% identical to SEQ ID NO: 4 (FIG. 2B) and having one or more of the above-identified substitutions. Certain of these β-glucosidase variants may be at least about 58% identical, at least about 59% identical, at least about 60% identical, at least about 61% identical, at least about 62% identical, at least about 63% identical, at least about 64% identical, at least about 65% identical, at least about 66% identical, at least about 67% identical, at least about 68% identical, at least about 69% identical, at least about 70% identical, at least about 71% identical, at least about 72% identical, at least about 73% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical or at least about 99% identical to SEQ ID NO: 4 (FIG. 2B).

The present invention further provides a β-glucosidase polypeptide variant (e.g., an isolated and/or recombinant variant) having an amino acid sequence encoded by a nucleic acid that hybridizes under stringent conditions over substantially the entire length of a nucleic acid corresponding to a sequence selected from the group consisting of (i) a polynucleotide that os complementary to a polynucleotide that encodes a β-glucosidase polypeptide having the amino acid sequence of SEQ ID NO 4 (e.g., SEQ ID NO: 3 (FIG. 2A)); and (ii) a polynucleotide that is complementary to a polynucleotide that encodes a C-terminally truncated variant of SEQ ID NO:4, wherein the encoded polypeptide has at least one or more substitutions or deletions at a position selected from the group consisting of T2, A3, I4, A5, Q6, E7, G8, A9, A10, P11, A12, A13, I14, L15, P17, E18, K19, W20, P21, P23, A24, T25, Q26, I29, D30, E34, K35, A39, L41, K42, Q43, L44, E47, V46, G51, Q52, V53, G56, G59, T60, I61, E64, L66, R67, K68, P70, S73, N79, N83, G84, D85, R87, A88, P89, K91, E92, A97, A98, L105, K107, P109, G110, H111, T112, P113, I114, F118, I120, G127, N128, I134, F135, L141, A143, T144, H145, D146, P147, E148, L150, R151, R152, I153, G154, E155, A158, V159, M161, A162, A163, G165, I166, W168, T169, A173, V177, D180, G188, S190, I195, A197, A198, A201, A202, I203, V204, E205, G206, V207, F211, G212, S213, K214, D215, F216, M217, A218, P219, G220, I222, S225, A226, F229, G233, D236, Q237, G238, D243, R245, I246, S247, E248, E250, R253, N256, A257, D264, A272, F274, Q278, I280, H282, H285, Q287, G295, M297, G298, F299, N300, V304, D311, Q312, P314, G315, F319, N320, T323, S324, I326, M331, A335, K339, Q340, Y342, E343, T345, A347, V349, K350, D351, T353, I354, M356, A357, R358, D360, A362, I366, V369, V371, L372, A373, E377, K378, P379, P381, K382, D383, G386, L387, L390, S395, P396, A400, G402, R403, K408, K417, S423, A426, D433, Q418, T419, R425, A426, D436, G439, K440, G444, T452, G453, R455, D457, E458, A460, G461, T463, G467, R470, A474, D475, A476, G478, S479, E481, F482, V484, A485, Q487, Y488, T490, K491, A495, R501, E502, F507, Q508, V511, E512, L514, Q517, P518, D519, Q520, Q522, L524, A525, K528, K529, K531, D532, Q533, G534, I535, A539, W548, P551, L553, S556, D557, A562, W563, L564, T567, G570, A573, V575, F577, K580, K583, Q585, H586, A589, G590, L592, Y594, S595, P597, T599, A600, A601, T603, T604, D609, D611, N613, A617, T623, Y624, K625, K627, K629, L633, P634, E635, E636, S637, G638, V639, P640, A641, E642, A643, R644, Q645, N646, A647, G648, I649, Y650, F651, R652, A653, G654, A655, L656, R657, L658, P659, G660, R661, F662, and L663, wherein amino acid position is determined by optimal alignment with SEQ ID NO: 4.

The C-terminally truncated variant of SEQ ID NO: 4 is typically truncated by from 1 to 40 amino acid residues from the C-terminus. more typically from 1 to 30 or 1 to 20 amino acid residues, and often by 16 amino acid residues. Exemplary C-terminally truncated variants of SEQ ID NO: 4 are provided in Examples 8 and 10-12. Illustrative polynucleotide sequences encoding a C-terminally truncated variant of SEQ ID NO: 4 are provided as SEQ ID NOs: 8, 10, and 12.

In some embodiments, the polynucleotide that hybridizes to the complement of a polynucleotide which encodes a polypeptide having the amino acid sequence of SEQ ID NO: 4 or C-terminally truncated variant thereof, does so under high or very high stringency conditions to the complement of a polynucleotide sequence that encodes a polypeptide having the sequence of SEQ ID NO: 4 or C-terminally truncated variant thereof.

In some embodiments, the β-glucosidase polypeptide variant of the present invention has at least one substitution selected from the group consisting of T2A, A3L/N/P/R/G, I4P/Q/R/S/T, A5L/N/T/Y, Q6A/D/G/N/P/S/T, E7A/G/H/L/P, G8A/C/D/P/Q/R/S/Y, A9E/G/I/K/T, A10G/N/P/S, P11A/E/L/R/S, A12E/F/N/R/S/Y/-, A13P/V, I14H/L/M/N/R/T/K, L15I/S, P17R, E18F/G/N/R, K19R, W20T, P21I/S, P23L, A24V, T25P, Q26P/R, A24V, T25A, I29V, D30E, E34D/K, K35E/P/Q/R, A39V, L41F, K42R, Q43P, L44S, E47K, V46F, G51P, Q52P, V53T, G56P, G59E/R/S, T60H/Y, I61V, E645, L66Q, R67C/H, K68E, P70S, S73A, N79D, N83H, G84A/E/Q, D85N, R87D, A88T, P89S, K91Q, E92D/G/S/V, A97G/T, A99E/K/R/S, L105Y, K107R, P109D/N, G110S, H111D, T112A/I/N, P113A/K/S/V, I114T/V, F118S/L, I120V, G127A/N/S, N128H/K, I134F/N, F135L, L141I, A143IM/Q/T, T144S, H145R, D146C/S, P147I/K/L/T/W/R, E148D/G/K, L150M, R151P/W, R152S, I153T, G154V, E155A/D/K/M/P/Q/W/G, A158T, V159E/I/L/A/Q/R, M161T/V, A162S/T/V, A163T, G165E, I166T/V, W168R, T169N, A173S/C, V177P, D180C, G188D, S190Y, I195L, A197D/M/N, A198C/E/L/M/N/Q/S/T/W/D, A201P/S/G, A202F/K/L/N/P/T/Y/S, I203F/H/Y, V204I, E205X (where "X" refers to any amino acid residue), G206S, V207A/E/F/I/L/Y, F211C/V/Y/W/Q, G212C/R/V/T, S213C/H/P/V, K214P/Y, D215K/L/N/S/G, F216L, M217L/T/V, A218K/P, P219C/E/I/L/M/T/Q/V, G220S/V I222A/C/G/I/S/V, S225C/F/N/S/T, A226G, F229I, G233P, D236G/Y, Q237R, G238R, D243G, R245K, I246C/V, S247P, E248K, E250G, R253K/Q, N256L/V, A257P/R, D264G, A272V/L, F274A/K/Q/S/T/Y/N, Q278N/R, I280V, H282N/D, H285D/N, Q287E/L/R, D291G, G295A/Q, M297I, G298R, F299S, N300D, V304L, A309G, D311E/G, Q312L, P314L/S, G315E, F319V, N320E/K/Q/S, T323A/D/G, S324V, I326S, M331L, A335P, K339E/R, Q340R, Y342C, E343A/G, T345S, A347G/K/M/V, V349A, K350F/L/T/Y/E/R, D351E, T353M/N/V/S/Y, I354T, M356K/Q/T, A357E/S/T, R358H, D360G, A362S, I366T, V369A, V371D/E/L/M/Y, L372S/W, A373T, E377D, K378R, P379G/V/Y, P381S, K382R, D383N/G, G386C/E/L/W, L387R, L390I/P, S395G/Q/K, P396N/S, A400K/T, G402S, R403S, K408I, K417R/S, S423D/N, A426S, D433G, Q418D, T419V, R425H, A426Q/S, D436N, G439P, K440N, G444P, T452A, G453R, R455K/P/S/T, D457H/E, E458N/D, A460S, G461K, T463P, G467K/Q, R470K, A474Q, D475K/S/E, A476K, G478P, S479A/H/V, E481G, F482Y, V484D, A485P/K, Q487D/K/N/R/L, Y488N, T490I, K491R, A495T, R501Q, E502G/K/N, F507G/S, Q508R/E, V511L, E512G, L514Q, Q517L, P518Q, D519G/N/K, Q520N/T/G/K, Q522K/R, L524W, A525K/S/T/M/G, K528R, K529R/E, K531E/R, D532G/R, Q533H/L, G534E, I535V/M, A539T/V, W548L, P551R, L553M, S556T, D557G, A562P, W563P, L564P, T567A, G570P, L372S, A573S/V, V575A, F577L, K580N/T, K583N/R/Q, Q585R, H586Y, A589R, G590P, L592F, Y594H/F, S595G, P597A, T599A, A600V, A601V, T603A/F/Y, T604P, D609E, D611C/E, N613D, A617D/P/V, T623S, Y624H, K625Q, K627R, K629C/R, L633D, P634S, E635D/-, E636D/G/-, S637-, G638-, V639-, P640-, A641-, E642A/-, A643P/-, R644-, Q645/-, N646K/-, Q645-, N646-A647-, G648-, I649T/-, Y650-, F651-, R652L/-, A653-, G654-, A655T/-, L656-, R657-, L658-, P659-, G660-, R661-, F662L/-, and L663P/Q/-, wherein amino acid position is determined by optimal alignment with SEQ ID NO: 4.

Particularly suitable are certain substitutions that were identified in variants that performed well with respect to the property of improved thermoactivity relative to the wildtype *Azospirillum irakense* β-glucosidase at pHs below the pH optimum for the wildtype enzyme (e.g., at a temperature and pH of 50° C. and pH 5.5, at a temperature of 50° C. and pH 5.0, at a temperature of 65° C. and pH 5.0, and the like). In addition, sequence-activity analyses indicated that certain of the above-described mutations (substitutions/deletions) appeared particularly favorable with respect to increasing thermoactivity relative to wildtype *Azospirillum irakense* β-glucosidase (SEQ ID NO: 4). Sequence-activity analysis was performed in accordance with the methods described in WO 03/075129, U.S. Ser. No. 10/379,378 filed Mar. 3, 2003, and R. Fox et al., "Optimizing the search algorithm for protein engineering by directed evolution," *Protein Eng.* 16(8): 589-597 (2003), both of which are incorporated herein by reference. See also R. Fox et al., "Directed molecular evolution by machine learning and the influence of nonlinear interactions," *J. Theor. Biol.* 234(2):187-199 (2005), which is incorporated herein by reference. The analysis identified substitutions in the following positions as being particularly beneficial for improved thermoactivity and low pH tolerance relative to the wildtype enzyme: A5, A9, I14, L41, N79, A88, P89, P109, G127, N128, M143, V159, A162, T169, V177, A198, A201, A202, I203, V207, F211, I222, S225, A272, N300, A309, D311, A335, D475, Q508, A525, Y594, and K625.

In certain embodiments, therefore, β-glucosidase variants of the present invention have an amino acid sequence that comprises substitutions in one or more positions selected from the group consisting of A5, A9, I14, L41, N79, A88, P89, P109, G127, N128, M143, V159, A162, T169, V177, A198, A201, A202, I203, V207, F211, I222, S225, A272, N300, A309, D311, A335, D475, Q508, A525, Y594, and K625. Typically, these β-glucosidase variants comprise one or more substitutions selected from the group consisting of A5T, A9G, I14M, L41F, N79D, A88T, P89S, P109D/N, G127N/S, N128K, M143T, V159E/Q, A162T, T169N, V177P, A198S, A201P, A202P, I203Y, V207Y, F211Y, I222A/S/V, S225C, A272L, N300D, A309G, D311G, A335P, D475E, Q508R, A525T, Y594F, and K625Q. All of these specific substitutions were identified as being particularly beneficial to improved thermoactivity and low pH tolerance relative to the wildtype *Azospirillum irakense* β-glucosidase.

In some embodiments, β-glucosidase variants of the present invention have an amino acid sequence that comprises substitutions in one or more positions identified by these analyses, i.e., T2, A3, I4, A5, A9, I14, K35R, L41, S73, N79, A88, P78, N79, P109, G127, N128, A143, H145, P147, V159, M161, A162, T169, V177, A197, A198, A201, A202, I203, V204, V207, F211, I222, S225, A272, H285, Q287, N300, A309, D311, A335, M356, D475, R501, Q508, V511, E512, A525, K529, T567, Y594, Y594, K625, and N646 (wherein amino acid position is determined by optimal alignment with SEQ ID NO: 4). Substitutions in these positions were either identified in variants having particularly improved thermostability relative to the wildtype *Azospirillum irakense* β-glucosidase or were identified from a sequence-activity analysis performed as described above.

In a specific embodiment, the variant comprises an amino acid sequence that has one or more substitutions selected from the group consisting of T2A, A3L/N/P/R/GR, I4P/Q/R/S/T, A5L/N/T/Y, A9E/G/I/K/T, I14H/L/M/N/R/T/K, K35E/P/Q/R, L41F, S73A, P78S, N79D, A88T, P109D/N, G127A/N/S, N128H/K, A143I/M/Q/T, H145R, P147I/K/L/T, V158E, V159E/I/L/A/Q/R, M161T/V, A162S/T/V, T169N, V177P, A197D/M/N, A198C/E/L/M/N/Q/S/T/W/D, A201P/S/G, A202F/K/L/N/P/T/Y/S, I203YF/H/Y, V204I, V207A/E/F/I/L/Y, F211C/V/Y/W/Q, I222A/C/G/I/S/V, S225C/V/N/S/T, A272V/L, H285D/N, Q287N/R, N300D, A309G, D311E/G, A335P, M356K/Q/T, D475K/S/E, R501Q, Q508R/E, V511L, E512G, A525K/S/T/M/G, K529R/E, T567A, Y594H/F, K625Q, Y594H/F, and N646K (wherein amino acid position is determined by optimal alignment with SEQ ID NO: 4).

In certain embodiments, the variant comprises an, amino acid sequence that has one or more substitutions selected from the group consisting of T2A, A3R, I4P/Q/R/S/T, A5T, A9G, I14M, K35E/P/Q/R, L41F, S73A, P78S, N79D, A88T, P109D, G127N, N128K, A143M/T, H145R, P147I/K/L/T, V158E, V159E, M161T/V, A162T, T169N, V177P, A197D/M/N, A198S, A201, A202P, I203Y, V204I, V207Y/F, F211Y, I222A/S/V, S225C, A272L, H285D/N, Q287R, N300D, A309G, D311G, A335P, M356K/Q/T, D475E, R501Q, Q508R, V511L, E512G, A525T, K529R/E, T567A, Y594F, K625Q, Y594H/F, and N646K (wherein amino acid position is determined by optimal alignment with SEQ ID NO: 4).

β-glucosidase variants of the present invention often have one or more substitutions that are selected from the group consisting of T2A, A3L/N/P/R/G, A5L/N/T/Y, I14H/L/M/R/T/K, T60H, S73A, N79D, G127A/N/S, N128H/K, A143I/M/Q/T, H145R, P147I/K/L/T/W/R, V159E/I/L/A/Q/RμM161T/V, T169N, V177P, Y186C, A197D/M/N, A198C/E/L/M/N/Q/S/T/W/D, A202F/K/L/N/P/T/Y, I203F/H/Y, V204I, V207A/E/F/I/L/Y, F211C/V/Y/W/Q, I222A/C/G/I/S/V, S225C/F/N/S/T, A272V/L, Q287E/L/R, D311E/G, A335P, M356K/Q/T, D475K/S/E, R501Q, Q508R/E, E512P, A525K/S/T/M/G, Y594H/F, and N646K. Often, variants of the present invention have at least one substitution selected from the group consisting of T2A, A5T, I14M, N79D, G127N, A142M, H145R, V158E, A197S, V207F, F210Y, I222A, S225C, Q508R, and A525T.

In certain embodiments, the variant exhibits greater thermoactivity relative to the wildtype *Azospirillum irakense* β-glucosidase at a temperature of 50° C. and pH of 6.5. Typically, these variants comprise an amino acid sequence that has a substitution in one or more amino acid positions selected from the group consisting of T2, A3, A5, I14, S73, N79, G127, A143, H145, V159, T169, V177, A198, A202, I203, V207, F211, I222, S225, A272, Q287, D311, Q508, E512, and A525, wherein amino acid position is determined by optimal alignment with SEQ ID NO: 4. In certain embodiments, these variants comprise an amino acid sequence that has one or more substitutions selected from the group consisting of T2A, A3R, A5T, I14M, S73A, N79D, G127N, A143M, H145R, V159E, T169N, V177P, A198S, A202P, I203Y, V207F, F211Y, I222A, S225C, A272L, Q287R, D311G, Q508R, E512G, and A525T.

The amino acid sequences of the β-glucosidase polypeptide variants described herein may have any combination of one or more substitutions at the following amino acid positions: T2, A3, I4, A5, Q6, E7, G8, A9, A10, P11, A12, A13, I14, L15, P17, E18, K19, W20, P21, P23, A24, T25, Q26, I29, D30, E34, K35, A39, L41, K42, Q43, L44, E47, V46, G51, Q52, V53, G56, G59, T60, I61, E64, L66, R67, K68, P70, S73, N79, N83, G84, D85, R87, A88, P89, K91, E92, A97, A98, L105, K107, P109, G110, H111, T112, P113, I114, F118, I120, G127, N128, I134, F135, L141, A143, T144, H145, D146, P147, E148, L150, R151, R152, I153, G154, E155, A158, V159, M161, A162, A163, G165, I166, W168, T169, A173, V177, D180, G188, S190, I195, A197, A198, A201, A202, I203, V204, E205, G206, V207, F211, G212, S213, K214, D215, F216, M217, A218, P219, G220, I222, S225, A226, F229, G233, D236, Q237, G238, D243, R245, I246, S247, E248, E250, R253, N256, A257, D264, A272, F274, Q278, I280, H282, H285, Q287, G295, M297, G298, F299, N300, V304, D311, Q312, P314, G315, F319, N320, T323, S324, I326, M331, A335, K339, Q340, Y342, E343, T345, A347, V349, K350, V351, T353, I354, M356, A357, R358, D360, A362, I366, V369, V371, L372, A373, E377, K378, P379, P381, K382, D383, G386, L387, L390, S395, P396, A400, G402, R403, K408, K417, S423, A426, D433, Q418, T419, R425, A426, D436, G439, K440, G444, T452, G453, R455, D456, E458, A460, G461, T463, G467, R470, A474, D475, A476, G478, S479, E481, F482, V484, A485, Q487, Y488, T490, K491, A495, R501, E502, F507, Q508, V511, E512, L514, Q517, P518, D519, Q520, Q522, L524, A525, K528, K529, K531, D532, Q533, G534, 1535, A539, W548, P551, L553, S556, D557, A562, W563, L564, T567, G570, A573, V575, F577, K580, K583, Q585, A589, H586, G590, L592, Y594, S595, P597, T599, A600, A601, T603, T604, D609, D611, N613, A617, T623, Y624, K625, K627, K629, L633, P634, E635, E636, S637, G638, V639, P640, A641, E642, A643, R644, Q645, N646, A647, G648, I649, Y650, F651, R652, A653, G654, A655, L656, R657, L658, P659, G660, R661, F662, and L663, wherein amino acid position is determined by optimal alignment with SEQ ID NO: 4. Suitable combinations include any combination of substitutions at any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more of the above-identified positions, up to a combination of substitutions at all 289 positions.

In certain embodiments, the variant exhibits greater thermoactivity relative to the wildtype *Azospirillum irakense* β-glucosidase at a temperature of 55° C. and pH of 5.3. Typically, these variants comprise an amino acid sequence that has one or more substitutions in a position selected from the group consisting of N79, A143, H145, V159, A98, and F211, wherein amino acid position is determined by optimal alignment with SEQ ID NO: 4. In some embodiments, these variants have an amino acid sequence that comprises one or more substitutions selected from the group consisting of N79D, A143M, H145R, V159E, A98S and F211Y. Typically, these variants have an amino acid sequence the comprises the substitutions N79D+A143M+H145R+V159E+A98S+F211Y. Exemplary variants are provided in Table 2C of Example 8.

In some embodiments, the variant exhibits greater thermoactivity relative to the wildtype *Azospirillum irakense* β-glucosidase at a temperature of 55° C. and pH 5.2. Typically, these variants comprise an amino acid sequence that has one or more substitutions in a position selected from the group consisting of T2, I14, N79, A143, H145, V159, F211, I222, S225, Q508, and A525, wherein amino acid position is determined by optimal alignment with SEQ ID NO: 4. In some embodiments, these variants have an amino acid sequence that comprises one or more substitutions selected from the group consisting of T2A, I14M, N79D, A143M, H145R, V159E, A198S, F211Y, I222A, S225C, Q508C, and A525T. Typically, these variants have an amino acid sequence that comprises the substitutions T2A+I14M+N79D+A143M+H145R+V159E+A198S+F211Y+I222A+S225C+Q508C+A525T. Exemplary variants are provided in Tables 2D and 3 of Example 8.

In some embodiments, the variant exhibits greater thermoactivity relative to the wildtype *Azospirillum irakense* β-glucosidase at a temperature of 65° C. and pH 5. Typically, these variants comprise an amino acid sequence that has one or more substitutions in a position selected from the group consisting of T2, A5, I14, N79, G127, A143, H145, V159, A198, V207, F211, I222, S225, Q508, and A525, wherein amino acid position is determined by optimal alignment with SEQ ID NO: 4. In some embodiments, these variants have an amino acid sequence that comprises one or more substitutions selected from the group consisting of T2A, A5T, I14M, N79D, G127N, A143M, H145R, V159E, A198S, V207F, F211Y, I222A, S225C, Q508R, and A525T. Typically these variants have an amino acid sequence that comprises the substitutions T2A+A5T+I14M+N79D+G127N+A143M+H145R+V159E+A198S+V207F+F211Y+I222A+S225C+Q508R+A525T. Exemplary variants are provided in Table 5 of Example 10.

In some embodiments, the variant exhibits greater thermoactivity relative to the wildtype *Azospirillum irakense* β-glucosidase at a temperature of 67° C. and pH 5. Typically, these variants comprise an amino acid sequence that has one or more substitutions in a position selected from the group consisting of T2, A3, A5, I14, S73, N79, G127, A143, H145, V159, V177, A198, I203, V207, F211, I222, S225, Q508, and A525, wherein amino acid position is determined by optimal alignment with SEQ ID NO: 4. In some embodiments, these variants have an amino acid sequence that comprises one or more substitutions selected from the group consisting of T2A, A5T, I14M, S73A, N79D, G127N, A143M, H145R, V159E, V177P, A198S, I203&, V207F, F211Y, I222A, S225C, Q508R, and A525T. Typically, these variants have an amino acid sequence that comprises the substitutions T2A+A5T+I14M+S73A+N79D+G127N+A143M+H145R+V159E+V177P+A198S+I203Y+V207F+F211Y+I222A+S225C+Q508R+A525T. Exemplary variants are provided in Table 6 of Example 11.

In some embodiments, the variant exhibits greater thermoactivity relative to the wildtype *Azospirillum irakense* β-glucosidase at a temperature of 72° C. and pH5. Typically, these variants comprise an amino acid sequence that has one or more substitutions in a position selected from the group consisting of T2, A3, A5, I14, S73, N79, G127, A143, H145, V159, T169, V177, A198, A202, I203, V207, F211, I222, S225, A272, Q287, D311, Q508, E512, A525, wherein amino acid position is determined by optimal alignment with SEQ ID NO: 4. In some embodiments, these variants have an amino acid sequence that comprises one or more substitutions selected from the group consisting of T2A, A3R, A5T, A14M, S73A, N79D, G127N, A143M, H145R, V159E, T169N, V177P, A198S, A202P, I203Y, V207F, F211Y, I222A, S225C, A272L, Q287R, D311G, Q508R, D311G, Q5084, E512G, and A525T. Typically these variants have an amino acid sequence that comprises the substitutions T2A+A3R+A5T+A14M+S73A+N79D+G127N+A143M+H145R+V159E+T169N+V177P+A198S+A202P+I203Y+V207F+F211Y+I222A+S225C+A272L+Q287R+D311G+Q508R+E512G+A525T. Exemplary variants are provided in Table 7 of Example 12.

β-glucosidase variants of the present invention may further have an amino acid sequence wherein no substitution is made at positions D309 and/or E509, i.e., the amino acid sequences have an aspartic acid residue at position 309 and/or glutamic acid residue at position 509.

Variants of the present invention may comprise any of the following exemplary combinations of substitutions relative to SEQ ID NO: 4: D311G+D532G+T599A; V46F+I222A; N128K+H145R+A201P+S225C; H145R+I222V; N128K+H145R; H145R+A201P+S225C; H145R+S225C; N128K+H145R+S225C; N128K+H145R+A162T+S225C; E18R+P23L+E34K+E47K+P70S+H145R+S225C; N128K+H145R+D146S+I222A+S225C; H145R+I222A+S225C+A525T; N128K+H145R+I222A; N79D+D85N+H145R+F211Y; A143M+H145R+A198S+P219M; N79D+A143M+H145R+A198S+F211Y; N79D+H145R; N79D+H145R+A198S+P219V; N79D+H145R+F211Y; N79D+A143M+H145R; A143M+H145R; H145R+F211Y; N79D+A143M+H145R+V159E+A198S+F211Y; H145R+V159Q+A198S+F211Y; A143M+H145R+V159E+F211Y; A143M+H145R+F211Y+E642A+A643P; T2A+H145R+A162T+A201P+I222A; N128K+H145R+I222S+S225C; N128K+H145R+A201P+I222S+S225C; H145R+A162T+I222A+S225C; H145R+A162T+S225C+A573S; N79D+N128K+A143M+H145R+V159E+A173C; N128K+A143M+H145R+V159Q+A201P+F211Y+S225C; N79D+A97T+N128K+A143M+H145R+V159E+A173C+F211Y+Q508R; N79D+N128K+H145R+A162T+A173C+A201P+F211Y+S225C+Q487R+A562P; N79D+N128K+H145R+A162T+F211Y+S225C+K625Q; N79D+N128K+H145R+A201P+F211Y; N79D+N128K+A143M+H145R+A162T+A198S+F211Y+I222S+S225C; H145R+V159Q+A201P+F211Y+S225C; N79D+H145R+A162T+A198S+L663P; H145R+D146S+A162T+A173C+A201P; N79D+N128K+H145R+V159E+A201P+F211Y+P219V+S225C; N79D+N128K+A143M+H145R+A162T+A201P+F211Y+P219V; N79D+H145R+D146S+V159E+A201P+F211Y+S225C+K339R; H145R+A201P+I222S+S225C; N79D+A143M+H145R+A162T+A201P+S225C+Q585R; N79D+H145R+D146S+A201P+F211Y+I222S+S225C; N79D+N128K+A143M+H145R+

V159E+A201P+F211Y+S225C; N79D+H145R+V159E+A162T+A201P+S225C+I535V; A24V+A143M+H145R+V159E+A201P+F211Y+I222S+S225C; N128K+H145R+V159E+A173C; N79D+K91Q+N128K+H145R+D146S+A201P+F211Y+I222A+S225C; N79D+N128K+F135L+A143M+H145R+A162T+A173C+A198S+P219V; N128K+A143M+H145R+V159E+A173C+A201P+F211Y+P219V; N79D+H145R+V159Q+F211Y+S225C; N128K+A143M+H145R+V159Q+A198S+F211Y+I222A+S225C+M297I+Q487R; N79D+N128K+H145R+A198S+F211Y+P219V+S225C; N79D+N128K+H145R+D146S+V159E+F211Y+I222S+S225C; A143M+H145R+A162T+F211Y+S225C; N68D+A143M+H145R+V159Q+A201P+F211Y+P219V+S225C; A143M+H145R+F211Y+P219V+S225C; N79D+N128K+H145R+A201P+P219V+K491R; A143M+H145R+A198S+F211Y+S225C; N128K+H145R+A162T+A198S+F211Y+P219V+S225C; N79D+H145R+D146S+V159E+A198S+F211Y+S225C; N79D+A143M+H145R+V159Q+A201P+S225C+K378R; N79D+N128K+H145R+A173C+A198S+F211Y+I222S; N79D+H145R+V159E+A198S+S225C; N79D+N128K+H145R+D146S+V159Q+A201P+F211Y+S225C; N79D+I114V+N128K+H145R+A162T+A198S+F211Y+S225C; A143M+H145R+A162T+A173C+A198S+F211Y+L514Q; N79D+H145R+V159Q+A201P+F211Y+I222A+S225C; N79D+E92V+N128K+A143M+H145R+A201P+F211Y+I222S+S225C; A143M+H145R+V159Q+A201P+F211Y+I222A+S225C+F229I; N79D+H145R+A198S+S225C; N79D+N128K+A143M+H145R+A162T+A198S+I222S+S225C+Q237R; N79D+G84A+N128K+H145R+A162T+A198S+F211Y+I222A+S225C; N79D+H145R+I166T+A198S+F211Y+S225C; N79D+H145R+A162T+A198S+S225C; H145R+D146S+V159Q+A201P+F11Y+I222A+S225C; A143M+H145R+A198S+F211Y+I222A+S225C+Q290R+D612E; H148R+A176C+A204P+F214Y+P222V; N79D+N128K+H145R+D146S+A162T+A173C+A198S+F211Y; N79D+N128K+H145R+D146S+S225C; A143M+H145R+A201P+S225C; N79D+H145R+G154V+F211Y+S225C; N79D+N128K+H145R; N128K+H145R+V159Q+A201P+F211Y+I222S+S225C; N79D+H145R+V159Q+A162T+A201P+F211Y+S225C; N128K+H145R+D146S+V159E+A201P+F211Y+S225C+A573V; N79D+H145R+V159E+A198S+F211Y+P219V; H145R+V159Q+F211Y+I222S+S225C+G534E; I14M+N79D+N128K+H145R+A162T+A201P+F211Y+S225C+Q487R; E34D+N79D+N128K+A143M+H145R+V159E+A201P+F211Y; N79D+H145R+D146S+A198S+F211Y+S225C; E7G+N79D+H145R+D146S+A198S+F211Y+I222S+S225C; N128K+A143T+H145R+V159Q+A201P+F211Y+I222S+S225C+E502G; H145R+A198S+F211Y+I222A+S225C+A373T; N79D+N128K+H145R+A173C+A198S+F211Y; N79D+N128K+H145R+D146S+S225C+A655T; N128K+A143M+H143R+V159E+F211Y+S225C; N79D+I114+N128K+H145R+V159Q+A173C+A198S+F211Y+P219V; N79D+H145R+D146S+A162T+A198S+F211Y+I222A+S225C+D311G+N320K+R358H+F662L; N79D+N128K+H145R+D146S+V159Q+A201P+F211Y+P219V+I280V; H145R+V159Q+A198S+F211Y+I222A+S225C+P381S; N79D+N128K+I134N+H145R+V159Q+S225C; N79D+N128K+H145R+V159Q+A198S+I222A+S225C+K628R; N79D+N128K+H145R+D146S+A162T+A198S+F211Y; H145R+F274K; H145R+F274Q; H145R+F274A+D436N; H145R+F274A; H145R+I326S; N79D+A143M+H145R+V159E+A198S+A257P+A485P; N79D+A143M+H145R+V159E+A198S+I222S+A257P+T604P; N79D+A143M+H145R+V159E+A198S+G570P+T604P; N79D+A143M+H145R+V159E+A198S+A485P+T604P; N79D+A143M+H145R+V159E+A198S+S213P+A485P; N79D+A143M+H145R+V159E+A198S+S213P+G220V; N79D+A143M+H145R+V159E+A198S; N79D+A143M+H145R+V159E+A198S+A539V; N79D+A143M+H145R+V159E+A198S+G570P; N79D+A143M+H145R+V159E+A198S+A485P; Q26R+N79D+A143M+H145R+V159E+A198S+T604P; N79D+A143M+H145R+V159E+A198S+S479A; N79D+A143M+H145R+V159E+A199S+S213P; N79D+A143M+H145R+V159E+A198S+T604P; G59R+N79D+A143M+H145R+V159E+A198S; N79D+A143M+H145R+V159E+A198S+M331L+A485P; N79D+I120V+A143M+H145R+V159E+A198S+Q517L+T604P; A12R+N79D+A143M+H145R+V159E+A198S+F211Y; A13P+N79D+A143M+H145R+V159E+A198S+F211Y; A10G+N79D+A143M+H145R+V159E+A198S+F211Y; A3L+N79D+A143M+H145R+V159E+A198S+F211Y; A10P+N79D+A143M+H145R+V159E+A198S+F211Y; I14T+N79D+A143M+H145R+V159E+A198S+F211Y; A10S+N79D+A143M+H145R+V159E+A198S+F211Y; A3N+N79D+A143M+H145R+V159E+A198S+F211Y; G8P+N79D+A143M+H145R+V159E+A198S+F211Y; A10N+N79D+A143M+H145R+V159E+A198S+F211Y; A9T+N79D+A143M+H145R+V159E+A198S+F211Y; A5T+N79D+A143M+H145R+V159E+A198S+F211Y; Q6D+N79D+A143M+H145R+V159E+A198S+F211Y; I4P+N79D+A143M+H145R+V159E+A198S+F211Y; G8Y+N79D+A143M+H145R+V159E+A198S+F211Y; E7H+N79D+A143M+H145R+V159E+A198S+F211Y; G8S+N79D+A143M+H145R+V159E+A198S+F211Y; G8R+N79D+A143M+H145R+V159E+A198S+F211Y; Q6T+N79D+A143M+H145R+V159E+A198S+F211Y; A12N+N79D+A143M+H145R+V159E+A198S+F211Y; P11E+N79D+A143M+H145R+V159E+A198S+F211Y; A3P+N79D+A143M+H145R+V159E+A198S+F211Y; A5N+N79D+A143M+H145R+V159E+A198S+F211Y; Q6P+N79D+A143M+H145R+V159E+A198S+F211Y; A3R+N79D+A143M+H145R+V159E+A198S+F211Y; Q6S+N79D+A143M+H145R+V159E+A198S+F211Y; A12Y+N79D+A143M+H145R+V159E+A198S+F211Y; Q6G+N79D+A143M+H145R+V159E+A198S+F211Y; A91+N79D+A143M+H145R+V159E+A198S+F211Y; G8A+N79D+A143M+H145R+V159E+A198S+F211Y; Q6A+N79D+A143M+H145R+V159E+A198S+F211Y; E7P+N79D+A143M+H145R+V159E+A198S+F211Y; A5L+N79D+A143M+H145R+V159E+A198S+F211Y; P11A+N79D+A143M+H145R+V159E+A198S+F211Y; I14R+N79D+A143M+H145R+V159E+A198S+F211Y; I4R+N79D+A143M+H145R+V159E+A198S+F211Y; A9G+N79D+A143M+H145R+V159E+A198S+F211Y; Q6N+N79D+A143M+H145R+V159E+A198S+F211Y; A9K+N79D+A143M+H145R+V159E+A198S+F211Y; A5Y+N79D+A143M+H145R+V159E+A198S+F211Y; I14M+N79D+K91Q+H145R+G154V+V159E+A198S+A201P+F211Y+S225C+A525T+K627R; I14M+N79D+K91Q+A143M+H145R+V159E+A198S+F211Y+I222A+Q508R+A525T+K627R; I14M+N79D+K91Q+A143M+H145R+V159E+A198S+F211Y+Q508R; N79D+K91Q+H145R+V159E+A198S+A201P+F211Y+I222S+Q508R+A525T; I14M+N79D+H145R+V159E+A198S+A201P+F211Y+S225C+A525T+K583R+K628R+L663P; T2A+I14M+N79D+K91Q+A143M+H145R+V159E+A198S+A201P+F211Y+S225C+A525T; I14M+N79D+K91Q+A143M+H145R+G154V+V159E+A198S+A201P+F211Y+S225C+Q508R+A525T; T2A+I14M+N79D+K91Q+A143M+H145R+V159E+A198S+A201P+F211Y+I222A+S225C+A525T+Y594H+K627R; I14M+N79D+K91Q+H145R+V159E+A198S+F211Y+I222A+S225C+Q508R+K627R; T2A+I14M+N79D+K91Q+A143M+H145R+V159E+

A198S+A201P+F211Y+S225C+L663P; I14M+N79D+A143M+H145R+V159E+A198S+F211Y+I14M+N79D+K91Q+H145R+V159E+A162S+A198S+A201P+F211Y+I222S+S225C+Q508R+A525T+K628R+L663P; T2A+I14M+N79D+A143M+H145R+V159E+A198S+F211Y+I222A+S225C+Q508R+A525T; T2A+N79D+K91Q+H145R+V159E+A198S+F211Y+S225C+Q508R+L663P; T2A+I14M+N79D+K91Q+H145R+V159E+A198S+A201P+F211Y+I222A+S225C+L514Q+K628R; T2A+I14M+N79D+A143M+H145R+V159E+A198S+A201 P+F211Y+I222A+S225C; I14M+N79D+K91Q+H145R+V159E+A198S+S225C+Q508R; N79D+A143M+H145R+V159E+A198S+V207Y+F211Y; N79D+G128N+A143M+H145R+V159E+A198S+F211Y; N79D+A143M+H145R+V159E+A198S+V207F+F211Y; N79D+A143M+H145R+V159E+A198S+V207L+F211Y; N79D+P109D+A143M+H145R+V159E+A198S+F211Y; N79D+A143M+H145R+V159E+M161T+A198S+F211Y; I14M+N79D+K91Q+H145R+V159E+A198S+F211Y+I222S+S225C+Q508R+A525T+L663P; T2A+I14M+N79D+H145R+V159E+A198S+A201P+V207I+F211Y+S225C+Q508R+K627R+L663P; I14M+N79D+K91Q+N128K+H145R+V159E+A198S+F211Y+I222A+Q508R; I14M+N79D+A143M+H145R+V159E+A198S+A201P+F211Y+Q508R+A525T+K627R; I14M+N79D+K91Q+A143M+H145R+V159E+A198S+F211Y+A525T+K627R; T2A+N79D+K91Q+H145R+V159E+A198S+A201P+F211Y+S225C+D236G+K627R; N79D+K91Q+H145R+V159E+A198S+F211Y+S225C+Q508R+A525T; N79D+A143M+H145R+V159E+A198S+F211Y+I246C; N79D+A143M+H145R+V159E+A198S+F211Y+V371M; N79D+A143M+H145R+V159E+A198S+F211Y+G298R+D311E; N79D+A143M+H145R+V159E+A198S+F211Y+G386E; N79D+A143M+H145R+V159E+A198S+F211Y+A358S; N79D+A143M+H145R+V159E+A198S+F211Y+D311G; N79D+A143M+H145R+V159E+A198S+F211Y+L372W; N79D+A143M+H145R+V159E+A198S+F211Y+P379G; T2A+I14M+N79D+A143M+H145R+P147K+V159E+A198S+F211Y+I222A+S225C+Q508R+A525T; T2A+I14M+N79D+A143M+H145R+V159E+A198S+F211Y+I222A+S225C+E377D+Q508R+A525T; T2A+I14M+N79D+A143M+H145R+P147T+V159E+A198S+F211Y+I223A+S225C+Q508R+A525T; T2A+I14M+N79D+A143M+H145R+V159E+A198S+F211Y+M217L+I222A+S225C+Q508R+A525T; T2A+I14M+N79D+A99K+A143M+H145R+V159E+A198S+F211Y+I222A+S225C+Q508R+A525T; T2A+I14M+N79D+A99R+A143M+H145R+V159E+A198S+F211Y+I222A+S225C+Q508R+A525T; T2A+I14M+D30E+N79D+A143M+H145R+V159E+A198S+F211Y+I222A+S225C+Q508R+A525T; T2A+I14M+N79D+A143M+H145R+P147L+V159E+A198S+F211Y+I222A+S225C+Q508R+A525T; T2A+I14M+N79D+A143M+H145R+V159E+A198S+F211Y+I222A+S225C+A347K+Q508R+A525T; T2A+I14M+N79D+N83H+A143M+H145R+V159E+A198S+F211Y+I222A+S225C+Q508R+A525T; T2A+I14M+N79D+A143M+H145R+V159E+A198S+F211Y+I222A+S225C+R455T+Q508R+A525T; T2A+I14M+N79D+A143M+H145R+V159E+A198S+F211Y+I222A+S225C+E502N+Q508R+A525T; T2A+I14M+N79D+N128H+A143M+H145R+V159E+A198S+F211Y+I222A+S225C+Q508R+A525T; T2A+I14M+S73A+N79D+A143M+H145R+V159E+A198S+F211Y+I222A+S225C+Q508R+A525T; T2A+I14M+N79D+A143M+H145R+V159E+A198S+I203Y+F211Y+I222A+S225C+Q508R+A525T; T2A+I14M+N79D+A143M+H145R+V159E+A198S+I203H+F211Y+I222A+S225C+Q508R+A525T; T2A+I14M+N79D+A143M+H145R+V159E+A198S+V204I+F211Y+I222A+S225C+Q508R+A525T; T2A+I14M+N79D+A143M+H145R+V159E+A198S+I203F+F211Y+I222A+S225C+Q508R+A525T; T2A+I14M+N79D+A143M+H145R+V159E+V177P+A198S+F211Y+I222A+S225C+Q508R+A525T; T2A+I14M+N79D+A143M+H145R+V159E+A198S+F211Y+I222A+S225C+Q508R+A525T+T603F; T2A+I14M+N79D+A143M+H145R+V159E+A198S+F211Y+I222A+S225C+Q508R+A525T+T603Y; T2A+I14M+N79D+A143M+H145R+V159E+A198S+F211Y+I222A+S225C+Q508R+A525T+L553M; T2A+E7P+A9G+A10N+I14M+N79D+N128K+A143M+H145R+V159E+A198S+F211Y+I222A+S225C+Q508R+A525T; T2A+A9G+A10N+I14M+N79D+N128K+A143M+H145R+V159E+A198S+F211Y+I222A+S225C+Q508R+A525T; T2A+Q6P+E7P+A9G+I14M+N79D+N128K+A143M+H145R+V159E+A198S+F211Y+I222A+S225C+Q508R+A525T; T2A+Q6P+A9K+A10N+I14M+N79D+N128K+A143M+H145R+V159E+A198S+F211Y+I222A+S225C+Q508R+A525T; T2A+Q6P+A10N+I14M+N79D+N128K+A143M+H145R+V159E+A198S+F211Y+I222A+S225C+Q508R+A525T; T2A+Q6P+I14M+N79D+N128K+A143M+H145R+V159E+A198S+F211Y+I222A+S225C+Q508R+A525T; T2A+Q6P+E7P+I14M+N79D+N128K+A143M+H145R+V159E+A198S+F211Y+I222A+S225C+Q508R+A525T; T2A+E7P+A9K+A10N+I14M+N79D+N128K+A143M+H145R+R152S+V159E+A298S+F211Y+I222A+S225C+Q508R+A525T; T2A+A9G+I14M+N79D+N128K+A143M+H145R+V159E+A198S+F211Y+I222A+S225C+Q508R+A525T; T2A+I14M+N79D+N128K+A143M+H145R+V159E+A198S+F211Y+I222A+S225C+Q508R+A525T; T2A+Q6P+I14M+N79D+A143M+H145R+V159E+A198S+F211Y+M217V+I222A+S225C+D311G+Q508R+A525T; T2A+I14M+I61V+N79D+G127N+A143M+H145R+V159E+A198T+F211Y+I222A+S225C+Q508R; T2A+A5T+A13P+I14M+N79D+N128K+A143M+H145R+V159E+A198S+F211Y+I222A+S225C+Q508R+A525T; T2A+I14M+N79D+N128K+A143M+H145R+V159E+M161V+A198S+V207L+F211Y+S225C+Q508R+A525T+I535V+N646K; T2A+A13P+I14M+N79D+A143M+H145R+V159E+A198S+V208F+F211Y+I222A+S225C+Q508R+A525T; T2A+I14M+N79D+G128N+A143M+H145R+V159E+A198S+V208I+F211Y+I222A+S225C+Y342C+Q508R+A525T+K583N+P634S; T2A+A5T+I14M+N79D+G128N+A143M+H145R+V159E+M161V+A198S+F211Y+I222A+S225C+Q508R+A525T; T2A+I14M+N79D+A143M+H145R+V159E+M161V+A198S+V207Y+F211Y+S225C+I354T+Q508R; T2A+I14M+N79D+A143M+H145R+V159E+A198S+V207Y+F211Y+I222A+S225C+Q508R+A525T; T2A+A5T+A13P+I14M+N79D+G127N+N128K+A143M+H145R+V159E+M161V+A198S+F211Y+S225C+Q508R+A525T+F577L; T2A+I4S+I14M+N79D+A143M+H145R+V159E+A198S+V207F+F211Y+I222A+S225C+Q508R+A525T; T2A+I4S+I14M+N79D+A143M+H145R+V159E+A198S+V207F+F211Y+I222A+S225C+Q508R+A525T; T2A+A9E+I14M+L66Q+N79D+A143M+H145R+V159E+M161V+A198S+V207L+F211Y+S225C+Q508R+A525T; T2A+A9G+I14M+N79D+P109D+G127N+A143M+H145R+G154V+V159E+A198S+V207F+F211Y+I222A+S225C+A525T; T2A+I14M+N79D+G127N+N128K+A143M+H145R+V159E+M161V+A198S+V207L+F211Y+S225C+Q508R+A525T; T2A+I14M+N79D+A143M+H145R+V159E+A198S+F211Y+I222A+S225C+Q508R; T2A+A5T+A13P+I14M+N79D+P109D+A143M+H145R+V159E+A198S+V207L+F211Y+I222A+S225C+Q508R; T2A+A3R+I14M+N79D+P109D+G127N+A143M+H145R+V159E+M161V+

A198S+V207F+F211Y+I222A+S225C+Q508R; T2A+A9G+I14M+N79D+G127N+N128K+A143M+H145R+V159E+A198S+V207F+F211Y+I222A+S225C+Q508R+A525T+Q533L+E636D; T2A+A5T+I14M+N79D+G127N+A143M+H145R+V159E+A198S+F211Y+I222A+S225C+Q508R+A525T; T2A+A3R+A9G+I14M+N79D+A143M+H145R+V159E+M161V+A198S+V207Y+F211Y+S225C+Q508R+A525T; T2A+I14M+N79D+N128K+A143M+H145R+V159E+A198S+V207Y+F211Y+I222A+S225C+Q508R+A525T+K583N; T2A+I14M+N79D+F119S+A143M+H145R+V159E+A198S+F211Y+I222A+S225C+L390P+Q508R+A525T; T2A+I14M+N79D+A143M+H145R+V159E+M161V+A198S+V207Y+F211Y+I222A+S225C+A525T+N646K; T2A+A13P+I14M+N79D+G127N+N128K+A143M+H145R+V159E+A198S+V207F+F211Y+I222A+S225C+Q508R+A525T; T2A+I14M+N79D+G127N+A143M+H145R+V159E+A198S+F211Y+I222A+S225C+Q508R+A525T; T2A+I14M+N79D+A143M+H145R+V159E+M161V+A198S+V207L+F211Y+I222A+S225C+Q508R; T2A+A5T+A9G+I14M+N79D+P89S+P109D+G127N+A143M+H145R+V159E+A198S+V207Y+F211Y+I222A+S225C+Q508R+A525T; T2A+A9G+A13P+I14M+N79D+G127N+A143M+H145R+V159E+A198S+F211Y+I222A+S225C+A525S; T2A+A9G+I14M+N79D+G127N+A143M+H145R+V159E+A2198S+V207Y+F211Y+I222A+S225C+Q508R+A525T; T2A+A5T+A9G+I14M+N79D+G127N+N128K+A143M+H145R+V159E+A198S+V207Y+F211Y+I222A+S225C+Q508R+A525T; T2A+I14M+N79D+A143M+H145R+V159E+A198S+V207F+F211Y+I222A+S225C+Q508R+A525T; T2A+A13P+I14M+N79D+A143M+H145R+V159E+A198S+V207F+F211Y+I222A+S225C+Q508R+A525T+N646K; T2A+I14M+N79D+A143M+H145R+V159E+M161V+A198S+F211Y+S225C+Q508R; T2A+I14M+N79D+A143M+H145R+V159E+A198S+F211Y+I222A+S225C+Q508R+A525T+Q585R; T2A+A9K+I14M+N79D+K107R+N128K+A143M+H145R+V159E+A198S+F211Y+I222A+S225C+Q508R+A525T; T2A+A9K+A10N+I14M+N79D+A143M+H145R+V159E+A198S+F211Y+I222A+S225C+Q508R+A525T; T2A+E7P+A10N+I14M+N79D+A143M+H145R+V159E+A198S+F211Y+I222A+S225C+M356T+Q508R+A525T+H586Y; T2A+E7P+A9G+A10N+I14M+N79D+A143M+H145R+V159E+A198S+F211Y+I222A+S225C+Q508R+A525T; T2A+I14M+N79D+A143M+H145R+V159E+A198S+F211Y+I222A+S225C+Q508R+A525T; T2A+Q6P+E7P+A9G+A10N+I14M+N79D+A143M+H145R+V159E+A198S+F211Y+I222A+S225C+Q508R+A525T; T2A+I14M+N79D+G127N+N128K+A143M+H145R+V159E+A198S+V207F+F211Y+I222A+S225C+I366T+Q508R; T2A+A3R+A5T+A9G+A13P+I14M+L44S+N79D+G127N+A143M+H145R+V159E+A198S+V207Y+F211Y+I222A+S225C+Q508R+P518Q+D519N+A525T; T2A+I14M+N79D+A143M+H145R+V159E+A198S+V207F+F211Y+I222A+S225C+Q508R+A525T+A600V; T2A+A5T+I14M+N79D+G127N+A143M+H145R+V159E+A198S+V207F+F211Y+I222A+S225C+Q508R+A525T; T2A+I14M+N79D+G127N+A143M+H145R+G154V+V159E+A198S+V207Y+F211Y+I222A+S225C+Q508R+A525I; T2A+I14M+N79D+A143M+H145R+V159E+A198S+F211Y+I222A+S225C+F274S+Q508R; T2A+A9G+I14M+N79D+G127S+A143M+H145R+V159E+A198S+F211Y+I222A+S225C+Q508R+A525T; T2A+A9G+A13P+I14M+N79D+P109D+N128K+A143M+H145R+V159E+A198S+V207I+F211Y+S225C+S247P+Q508R+A525S; T2A+I14M+N79D+A143M+H145R+V159E+A198S+V207Y+F211Y+I222A+S225C+Q508R+A525T+D611E; T2A+I14M+N79D+A143M+H145R+V159E+M161V+A198S+V207Y+F211Y+I222A+S225C+Q508R+A525T; T2A+A5T+I14M+N79D+P109N+A143M+H145R+V159E+M161V+A198S+V207Y+F211Y+I222A+Q508R+A525T; and T2A+A9G+I14M+N79D+A143M+H145R+V159E+A198S+V207F+F211Y+I222A+S225C+A525T.

Some variant polypeptides of the present invention may have the following exemplary combinations of substitutions: T2A+A5T+I14M+N79D+G127N+A143M+H145R+V159E+A198S+V207F+F211Y+I222A+S225C+Q508R+A525T+P109D+V177P+Q287R+A600V; T2A+A5T+I14M+N79D+G127N+A143M+H145R+V159E+A198S+V207F+F211Y+I222A+S225C+Q508R+A525T+I4S+I61V+V177P+I535V; T2A+A5T+I14M+N79D+G127N+A143M+H145R+V159E+A198S+V207F+F211Y+I222A+S225C+Q508R+A525T+A3R+I4S+I61V+V177P+I203Y+I535V; T2A+A5T+I14M+N79D+G127N+A143M+H145R+V159E+A198S+V207F+F211Y+I222A+S225C+Q508R+A525T+I4S+V177P+N320S+K350E; T2A+A5T+I14M+N79D+G127N+A143M+H145R+V159E+A198S+V207F+F211Y+I222A+S225C+Q508R+A525T+A3R+V177P+I535V; T2A+A5T+I14M+N79D+G127N+A143M+H145R+V159E+A198S+V207F+F211Y+I222A+S225C+Q508R+A525T+P89S+V177P+D236Y; T2A+A5T+I14M+N79D+G127N+A143M+H145R+V159E+A198S+V207F+F211Y+I222A+S225C+Q508R+A525T+I4S+V177P+A600V; T2A+A5T+I14M+N79D+G127N+A143M+H145R+V159E+A198S+V207F+F211Y+I222A+S225C+Q508R+A525T+I4S+P89S+V177P+I535V+Q585R; T2A+A5T+I14M+N79D+G127N+A143M+H145R+V159E+A198S+V207F+F211Y+I222A+S225C+Q508R+A525T+I4S+I61V+S73A+V177P+N613D+A617V; T2A+A5T+I14M+N79D+G127N+A143M+H145R+V159E+A198S+V207F+F211Y+I222A+S225C+Q508R+A525T+V177P+I535V; T2A+A5T+I14M+N79D+G127N+A143M+H145R+V159E+A198S+V207F+F211Y+I222A+S225C+Q508R+A525T+A3R+S73A+V177P+I203Y+A600V; T2A+A5T+I14M+N79D+G127N+A143M+H145R+V159E+A198S+V207F+F211Y+I222A+S225C+Q508R+A525T+I4S+P89S+V177P+A600V; T2A+A5T+I14M+N79D+G127N+A143M+H145R+V159E+A198S+V207F+F211Y+I222A+S225C+Q508R+A525T+P89S+V177P; T2A+A5T+I14M+N79D+G127N+A143M+H145R+V159E+A198S+V207F+F211Y+I222A+S225C+Q508R+A525T+K35Q+S73A+I203Y; T2A+A5T+I14M+N79D+G127N+A143M+H145R+V159E+A198S+V207F+F211Y+I222A+S225C+Q508R+A525T+I203Y+I535V; T2A+A5T+I14M+N79D+G127N+A143M+H145R+V159E+A198S+V207F+F211Y+I222A+S225C+Q508R+A525T+P89S+V177P+I203Y+Y594F; T2A+A5T+I14M+N79D+G127N+A143M+H145R+V159E+A198S+V207F+F211Y+I222A+S225C+Q508R+A525T+S73A+I203Y; T2A+A5T+I14M+N79D+G127N+A143M+H145R+V159E+A198S+V207F+F211Y+I222A+S225C+Q508R+A525T+A3R+I4S+V177P; T2A+A5T+I14M+N79D+G127N+A143M+H145R+V159E+A198S+V207F+F211Y+I222A+S225C+Q508R+A525T+A3R+I4S+S73A+V177P+I535M; T2A+A5T+I14M+N79D+G127N+A143M+H145R+V159E+A198S+V207F+F211Y+I222A+S225C+Q508R+A525T+A3R+I61V+V177P; T2A+A5T+I14M+N79D+G127N+A143M+H145R+V159E+A198S+V207F+F211Y+I222A+S225C+Q508R+A525T+I4S+V177P+A601V; T2A+A5T+I14M+N79D+G127N+A143M+H145R+V159E+A198S+V207F+F211Y+I222A+S225C+Q508R+A525T+A3R+M161V+I203Y+A222I+D383G; T2A+A5T+I14M+N79D+G127N+A143M+H145R+V159E+A198S+V207F+F211Y+I222A+

S225C+Q508R+A525T+A3R+V177P+S213T; T2A+A5T+I14M+N79D+G127N+A143M+H145R+V159E+A198S+V207F+F211Y+I222A+S225C+Q508R+A525T+A3R+P109D+V177P+M356T; T2A+A5T+I14M+N79D+G127N+A143M+H145R+V159E+A198S+V207F+F211Y+I222A+S225C+Q508R+A525T+I203Y+M356T+N646K; T2A+A5T+I14M+N79D+G127N+A143M+H145R+V159E+A198S+V207F+F211Y+I222A+S225C+Q508R+A525T+T25A+N128H+V177P+I203Y+T525S; T2A+A5T+I14M+N79D+G127N+A143M+H145R+V159E+A198S+V207F+F211Y+I222A+S225C+Q508R+A525T+A3R+A13P+P147T+V177P+I203Y+T525S+H586Y; T2A+A5T+I14M+N79D+G127N+A143M+H145R+V159E+A198S+V207F+F211Y+I222A+S225C+Q508R+A525T+A13P+P109D+V177P; T2A+A5T+I14M+N79D+G127N+A143M+H145R+V159E+A198S+V207F+F211Y+I222A+S225C+Q508R+A525T+A13P+P109D+N128K+V177P+P597A; T2A+A5T+I14M+N79D+G127N+A143M+H145R+V159E+A198S+V207F+F211Y+I222A+S225C+Q508R+A525T+A13P+V177P+A400T+H586Y; T2A+A5T+I14M+N79D+G127N+A143M+H145R+V159E+A198S+V207F+F211Y+I222A+S225C+Q508R+A525T+A3R+A13P+P147T+E159G+V177P; T2A+A5T+I14M+N79D+G127N+A143M+H145R+V159E+A198S+V207F+F211Y+I222A+S225C+Q508R+A525T+P109D+P147T+V177P+E502N+H586Y; T2A+A5T+I14M+N79D+G127N+A143M+H145R+V159E+A198S+V207F+F211Y+I222A+S225C+Q508R+A525T+A13P+P147T+V177P+A226G+H586Y; T2A+A5T+I14M+N79D+G127N+A143M+H145R+V159E+A198S+V207F+F211Y+I222A+S225C+Q508R+A525T+P109D+P147T+V177P+T525S; T2A+A5T+I14M+N79D+G127N+A143M+H145R+V159E+A198S+V207F+F211Y+I222A+S225C+Q508R+A525T+V177P+E502N+T525S; T2A+A5T+I14M+N79D+G127N+A143M+H145R+V159E+A198S+V207F+F211Y+I222A+S225C+Q508R+A525T+V177P+L372S; T2A+A5T+I14M+N79D+G127N+A143M+H145R+V159E+A198S+V207F+F211Y+I222A+S225C+Q508R+A525T+V177P+E502N+R508Q; T2A+A5T+I14M+N79D+G127N+A143M+H145R+V159E+A198S+V207F+F211Y+I222A+S225C+Q508R+A525T+A3R+A13P+P147T+V177P+E502N+H586Y; T2A+A5T+I14M+N79D+G127N+A143M+H145R+V159E+A198S+V207F+F211Y+I222A+S225C+Q508R+A525T+A3R+I203Y+A400T+E502N+T525S; T2A+A5T+I14M+N79D+G127N+A143M+H145R+V159E+A198S+V207F+F211Y+I222A+S225C+Q508R+A525T+A13P+N128H+V177P+E502N+R508Q; T2A+A5T+I14M+N79D+G127N+A143M+H145R+V159E+A198S+V207F+F211Y+I222A+S225C+Q508R+A525T+P109D+V177P+D351E+H586Y; T2A+A5T+I14M+N79D+G127N+A143M+H145R+V159E+A198S+V207F+F211Y+I222A+S225C+Q508R+A525T+V177P+R508Q; T2A+A5T+I14M+N79D+G127N+A143M+H145R+V159E+A198S+V207F+F211Y+I222A+S225C+Q508R+A525T+A3R+A13P+I203Y+A400T; T2A+A5T+I14M+N79D+G127N+A143M+H145R+V159E+A198S+V207F+F211Y+I222A+S225C+Q508R+A525T+A3R+P109D+P147T+V177P+H586Y; T2A+A5T+I14M+N79D+G127N+A143M+H145R+V159E+A198S+V207F+F211Y+I222A+S225C+Q508R+A525T+A13P+N128H+V177P; T2A+A5T+I14M+N79D+G127N+A143M+H145R+V159E+A198S+V207F+F211Y+I222A+S225C+Q508R+A525T+P109D+V177P+A400T+E502N+H586Y; T2A+A5T+I14M+N79D+G127N+A143M+H145R+V159E+A198S+V207F+F211Y+I222A+S225C+Q508R+A525T+A13P+P147T+V177P+A400T+E502N+R508Q; T2A+A5T+I14M+N79D+G127N+A143M+H145R+V159E+A198S+V207F+F211Y+I222A+S225C+Q508R+A525T+P109D+V177P+A400T; T2A+A5T+I14M+N79D+G127N+A143M+H145R+V159E+A198S+V207F+F211Y+I222A+S225C+Q508R+A525T+A13P+V177P+V204I+D291G; T2A+A5T+I14M+N79D+G127N+A143M+H145R+V159E+A198S+V207F+F211Y+I222A+S225C+Q508R+A525T+A3R+P147T+V177P+A400T+E502N; T2A+A5T+I14M+N79D+G127N+A143M+H145R+V159E+A198S+V207F+F211Y+I222A+S225C+Q508R+A525T+V177P A400T; T2A+A5T+I14M+N79D+G127N+A143M+H145R+V159E+A198S+V207F+F211Y+I222A+S225C+Q508R+A525T+N128H+V177P+E502N+H586Y; T2A+A5T+I14M+N79D+G127N+A143M+H145R+V159E+A198S+V207F+F211Y+I222A+S225C+Q508R+A525T+V177P+A400T+R508Q; T2A+A5T+I14M+N79D+G127N+A143M+H145R+V159E+A198S+V207F+F211Y+I222A+S225C+Q508R+A525T+A13P+P147T+I203Y+H586Y; T2A+A5T+I14M+N79D+G127N+A143M+H145R+V159E+A198S+V207F+F211Y+I222A+S225C+Q508R+A525T+P109D+V177P; T2A+A5T+I14M+N79D+G127N+A143M+H145R+V159E+A198S+V207F+F211Y+I222A+S225C+Q508R+A525T+A13P+P109D+V177P+T525S; T2A+A5T+I14M+N79D+G127N+A143M+H145R+V159E+A198S+V207F+F211Y+I222A+S225C+Q508R+A525T+A3R+P147T+V177P+I203Y+E502N+H586Y; T2A+A5T+I14M+N79D+G127N+A143M+H145R+V159E+A198S+V207F+F211Y+I222A S225C+Q508R+A525T+A3R+V177P; T2A+A5T+I14M+N79D+G127N+A143M+H145R+V159E+A198S+V207F+F211Y+I222A+S225C+Q508R+A525T+A13P+I203Y+A400T+E502N; T2A+A5T+I14M+N79D+G127N+A143M+H145R+V159E+A198S+V207F+F211Y+I222A+S225C+Q508R+A525T+A3R+A13P+V177P+A400T+H586Y; T2A+A5T+I14M+N79D+G127N+A143M+H145R+V159E+A198S+V207F+F211Y+I222A+S225C+Q508R+A525T+A3R+V177P+E502N; T2A+A5T+I14M+N79D+G127N+A143M+H145R+V159E+A198S+V207F+F211Y+I222A+S225C+Q508R+A525T+A3R+P147T+I203Y+E502N; T2A+A5T+I14M+N79D+G127N+A143M+H145R+V159E+A198S+V207F+F211Y+I222A+S225C+Q508R+A525T+A3R+T25A+V177P+A400T+R508Q; T2A+A5T+I14M+N79D+G127N+A143M+H145R+V159E+A198S+V207F+F211Y+I222A+S225C Q508R+A525T+A3R+V177P+A400T; T2A+A5T+I14M+N79D+G127N+A143M+H145R+V159E+A198S+V207F+F211Y+I222A+S225C+Q508R+A525T+A3R+M14K+N128H+V177P+R508Q; T2A+A5T+I14M+N79D+G127N+A143M+H145R+V159E+A198S+V207F+F211Y+I222A+S225C+Q508R+A525T+A13P+P147T+E502N; T2A+A5T+I14M+N79D+G127N+A143M+H145R+V159E+A198S+V207F+F211Y+I222A+S225C+Q508R+A525T+V177P; T2A+A5T+I14M+N79D+G127N+A143M+H145R+V159E+A198S+V207F+F211Y+I222A+S225C+Q508R+A525T+A3R+N128H+V177P; T2A+A5T+I14M+N79D+G127N+A143M+H145R+V159E+A198S+V207F+F211Y+I222A+S225C+Q508R+A525T+N128H+P147T+V177P+T603A; T2A+A5T+I14M+N79D+G127N+A143M+H145R+V159E+A198S+V207F+F211Y+I222A+S225C+Q508R+A525T+P147T+I203Y+H586Y; T2A+A5T+I14M+N79D+G127N+A143M+H145R+V159E+A198S+V207F+F211Y+I222A+S225C+Q508R+A525T+T169N; T2A+A5T+I14M+N79D+G127N+A143M+H145R+V159E+A198S+V207F+F211Y+I222A+S225C+Q508R+A525T+R508E; T2A+A5T+I14M+N79D+G127N+A143M+H145R+V159E+A198S+V207F+F211Y+I222A+S225C+Q508R+A525T+F274K; T2A+A5T+I14M+N79D+G127N+A143M+H145R+V159E+A198S+V207F+

F211Y+I222A+S225C+Q508R+A525T+F274N; T2A+A5T-+I14M+N79D+G127N+A143M+H145R+V159E+A198S+V207F+F211Y+I222A+S225C+Q508R+A525T+F274S; T2A+A5T+I14M+N79D+G127N+A143M+H145R+V159E+A198S+V207F+F211Y+I222A+S225C+Q508R+A525T+L41F+A335P; T2A+A5T+I14M+N79D+G127N+A143M+H145R+V159E+A198S+V207F+F211Y+I222A+S225C+Q508R+A525T+A272L+N300D; T2A+A5T+I14M+N79D+G127N+A143M+H145R+V159E+A198S+V207F+F211Y+I222A+S225C+Q508R+A525T+A309G; T2A+A5T+I14M+N79D+G127N+A143M+H145R+V159E+A198S+V207F+F211Y+I222A+S225C+Q508R+A525T+V304L; T2A+A5T+I14M+N79D+G127N+A143M+H145R+V159E+A198S+V207F+F211Y+I222A+S225C+Q508R+A525T+T60H+H285N; T2A+A5T+I14M+N79D+G127N+A143M+H145R+V159E+A198S+V207F+F211Y+I222A+S225C+Q508R+A525T+S198W+T525M; T2A+A5T+I14M+N79D+G127N+A143M+H145R+V159E+A198S+V207F+F211Y+I222A+S225C+Q508R+A525T+S198A+T525G; T2A+A5T+I14M+N79D+G127N+A143M+H145R+V159E+A198S+V207F+F211Y+I222A+S225C+Q508R+A525T+D311G+D475E; T2A+A5T+I14M+N79D+G127N+A143M+H145R+V159E+A198S+V207F+F211Y+I222A+S225C+Q508R+A525T+T169N+Q287R+A309G+D311G; T2A+A5T+I14M+N79D+G127N+A143M+H145R+V159E+A198S+V207F+F211Y+I222A+S225C+Q508R+A525T+L41F+A309G+D311G+A335P; T2A+A5T+I14M+N79D+G127N+A143M+H145R+V159E+A198S+V207F+F211Y+I222A+S225C+Q508R+A525T+D311G+K529E; T2A+A5T+I14M+N79D+G127N+A143M+H145R+V159E+A198S+V207F+F211Y+I222A+S225C+Q508R+A525T+Y211Q; T2A+A5T+I14M+N79D+G127N+A143M+H145R+V159E+A198S+V207F+F211Y+I222A+S225C+Q508R+A525T+T169N+A202P+A272L+Q287R+D311G+E512G; T2A+A5T+I14M+N79D+G127N+A143M+H145R+V159E+A198S+V207F+F211Y+I222A+S225C+Q508R+A525T+T169N+A202P+N300D A309G+D311G+Y594F; T2A+A5T+I14M+N79D+G127N+A143M+H145R+V159E+A198S+V207F+F211Y+I222A+S225C+Q508R+A525T+R67H+T169N+A202P+A335P; T2A+A5T+I14M+N79D+G127N+A143M+H145R+V159E+A198S+V207F+F211Y+I222A+S225C+Q508R+A525T+V304L+A335P; T2A+A5T+I14M+N79D+G127N+A143M+H145R+V159E+A198S+V207F+F211Y+I222A+S225C+Q508R+A525T+A272L+A335P+A357S; T2A+A5T+I14M+N79D+G127N+A143M+H145R+V159E+A198S+V207F+F211Y+I222A+S225C+Q508R+A525T+A272L; T2A+A5T+I14M+N79D+G127N+A143M+H145R+V159E+A198S+V207F+F211Y+I222A+S225C+Q508R+A525T+L41F+T169N+A272L+N300D+D311G+A335P+D475E+Y594F; T2A+A5T+I14M+N79D+G127N+A143M+H145R+V159E+A198S+V207F+F211Y+I222A+S225C+Q508R+A525T+A202P+N300D+A309G+D311G+A335P+K350R+Q487L; T2A+A5T+I14M+N79D+G127N+A143M+H145R+V159E+A198S+V207F+F211Y+I222A+S225C+Q508R+A525T+T169N+D311G+A335P+V349A+T452A; T2A+A5T+I14M+N79D+G127N+A143M+H145R+V159E+A198S+V207F+F211Y+I222A+S225C+Q508R+A525T+T169N+A335P+Y594F; T2A+A5T+I14M+N79D+G127N+A143M+H145R+V159E+A198S+V207F+F211Y+I222A+S225C+Q508R+A525T+L41F+A309G+D311G+A335P+E343G; T2A+A5T+I14M+N79D+G127N+A143M+H145R+V159E+A198S+V207F+F211Y+I222A+S225C+Q508R+A525T+D311G; T2A+A5T+I14M+N79D+G127N+A143M+H145R+V159E+A198S+V207F+F211Y+I222A+S225C+Q508R+A525T+A335P; T2A+A5T+I14M+N79D+G127N+A143M+H145R+V159E+A198S+V207F+F211Y+I222A+S225C+Q508R+A525T+T169N+A335P; T2A+A5T+I14M+N79D+G127N+A143M+H145R+V159E+A198S+V207F+F211Y+I222A+S225C+Q508R+A525T+N300D+A309G+A335P; T2A+A5T+I14M+N79D+G127N+A143M+H145R+V159E+A198S+V207F+F211Y+I222A+S225C+Q508R+A525T+A335P; T2A+A5T+I14M+N79D+G127N+A143M+H145R+V159E+A198S+V207F+F211Y+I222A+S225C+Q508R+A525T+A202P+A335P+Y594F; T2A+A5T+I14M+N79D+G127N+A143M+H145R+V159E+A198S+V207F+F211Y+I222A+S225C+Q508R+A525T+V511L; T2A+A5T+I14M+N79D+G127N+A143M+H145R+V159E+A198S+V207F+F211Y+I222A+S225C+Q508R+A525T+T169N+A335P; T2A+A5T+I14M+N79D+G127N+A143M+H145R+V159E+A198S+V207F+F211Y+I222A+S225C+Q508R+A525T+D264G+A272L+A309G+A335P; T2A+A5T+I14M+N79D+G127N+A143M+H145R+V159E+A198S+V207F+F211Y+I222A+S225C+Q508R+A525T+A202P+N300D+D311G+A335P; T2A+A5T+I14M+N79D+G127N+A143M+H145R+V159E+A198S+V207F+F211Y+I222A+S225C+Q508R+A525T+T169N+D311G+K531R; T2A+A5T+I14M+N79D+G127N+A143M+H145R+V159E+A198S+V207F+F211Y+I222A+S225C+Q508R+A525T+L41F+Q287R+A335P; T2A+A5T+I14M+N79D+G127N+A143M+H145R+V159E+A198S+V207F+F211Y+I222A+S225C+Q508R+A525T+T169N+A202P+D215G+A272L+A309G+A335P+Y594F; T2A+A5T+I14M+N79D+G127N+A143M+H145R+V159E+A198S+V207F+F211Y+I222A+S225C+Q508R+A525T+A202P+A335P-des[A647-L663]; T2A+A5T+I14M+N79D+G127N+A143M+H145R+V159E+A198S+V207F+F211Y+I222A+S225C+Q508R+A525T+L41F+T169N+A202P+A272L+D311G+K339R+Y594F; T2A+A5T+I14M+N79D+G127N+A143M+H145R+V159E+A198S+V207F+F211Y+I222A+S225C+Q508R+A525T+H282N; T2A+A5T+I14M+N79D+G127N+A143M+H145R+V159E+A198S+V207F+F211Y+I222A+S225C+Q508R+A525T+F118L+T169N+A272L+A335P; T2A+A5T+I14M+N79D+G127N+A143M+H145R+V159E+A198S+V207F+F211Y+I222A+S225C+Q508R+A525T+P219Q; T2A+A5T+I14M+N79D+G127N+A143M+H145R+V159E+A198S+V207F+F211Y+I222A+S225C+Q508R+A525T+D519G; T2A+A5T+I14M+N79D+G127N+A143M+H145R+V159E+A198S+V207F+F211Y+I222A+S225C+Q508R+A525T+Q522K; T2A+A5T+I14M+N79D+G127N+A143M+H145R+V159E+A198S+V207F+F211Y+I222A+S225C+Q508R+A525T+G59S; T2A+A5T+I14M+N79D+G127N+A143M+H145R+V159E+A198S+V207F+F211Y+I222A+S225C+Q508R+A525T+P147W+D475E; T2A+A5T+I14M+N79D+G127N+A143M+H145R+V159E+A198S+V207F+F211Y+I222A+S225C+Q508R+A525T+Q522R; T2A+A5T+I14M+N79D+G127N+A143M+H145R+V159E+A198S+V207F+F211Y+I222A+S225C+Q508R+A525T+A309G; T2A+A5T+I14M+N79D+G127N+A143M+H145R+V159E+A198S+V207F+F211Y+I222A+S225C+Q508R+A525T+A226G+E502N; T2A+A5T+I14M+N79D+G127N+A143M+H145R+V159E+A198S+V207F+F211Y+I222A+S225C+Q508R+A525T+E502N+R508Q+N646K; T2A+A5T+I14M+N79D+G127N+A143M+H145R+V159E+A198S+V207F+F211Y+I222A+S225C+Q508R+A525T+Q520T; T2A+A5T+I14M+N79D+G127N+A143M+H145R+V159E+A198S+V207F+F211Y+I222A+S225C+Q508R+A525T+Q520G; T2A+A5T+I14M+N79D+G127N+A143M+H145R+V159E+A198S+V207F+F211Y+I222A+S225C+Q508R+A525T+T5A+A589R; T2A+A5T+

I14M+N79D+G127N+A143M+H145R+V159E+A198S+V207F+F211Y+I222A+S225C+Q508R+A525T+Q522K; T2A+A5T+I14M+N79D+G127N+A143M+H145R+V159E+A198S+V207F+F211Y+I222A+S225C+Q508R+A525T+A202P; T2A+A5T+I14M+N79D+G127N+A143M+H145R+V159E+A198S+V207F+F211Y+I222A+S225C+Q508R+A525T+A485K; T2A+A5T+I14M+N79D+G127N+A143M+H145R+V159E+A198S+V207F+F211Y+I222A+S225C+Q508R+A525T+D519K; T2A+A5T+I14M+N79D+G127N+A143M+H145R+V159E+A198S+V207F+F211Y+I222A+S225C+Q508R+A525T+S198D; T2A+A5T+I14M+N79D+G127N+A143M+H145R+V159E+A198S+V207F+F211Y+I222A+S225C+Q508R+A525T+Q520N; T2A+A5T+I14M+N79D+G127N+A143M+H145R+V159E+A198S+V207F+F211Y+I222A+S225C+Q508R+A525T+S198N+T525A; T2A+A5T+I14M+N79D+G127N+A143M+H145R+V159E+A198S+V207F+F211Y+I222A+S225C+Q508R+A525T+N83H+D457E; T2A+A5T+I14M+N79D+G127N+A143M+H145R+V159E+A198S+V207F+F211Y+I222A+S225C+Q508R+A525T+E155G; T2A+A5T+I14M+N79D+G127N+A143M+H145R+V159E+A198S+V207F+F211Y+I222A+S225C+Q508R+A525T+R3G; T2A+A5T+I14M+N79D+G127N+A143M+H145R+V159E+A198S+V207F+F211Y+I222A+S225C+Q508R+A525T+S395K+D519G; T2A+A5T+I14M+N79D+G127N+A143M+H145R+V159E+A198S+V207F+F211Y+I222A+S225C+Q508R+A525T+P147R+E502N+N646K; T2A+A5T+I14M+N79D+G127N+A143M+H145R+V159E+A198S+V207F+F211Y+I222A+S225C+Q508R+A525T+Q520K; T2A+A5T+I14M+N79D+G127N+A143M+H145R+V159E+A198S+V207F+F211Y+I222A+S225C+Q508R+A525T+P219E; T2A+A5T+I14M+N79D+G127N+A143M+H145R+V159E+A198S+V207F+F211Y+I222A+S225C+Q508R+A525T+E502N; T2A+A5T+I14M+N79D+G127N+A143M+H145R+V159E+A198S+V207F+F211Y+I222A+S225C+Q508R+A525T+G386W; T2A+A5T+I14M+N79D+G127N+A143M+H145R+V159E+A198S+V207F+F211Y+I222A+S225C+Q508R+A525T+E502N+N646K; T2A+A5T+I14M+N79D+G127N+A143M+H145R+V159E+A198S+V207F+F211Y+I222A+S225C+Q508R+A525T+D532R; T2A+A5T+I14M+N79D+G127N+A143M+H145R+V159E+A198S+V207F+F211Y+I222A+S225C+Q508R+A525T+A226G+T525S; T2A+A5T+I14M+N79D+G127N+A143M+H145R+V159E+A198S+V207F+F211Y+I222A+S225C+Q508R+A525T+K35R+E502N+N646K; T2A+A5T+I14M+N79D+G127N+A143M+H145R+V159E+A198S+V207F+F211Y+I222A+S225C+Q508R+A525T+P147R+E502N+R508Q; T2A+A5T+I14M+N79D+G127N+A143M+H145R+V159E+A198S+V207F+F211Y+I222A+S225C+Q508R+A525T+E92D; T2A+A5T+I14M+N79D+G127N+A143M+H145R+V159E+A198S+V207F+F211Y+I222A+S225C+Q508R+A525T+P109D+H282D+L372S+E458D+E502N; T2A+A5T+I14M+N79D+G127N+A143M+H145R+V159E+A198S+V207F+F211Y+I222A+S225C+Q508R+A525T+T60H; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+D475E+V511L+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G+D475E+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+D475E+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A335P+D475E; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A309G+A335P+D475E+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A309G+A335P+T567A; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A309G+A335P+D475E+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+H285N+A335P+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+K529E+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+K529E+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G+A335P; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+Y594F; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+K35R+T60H+A335P+Y594F+K627R; and T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G+A335P+V511L. Exemplary sequences comprising these combinations are provided in the Examples hereinbelow.

In accordance with the present invention, β-glucosidase activity can be determined by methods known in the art. Preferred assays for determining activity include the assays of Examples 5 and 7 for β-glucosidase activity using either pNPG or cellobiose as a substrate.

In some embodiments, β-glucosidase polypeptide variants of the present invention include those having improved (e.g., greater) β-glucosidase activity relative to wildtype *Azospir-*

*illum irakense* β-glucosidase (SEQ ID NO: 4). Improved β-glucosidase activity may be measured by the assays described in either Example 5 or Example 7. For example, β-glucosidase polypeptides of the present invention often have β-glucosidase activity that is at least about 1-fold, at least about 2-fold, up to about 3-fold or greater β-glucosidase activity as compared to wildtype *Azospirillum irakense* β-glucosidase (SEQ ID NO: 4), as measured for example in the assays described in either Example 5 or Example 7. Exemplary β-glucosidase polypeptide variants having improved β-glucosidase activity relative to wildtype *Azospirillum irakense* β-glucosidase are identified in the Tables in Examples 8, 9, 10, 11, and 12.

The control β-glucosidase utilized in conjunction with the assays conducted on the variants listed in Tables 2B-D, 3, 5, 6, and 7 were other improved variants (i.e., not wildtype *A. irakense* CelA, which exhibited poor activity compared to the variants used as controls). Many of the β-glucosidase polypeptide variants of the present invention exhibit at least about 1.1 to about 6-fold and up to about 15-fold or greater β-glucosidase activity as compared to Variant No. 5 [H145R] CelA (SEQ ID NO: 5, described hereinbelow in Table 2A of Example 8) which itself exhibited greater β-glucosidase activity as compared to wildtype *A. irakense* β-glucosidase in the assay of Example 7 under conditions of 55° C. and pH 6.0. β-glucosidase polypeptide variants of the present invention exhibit even further improved activity, as demonstrated in Tables 2C and 2D of Example 8, hereinbelow. The present invention therefore provides β-glucosidase polypeptide variants that have at least about 1.1-fold to about 1.5-fold, and up to about 3-fold or greater β-glucosidase activity as compared to Variant No. 94 [N79D+A143M+H145R+V159E+A198S+F211Y]CelA (SEQ ID NO: 6, described hereinbelow in Table 2C of Example 8) under conditions of 55° C. and pH 5.3, and at least about 1.1-fold to about 3-fold and up to about 12-fold or greater β-glucosidase activity as compared to Variant No. 264 [T2A+I14M+N79D+A143M+H145R+V159E+A198S+F211Y+I222A+S225C+Q508R+A525T]CelA-des[A647-L663]] (SEQ ID NO: 7, described hereinbelow in Table 2D of Example 8) as measured in the assay of Example 7 under conditions of 55° C. and pH 5.2. Variant Nos. 5, 94, and 264 all exhibited improved activity (e.g., thermoactivity) over the wildtype *A. irakense* β-glucosidase.

The present invention further provides β-glucosidase polypeptide variants that exhibit at least about 1.2 to 2.0 fold and from about 2.1 to about 3.0 fold greater β-glucosidase activity as compared to Variant No. 366 [T2A+A5T+I14M+N79D+G127N+A143M+h145R+V159E+A198S+V207F+F211Y+I222A+S225C+Q508R+A525T]CelA-des[A647-L664] (SEQ ID NO: 9, described hereinbelow in Table 5 of Example 10) under conditions of 65° C. and pH5. In other embodiments, β-glucosidase polypeptide variants of the present invention exhibit at least about 0.5 to about 1.0 fold, about 1.1 to about 2.0 fold, about 2.1 to about 3.0 fold, about 3.1 to about 4.1 fold greater β-glucosidase activity as compared to Variant No. 391 [T2A+A5T+I14M+S73A+N79D+G127N+A143M+H145R+V159E+V177P+A198S+I203Y+V207F+F211Y+I222A+S225C+Q508R+A525T]CelA-des [A647-L664] (SEQ ID NO: 11, described hereinbelow in Table 6 of Example 11) under conditions of 67° C. and pH 5. In certain embodiments β-glucosidase polypeptide variants of the present invention exhibit at least about 1.0 to 2.0 fold or greater -glucosidase activity as compared to Variant No. 463 [T2A+A3R+A5T+I14M+S73A+N79D+G127N+A143M+H145R+V159E+T169N+V177P+A198S+A202P+I203Y+V207F+F211Y+I222A+S225C+A272L+Q287R+D311G+Q508R+E512G+A525T]CelA-des[A147-L663] (SEQ ID NO: 13, described hereinbelow in Table 7 of Example 12) under conditions of 72° C. and pH 5. Variant Nos. 366, 391, and 463 all exhibited improved activity (e.g., thermoactivity) over the wildtype *A. irakense* β-glucosidase, as demonstrated indirectly by showing improvement over a chain of controls, one of which, Variant No. 5 has been directly compared to the wildtype enzyme.

The variants of the present invention will, in some instances, produce at least about 2-times up to at least about 3 times more glucose as compared to the amount of glucose produced from the hydrolysis of a cellobiose substrate by the wildtype *A. irakense* β-glucosidase (SEQ ID NO: 4) under substantially the same conditions. Some of the variants of the present invention will produce at least about 1.1 to 6 times and up to 15 times more glucose as compared to Variant No. 5 [H145R]CelA; at least about 1.1 times to about 1.5 times, and up to about 3 times or more glucose as compared to Variant No. 94 [N79D+A143M+H145R+V159E+A198S+F211Y] CelA; and at least about 1.1 times to about 3 times and up to about 12 times more glucose as compared to Variant No. 264 [T2A+I14M+N79D+A143M+H145R+V159E+A198S+F211y+I222A+S225C+Q508R+A525T]CelA-des[A647-L663].

The present invention further provides an isolated or recombinant β-glucosidase polypeptide variant having an amino acid sequence that has a substitution, deletion, and/or insertion of from one to forty amino acid residues in SEQ ID NO: 4, wherein the variant exhibits at least about 2-fold greater β-glucosidase activity than wild type *A. irakense* β-glucosidase (SEQ ID NO: 4), as measured in the assay of for example, Examples 5 or 7 (using either pNPG or cellobiose as substrate). These β-glucosidase polypeptides may have a substitution, deletion, and/or insertion of from 1 to 2, or from 1 or 2 to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and up to 40 residues.

Typically, these β-glucosidases exhibit β-glucosidase activity that is at least about 2-fold up to at least about 3-fold greater than that of wildtype *A. irakense* CelA (SEQ ID NO: 4) and/or at least about 1.1 to about 6-fold and up to about 15-fold or greater β-glucosidase activity as compared to Variant No. 5: [H145A] CelA (under conditions of 55° C. and pH 6.0) and/or at least about 1.1-fold to about 1.5-fold and up to about 3-fold or greater β-glucosidase activity as compared to Variant No. 94, [N79D+A143M+H145R+V159E+A198S+F211Y] and/or at least about 1.1-fold to about 3-fold and up to about 12-fold or greater β-glucosidase activity as compared to Variant No. 264: [T2A+I14M+N79D+A143M+H145R+V159E+A198S+F211Y+I222A+S225C+Q508R+A525T]CelA des[A647-L663], as measured in the assays described in either Example 5 or 7.

In another embodiment, the present invention also provides a fragment of the β-glucosidase polypeptide variants described herein having β-glucosidase activity such as those detected for example in the assays of either Example 5 or 7. These fragments are referred to herein as "β-glucosidase fragments". As used herein, the term "fragment" refers to a polypeptide having a deletion of from 1 to 50 amino acid residues from the carboxy (C-) terminus, the amino (N-) terminus, or both (i.e., a deletion of 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues from either or both the N- or C-terminus). In certain embodiments, the deletion will be from 1 to 15 amino acid residues from the —N-terminus and from 1 to 40 amino acid residues from the C-terminus. These β-glucosidase fragments are also referred to herein as N-terminally truncated and C-terminally truncated β-glucosidase polypeptide variants, respectively. In some embodiments, the deletion may be from 1 to 30, or 1 to 20, or 1 to 10 residues, or 1 to 5 residues from the C-terminus, the N-terminus, or both. Exemplary C-terminally truncated β-glucosidase variants are provided in Examples 8 and 10-12. The C-terminal truncation of 16 amino acid residues appeared particularly beneficial for expression and secretion.

β-glucosidase fragments of the present invention include those that have at least about 2-fold up to at least about 3-fold greater β-glucosidase activity as compared to wildtype *A. irakense* CelA (SEQ ID NO: 4) (under conditions of 50° C. and pH 6.5) and/or at least about 1.1 to about 6-fold and up to about 15-fold or greater β-glucosidase activity as compared to Variant No. 5 [N79D+A143M+H145R+V159E+A198S+F211Y]CelA and/or at least about 1.1-fold to about 1.5-fold and up to about 3-fold or greater β-glucosidase activity as compared to Variant No. 94 [N79D+A143M+H145R+V159E+A198S+F211Y] (under conditions of 55° C. and pH 5.3) and/or at least about 1.1-fold to about 3-fold and up to about 12-fold or greater β-glucosidase activity as compared to Variant No. 264 [T2A+I14M+N79D+A143M+H145R+V159E+A198S+F211Y+I222A+S225C+Q508R+A525T] CelA des[A647-L663] (under conditions of 55° C. and pH 5.2), as measured in the assay described in Example 7. β-glucosidase fragments of the present invention may have any of the substitutions or combinations thereof described herein.

Particularly useful variants include those having C-terminal truncations. C-terminally truncated CelA variants may further have any one or combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 and/or more of the substitutions described herein.

Exemplary C-terminally truncated variants having various combinations of the above-described substitutions include: T2A+A5T+I14M+N79D+G127N+A143M+H145R+V159E+A198S+V207F+F211Y+I222A+S225C+Q508R+A525T+P109D+V177P+Q287R+A600V-des[A647-L663]; T2A+A5T+I14M+N79D+G127N+A143M+H145R+V159E+A198S+V207F+F211Y+I222A+S225C+Q508R+A525T+I4S+I61V+V177P+I535V-des[A647-L663]; T2A+A5T+I14M+N79D+G127N+A143M+H145R+V159E+A198S+V207F+F211Y+I222A+S225C+Q508R+A525T+A3R+I4S+I61V+V177P+I203Y+I535V-des[A647-L663]; T2A+A5T+I14M+N79D+G127N+A143M+H145R+V159E+A198S+V207F+F211Y+I222A+S225C+Q508R+A525T+I4S+V177P+N320S+K350E-des[A647-L663]; T2A+A5T+I14M+N79D+G127N+A143M+H145R+V159E+A198S+V207F+F211Y+I222A+S225C+Q508R+A525T+A3R+V177P+I535V-des[A647-L663]; T2A+A5T+I14M+N79D+G127N+A143M+H145R+V159E+A198S+V207F+F211Y+I222A+S225C+Q508R+A525T+P89S+V177P+D236Y-des[A647-L663]; T2A+A5T+I14M+N79D+G127N+A143M+H145R+V159E+A198S+V207F+F211Y+I222A+S225C+Q508R+A525T+I4S+V177P+A600V-des[A647-L663]; T2A+A5T+I14M+N79D+G127N+A143M+H145R+V159E+A198S+V207F+F211Y+I222A+S225C+Q508R+A525T+I4S+P89S+V177P+I535V+Q585R-des[A647-L663]; T2A+A5T+I14M+N79D+G127N+A143M+H145R+V159E+A198S+V207F+F211Y+I222A+S225C+Q508R+A525T+I4S+I61V+S73A+V177P+N613D+A617V-des[A647-L663]; T2A+A5T+I14M+N79D+G127N+A143M+H145R+V159E+A198S+V207F+F211Y+I222A+S225C+Q508R+A525T+V177P+I535V-des[A647-L663]; T2A+A5T+I14M+N79D+G127N+A143M+H145R+V159E+A198S+V207F+F211Y+I222A+S225C+Q508R+A525T+A3R+S73A+V177P+I203Y+A600V-des[A647-L663]; T2A+A5T+I14M+N79D+G127N+A143M+H145R+V159E+A198S+V207F+F211Y+I222A+S225C+Q508R+A525T+I4S+P89S+V177P+A600V-des[A647-L663]; T2A+A5T+I14M+N79D+G127N+A143M+H145R+V159E+A198S+V207F+F211Y+I222A+S225C+Q508R+A525T+P89S+V177P-des[A647-L663]; T2A+A5T+I14M+N79D+G127N+A143M+H145R+V159E+A198S+V207F+F211Y+I222A+S225C+Q508R+A525T+K35Q+S73A+I203Y-des[A647-L663]; T2A+A5T+I14M+N79D+G127N+A143M+H145R+V159E+A198S+V207F+F211Y+I222A+S225C+Q508R+A525T+I203Y+I535V-des[A647-L663]; T2A+A5T+I14M+N79D+G127N+A143M+H145R+V159E+A198S+V207F+F211Y+I222A+S225C+Q508R+A525T+P89S+V177P+I203Y+Y594F-des[A647-L663]; T2A+A5T+I14M+N79D+G127N+A143M+H145R+V159E+A198S+V207F+F211Y+I222A+S225C+Q508R+A525T+S73A+I203Y-des[A647-L663]; T2A+A5T+I14M+N79D+G127N+A143M+H145R+V159E+A198S+V207F+F211Y+I222A+S225C+Q508R+A525T+A3R+I4S+V177P-des[A647-L663]; T2A+A5T+I14M+N79D+G127N+A143M+H145R+V159E+A198S+V207F+F211Y+I222A+S225C+Q508R+A525T+A3R+I4S+S73A+V177P+I535M-des[A647-L663]; T2A+A5T+I14M+N79D+G127N+A143M+H145R+V159E+A198S+V207F+F211Y+I222A+S225C+Q508R+A525T+A3R+I61V+V177P-des[A647-L663]; T2A+A5T+I14M+N79D+G127N+A143M+H145R+V159E+A198S+V207F+F211Y+I222A+S225C+Q508R+A525T+I4S+V177P+A601V-des[A647-L663]; T2A+A5T+I14M+N79D+G127N+A143M+H145R+V159E+A198S+V207F+F211Y+I222A+S225C+Q508R+A525T+A3R+M161V+I203Y+A222I+D383G-des[A647-L663]; T2A+A5T+I14M+N79D+G127N+A143M+H145R+V159E+A198S+V207F+F211Y+I222A+S225C+Q508R+A525T+A3R+V177P+S213T-des[A647-L663]; T2A+A5T+I14M+N79D+G127N+A143M+H145R+V159E+A198S+V207F+F211Y+I222A+S225C+Q508R+A525T+A3R+P109D+V177P+M356T-des[A647-L663]; T2A+A5T+I14M+N79D+G127N+A143M+H145R+V159E+A198S+V207F+F211Y+I222A+S225C+Q508R+A525T+I203Y+M356T+N646K-des[A647-L663]; T2A+A5T+I14M+N79D+G127N+A143M+H145R+V159E+A198S+V207F+F211Y+I222A+S225C+Q508R+A525T+T25A+N128H+V177P+I203Y+T525S-des[A647-L663]; T2A+A5T+I14M+N79D+G127N+A143M+H145R+V159E+A198S+V207F+F211Y+I222A+S225C+Q508R+A525T+A3R+A13P+P147T+V177P+I203Y+T525S+H586Y-des[A647-L663]; T2A+A5T+I14M+N79D+G127N+A143M+H145R+V159E+A198S+V207F+F211Y+I222A+S225C+Q508R+A525T+A13P+P109D+V177P-des[A647-L663]; T2A+A5T+I14M+N79D+G127N+A143M+H145R+V159E+A198S+V207F+F211Y+I222A+S225C+Q508R+A525T+A13P+P109D+N128K+V177P+P597A-des[A647-L663]; T2A+A5T+I14M+N79D+G127N+A143M+H145R+V159E+A198S+V207F+F211Y+I222A+S225C+Q508R+A525T+A13P+V177P+A400T+H586Y-des[A647-L663]; T2A+A5T+I14M+N79D+G127N+A143M+H145R+V159E+A198S+V207F+F211Y+I222A+S225C+Q508R+A525T+A3R+A13P+P147T+E159G+V177P-des[A647-L663]; T2A+A5T+I14M+N79D+G127N+A143M+H145R+V159E+A198S+V207F+F211Y+I222A+S225C+Q508R+A525T+P109D+P147T+V177P+E502N+H586Y-des[A647-L663]; T2A+A5T+I14M+N79D+G127N+A143M+H145R+V159E+A198S+V207F+F211Y+I222A+S225C+Q508R+A525T+A13P+P147T+V177P+A226G+H586Y-des[A647-L663]; T2A+A5T+I14M+N79D+G127N+A143M+H145R+V159E+A198S+V207F+F211Y+I222A+S225C+Q508R+A525T+P109D+P147T+V177P+T525S- des[A647-L663]; T2A+A5T+I14M+N79D+G127N+A143M+H145R+V159E+A198S+V207F+F211Y+I222A+S225C+Q508R+A525T+V177P+E502N+T525S-des[A647-L663]; T2A+A5T+I14M+N79D+G127N+A143M+H145R+V159E+A198S+V207F+F211Y+I222A+S225C+Q508R+A525T+V177P+L372S-des[A647-L663]; T2A+A5T+I14M+N79D+G127N+A143M+H145R+V159E+A198S+V207F+F211Y+I222A+S225C+Q508R+A525T+V177P+E502N+R508Q-des[A647-L663]; T2A+A5T+I14M+N79D+G127N+A143M+H145R+V159E+A198S+V207F+F211Y+I222A+S225C+Q508R+A525T+A3R+A13P+P147T+V177P+E502N+H586Y-des[A647-L663]; T2A+A5T+I14M+N79D+G127N+A143M+H145R+V159E+A198S+V207F+F211Y+I222A+S225C+Q508R+A525T+A3R+I203Y+A400T+E502N+T525S-des[A647-L663]; T2A+A5T+I14M+N79D+G127N+A143M+H145R+V159E+A198S+V207F+F211Y+I222A+S225C+Q508R+A525T+A13P+N128H+V177P+E502N+R508Q-des[A647-L663]; T2A+A5T+I14M+N79D+G127N+A143M+H145R+V159E+A198S+V207F+F211Y+I222A+S225C+Q508R+A525T+P109D+V177P+D351E+H586Y-des[A647A-L663]; T2A+A5T+I14M+N79D+G127N+A143M+H145R+V159E+A198S+V207F+F211Y+I222A+S225C+Q508R+A525T+V177P+R508Q-des[A647-L663]; T2A+A5T+I14M+N79D+G127N+A143M+H145R+V159E+A198S+V207F+F211Y+I222A+S225C+Q508R+A525T+A3R+A13P+I203Y+A400T-des[A647-L663]; T2A+A5T+I14M+N79D+G127N+A143M+H145R+V159E+A198S+V207F+F211Y+I222A+S225C+Q508R+A525T+A3R+P109D+P147T+V177P+H586Y-des[A647-L663]; T2A+A5T+I14M+N79D+G127N+A143M+H145R+V159E+A198S+V207F+F211Y+I222A+S225C+Q508R+A525T+A13P+N128H+V177P-des[A647-L663]; T2A+A5T+I14M+N79D+G127N+A143M+H145R+V159E+A198S+V207F+F211Y+I222A+S225C+Q508R+A525T+P109D+V177P+A400T+E502N+H586Y-des[A647-L663]; T2A+A5T+I14M+N79D+G127N+A143M+H145R+V159E+A198S+V207F+F211Y+I222A+S225C+Q508R+A525T+A13P+P147T+V177P+A400T+E502N+R508Q-des[A647-L663]; T2A+A5T+I14M+N79D+G127N+A143M+H145R+V159E+A198S+V207F+F211Y+I222A+S225C+Q508R+A525T+P109D+V177P+A400T-des[A647-L663]; T2A+A5T+I14M+N79D+G127N+A143M+H145R+V159E+A198S+V207F+F211Y+I222A+S225C+Q508R+A525T+A13P+V177P+V204I+D291G-des[A647-L663]; T2A+A5T+I14M+N79D+G127N+A143M+H145R+V159E+A198S+V207F+F211Y+I222A+S225C+Q508R+A525T+A3R+P147T+V177P+A400T+E502N-des[A647-L663]; T2A+A5T+I14M+N79D+G127N+A143M+H145R+V159E+A198S+V207F+F211Y+I222A+S225C+Q508R+A525T+V177P+A400T-des[A647-L663]; T2A+A5T+I14M+N79D+G127N+A143M+H145R+V159E+A198S+V207F+F211Y+I222A+S225C+Q508R+A525T+N128H+V177P+E502N+H586Y-des[A647-L663]; T2A+A5T+I14M+N79D+G127N+A143M+H145R+V159E+A198S+V207F+F211Y+I222A+S225C+Q508R+A525T+V177P+A400T+R508Q-des[A647-L663]; T2A+A5T+I14M+N79D+G127N+A143M+H145R+V159E+A198S+V207F+F211Y+I222A+S225C+Q508R+A525T+A13P+P147T+I203Y+H586Y-des[A647-L663]; T2A+A5T+I14M+N79D+G127N+A143M+H145R+V159E+A198S+V207F+F211Y+I222A+S225C+Q508R+A525T+P109D+V177P-des[A647-L663]; T2A+A5T+I14M+N79D+G127N+A143M+H145R+V159E+A198S+V207F+F211Y+I222A+S225C+Q508R+A525T+A13P+P109D+V177P+T525S-des[A647-L663]; T2A+A5T+I14M+N79D+G127N+A143M+H145R+V159E+A198S+V207F+F211Y+I222A+S225C+Q508R+A525T+A3R+P147T+V177P+I203Y+E502N+H586Y-des[A647-L663]; T2A+A5T+I14M+N79D+G127N+A143M+H145R+V159E+A198S+V207F+F211Y+I222A+S225C+Q508R+A525T+A3R+V177P-des[A647-L663]; T2A+A5T+I14M+N79D+G127N+A143M+H145R+V159E+A198S+V207F+F211Y+I222A+S225C+Q508R+A525T+A13P+I203Y+A400T+E502N-des[A647-L663]; T2A+A5T+I14M+N79D+G127N+A143M+H145R+V159E+A198S+V207F+F211Y+I222A+S225C+Q508R+A525T+A3R+A13P+V177P+A400T+H586Y-des[A647-L663]; T2A+A5T+I14M+N79D+G127N+A143M+H145R+V159E+A198S+V207F+F211Y+I222A+S225C+Q508R+A525T+A3R+V177P+E502N-des[A647-L663]; T2A+A5T+I14M+N79D+G127N+A143M+H145R+V159E+A198S+V207F+F211Y+I222A+S225C+Q508R+A525T+A3R+P147T+I203Y+E502N-des[A647-L663]; T2A+A5T+I14M+N79D+G127N+A143M+H145R+V159E+A198S+V207F+F211Y+I222A+S225C+Q508R+A525T+A3R+T25A+V177P+A400T+R508Q-des[A647-L663]; T2A+A5T+I14M+N79D+G127N+A143M+H145R+V159E+A198S+V207F+F211Y+I222A+S225C+Q508R+A525T+A3R+V177P+A400T-des[A647-L663]; T2A+A5T+I14M+N79D+G127N+A143M+H145R+V159E+A198S+V207F+F211Y+I222A+S225C+Q508R+A525T+A3R+M14K+N128H+V177P+R508Q-des[A647-L663]; T2A+A5T+I14M+N79D+G127N+A143M+H145R+V159E+A198S+V207F+F211Y+I222A+S225C+Q508R+A525T+A13P+P147T+E502N-des[A647-L663]; T2A+A5T+I14M+N79D+G127N+A143M+H145R+V159E+A198S+V207F+F211Y+I222A+S225C+Q508R+A525T+V177P-des[A647-L663]; T2A+A5T+I14M+N79D+G127N+A143M+H145R+V159E+A198S+V207F+F211Y+I222A+S225C+Q508R+A525T+A3R+N128H+V177P-des[A647-L663]; T2A+A5T+I14M+N79D+G127N+A143M+H145R+V159E+A198S+V207F+F211Y+I222A+S225C+Q508R+A525T+N128H+P147T+V177P+T603A-des[A647-L663]; T2A+A5T+I14M+N79D+G127N+A143M+H145R+V159E+A198S+V207F+F211Y+I222A+S225C+Q508R+A525T+P147T+I203Y+H586Y-des[A647-L663]; T2A+A5T+I14M+N79D+G127N+A143M+H145R+V159E+A198S+V207F+F211Y+I222A+S225C+Q508R+A525T+T169N-des[A647-L663]; T2A+A5T+I14M+N79D+G127N+A143M+H145R+V159E+A198S+V207F+F211Y+I222A+S225C+Q508R+A525T+R508E-des[A647-L663]; T2A+A5T+I14M+N79D+G127N+A143M+H145R+V159E+A198S+V207F+F211Y+I222A+S225C+Q508R+A525T+F274K-des[A647-L663]; T2A+A5T+I14M+N79D+G127N+A143M+H145R+V159E+A198S+V207F+F211Y+I222A+S225C+Q508R+A525T+F274N-des[A647-L663]; T2A+A5T+I14M+N79D+G127N+A143M+H145R+V159E+A198S+V207F+F211Y+I222A+S225C+Q508R+A525T+F274S-des[A647-L663]; T2A+A5T+I14M+N79D+G127N+A143M+H145R+V159E+A198S+V207F+F211Y+I222A+S225C+Q508R+A525T+L41F+A335P-des[A647-L663]; T2A+A5T+I14M+N79D+G127N+A143M+H145R+V159E+A198S+V207F+F211Y+I222A+S225C+Q508R+A525T+A272L+N300D-des[A647-L663]; T2A+A5T+I14M+N79D+G127N+A143M+H145R+V159E+A198S+V207F+F211Y+I222A+S225C+Q508R+A525T+A309G-des[A647-L663]; T2A+A5T+I14M+N79D+G127N+A143M+H145R+V159E+A198S+V207F+F211Y+I222A+S225C+Q508R+A525T+V304L-des[A647-L663]; T2A+A5T+I14M+N79D+G127N+A143M+H145R+V159E+A198S+V207F+F211Y+I222A+S225C+Q508R+A525T+T60H+H285N-des[A647-L663]; T2A+A5T+I14M+N79D+G127N+A143M+H145R+V159E+A198S+V207F+F211Y+I222A+S225C+Q508R+A525T+S198W+T525M-des

[A647-L663]; T2A+A5T+I14M+N79D+G127N+A143M+H145R+V159E+A198S+V207F+F211Y+I222A+S225C+Q508R+A525T+S198A+T525G-des[A647-L663]; T2A+A5T+I14M+N79D+G127N+A143M+H145R+V159E+A198S+V207F+F211Y+I222A+S225C+Q508R+A525T+D311G+D475E-des[A647-L663]; T2A+A5T+I14M+N79D+G127N+A143M+H145R+V159E+A198S+V207F+F211Y+I222A+S225C+Q508R+A525T+T169N+Q287R+A309G+D311G-des[A647-L663]; T2A+A5T+I14M+N79D+G127N+A143M+H145R+V159E+A198S+V207F+F211Y+I222A+S225C+Q508R+A525T+L41F+A309G+D311G+A335P-des[A647-L663]; T2A+A5T+I14M+N79D+G127N+A143M+H145R+V159E+A198S+V207F+F211Y+I222A+S225C+Q508R+A525T+D311G+K529E-des[A647-L663]; T2A+A5T+I14M+N79D+G127N+A143M+H145R+V159E+A198S+V207F+F211Y+I222A+S225C+Q508R+A525T+Y211Q-des[A647-L663]; T2A+A5T+I14M+N79D+G127N+A143M+H145R+V159E+A198S+V207F+F211Y+I222A+S225C+Q508R+A525T+T169N+A202P+A272L+Q287R+D311G+E512G-des[A647-L663]; T2A+A5T+I14M+N79D+G127N+A143M+H145R+V159E+A198S+V207F+F211Y+I222A+S225C+Q508R+A525T+T169N+A202P+N300D A309G+D311G+Y594F-des[A647-L663]; T2A+A5T+I14M+N79D+G127N+A143M+H145R+V159E+A198S+V207F+F211Y+I222A+S225C+Q508R+A525T+R67H+T169N+A202P+A335P-des[A647-L663]; T2A+A5T+I14M+N79D+G127N+A143M+H145R+V159E+A198S+V207F+F211Y+I222A+S225C+Q508R+A525T+V304L+A335P-des[A647-L663]; T2A+A5T+I14M+N79D+G127N+A143M+H145R+V159E+A198S+V207F+F211Y+I222A+S225C+Q508R+A525T+A272L+A335P+A357S-des[A647-L663]; T2A+A5T+I14M+N79D+G127N+A143M+H145R+V159E+A198S+V207F+F211Y+I222A+S225C+Q508R+A525T+A272L-des[A647-L663]; T2A+A5T+I14M+N79D+G127N+A143M+H145R+V159E+A198S+V207F+F211Y+I222A+S225C+Q508R+A525T+L41F+T169N+A272L+N300D+D311G+A335P+D475E+Y594F-des[A647-L663]; T2A+A5T+I14M+N79D+G127N+A143M+H145R+V159E+A198S+V207F+F211Y+I222A+S225C+Q508R+A525T+A202P+N300D+A309G+D311G+A335P+K350R+Q487L-des[A647-L663]; T2A+A5T+I14M+N79D+G127N+A143M+H145R+V159E+A198S+V207F+F211Y+I222A+S225C+Q508R+A525T+T169N+D311G+A335P+V349A+T452A-des[A647-L663]; T2A+A5T+I14M+N79D+G127N+A143M+H145R+V159E+A198S+V207F+F211Y+I222A+S225C+Q508R+A525T+T169N+A335P+Y594F-des[A647-L663]; T2A+A5T+I14M+N79D+G127N+A143M+H145R+V159E+A198S+V207F+F211Y+I222A+S225C+Q508R+A525T+L41F+A309G+D311G+A335P+E343G-des[A647-L663]; T2A+A5T+I14M+N79D+G127N+A143M+H145R+V159E+A198S+V207F+F211Y+I222A+S225C+Q508R+A525T+D311G-des[A647-L663]; T2A+A5T+I14M+N79D+G127N+A143M+H145R+V159E+A198S+V207F+F211Y+I222A+S225C+Q508R+A525T+A335P-des[A647-L663]; T2A+A5T+I14M+N79D+G127N+A143M+H145R+V159E+A198S+V207F+F211Y+I222A+S225C+Q508R+A525T+T169N+A335P-des[A647-L663]; T2A+A5T+I14M+N79D+G127N+A143M+H145R+V159E+A198S+V207F+F211Y+I222A+S225C+Q508R+A525T+N300D+A309G+A335P-des[A647-L663]; T2A+A5T+I14M+N79D+G127N+A143M+H145R+V159E+A198S+V207F+F211Y+I222A+S225C+Q508R+A525T+A335P-des[A647-L663]; T2A+A5T+I14M+N79D+G127N+A143M+H145R+V159E+A198S+V207F+F211Y+I222A+S225C+Q508R+A525T+A202P+A335P+Y594F-des[A647-L663]; T2A+A5T+I14M+N79D+G127N+A143M+H145R+V159E+A198S+V207F+F211Y+I222A+S225C+Q508R+A525T+V511L-des[A647-L663]; T2A+A5T+I14M+N79D+G127N+A143M+H145R+V159E+A198S+V207F+F211Y+I222A+S225C+Q508R+A525T+T169N+A335P-des[A647-L663]; T2A+A5T+I14M+N79D+G127N+A143M+H145R+V159E+A198S+V207F+F211Y+I222A+S225C+Q508R+A525T+D264G+A272L+A309G+A335P-des[A647-L663]; T2A+A5T+I14M+N79D+G127N+A143M+H145R+V159E+A198S+V207F+F211Y+I222A+S225C+Q508R+A525T+A202P+N300D+D311G+A335P-des[A647-L663]; T2A+A5T+I14M+N79D+G127N+A143M+H145R+V159E+A198S+V207F+F211Y+I222A+S225C+Q508R+A525T+T169N+D311G+K531R-des[A647-L663]; T2A+A5T+I14M+N79D+G127N+A143M+H145R+V159E+A198S+V207F+F211Y+I222A+S225C+Q508R+A525T+L41F+Q287R+A335P-des[A647-L663]; T2A+A5T+I14M+N79D+G127N+A143M+H145R+V159E+A198S+V207F+F211Y+I222A+S225C+Q508R+A525T+T169N+A202P+D215G+A272L+A309G+A335P+Y594F-des[A647-L663]; T2A+A5T+I14M+N79D+G127N+A143M+H145R+V159E+A198S+V207F+F211Y+I222A+S225C+Q508R+A525T+A202P+A335P-des[A647-L663]; T2A+A5T+I14M+N79D+G127N+A143M+H145R+V159E+A198S+V207F+F211Y+I222A+S225C+Q508R+A525T+L41F+T169N+A202P+A272L+D311G+K339R+Y594F-des[A647-L663]; T2A+A5T+I14M+N79D+G127N+A143M+H145R+V159E+A198S+V207F+F211Y+I222A+S225C+Q508R+A525T+H282N-des[A647-L663]; T2A+A5T+I14M+N79D+G127N+A143M+H145R+V159E+A198S+V207F+F211Y+I222A+S225C+Q508R+A525T+F118L+T169N+A272L+A335P-des[A647-L663]; T2A+A5T+I14M+N79D+G127N+A143M+H145R+V159E+A198S+V207F+F211Y+I222A+S225C+Q508R+A525T+P219Q-des[A647-L663]; T2A+A5T+I14M+N79D+G127N+A143M+H145R+V159E+A198S+V207F+F211Y+I222A+S225C+Q508R+A525T+D519G-des[A647-L663T2A+A5T+I14M+N79D+G127N+A143M+H145R+V159E+A198S+V207F+F211Y+I222A+S225C+Q508R+A525T+Q522K-des[A647-L663T2A+A5T+I14M+N79D+G127N+A143M+H145R+V159E+A198S+V207F+F211Y+I222A+S225C+Q508R+A525T+G59S-des[A647-L663]; T2A+A5T+I14M+N79D+G127N+A143M+H145R+V159E+A198S+V207F+F211Y+I222A+S225C+Q508R+A525T+P147W+D475E-des[A647-L663]; T2A+A5T+I14M+N79D+G127N+A143M+H145R+V159E+A198S+V207F+F211Y+I222A+S225C+Q508R+A525T+Q522R-des[A647-L663]; T2A+A5T+I14M+N79D+G127N+A143M+H145R+V159E+A198S+V207F+F211Y+I222A+S225C+Q508R+A525T+A309G-des[A647-L663]; T2A+A5T+I14M+N79D+G127N+A143M+H145R+V159E+A198S+V207F+F211Y+I222A+S225C+Q508R+A525T+A226G+E502N-des[A647-L663]; T2A+A5T+I14M+N79D+G127N+A143M+H145R+V159E+A198S+V207F+F211Y+I222A+S225C+Q508R+A525T+E502N+R508Q+N646K-des[A647-L663]; T2A+A5T+I14M+N79D+G127N+A143M+H145R+V159E+A198S+V207F+F211Y+I222A+S225C+Q508R+A525T+Q520T-des[A647-L663]; T2A+A5T+I14M+N79D+G127N+A143M+H145R+V159E+A198S+V207F+F211Y+I222A+S225C+Q508R+A525T+Q520G-des[A647-L663]; T2A+A5T+I14M+N79D+G127N+A143M+H145R+V159E+A198S+V207F+F211Y+I222A+S225C+Q508R+A525T+T5A+A589R-des[A647-L663]; T2A+A5T+I14M+N79D+G127N+A143M+H145R+V159E+A198S+V207F+F211Y+I222A+S225C+Q508R+A525T+Q522K-des[A647-L663]; T2A+A5T+I14M+N79D+G127N+A143M+H145R+V159E+A198S+V207F+

F211Y+I222A+S225C+Q508R+A525T+A202P-des[A647-L663]; T2A+A5T+I14M+N79D+G127N+A143M+H145R+V159E+A198S+V207F+F211Y+I222A+S225C+Q508R+A525T+A485K-des[A647-L663]; T2A+A5T+I14M+N79D+G127N+A143M+H145R+V159E+A198S+V207F+F211Y+I222A+S225C+Q508R+A525T+D519K-des[A647-L663]; T2A+A5T+I14M+N79D+G127N+A143M+H145R+V159E+A198S+V207F+F211Y+I222A+S225C+Q508R+A525T+S198D-des[A647-L663]; T2A+A5T+I14M+N79D+G127N+A143M+H145R+V159E+A198S+V207F+F211Y+I222A+S225C+Q508R+A525T+Q520N-des[A647-L663]; T2A+A5T+I14M+N79D+G127N+A143M+H145R+V159E+A198S+V207F+F211Y+I222A+S225C+Q508R+A525T+S198N+T525A-des[A647-L663]; T2A+A5T+I14M+N79D+G127N+A143M+H145R+V159E+A198S+V207F+F211Y+I222A+S225C+Q508R+A525T+N83H+D457E-des[A647-L663]; T2A+A5T+I14M+N79D+G127N+A143M+H145R+V159E+A198S+V207F+F211Y+I222A+S225C+Q508R+A525T+E155G-des[A647-L663]; T2A+A5T+I14M+N79D+G127N+A143M+H145R+V159E+A198S+V207F+F211Y+I222A+S225C+Q508R+A525T+R3G-des[A647-L663]; T2A+A5T+I14M+N79D+G127N+A143M+H145R+V159E+A198S+V207F+F211Y+I222A+S225C+Q508R+A525T+S395K+D519G-des[A647-L663]; T2A+A5T+I14M+N79D+G127N+A143M+H145R+V159E+A198S+V207F+F211y+I222A+S225C+Q508R+A525T+P147R+E502N+N646K-des[A647-L663]; T2A+A5T+I14M+N79D+G127N+A143M+H145R+V159E+A198S+V207F+F211Y+I222A+S225C+Q508R+A525T+Q520K-des[A647-L663]; T2A+A5T+I14M+N79D+G127N+A143M+H145R+V159E+A198S+V207F+F211Y+I222A+S225C+Q508R+A525T+P219E-des[A647-L663]; T2A+A5T+I14M+N79D+G127N+A143M+H145R+V159E+A198S+V207F+F211Y+I222A+S225C+Q508R+A525T+E502N-des[A647-L663]; T2A+A5T+I14M+N79D+G127N+A143M+H145R+V159E+A198S+V207F+F211Y+I222A+S225C+Q508R+A525T+G386W-des[A647-L663]; T2A+A5T+I14M+N79D+G127N+A143M+H145R+V159E+A198S+V207F+F211Y+I222A+S225C+Q508R+A525T+E502N+N646K-des[A647-L663]; T2A+A5T+I14M+N79D+G127N+A143M+H145R+V159E+A198S+V207F+F211Y+I222A+S225C+Q508R+A525T+D532R-des[A647-L663]; T2A+A5T+I14M+N79D+G127N+A143M+H145R+V159E+A198S+V207F+F211Y+I222A+S225C+Q508R+A525T+A226G+T525S-des[A647-L663]; T2A+A5T+I14M+N79D+G127N+A143M+H145R+V159E+A198S+V207F+F211Y+I222A+S225C+Q508R+A525T+K35R+E502N+N646K-des[A647-L663]; T2A+A5T+I14M+N79D+G127N+A143M+H145R+V159E+A198S+V207F+F211Y+I222A+S225C+Q508R+A525T+P147R+E502N+R508Q-des[A647-L663]; T2A+A5T+I14M+N79D+G127N+A143M+H145R+V159E+A198S+V207F+F211Y+I222A+S225C+Q508R+A525T+E92D-des[A647-L663]; T2A+A5T+I14M+N79D+G127N+A143M+H145R+V159E+A198S+V207F+F211Y+I222A+S225C+Q508R+A525T+P109D+H282D+L372S+E458D+E502N-des[A647-L663]; T2A+A5T+I14M+N79D+G127N+A143M+H145R+V159E+A198S+V207F+F211Y+I222A+S225C+Q508R+A525T+T60H-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+D475E+V511L+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G+D475E+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+D475E+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A335P+D475E-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A309G+A335P+D475E+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A309G+A335P+T567A-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+A309G+A335P+D475E+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+H285N+A335P+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+K529E+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+K529E+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G+A335P des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A335P+Y594F-des[A647-L663]; T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+K35R+T60H+A335P+Y594F+K627R-des[A647-L663]; and T2A+A3R+A5T+I14M+S73A+N79D+G127N+I14M+S73A+N79D+G127N+I143M+H145R+V159E+T169N+V177P+A198S+A202P+I203Y+V207F+F2117+I222A+S225C+A272L+Q287R+D311G+Q508R+E512G+A525T+T60H+A309G+A335P+V511L-des[A647-L663], where amino acid position is determined by optimal alignment with SEQ ID NO: 4. Other illustrative C-terminally truncated β-glucosidase polypeptide variants are provided in the Tables of Examples 8-12.

The present invention also provides β-glucosidase polypeptide variants having improved thermoactivity, including improved thermostability, and/or improved stability at low and high pHs, particularly low pHs (typically greater than 4.5 and less than 6.0, more typically in the range of from 5.0 to 5.5) relative to wildtype *A. irakense* β-glucosidase. β-glucosidase polypeptide variants of the present invention may exhibit a half life at a pH of about 6 or less (such as, for example, about 5.5, about 5, about 4.5 etc.) and a temperature of about 60° C. or more (such as, for example, 65° C., 70° C., 75° C., 80° C., etc.) of at least about 24 hours, at least about 36 hours, at least about 48 hours, up to at least about 72 hours or more as measured using the assay of Example 5A. β-glucosidase polypeptide variants of the present invention may exhibit a half life at a pH of about 8 or more (such as, for example; about 8.5, about 9, etc.) and a temperature of about 60° C. or more (such as, for example, 65° C., 70° C., etc.) of at least about 24 hours, at least about 36 hours, at least about 48 hours, up to at least about 72 hours or more as measured using the assay of Example 5A.

In some embodiments, β-glucosidase polypeptide variants of the present invention exhibit a percent residual activity of at least about 50%, at least about 60%, at least about 70%, at least about 75%, at least about 80%, at least about 85%, and at least about 90% after 48 hours at 55 C, pH 5.0, using, for example the method of Example 5A.

The present invention includes conservatively modified variants of the (3-glucosidases described herein. These variants have conservative substitutions made in their amino acid sequences. Examples of conservative substitutions are within the group of basic amino acids (arginine, lysine and histidine), acidic amino acids (glutamic acid and aspartic acid), polar amino acids (glutamine and asparagines), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are known in the art and are described, for example, by H. Neurath and R. L. Hill, 1979, in "The Proteins," Academic Press, New York, which is incorporated herein by reference. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Conservatively substituted variations of the β-glucosidase polypeptide variants of the present invention include substitutions of a small percentage, typically less than 5%, more typically less than 2%, and often less than 1% of the amino acids of the polypeptide sequence, with a conservatively selected amino acid of the same conservative substitution group. The addition of sequences which do not alter the encoded activity of a β-glucosidase, such as the addition of a non-functional or non-coding sequence, is considered a conservative variation of the β-glucosidase polynucleotide.

The amino acid and polynucleotide sequences of β-glucosidase polypeptides not specifically described herein can be readily generated and identified using methods that are well known to those having ordinary skill in the art. Libraries of these β-glucosidase polypeptide variants may be generated and screened using the high throughput screen for presence of β-glucosidase activity described in either Example 5 or Example 7.

Methods for generating variant libraries are well known in the art. For example, mutagenesis and directed evolution methods can be readily applied to polynucleotides (such as, for example, wildtype *Azospirillum irakense* β-glucosidase encoding polynucleotides (e.g., SEQ ID NO: 3, FIG. 2A) or the polynucleotides of the present invention (described hereinbelow) to generate variant libraries that can be expressed, screened, and assayed using the methods described herein. Mutagenesis and directed evolution methods are well known in the art. See, e.g., Ling, et al., "Approaches to DNA mutagenesis: an overview," *Anal. Biochem.,* 254(2):157-78 (1997); Dale, et al., "Oligonucleotide-directed random mutagenesis using the phosphorothioate method," *Methods Mol. Biol.,* 57:369-74 (1996); Smith, "In vitro mutagenesis," *Ann. Rev. Genet.,* 19:423-462 (1985); Botstein, et al., "Strategies and applications of in vitro mutagenesis," *Science,* 229:1193-1201 (1985); Carter, "Site-directed mutagenesis," *Biochem. J.,* 237:1-7 (1986); Kramer, et al., "Point Mismatch Repair," *Cell,* 38:879-887 (1984); Wells, et al., "Cassette mutagenesis: an efficient method for generation of multiple mutations at defined sites," *Gene,* 34:315-323 (1985); Minshull, et al., "Protein evolution by molecular breeding," *Current Opinion in Chemical Biology,* 3:284-290 (1999); Christians, et al., "Directed evolution of thymidine kinase for AZT phosphorylation using DNA family shuffling," *Nature Biotechnology,* 17:259-264 (1999); Crameri, et al., "DNA shuffling of a family of genes from diverse species accelerates directed evolution," *Nature,* 391:288-291; Crameri, et al., "Molecular evolution of an arsenate detoxification pathway by DNA shuffling," *Nature*_Biotechnology, 15:436-438 (1997); Zhang, et al., "Directed evolution of an effective fucosidase from a galactosidase by DNA shuffling and screening," *Proceedings of the National Academy of Sciences, U.S.A.,* 94:45-4-4509; Crameri, et al., "Improved green fluorescent protein by molecular evolution using DNA shuffling," *Nature Biotechnology,* 14:315-319 (1996); Stemmer, "Rapid evolution of a protein in vitro by DNA shuffling," *Nature,* 370:389-391 (1994); Stemmer, "DNA shuffling by random fragmentation and reassembly: In vitro recombination for molecular evolution," *Proceedings of the National Academy of Sciences, U.S.A.,* 91:10747-10751 (1994); WO 95/22625; WO 97/0078; WO 97/35966; WO 98/27230; WO 00/42651; WO 01/75767; US 2009/0312196; U.S. Ser. No. 12/562,988, filed Sep. 18, 2009; and WO 2009/152336, all of which are incorporated herein by reference.

Exemplary βl-glucosidase polypeptide variants of the invention include those described in the Tables of Example 8-12. These variants exhibited improved thermoactivity and low pH tolerance relative to the wildtype *Azospirillum irakense* β-glucosidase.

The present invention also provides β-glucosidase variant fusion polypeptides, wherein the fusion polypeptide comprises an amino acid sequence encoding a β-glucosidase variant polypeptide of the present invention or fragment thereof, linked either directly or indirectly through the N- or C-terminus of the β-glucosidase variant polypeptide to an amino acid sequence encoding at least a second (additional) polypeptide. The β-glucosidase variant fusion polypeptide may further include amino acid sequence encoding a third, fourth, fifth, or additional polypeptides. Typically, each additional polypeptide has a biological activity, or alternatively, is a portion of a polypeptide that has a biological activity, wherein the portion has the effect of improving expression and/or secretion of the fusion polypeptide from the desired expression host. These sequences may be fused, either directly or indirectly, to the N- or C-terminus of the β-glucosidase variant polypeptide or fragment thereof, or alternatively, to the N- or C-terminus of the additional polypeptides having biological activity.

Typically, the additional polypeptide(s) encode an enzyme or active fragment thereof, and/or a polypeptide that improves expression and/or secretion of the fusion polypeptide from the desired expression host cell. More typically, the additional polypeptide(s) encode(s) a cellulase (for example, a β-glucosidase having a different amino acid sequence from the β-glucosidase variant polypeptide in the fusion polypeptide (e.g., a wildtype β-glucosidase or a variant thereof, including a different CelA β-glucosidase variant polypeptide), or a polypeptide exhibiting cellobiohydrolase or endoglucanse activity) and/or a polypeptide that improves expression and secretion from the desired host cell, such as, for example, a polypeptide that is normally expressed and secreted from the desired expression host, such as a secreted polypeptide normally expressed from filamentous fungi. These include glucoamylase, α-amylase and aspartyl proteases from *Aspergillus niger, Aspergillus niger* var. *awamori*, and *Aspergillus oryzae*, cellobiohydrolase I, cellobiohydrolase II, endoglucanase I and endoglucase III from *Trichoderma* and glucoamylase from *Neurospora* and *Humicola* sp. See WO 98/31821, which is incorporated herein by reference.

The polypeptide components of the fusion polypeptide may be linked to each other indirectly via a linker. Linkers suitable for use in the practice of the present invention are described in WO 2007/075899, which is incorporated herein by reference. Exemplary linkers include peptide linkers of from 1 to about 40 amino acid residues in length, including those from about 1 to about 20 amino acid residues in length, and those from about 1 to about 10 amino acid residues in length. In some embodiments, the linkers may be made up of a single amino acid residue, such as, for example, a Gly, Ser, Ala, or Thr residue or combinations thereof, particularly Gly and Ser. Linkers employed in the practice of the present invention may be cleavable. Suitable cleavable linkers may contain a cleavage site, such as a protease recognition site. Exemplary protease recognition sites are well known in the art and include, for example, Lys-Arg (the KEX2 protease recognition site, which can be cleaved by a native *Aspergillus* KEX2-like protease), and Lys and Arg (the trypsin protease recognition sites). See, for example, WO 2007/075899, which is incorporated herein by reference.

β-Glucosidase Polynucleotides

The present invention provides isolated or recombinant polynucleotides that encode any of the above-described β-glucosidase polypeptide variants.

Those having ordinary skill in the art will readily appreciate that due to the degeneracy of the genetic code, a multitude of nucleotide sequences encoding β-glucosidase polypeptides of the present invention exist. Table 1 is a Codon Table that provides the synonymous codons for each amino acid. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Such "silent variations" are one species of "conservative" variation. One of ordinary skill in the art will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention contemplates and provides each and every possible variation of nucleic acid sequence encoding a polypeptide of the invention that could be made by selecting combinations based on possible codon choices. These combinations are made in accordance with the standard triplet genetic code (set forth in Table 1), as applied to the polynucleotide sequences of the present invention.

A group of two or more different codons that, when translated in the same context, all encode the same amino acid, are referred to herein as "synonymous codons." β-glucosidase polynucleotides of the present invention may be codon optimized for expression in a particular host organism by modifying the polynucleotides to conform with the optimum codon usage of the desired host organism. Those having ordinary skill in the art will recognize that tables and other references providing preference information for a wide range of organisms are readily available See e.g., Henaut and Danchin in "*Escherichia coli* and *Salmonella*," Neidhardt, et al. Eds., ASM Pres, Washington D.C. (1996), pp. 2047-2066, which is incorporated herein by reference.

The terms "conservatively modified variations" and "conservative variations" are used interchangeably herein to refer to those nucleic acids that encode identical or essentially identical amino acid sequences, or in the situation where the nucleic acids are not coding sequences, the term refers to nucleic acids that are identical. One of ordinary skill in the art will recognize that individual substitutions, deletions or additions which alter, add or delete a single amino acid or a small percentage of amino acids in an encoded sequence are considered conservatively modified variations where the alterations result in one or more of the following: the deletion of an amino acid, addition of an amino acid, or substitution of an amino acid with a chemically similar amino acid. When more than one amino acid is affected, the percentage is typically less than 5% of amino acid residues over the length of the encoded sequence, and more typically less than 2%. References providing amino acids that are considered conservative substitutions for one another are well known in the art.

An exemplary β-glucosidase polynucleotide sequence of the present invention is provided as SEQ ID NO: 3, which is a polynucleotide sequence that encodes wild type *Azospirillum irakense* β-glucosidase (SEQ ID NO: 4), but which has been codon optimized to express well in both *Bacillus megaterium* and *Escherichia coli*, as described in Example 1, hereinbelow. Other specific changes have been identified in polynucleotides of the present invention that differ from the corresponding wild type *Azospirillum irakense* β-glucosidase polynucleotide sequence. The present invention further provides an isolated or recombinant β-glucosidase polynucleotide having a polynucleotide sequence comprising one or more substitutions selected from the group consisting of t3c, c12t, a24t, a27t/g, t30c, g33a, c36t, t43c, t69c, g72a, g93n, g93a, a96g, t99g/c, a102g, a104g, t111a/c, g120t, t135c, t138g, a147g, a150g, t171c, a186t, c195t, c199a, t216c, t222c, t249c, a252g, c259a, a270g, t282c, t291c, c303t, a309g, g324a, c330t, g348a, t351c, a366g, t408c, t417c, a426g, a429g, a441t/g, a450t/g, t462a/c, a468g, t489c, g492t, a495g, t501c, g513a, t516c, t528c, a543t/g, a555g, a570g, t576c, t585c, t591c, a600t/g, a606g, t609a, g612t, a615g, a621t, g654c, t666a, a675t, a678g, t688c, t693c, a702g, a714t, a726g, t729c, a732g/t, c735t, a741g, a744g, c747t, t756a, t756c, t762a, t771a, t783c, g786a, t789a, a798g, g804t, t819a, c828t, t849c, a861g, t873c, a882g, a885g, g894t, t897c, a903g, g912t, g915a, t924c, c933t, a939t, t951c, t963c, a969g, g981a, a987g, c1002t/g, t1008c, c1011a, g1017a, a1029g, a1044g, a1050g, t1053c, t1065c, t1036c, a1044g, t1062a, a1071g, a1077g/t, c1086t, a1092g, t1114c, t1137c, a1173g, a1176g, a1179g, a1185g, t1188c, a1197g, a1203g, c1206t, t1218c, t1220c, a1221g, c1227t, t1233c, a1230g, t1254c, t1260c, a1269g, t1290c, a1293, t1296c, a1302t, a1305g, t1324a, g1329a, a1350g, a1353g, t1356c, a1359g, t1371c, t1377c, t1386c, a1398g, t1401a, c1413t, t1425c, a1428t, a1431g, g1434t/a, c1437t, a1443g, t1446c, a1473g, t1476c, t1494c, t1497c, c1500t, a1506g, t1530c, g1536t/a, a1539g, a1545g, a1554g, t1569c, t1575g, t1575c, c1581t, c1588t, a1602c, t1617c, t1620c, t1626c, t1629c, a1635g, a1656g, t1650c, c1668t, t1674a, a1683g, c1698a, a1704g, t1707c, a1725g, a1734g, c1737t, a1749g, a1767g, a1770g, g1776a, t1782c, g1791a/t, t1794c, a1812g, t1821g, t1839c, g1851a, t1854c, t1857c, t1864c, t1878c, t1896c, a1899g, t1902c, a1905g, t1911c, a1914g, t1923g, c1930a, and a1932c, wherein nucleotide position is determined by optimal alignment with SEQ ID NO: 3. Illustrative variants having these silent mutations are provide in Examples 8-12, hereinbelow.

β-glucosidase polynucleotides of the present invention may further comprise a polynucleotide encoding a signal peptide as described in more detail below under the heading "Vectors, Promoters, and Expression Systems".

Polynucleotides of the present invention can be prepared using methods that are well known in the art. Typically, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al. (1981) *Tetrahedron Letters,* 22:1859-69, or the method described by Matthes, et al. (1984) *EMBO J.,* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, et al., *Cold Spring Harbor Symp. Quant. Biol.,* 47:411-418 (1982) and Adams, et al., *J. Am. Chem. Soc.,* 105:661 (1983), both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel"), all of which are incorporated herein by reference. Examples of protocols sufficient to direct persons of skill through in vitro amplification methods, including the polymerase chain reaction (PCR) and the ligase chain reaction (LCR). Reference is made to Berger, Sambrook, and Ausubel, as well as Mullis et al., (1987) U.S. Pat. No. 4,683,202*; PCR Protocols A Guide to Methods and Applications* (Innis et al. eds) Academic Press Inc. San Diego, Calif. (1990) (Innis); Arnheim & Levinson (Oct. 1, 1990) *C&EN*36-47*; The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564, all of which are incorporated herein by reference. Improved methods for cloning in vitro amplified nucleic acids are described in Wallace et al., U.S. Pat. No. 5,426,039, which is incorporated herein by reference.

Vectors, Promoters, and Expression Systems

The present invention also includes recombinant constructs comprising one or more of the β-glucosidase polynucleotide sequences as broadly described above. The term "construct", "DNA construct", or "nucleic acid construct" refers herein to a nucleic acid, either single- or double-stranded, which is isolated from a naturally occurring gene or which has been modified to contain segments of nucleic acids in a manner that would not otherwise exist in nature. The term "nucleic acid construct" is synonymous with the term "expression cassette" when the nucleic acid construct contains the control sequences required for expression of a β-glucosidase coding sequence of the present invention.

The present invention also provides an expression vector comprising β-glucosidase polynucleotide of the present invention operably linked to a promoter. Example 1 provides a description of how to make constructs for expression of β-glucosidase. However, one skilled in the art is aware of means for making DNA constructs. The term "control sequences" refers herein to all the components that are necessary or advantageous for the expression of a polypeptide of the present invention. Each control sequence may be native or foreign to the nucleotide sequence encoding the polypeptide. Such control sequences include, but are not limited to, a leader, promoter, signal peptide sequence, and transcription terminator. At a minimum, the control sequences include a promoter and transcriptional and translational stop signals. In some embodiments, the control sequence may include a polyadenylation sequence. The control sequences may be provided with linkers for the purpose of introducing specific restriction sites facilitating ligation of the control sequences with the coding region of the nucleotide sequence encoding a polypeptide.

The term "operably linked" refers herein to a configuration in which a control sequence is appropriately placed at a position relative to the coding sequence of the DNA sequence such that the control sequence influences the expression of a polypeptide. When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

Polynucleotides of the present invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

When incorporated into an expression vector, a β-glucosidase polynucleotide of the invention is operatively linked to an appropriate transcription control sequence (promoter) to direct mRNA synthesis, e.g., T5 promoter. Examples of such transcription control sequences particularly suited for use in transgenic plants include the cauliflower mosaic virus (CaMV) and figwort mosaic virus (FMV). Other promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. Examples of suitable promoters useful for directing the transcription of the nucleotide constructs of the present invention in a filamentous fungal host cell are promoters such as cbh1, cbh2, egl1, egl2, pepA, hfb1, hfb2, xyn1, amy, and glaA (Nunberg et al., Mol. Cell Biol., 4:2306-2315 (1984), Boel et al., *EMBO J.* 3:1581-1585 ((1984) and EPA 137280, which are incorporated herein by reference). In bacterial host cells, suitable promoters include the promoters obtained from the *E. coli* lac operon, *Streptomyces coelicolor* agarase gene (dagA), a gene from a *Bacillus* sp., such as, for example, the *Bacillus subtilis* levansucranse gene (sacB), the *Bacillus licheniformis* alpha-amylase gene (amyl), the *Bacillus megaterium* InhA gene (which is described in U.S. Ser. No. 61/169,848, filed Apr. 16, 2009 and U.S. Ser. No. 12/760,827, filed Apr. 15, 2010, both of which are incorporated herein by reference), the *Bacillus stearothermophilus* maltogenic amylase gene (amyM), the *Bacillus amyloliquefaciens* alpha-amylase gene (amyQ), *Bacillus subtilis* xylA and xylB genes, the xylose promoter (Pxyl) from *Bacillus megaterium*, and the promoter obtained from the prokaryotic beta-lactamase gene.

An expression vector optionally contains a ribosome binding site for translation initiation, and a transcription terminator, such as PinII. The vector also optionally includes appropriate sequences for amplifying expression, e.g., an enhancer.

The vector or DNA construct may also generally include a signal peptide coding region that codes for an amino acid sequence linked to the amino terminus of a polypeptide and which directs the encoded polypeptide into the cells secretory pathway. Signal peptides that are suitable for use in the practice of the present invention include the *Bacillus megaterium* penicillin G acylase signal peptide sequence (amino acid residues −1 to −24 of SEQ ID NO: 2, as shown in FIG. 1B, encoded by nucleic acids −1 to −72 of SEQ ID NO: 1, as depicted in FIG. 1A).

Variants of the *Bacillus megaterium* penicillin G acylase signal peptide that are effective at directing the β-glucosidase to the secretory pathway of *Bacillus megaterium* are also suitable. Exemplary variants are described in Tables 3, 5, 6, and 7 in Examples 8 (e.g., F-8E L-19Q, and F-10T), 10 (e.g., F-10T, K-21R, N-5H/S, and I-14V), 11 (e.g., N-5D and I-15V), and 12 (e.g., F-10T), respectively. The numbering of amino acid substitutions in the signal sequence is indicated in FIG. 1B.

Other effective signal peptide coding regions for bacterial host cells may be obtained from the genes of *Bacillus* NCIB 11837 maltogenic amylase, *B. stearothermophilus* alpha-amylase, *B. licheniformis* subtilisin, *B. licheniformis* beta-lactamase, *B. stearothermophilus* neutral proteases (nprT, nprS, nprM) and *B. subtilis* prsS. Further signal sequences are described in Simonen and Palva (1993), *Microbiological Reviews* 57:109-137, which is incorporated herein by reference. Effective signal peptide coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase and *Humicola lanuginosa* lipase. Variants of these signal peptides and other signal peptides are suitable, as well as expression mutants thereof having one or more silent mutations. An exemplary *Bacillus megaterium* penicillin G acylase signal peptide having a silent mutation is described in Table 3, with the mutation c-46g relative to SEQ ID NO: 1 (depicted in FIG. 1A). Additional illustrative silent mutations in the *Bacillus megaterium* penicillin G acylase signal peptide are provided in Table 6: g-67a, g-61a, c-57t, c-46t, a-43t, and c-39t.

In addition, expression vectors of the present invention optionally contain one or more selectable marker genes to provide a phenotypic trait for selection of transformed host cells. Suitable marker genes include those coding for antibiotic resistance such as, ampicillin, kanamycin, chloramphenicol, or tetracycline resistance. Further examples include the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Additional selectable marker genes include dihydrofolate reductase or neomycin resistance for eukaryotic cell culture, and tetracycline or ampicillin resistance in *E. coli*.

The vector may further contain genetic elements that facilitate integration by either homologous or non-homologous recombination. Genetic elements that facilitate integration by homologous recombination have sequence homology to targeted integration sites in the genomic sequence of the desired expression host cell. Genetic elements or techniques which facilitate integration by non-homologous recombination include restriction enzyme-mediated integration (REMI) (see Manivasakam et al., *Mol. Cell Biol.* (1998) 18(3):1736-1745, which is incorporated herein by reference), transposon-mediated integration, and other elements and methods that are well known in the art.

An exemplary expression vector for the expression of β-glucosidase polypeptides of the present invention is described in Example 1, hereinbelow. Vectors of the present invention can be employed to transform an appropriate host to permit the host to express an invention protein or polypeptide.

β-glucosidase polynucleotides of the invention can also be fused, for example, in-frame to nucleic acids encoding a secretion/localization sequence, to target polypeptide expression to a desired cellular compartment, membrane, or organelle of a cell, or to direct polypeptide secretion to the periplasmic space or into the cell culture media. Such sequences are known to those of skill, and include secretion leader peptides, organelle targeting sequences (e.g., nuclear localization sequences, endoplasmic reticulum (ER) retention signals, mitochondrial transit sequences, peroxisomal transit sequences, and chloroplast transit sequences), membrane localization/anchor sequences (e.g., stop transfer sequences, GPI anchor sequences), and the like.

Expression Hosts

The present invention also provides engineered (recombinant) host cells that are transformed with a vector or DNA construct of the invention (e.g., an invention cloning vector or an invention expression vector), as well as the production of β-glucosidase polypeptide variants of the invention. Thus, the present invention is directed to a (non-human) host cell comprising any β-glucosidase polynucleotide of the present invention that is described hereinabove. As used herein, a genetically modified or recombinant host cell includes the progeny of said host cell that comprises a β-glucosidase polynucleotide which encodes a variant polypeptide of the invention.

In some embodiments, the genetically modified or recombinant host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. Particularly preferred fungal host cells are yeast cells and filamentous fungal cells. The filamentous fungi host cells of the present invention include all filamentous forms of the subdivision Eumycotina and Oomycota. (see, for example, Hawksworth et al., In Ainsworth and Bisby's Dictionary of The Fungi, 8th edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells of the present invention are morphologically distinct from yeast.

In the present invention a filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof.

In some embodiments of the invention, the filamentous fungal host cell is of the, *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species.

In some embodiments of the invention, the filamentous fungal host cell is of the *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof—See Sheir-Neiss et al., Appl. Microbiol. Biotechnology, 20 (1984) pp 46-53), *T. koningii*, and *T. harzianum*. In addition, the term "*Trichoderma*" refers to any fungal strain that was previously classified as *Trichoderma* or currently classified as *Trichoderma*.

In some embodiments of the invention, the filamentous fungal host cell is of the *Aspergillus* species, e.g., *A. awamori, A. funigatus, A. japonicus, A. nidulans, A. niger, A. aculeatus, A. foetidus, A. oryzae, A. sojae*, and *A. kawachi*. (Reference is made to Kelly and Hynes (1985) *EMBO J.* 4,475479; NRRL 3112, ATCC 11490, 22342, 44733, and 14331; Yelton M., et al., (1984) *Proc. Natl. Acad. Sci. USA,* 81, 1470-1474; Tilburn et al., (1982) *Gene* 26, 205-221; and Johnston, I. L. et al. (1985) *EMBO J.* 4, 1307-1311, all of which are incorporated herein by reference).

In some embodiments of the invention, the filamentous fungal host cell is of the *Chrysosporium* species, e.g., *C. lucknowense, C. keratinophilum, C. tropicum, C. merdarium, C. inops, C. pannicola*, and *C. zonatum*.

In some embodiments of the invention, the filamentous fungal host cell is of the *Fusarium* species, e.g., *F. bactridio-*

*ides, F. cerealis, F. crookwellense, F. culmorum, F. graminearum, F. graminum. F. oxysporum, F. roseum*, and *F. venenatum*. In some embodiments of the invention, the filamentous fungal host cell is of the *Neurospora* species, e.g., *N. crassa*. Reference is made to Case, M. E. et al., (1979) *Proc. Natl. Acad. Sci. USA,* 76, 5259-5263; U.S. Pat. No. 4,486, 553; and Kinsey, J. A. and J. A. Rambosek (1984) *Molecular and Cellular Biology* 4, 117-122, all of which are incorporated herein by reference. In some embodiments of the invention, the filamentous fungal host cell is of the *Humicola* species, e.g., *H. insolens, H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum, P. chrysogenum*, and *P. verruculosum*. In some embodiments of the invention, the filamentous fungal host cell is of the *Thielavia* species, e.g., *T. terrestris*. In some embodiments of the invention, the filamentous fungal host cell is of the *Tolypocladium* species, e.g., *T. inflatum* and *T. geodes* or of the *Trichoderma* species, e.g., *T. reesei*. In some embodiments of the invention, the filamentous fungal host cell is of the *Trametes* species, e.g., *T. villosa* and *T. versicolor.*

In the present invention a yeast host cell may be a cell of a species of but not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccaromyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, and *Yarrowia lipolytica.*

In some embodiments on the invention, the host cell is an algal such as, *Chlamydomonas* (e.g., *C. Reinhardtii*) and *Phormidium* (*P.* sp. ATCC29409).

In other embodiments, the host cell is a prokaryotic cell. Suitable prokaryotic cells include gram positive, gram negative and gram-variable bacterial cells. The host cell may be a species of, but not limited to *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas.*

In some embodiments, the host cell is a species of *Agrobacterium, Acinetobacter, Azobacter, Bacillus, Bifidobacterium, Buchnera, Geobacillus, Campylobacter, Clostridium, Corynebacterium, Escherichia, Enterococcus, Erwinia, Flavobacterium, Lactobacillus, Lactococcus, Pantoea, Pseudomonas, Staphylococcus, Salmonella, Streptococcus, Streptomyces*, and *Zymomonas.*

In yet other embodiments, the bacterial host strain is non-pathogenic to humans. In some embodiments the bacterial host strain is an industrial strain. Numerous bacterial industrial strains are known and suitable in the present invention.

In some embodiments of the invention the bacterial host cell is of the *Agrobacterium* species, e.g., *A. radiobacter, A. rhizogenes*, and *A. rubi*. In some embodiments of the invention the bacterial host cell is of the *Arthrobacter* species, e.g., *A. aurescens, A. citreus, A. globformis, A. hydrocarboglutamicus, A. mysorens, A. nicotianae, A. paraffineus, A. protophonniae, A. roseoparaffinus, A. sulfureus*, and *A. ureafaciens*. In some embodiments of the invention the bacterial host cell is of the *Bacillus* species, e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. Some preferred embodiments of a *Bacillus* host cell include *B. subtilis, B. licheniformis, B. megaterium, B. stearothermophilus* and *B. amyloliquefaciens*. In some embodiments the bacterial host cell is of the *Clostridium* species, e.g., *C. acetobutylicum, C. tetani* E88, *C. lituseburense, C. saccharobutylicum, C. perfringens*, and *C. beijerinckii*. In some embodiments the bacterial host cell is of the *Corynebacterium* species e.g., *C. glutamicum* and *C. acetoacidophilum*. In some embodiments the bacterial host cell is of the *Escherichia* species, e.g., *E. coli*. In some embodiments the bacterial host cell is of the *Erwinia* species, e.g., *E. uredovora, E. carotovora, E. ananas, E. herbicola, E. punctata*, and *E. terreus*. In some embodiments the bacterial host cell is of the *Pantoea* species, e.g., *P. citrea*, and *P. agglomerans*. In some embodiments the bacterial host cell is of the *Pseudomonas* species, e.g., *P. putida, P. aeruginosa, P. mevalonii*, and *P.* sp. D-01 10. In some embodiments the bacterial host cell is of the *Streptococcus* species, e.g., *S. equisimiles, S. pyogenes*, and *S. uberis*. In some embodiments the bacterial host cell is of the *Streptomyces* species, e.g., *S. ambofaciens, S. achromogenes, S. avermitilis, S. coelicolor, S. aureofaciens, S. aureus, S. fungicidicus, S. griseus*, and *S. lividans*. In some embodiments the bacterial host cell is of the *Zymomonas* species, e.g., *Z. mobilis*, and *Z. lipolytica.*

Strains that may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Introduction of a vector or DNA construct into a host cell can be effected by calcium phosphate transfection, DEAE-Dextran mediated transfection, electroporation, or other common techniques (See Davis, L., Dibner, M. and Battey, I. (1986) *Basic Methods in Molecular Biology*, which is incorporated herein by reference). The engineered host cells can be cultured in conventional nutrient media modified as appropriate for activating promoters, selecting transformants, or amplifying the β-glucosidase polynucleotide. Culture conditions, such as temperature, pH and the like, are those previously used with the host cell selected for expression, and will be apparent to those skilled in the art and in the references cited herein, including, for example, Sambrook, Ausubel and Berger, as well as, for example, Freshney (1994) *Culture of Animal Cells, a Manual of Basic Technique*, third edition, Wiley-Liss, New York; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla., all of which are incorporated herein by reference.

Production and Recovery of β-Glucosidase Polypeptide Variants

The present invention is directed to a method of making a polypeptide having β-glucosidase activity, the method comprising providing a host cell transformed with any one of the described β-glucosidase polynucleotides of the present invention; culturing the transformed host cell in a culture medium under conditions that cause said polynucleotide to express the encoded β-glucosidase polypeptide variant; and optionally recovering or isolating the expressed β-glucosidase polypeptide variant, or recovering or isolating the culture medium containing the expressed β-glucosidase polypeptide variant. The method further provides optionally lysing the transformed host cells after expressing the encoded β-glucosidase polypeptide variant and optionally recovering or isolating the expressed β-glucosidase polypeptide variant from the cell lysate. The present invention further provides a method of making a β-glucosidase polypeptide variant, said method comprising cultivating a host cell transformed with a β-glucosidase polynucleotide under conditions suitable for the production of the β-glucosidase polypeptide variant and recovering the β-glucosidase polypeptide variant.

Typically, recovery or isolation of the β-glucosidase polypeptide variant is from the host cell culture medium, the host cell or both, using protein recovery techniques that are well known in the art, including those described herein.

Following transformation of a suitable host strain and growth (cultivating or culturing) of the host strain to an appropriate cell density, the selected promoter may be induced by appropriate means (e.g., temperature shift or chemical induction) and cells are cultured for an additional period. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In vitro Cell Dev. Biol.* 25:1016-1024, all of which are incorporated herein by reference. For plant cell culture and regeneration, Payne et al. (1992) *Plant Cell and Tissue Culture in Liquid Systems*_John Wiley & Sons, Inc. New York, N.Y.; Gamborg and Phillips (eds) (1995) *Plant Cell,*__*Tissue and Organ Culture*; Fundamental Methods Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

In some embodiments, cells expressing the β-glucosidase polypeptide variants of the invention are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady sate growth conditions. Methods for modulating nutrients and growth factors for continuous fermentation processes as well as techniques for maximizing the rate of product formation are well known in the art of industrial microbiology.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic, chromatofocusing, and size exclusion), or precipitation. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, for example, those set forth in Sandana (1997) *Bioseparation of Proteins*, Academic Press, Inc.; Bollag et al. (1996) *Protein Methods, 2nd* Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* 3rd *Edition*, Springer Verlag, NY; Janson and Ryden (1998) *Protein Purification: Principles, High Resolution Methods and Applications, Second Edition*, Wiley-VCH, NY; and Walker (1998) *Protein Protocols on CD-ROM*, Humana Press, NJ, all of which are incorporated herein by reference. An exemplary procedure for producing β-glucosidases is provided in Example 4, hereinbelow. The skilled artisan will readily appreciate that this procedure can be used to produce the β-glycosidase polypeptide variants of the present invention.

Cell-free transcription/translation systems can also be employed to produce β-glucosidase polypeptides using the polynucleotides of the present invention. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

Methods of Using β-Glucosidase Polypeptides and Related Compositions

As described supra, β-glucosidase polypeptide variants of the present invention can be used to catalyze the hydrolysis of a sugar dimer with the release of the corresponding sugar monomer, for example, the conversion of cellobiose with the release of glucose. Thus, the present invention provides a method for producing glucose, said method comprising: (a) providing a cellobiose; and (b) contacting the cellobiose with a β-glucosidase polypeptide variant of the invention under conditions sufficient to form a reaction mixture for converting the cellobiose to glucose. The β-glucosidase polypeptide variant may be utilized in such methods in either isolated form or as part of a composition, such as any of those described herein. The β-glucosidase polypeptide variant may also be provided in cell culturing media or in a cell lysate. For example, after producing the β-glucosidase polypeptide variant by culturing a host cell transformed with a β-glucosidase polynucleotide or vector of the present invention, the β-glucosidase need not be isolated from the culture medium (i.e., if the β-glucosidase is secreted into the culture medium) or cell lysate (i.e., if the β-glucosidase is not secreted into the culture medium) or used in purified form to be useful in further methods of using the β-glucosidase polypeptide variant. Any composition, cell culture medium, or cell lysate containing a β-glucosidase polypeptide variant of the present invention may be suitable for using in methods that utilize a β-glucosidase. Therefore, the present invention further provides a method for producing glucose, the method comprising: (a) providing a cellobiose; and (b) contacting the cellobiose with a culture medium or cell lysate or composition comprising a β-glucosidase polypeptide variant of the present invention under conditions sufficient to form a reaction mixture for converting the cellobiose to glucose.

The present invention further provides compositions that are useful for the enzymatic conversion of cellobiose to glucose. For example, one or more β-glucosidase polypeptide variants of the present invention may be combined with another enzyme and/or an agent that alters the bulk material handling properties or further processability of the β-glucosidase(s) (e.g., a flow aid agent, water, buffer, a surfactant, and the like) or that improves the efficiency of the conversion of cellobiose to glucose, as described in more detail hereinbelow. The other enzyme may be a different β-glucosidase or another cellulase enzyme. For example, in some embodiments, the β-glucosidase is combined with other cellulases to form a cellulase mixture. The cellulase mixture may include cellulases selected from CBH and EG cellulases (e.g., cellulases from *Trichoderma reesei* (e.g., C2730 Cellulase from *Trichoderma reesei* ATCC No. 25921, Sigma-Aldrich, Inc.), C9870 ACCELLERASE™ 1500, Genencor, Inc., and the like), *Acidothermus cellulolyticus, Thermobifida fusca, Humicola grisea* and *Chrysosporium* sp.). The enzymes of the cellulase mixture work together resulting in decrystallization and hydrolysis of the cellulose from a biomass substrate to yield soluble sugars, such as but not limited to glucose (See Brigham et al., (1995) in Handbook on Bioethanol (C. Wyman ed.) pp 119-141, Taylor and Francis, Washington D.C., which is incorporated herein by reference).

β-glucosidase polypeptide variants of the present invention may be used in combination with other optional ingredients such as water, a buffer, a surfactant, and/or a scouring agent. A buffer may be used with a β-glucosidase polypeptide variant of the present invention (optionally combined with other cellulases, including another β-glucosidase) to maintain a desired pH within the solution in which the β-glucosidase is employed. The exact concentration of buffer employed will depend on several factors which the skilled artisan can determine. Suitable buffers are well known in the art. A surfactant may further be used in combination with the cellulases of the present invention. Suitable surfactants include any surfactant compatible with the β-glucosidase and optional other cellulases being utilized. Exemplary surfactants include an anionic, a non-ionic, and ampholytic surfactants.

Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants can also be employed as is known in the art.

β-glucosidase polypeptide variants of the present invention, as well as any composition, culture medium, or cell lysate comprising such variants, may be used in the production of monosaccharides, disaccharides, or oligomers of a mono- or di-saccharide as chemical or fermentation feedstock from biomass. As used herein, the term "biomass" refers to living or dead biological material that contains a polysaccharide substrate, such as, for example, cellulose, starch, and the like. Therefore, the present invention provides a method of converting a biomass substrate to a fermentable sugar, the method comprising contacting a culture medium or cell lysate containing a β-glucosidase polypeptide variant according to the invention, with the biomass substrate under conditions suitable for the production of the fermentable sugar. The present invention further provides a method of converting a biomass substrate to a fermentable sugar, the method comprising: (a) pretreating a cellulose substrate to increase its susceptibility to hydrolysis; (b) contacting the pretreated cellulose substrate of step (a) with a composition, culture medium or cell lysate containing a β-glucosidase polypeptide variant of the present invention under conditions suitable for the production of the fermentable sugar.

In some embodiments, the biomass includes cellulosic substrates including but not limited to, wood, wood pulp, paper pulp, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof. The biomass may optionally be pretreated to increase the susceptibility of cellulose to hydrolysis using methods known in the art such as chemical, physical and biological pretreatments (e.g., steam explosion, pulping, grinding, acid hydrolysis, solvent exposure, and the like, as well as combinations thereof).

In some embodiments, the β-glucosidase polypeptide variants and β-glucosidase polypeptide variant-containing compositions, cell culture media, and cell lysates may be reacted with the biomass or pretreated biomass at a temperature in the range of about 25° C. to about 100° C., about 30° C. to about 90° C., about 30° C. to about 80° C., about 40° C. to about 80° C. and about 35° C. to about 75° C. Also the biomass may be reacted with the β-glucosidase polypeptide variants and β-glucosidase polypeptide variant-containing compositions, cell culture media, and cell lysates at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. In addition to the temperatures described above, conditions suitable for converting a biomass substrate to a fermentable sugar that employ a β-glucosidase polypeptide variant of the present invention (optionally in a composition, cell culture medium, or cell lysate) include carrying out the process at a pH in a range from about pH 3.0 to about 8.5, about pH 3.5 to about 8.5, about pH 4.0 to about 7.5, about pH 4.0 to about 7.0, about pH 4.0 to about 6.5, about pH 5.0 to about 6.0, and about pH 5.0 to about 5.5. Those having ordinary skill in the art will appreciate that the reaction times for converting a particular biomass substrate to a fermentable sugar may vary but the optimal reaction time can be readily determined. Exemplary reaction times may be in the range of from about 1.0 to about 240 hours, from about 5.0 to about 180 hrs and from about 10.0 to about 150 hrs. For example, the incubation time may be at least 1 hr, at least 5 hrs, at least 10 hrs, at least 15 hrs, at least 25 hrs, at least 50 hr, at least 100 hrs, at least 180 and the like.

Reaction of the β-glucosidase with biomass substrate or pretreated biomass substrate under these conditions may result in the release of substantial amounts of the soluble sugars from the substrate. For example at least 20%, at least 30%, at least 40%, at least 50%, at least 60%, at least 70%, at least 80%, at least 90% or more soluble sugar may be available as compared to the release of sugar by the wildtype *Azospirillum irakense* CelA (SEQ ID NO: 4). In some embodiments, the soluble sugars will comprise glucose.

The soluble sugars produced by the methods of the present invention may be used to produce an alcohol (such as, for example, ethanol, butanol, and the like). The present invention therefore provides a method of producing an alcohol, where the method comprises (a) providing a fermentable sugar, such as one produced using a β-glucosidase polypeptide variant of the present invention in the methods described supra; (b) contacting the fermentable sugar with a fermenting microorganism to produce the alcohol; and (c) recovering the alcohol.

In some embodiments, the β-glucosidase polypeptide variant of the present invention, or composition, cell culture medium, or cell lysate containing such variant(s) may be used to catalyze the hydrolysis of a biomass substrate to a fermentable sugar in the presence of a fermenting microorganism such as a yeast (e.g., *Saccharomyces* sp., such as, for example, *S. cerevisiae, Pichia* sp., and the like) or other C5 or C6 fermenting microorganisms that are well known in the art, to produce an end-product such as ethanol. In this simultaneous saccharification and fermentation (SSF) process, the fermentable sugars (e.g., glucose and/or xylose) are removed from the system by the fermentation process.

The soluble sugars produced by the use of a β-glucosidase variant polypeptide of the present invention may also be used in the production of other end-products. such as, for example, acetone, an amino acid (e.g., glycine, lysine, and the like), an organic acid (e.g., lactic acid, and the like), glycerol, a diol (e.g., 1,3 propanediol, butanediol, and the like) and animal feeds.

One of skill in the art will readily appreciate that the β-glucosidase polypeptide variant compositions of the present invention may be used in the form of an aqueous solution or a solid concentrate. When aqueous solutions are employed, the β-glucosidase solution can easily be diluted to allow accurate concentrations. A concentrate can be in any form recognized in the art including, for example, liquids, emulsions, suspensions, gel, pastes, granules, powders, an agglomerate, a solid disk, as well as other forms that are well known in the art. Other materials can also be used with or included in the β-glucosidase composition of the present invention as desired, including stones, pumice, fillers, solvents, enzyme activators, and anti-redeposition agents depending on the intended use of the composition.

β-glucosidase polypeptide variants and compositions thereof may also be used in the food and beverage industry for example in the process of wine making for the efficient release of monoterpenols (see, for example, Yanai and Sato (1999) *Am. J. Enol. Eitic.,* 50:231-235, which is incorporated herein by reference) and for the preparation of glycon isoflavone-enriched tofu (see, for example, Mase et al., (2004) *J. Appl. Glycosci.,* 51:211-216, which is incorporated herein by reference). β-glucosidase polypeptide variants of the present invention may also be employed in detergent compositions for improved cleaning performance (see, for example, U.S. Pat. No. 7,244,605; U.S. Pat. No. 5,648,263 and WO 2004/048592, which are incorporated herein by reference).

The foregoing and other aspects of the invention may be better understood in connection with the following non-limiting examples.

EXAMPLES

The following examples are offered to illustrate, but not to limit the claimed invention.

Example 1

Wild type *Azospirillum irakense* CelA Gene Acquisition and Construction of Expression Vectors A gene coding for *Azospirillum irakense* CelA was codon optimized for expression in *B. megaterium* and *E. coli* based on the reported amino acid sequence (AAG43575.1) and a codon optimization algorithm incorporated as described in Example 1 of PCT publication WO2008/042876, which is incorporated herein by reference. The gene was synthesized by GenScript Corporation (GenScript Corporation, 120 Centennial Ave., Piscataway, N.J. 08854, USA) and the DNA sequence verified. The gene was cloned behind a nucleotide sequence encoding the *Bacillus megaterium* penicillin G acylase signal peptide plus a spacer region (encoding the signal peptide cleavage site and nucleotides corresponding to a SpeI restriction site) into an *E. coli/B. megaterium* shuttle vector pSSBm28 using the BsrGI/NgoMIV cloning sites. The polynucleotide sequence encoding wildtype *A. irakense* CelA is shown in FIG. 1A (SEQ ID NO: 1). Nucleotides −72 to −1 encode the *B. megaterium* penicillin G acylase signal peptide. Nucleotides 1-3 encode part of the signal peptide cleavage site. Nucleotides 4-9 correspond to a SpeI restriction site. The vector pSSBm28 is a modified vector based on the *Bacillus megaterium* shuttle vector pMM1525 (Boca Scientific Inc., Boca Raton, Fla.). pSSBm28 differs from pMM1525 in that it has the penicillin G acylase signal peptide instead of the LipA signal peptide that pMM1625 has. In both vectors, the signal peptide and gene are under the control of and xylose promoter (Pxyl) regulated by the xylose repressor gene (xylR) present on the shuttle vector. The vector contained the 'rep U' origin of replication for *Bacillus* and a tetracycline ampicillin resistance marker. The vector also contained the pBR322 origin of replication and an ampicillin resistance marker for maintenance in *E. coli*. The resulting plasmid (pSSBm28-CelA) was transformed by a standard PEG-mediated method of DNA transfer into *B. megaterium* protoplasts. The CelA sequence from the transformants was verified. The amino acid sequence of the encoded polypeptide is shown in FIG. 1B (SEQ ID NO: 2). Amino acid residues −1 to −24 correspond to the *B. megaterium* penicillin G acylase signal peptide. The signal peptide is cleaved between amino acid residues −1 and +1. The amino acid residue at position +1, glycine, was engineered into the polypeptide to signal peptide processing in *B. megaterium*. The amino acid residues at positions 2 and 3, threonine and serine, respectively, are encoded by a nucleotide sequence that corresponds to a SpeI restriction site. The wildtype CelA catalytic domain is encoded by amino acid residues +4 to +666 of SEQ ID NO: 2 (using the numbering convention depicted in FIG. 1B) and also amino acid residues 1-663 of SEQ ID NO: 4 (FIG. 2B) and is encoded by the polynucleotide sequence defined by nucleic acids 10-2001 of SEQ ID NO: 1 (using the numbering convention depicted in FIG. 1A) and nucleic acids 1-1992 of SEQ ID NO: 3 (FIG. 2A).

Example 2

Shake Flask Procedure for Producing CelA

A single microbial colony of *Bacillus megaterium* containing the vector prepared in Example 1 with the CelA gene was inoculated into 3 ml Luria-Bertani (LB) Broth (0.01 g/L Peptone from casein, 0.005 g/L yeast extract, 0.01 g/L sodium chloride) containing 10 μg/mL tetracycline. Cells were grown overnight (at least 16 hrs) in an incubator at 37° C. with shaking at 250 rpm. 0.5 mls of this culture was then diluted into 50 mL A5 media (2 g/L $(NH4)_2SO_4$, 3.5 g/L $KH_2HPO_4$, 7.3 g/L $Na_2HPO_4$, 1 g/L yeast extract, pH to 6.8), 50 μL of trace elements solution (49 g/L $MnCl_2.4H_2O$, 45 g/L $CaCl_2$, 2.5 g/L $(NH_4)Mo_7.O_{24}.H_2O$, 2.5 g/L $CoCl_2.6H_2O$), 750 μL of 20% glucose, 1.25 ml of 20% xylose, 75 μl of 1M $MgSO_4$, 50 μL of 10 mg/mL tetracycline, 50 μL of 2.5 g/L $FeSO_4.7H_2O$ in a 250 ml flask. It was allowed to grow at 37° C. for 24 hours. Cells were pelleted by centrifugation (4000 rpm, 15 min, 4° C.). The clear media supernatant containing the secreted CelA enzyme was collected and stored at 4° C. The activity of wild-type CelA was confirmed using pNPG (p-nitrophenyl-β-D-glucopyranoside) as substrate as described by Breves et al. (1997) *Appl. Environmental Microbiol.* 63:3902, which is incorporated herein by reference.

Example 3

Inoculation Shake Flask Procedure for Producing CelA

A single microbial colony of *B. megaterium* containing a vector coding for CelA was inoculated into 250 ml A5 broth (2.0 g/L ammonium sulfate, 7.26 g/L of disodium monohydrogen phosphate, 3.52 g/L of potassium dihydrogen phosphate, 1.0 g/L of Tastone-154 yeast extract, 1.5 ml/L of 1M magnesium sulfate solution, 1.0 ml of 2.5 g/L iron sulfate septahydrate solution, and 1.0 ml/L of trace element solution containing 45.0 g/L of calcium chloride, 49.0 g/L manganese chloride tetrahydrate, 2.5 g/L cobalt chloride hexahydrate, and 2.5 g/L ammonium molybdate hydrate) containing 10 μg/ml tetracycline and 0.5% glucose. The vector that was utilized was the same as that described in Example 1 except that the promoter from *Bacillus megaterium* InhA was used. This promoter is described in U.S. Ser. No. 61/169,848, filed Apr. 16, 2009 and U.S. Ser. No. 12/760,827, filed Apr. 15, 2010, both of which are incorporated herein by reference. Cells were grown overnight (at least 12 hrs) in an incubator at 30° C. with shaking at 250 rpm. When the OD600 of the culture was 3.0 to 5.0, the cells were removed from the incubator and used immediately for inoculating the fermentor, or stored at 4° C. until used.

Example 4

Reference Cellobiase Expression; Fermentation Procedure

In an aerated agitated 15 L fermentor, 6.0 L of growth medium containing 0.88 g/L ammonium sulfate, 1.0 g/L of sodium citrate, 12.5 g/L of dipotassium monohydrogen phosphate trihydrate, 6.25 g/L of potassium dihydrogen phosphate, 3.3 g/L of Tastone-154 yeast extract, 2.0 g/L of Phytone peptone, and 1.0 ml/L of trace element solution containing 45.0 g/L of calcium chloride, 49.0 g/L manganese chloride tetrahydrate, 2.5 g/L cobalt chloride hexahydrate, and 2.5 g/L ammonium molybdate hydrate was sterilized and brought to a temperature of 37° C. 120.0 mL of a feed solution containing 500 g/L glucose monohydrate, 12 g/L ammonium chloride and 5.0 g/L magnesium sulfate anhydrous was added. 0.083 g/L ferric ammonium citrate and 10 μg/mL tetracycline were added. The fermentor was inoculated with a late exponential culture of *B. megaterium*, containing a vector coding for CelA, grown in a shake flask as described in Example 3 to a starting OD600 of 3.0 to 5.0. The vector that was utilized was the same as that described in Example 1 except that the promoter from *Bacillus megaterium* InhA was used. This promoter is described in U.S. Ser. No. 61/169,848, filed Apr. 16, 2009 and U.S. Ser. No. 12/760,827, filed Apr. 16, 2010, both of, which are incorporated herein by reference. The fermentor was agitated at 500-1200 rpm and air was supplied to the fermentation vessel at 0.6-25.0 L/min to maintain dissolved oxygen level of 50% saturation. The pH of the culture was controlled at 7.0 by addition of 28% v/v ammonium hydroxide. Growth of the culture was maintained by the addition of a feed solution containing 500 g/L glucose monohydrate, 12 g/L ammonium chloride and 5.0 g/L magnesium sulfate anhydrous. After the culture reached an OD600 of 70±10, the expression of CelA was induced by the addition of xylose to obtain and maintain a concentration of 0.5%. The culture was grown for another 12 hours. The culture was then chilled to 4° C. and maintained at 4° C. until harvested. Media supernatant was harvested by centrifugation at 5000G for 30 minutes in a Sorval RC12BP centrifuge at 4° C.

The clear supernatant was decanted and concentrated ten-fold using a polyethersulfone polymer ultrafiltration membrane with a molecular weight cut off of 10 kDa. The concentrate was diafiltered using at least 3 volumes of 100 mM sodium phosphate buffer pH 6.5. The final concentrate was stored at 4° C.

Example 5

High Throughput Assays to Determine β-Glucosidase and Cellobiase Activity

Beta-glucosidase activity may be determined either by a para-nitrophenyl-β-D-glucopyranoside (pNPG) assay, or a cellobiose assay.

A. Para-Nitrophenyl Glucopyranoside (pNPG) Assay

A colorimetric pNPG (p-nitrophenyl-(β-D-glucopyranoside)-based assay was used for measuring β-glucosidase activity. In a total volume of 100 μL, 20 μL clear media supernatant containing β-glucosidase enzyme was added to 4 mM pNPG (Sigma-Aldrich, Inc. St. Louis, Mo.) solution in 50 mM sodium phosphate buffer at pH6.5. The reactions were incubated at pH 6.5, 45° C. for 1 hour. The reaction mixture was quenched with 100 μL of 1M sodium carbonate pH 11 solution. The absorbance of the solution was measured at 405 nm to determine the conversion of pNPG to p-nitrophenol. The release of p-nitrophenol (ϵ=17,700 M−1 cm−1) was measured at 405 nm to calculate β-glucosidase activity. Detectable β-glucosidase activity was observed under high throughput screening conditions (pH 7, 50° C.).

B. Cellobiose Assay

β-glucosidase activity was also determined using a cellobiose assay, which used cellobiose as substrate. In a total volume of 100 μL, 25 μL clear media supernatant containing CelA enzyme was added to 10 g/L cellobiose (Fluka Cat. No. 22150, Sigma-Aldrich, Inc., St. Louis, Mo.) in 100 mM sodium phosphate buffer (pH 6-7) or sodium acetate buffer (pH 5-5.5). The reaction was incubated at 45-70° C. for an appropriate time (25 minutes to overnight depending on the enzyme concentration) while shaking. Glucose production was determined using an enzymatic glucose assay (K-GLUC, Megazyme, Ireland). 10 μl of each reaction was added to 190 μl GOPOD reagent (supplied as part of the K-GLUC assay kit). The reaction was incubated at 45° C. for 20 minutes and the absorbance of the solution was measured at 510 nm. The GOPOD reagent contains 50 mM Potassium phosphate buffer pH7.4, 0.011M p-hydroxybenzoic acid, 0.008% w/v sodium azide, glucose oxidase (>12,000 U/L), peroxidase (>650 U/L) and 80 mg/L 4-aminoantipyrine. The glucose oxidase enzyme in the reagent reacts with any glucose present in the sample and produces hydrogen peroxide which then reacts with the 4-aminoantipyrine to produce a quinoneimine dye in quantities proportionate with the amount of glucose present and can be measured spectrophotometrically at 510 nm. Detectable β-glucosidase activity was observed under high throughput screening conditions (i.e., pH 7, 50° C.).

Example 6

Evaluation of Optimal CelA Activity

The native CelA activity profile was investigated at different temperatures (40-55° C.) and pH (5.0-8.0) using cellobiose (10 g/L) as a substrate. The experimental and analytical procedures are described in Example 5. CelA exhibited optimum activity at pH 6.0 and 47° C., and detectable CelA activity was observed at pH 4 and 70° C. as shown in FIG. 6.

Example 7

High Throughput Assays to Identify Improved CelA Variants

Plasmid libraries containing variant CelA genes were transformed into *B. megaterium* and plated on Luria-Bertani (LB) agar plates containing 3 μg/mL tetracycline with a DM3 regeneration media overlay (400 mM sodium succinate dibasic, pH 7.3, 0.5% casamino acids, 0.5% yeast extract, 0.4% $K_2HPO_4$, 0.2% $KH_2PO_4$, 20 mM $MgCl_2$, 0.5% glucose and 0.2% BSA). After incubation for at least 18 hours at 30° C., colonies were picked using a Q-bot® robotic colony picker (Genetix USA, Inc., Beaverton, Oreg.) into shallow, 96-well well microtiter plates containing 180 μL, LB and 10 μg/mL tetracycline. Cells were grown overnight at 37° C. with shaking at 200 rpm and 85% humidity. 10 μL of this culture was then transferred into 96-well microtiter plates (deep well) containing 390 μL A5-glucose-xylose medium and 10 μg/mL tetracycline as described in example 2. The plates were then incubated at 37° C. with shaking at 250 rpm and 85% humidity overnight (~18-24 hours). The deep plates were centrifuged at 4000 rpm for 15 minutes and the clear media supernatant containing the secreted CelA enzyme was used for the high throughput pNPG or cellobiose assay of Example 5.

The CelA libraries were screened in high throughput using the cellobiose assay of Example 5 (Substrate: cellobiose; pH: 5-7; temperature: 45-72° C.; time: 2-24 hrs) for the identification of improved variants.

In shallow, 96-well microtiter plates 25 μL of media supernatant was added to 75 μL of 10 g/l cellobiose in 150 mM sodium acetate buffer pH 5-5.5 or 150 mM sodium phosphate buffer pH6-7. After sealing with aluminum/polypropylene laminate heat seal tape (Velocity 11 (Menlo Park, Calif.), Cat#06643-001), the plates were shaken at 45-65° C. for up to 24 hrs. The plates were centrifuged for 5 minutes at 4000 rpm. In shallow well clear microtiter plates, 10 μL of the reaction mixture was added to 190 μL of GOPOD reagent (as in example 5B) per well. The solutions were incubated at 45° C. for 1 hour and absorbance was measured at 510 nm for the identification of active CelA variants.

Example 8

Improved (3-Glucosidase Activities of Engineered CelA Variants

Improved CelA variants were identified from the high throughput screening of various CelA variant libraries as described in Example 7, using the cellobiose assay of Example 5 using 3.3 g/l cellobiose at temperatures from 50°-55° C. at a pH in the range of 5.3-6.5. Tables 2A, 2B, 2C, and 2D and Table 3 depict the improvement in activities of CelA variants encompassed by the invention. The assay conditions are indicated in each table. Each subsequent table provides variants that are improved over variants in a previous table (and therefore the wildtype CelA) with respect to thermoactivity. Assay conditions were selected outside of the temperature and pH optimum of the reference enzyme (i.e., wildtype CelA in Table 2A; Variant No. 5 in Table 2B; Variant No. 94 in Table 2C; and Variant No. 264 in Tables 2D and Table 3). Table 2A provides the fold improvement in cellobiase activity for illustrative variants relative to wildtype CelA. The wildtype CelA and variants were prepared in accordance with the method of Example 1. Tables 2B, 2C, and 2D report fold improvement in cellobiase activity for further improved variants relative to Variant 5 ([H145R]CelA, reported in Table 2A), Variant 94 ([N79D+A143M+H145R+V159E+A198S+F211Y]CelA, reported in Table 2B), and Variant 264 ([T2A+I14M+N79D+A143M+H145R+V159E+A198S+F211Y+I223A+S225C+Q508R+A525T]CelA-des[A647-L663], reported in Table 2C), respectively. The native *B. megaterium* penicillin G acylase signal sequence, amino acid residues −1 to −24 of SEQ ID NO: 2, was used in connection with the expression of wildtype CelA and the variants listed in the Tables. The mutations listed in the tables are indicated relative to SEQ ID NO: 4, the wildtype CelA. All of the sequences described in the tables below, including the wildtype CelA, included residues GTS prior to the N-terminus of SEQ ID NO: 4 (prepared as described in Example 1, and shown as amino acid residues 1-3 in SEQ. ID NO: 2), unless otherwise noted.

TABLE 2A

Improved CelA variants derived from the native CelA (SEQ ID NO: 4). These variants were directly compared to native CelA (SEQ ID NO: 4) (expressed from codon optimized CelA, SEQ ID NO: 1) in screening. Assay conditions: 3.3 g/l cellobiose, 50° C. and pH 6.5.

| Sample No. | Amino Acid Substitutions[1] | Silent Mutations[2] | Fold improvement[3] over wildtype CelA |
|---|---|---|---|
| Control Wildtype CelA | | | |
| 1 | G206S | a426g | + |
| 2 | N128K | | + |
| 3 | Q287E | | + |
| 4 | D311G + D532G + T599A | | + |
| 5 | *H145R | t489c | + |
| 6 | A162S | | + |
| 7 | F211Y | | ++ |
| 8 | A162T | | + |
| 9 | A201G | | + |
| 10 | A198M | | + |
| 11 | V159L | | + |
| 12 | A202N | | + |
| 13 | A198C | | + |
| 14 | D146S | | ++ |
| 15 | R151P | | + |
| 16 | A198S | | + |
| 17 | P219M | | + |
| 18 | V159A | | + |
| 19 | A198L | | + |
| 20 | A198N | | + |
| 21 | V159Q | | + |
| 22 | V159I | | + |
| 23 | A202P | | + |
| 24 | P219V | | + |
| 25 | R151P | | + |
| 26 | A202F | | + |
| 27 | A202Y | | + |
| 28 | F211W | | ++ |
| 29 | A201P | | ++ |
| 30 | E155D | | + |
| 31 | A198Q | | + |
| 32 | I222G | | + |
| 33 | V159R | | + |
| 34 | I222S | | + |

TABLE 2A-continued

Improved CelA variants derived from the native CelA (SEQ ID NO: 4). These variants were directly compared to native CelA (SEQ ID NO: 4) (expressed from codon optimized CelA, SEQ ID NO: 1) in screening. Assay conditions: 3.3 g/l cellobiose, 50° C. and pH 6.5.

| Sample No. | Amino Acid Substitutions[1] | Silent Mutations[2] | Fold improvement[3] over wildtype CelA |
|---|---|---|---|
| 35 | A202K | | + |
| 36 | A143M | | + |
| 37 | I195L | | + |
| 38 | A173S | | + |
| 39 | A143Q | | + |
| 40 | A173C | | ++ |
| 41 | S225C | | ++ |
| 42 | I222A | | + |
| 43 | G467Q | | + |
| 44 | F482Y | | + |
| 45 | Q487N | | + |
| 46 | L387R | | + |
| 47 | D475K | | + |
| 48 | N79D | | ++ |
| 49 | Q487D | | + |
| 50 | K629C | | + |
| 51 | D519G | | + |
| 52 | L141I | c1698a | + |
| 53 | I153T | t528c | + |
| 54 | L663Q | | + |
| 55 | S225T | | + |
| 56 | S225F | c747t | + |
| 57 | I222C | | + |
| 58 | E155M | | + |
| 59 | E155Q | | + |
| 60 | E155K | | + |
| 61 | E155A | | + |
| 62 | E155W | | + |
| 63 | R151W | | + |
| 64 | A162V | | + |
| 65 | P219Q | | + |
| 66 | P219E | | + |
| 67 | P219C | | + |
| 68 | P219I | | + |
| 69 | P219T | | + |
| 70 | P219L | | + |
| 71 | A202L | | + |
| 72 | V46F + I222A | | + |
| 73 | I222V | | + |
| 73a | T60Y | | + |
| 73b | A202S | | + |

[1]Amino acid position determined by optimal alignment with SEQ ID NO: 4.
[2]Nucleotide position determined by optimal alignment with SEQ ID NO: 3.
[3]Fold improvement over wildtype CelA (SEQ ID NO: 4) is represented as follows: + = 1.1 to 2.0 fold improvement over native CelA (SEQ ID NO: 4) and ++ = 2.1 to 2.6 fold improvement over native CelA (SEQ ID NO: 4).
*Variant used for comparison of the further improved variants described in Table 2B.

TABLE 2B

Improved CelA variants and comparison to Control #2, Variant No. 5 ([H145R]CelA) (SEQ ID NO: 5, FIG. 3). Assay conditions: 3.3 g/l cellobiose, 55° C. and pH 6.0.

| Variant No. | Amino Acid Substitutions[1] | Silent Mutations[2] | Fold improvement[3] over Control Variant No. 5 from Table 2A |
|---|---|---|---|
| 5 Control #2 | H145R | | |
| 74 | N128K + H145R + A201P + S225C | t489c | ++ |
| 75 | H145R + I222V | t489c | ++ |
| 76 | N128K + H145R | t489c | ++ |
| 77 | H145R + A201P + S225C | t489c | ++ |
| 78 | H145R + S225C | t489c | ++ |
| 79 | N128K + H145R + S225C | t489c | ++ |
| 80 | N128K + H145R + A162T + S225C | t489c | +++ |

TABLE 2B-continued

Improved CelA variants and comparison to Control #2, Variant No. 5 ([H145R]CelA) (SEQ ID NO: 5, FIG. 3). Assay conditions: 3.3 g/l cellobiose, 55° C. and pH 6.0.

| Variant No. | Amino Acid Substitutions[1] | Silent Mutations[2] | Fold improvement[3] over Control Variant No. 5 from Table 2A |
|---|---|---|---|
| 81 | E18R + P23L + E34K + E47K + P70S + H145R + S225C | | ++ |
| 82 | N128K + H145R + D146S + I222A + S225C | a450t + t489c; | +++ |
| 83 | H145R + I222A + S225C + A525T | t489c | +++ |
| 84 | N128K + H145R + I222A | t489c | +++ |
| 85 | N79D + D85N + H145R + F211Y | t489c | ++ |
| 86 | A143M + H145R + A198S + P219M | t489c | ++ |
| 87 | N79D + A143M + H145R + A198S + F211Y | t489c | +++ |
| 88 | N79D + H145R | t489c | ++ |
| 89 | N79D + H145R + A198S + P219V | t489c + t666a | ++ |
| 90 | N79D + H145R + F211Y | t489c | ++ |
| 91 | N79D + A143M + H145R | t489c | +++ |
| 92 | A143M + H145R | t489c | ++ |
| 93 | H145R + F211Y | t489c | ++ |
| 94 | **N79D + A143M + H145R + V159E + A198S + F211Y | t489c | +++ |
| 95 | H145R + V159Q + A198S + F211Y | t489c | ++ |
| 96 | A143M + H145R + V159E + F211Y | t489c + g492t | ++ |
| 97 | A143M + H145R + F211Y + E642A + A643P | t489c + t1923g + a1932c | +++ |
| 98 | T2A + H145R + A162T + A201P + I222A | t111a + t489c; a675t; a1352g | +++ |
| 99 | N128K + H145R + I222S + S225C | t489c; c1437t + a1539g | +++ |
| 100 | N128K + H145R + A201 + I222S + S225C | t489c + t771a + t1065c | +++ |
| 101 | H145R + A162T + I222A + S225C | t489c | +++ |
| 102 | H145R + A162T + S225C + A573S | t489c | ++ |
| 103 | H145R-des[A647-L663] | t489c | ++ |
| 104 | H145R-des[F651-L663] | t489c | ++ |
| 105 | H145R-des[E635-L663] | t489c | ++ |
| 106 | H145R-des[S637-L663] | t489c | ++ |
| 107 | H145R-des[Q645-L663] | t489c | ++ |
| 108 | H145R-des[A641-L663] | t489c | ++ |
| 109 | H145R-des[L663] | t489c | ++ |
| 110 | H145R-des[A643-L663] | t489c | ++ |
| 111 | H145R-des[A653-L663] | t489c | ++ |
| 112 | N79D + N128K + A143M + H145R + V159E + A173C | t489c | +++ |
| 113 | N128K + A143M + H145R + V159Q + A201P + F211Y + S225C | t489c | +++ |
| 114 | N79D + A97T + N128K + A143M + H145R + V159E + A173C + F211Y + Q508R | t249c + t489c | +++ |
| 115 | N79D + N128K + H145R + A163T + A173C + A201P + F211Y + S225C + Q487R + A562P | t489c + a1050g | ++ |
| 116 | N79D + N128K + H145R + A162T + F211Y + S225C + K625Q | t489c + a1221g | +++ |
| 117 | N79D + N128K + H145R + A201P + F213Y | t489c + a798g | +++ |
| 118 | N79D + N128K + A143M + H145R + A162T + A198S + F211Y + I222S + S225C | t489c | +++ |
| 119 | H145R + V159Q + A201P + F211Y + S225C | t489c | +++ |
| 120 | N79D + H145R + A162T + A198S + L663P | t489c + a570g + t1497c; + t1878c | +++ |
| 121 | H145R + D146S + A162T + A173C + A201P | t489c | ++ |
| 122 | N79D + N128K + H145R + V159E + A201P + F211Y + P219V + S225C | t489c | +++ |
| 123 | N79D + N128K + A143M + H145R + A162T + A201P + F211Y + P219V | t489c + g1851a + a1905g | ++ |
| 124 | N79D + H145R + D146S + V159E + A201P + F211Y + S225C + K339R | t489c | +++ |
| 125 | H145R + A201P + I222S + S225C | t489c + t1617c | +++ |
| 126 | N79D + A143M + H145R + A162T + A201P + S225C + Q585R | t489c | ++ |
| 127 | N79D + H145R + D146S + A201P + F211Y + I222S + S225C | t489c | +++ |
| 128 | N79D + N128K + A143M + H145R + V159E + A201P + F211Y + S225C | t489c + t756c + t1575c | +++ |

TABLE 2B-continued

Improved CelA variants and comparison to Control #2, Variant No. 5 ([H145R]CelA) (SEQ ID NO: 5, FIG. 3). Assay conditions: 3.3 g/l cellobiose, 55° C. and pH 6.0.

| Variant No. | Amino Acid Substitutions[1] | Silent Mutations[2] | Fold improvement[3] over Control Variant No. 5 from Table 2A |
|---|---|---|---|
| 129 | N79D + H145R + V159E + A162T + A201P + S225C + I535V | t489c | +++ |
| 130 | A24V + A143M + H145R + V159E + A201P + F211Y + I222S + S225C | t489c + a939t | +++ |
| 131 | N128K + H145R + V159E + A173C | t489c | ++ |
| 132 | N79D + K91Q + N128K + H145R + D146S + A201P + F211Y + I222A + S225C | t489c + a1899g | +++ |
| 133 | N79D + N128K + F135L + A143M + H145R + A162T + A173C + A198S + P219V | t489c | ++ |
| 134 | N128K + A143M + H145R + V159E + A173C + A201P + F211Y + P219V | t489c | ++ |
| 135[4] | N82D + H148R + V162Q + F214Y + S228C | t489c + t528c + a1104g | +++ |
| 136 | N128K + A143M + H145R + V159Q + A198S + F211Y + I222A + S225C + M297I + Q487R | t489c | ++ |
| 137 | N79D + N128K + H145R + A298S + F211Y + P219V + S225C | t489c | +++ |
| 138 | N79D + N128K + H145R + D146S + V159E + F211Y + I222S + S225C | t489c | +++ |
| 139 | A143M + H145R + A162T + F211Y + S225C | t489c | +++ |
| 140 | N79D + A143M + H145R + V159Q + A201P + F211Y + P219V + S225C | t111c + t489c + t1218c | +++ |
| 141 | A143M + H145R + F211Y + P219V + S225C | t489c | +++ |
| 142 | N79D + N128K + H145R + A201P + P219V + K491R | t489c + a861g | +++ |
| 143 | A143M + H145R + A198S + F211Y + S225C | t489c | +++ |
| 144 | N128K + H145R + A162T + A198S + F211Y + P219V + S225C | t489c + t1650c | +++ |
| 145 | N79D + H145R + D146S + V159E + A198S + F211Y + S225C | t489c + g981a | +++ |
| 146 | N79D + A143M + H145R + V159Q + A201P + S225C + K378R | t489c | +++ |
| 147 | N79D + N128K + H145R + A173C + A198S + F211Y + I222S | t489c + c1227t + a1770g | +++ |
| 148 | N79D + H145R + V159E + A198S + S225C | a309g + t489c + a1359g | +++ |
| 149 | N79D + N128K + H145R + D146S + V159Q + A201P + F211Y + S225C | t489c + a1749g | +++ |
| 150 | N79D + I114V + N128K + H145R + A162T + A198S + F211Y + S225C | t489c + a1269g | +++ |
| 151 | A143M + H145R + A162T + A173C + A198S + F211Y + L514Q | t489c | +++ |
| 152 | N79D + H145R + V159Q + A201P + F211Y + I222A + S225C | t489c | +++ |
| 153 | N79D + E92V + N128K + A143M + H145R + A201P + F211Y + I222S + S225C | g33a + t489c | ++ |
| 154 | A143M + H145R + V159Q + A201P + F211Y + I222A + S225C + F229I | t489c | ++ |
| 155 | N79D + H145R + A198S + S225C | a270g + t498c | +++ |
| 156 | N79D + N128K + A143M + H145R + A162T + A198S + I222S + S225C + Q237R | t489c | +++ |
| 157 | N79D + G84A + N128K + H145R + A162T + A198S + F211Y + I223A + S225C | t111c + t489c + a1230g | +++ |
| 158 | N79D + H145R + I166T + A198S + F211Y + S225C | t489c + t1878c | ++ |
| 159 | N79D + H145R + A162T + A198S + S225C | t489c | +++ |
| 160 | H145R + D146S + V159Q + A201P + F211Y + I222A + S225C | t489c | +++ |
| 161 | A143M + H145R + A198S + F213Y + I222A + S225C + Q287R + D609E | t489c | +++ |
| 162 | H145R + A173C + A201P + F211Y + P219V | a151g + t489c + a543t | +++ |
| 163 | N79D + N128K + H145R + D146S + A162T + A173C + A198S + F211Y | t489c | +++ |
| 164 | N79D + N128K + H145R + D146S + S225C | t489c | +++ |
| 165 | A143M + H145R + A201P + S225C | t489c | +++ |

TABLE 2B-continued

Improved CelA variants and comparison to Control #2, Variant No. 5 ([H145R]CelA) (SEQ ID NO: 5, FIG. 3). Assay conditions: 3.3 g/l cellobiose, 55° C. and pH 6.0.

| Variant No. | Amino Acid Substitutions[1] | Silent Mutations[2] | Fold improvement[3] over Control Variant No. 5 from Table 2A |
|---|---|---|---|
| 166 | N79D + H145R + G154V + F211Y + S225C | t489c | +++ |
| 167 | N79D + N128K + H145R | t489c + t1356c | ++ |
| 168 | N128K + H145R + V159Q + A201P + F211Y + I222S + S225C | t489c + a714t | +++ |
| 169 | N79D + H145R + V159Q + A162T + A201P + F211Y + S225C | t489c | +++ |
| 170 | N128K + H145R + D146S + V159E + A201P + F211Y + S225C + A573V | t462a + t489c + a600t | ++ |
| 171 | N79D + H145R + V159E + A198S + F211Y + P219V | t291c + t489c + a1077g | +++ |
| 172 | H145R + V159Q + F211Y + I222S + S225C + G534E | t489c | +++ |
| 173 | I14M + N79D + N128K + H145R + A162T + A201P + F211Y + S225C + Q487R | t489c | +++ |
| 174 | E34D + N79D + N128K + A143M + H145R + V159E + A201P + F211Y | t489c + t1114c | ++ |
| 175 | N79D + H145R + D146S + A198S + F211Y + S225C | t489c + t756a | +++ |
| 176 | E7G + N79D + H145R + D146S + A198S + F211Y + I223S + S225C | t489c | +++ |
| 177 | N128K + A143T + H145R + V159Q + A201P + F211Y + I223S + S225C + E502G | t489c + a702g | ++ |
| 178 | H145R + A198S + F211Y + I222A + S225C + A373T | c36t + t489c + a744g + a1071g + a1179g + a1602c | +++ |
| 179 | N79D + N128K + H145R + A173C + A198S + F211Y | t489c + a615g + a1071g + t1188c | +++ |
| 180 | N79D + N128K + H145R + D146S + S225C + A655T | t489c + t1036c + t1857c | +++ |
| 181 | N128K + A143M + H145R + V159E + F211Y + S225C | t171c + t489c + a1767g | +++ |
| 182 | N79D + I114T + N128K + H145R + V159Q + A173C + A198S + F211Y + P219V | t489c | ++ |
| 183 | N79D + H145R + D146S + A162T + A198S + F211Y + I222A + S225C + D311G + N320K + R358H + F662L | t489c | ++ |
| 184 | N79D + N128K + H145R + D146S + V159Q + A201P + F211Y + P219V + I280V | t489c | +++ |
| 185 | H145R + V159Q + A198S + F211Y + I222A + S225C + P381S | t489c + a885g + t1293c | ++ |
| 186 | N79D + N128K + I134N + H145R + V159Q + S225C | t489c | +++ |
| 187 | N79D + N128K + H145R + V159Q + A198S + I223A + S225C + K627R | t489c | +++ |
| 188 | N79D + N128K + H145R + D146S + A162T + A198S + F211Y | t489c | ++ |
| 189 | H145R + F274K | | ++ |
| 190 | H145R + F274Q | | ++ |
| 191 | H145R + F274A + D436N | | ++ |
| 192 | H145R + F274A | | ++ |
| 193 | H145R + I326S | | ++ |
| 194 | N79D + A143M + H145R + V159E + A198S + A257P + A485P | t489c + a882g | ++ |
| 195 | N79D + A143M + H145R + V159E + A198S + I223S + A257P + T604P | t489c | ++ |
| 196 | N79D + A143M + H145R + V159E + A198S + G570P + T604P | t489c + a1914g | ++ |
| 197 | N79D + A143M + H145R + V159E + A198S + A485P + T604P | t489c | ++ |
| 198 | N79D + A143M + H145R + V159E + A198S + S213P + A485P | t489c + t1254c | ++ |
| 199 | N79D + A143M + H145R + V159E + A198S + S213P + G220V | t489c | ++ |
| 200 | N79D + A143M + H145R + V159E + A198S | t498c | +++ |
| 201 | N79D + A143M + H145R + V159E + A198S + A539V | t489c | ++ |

TABLE 2B-continued

Improved CelA variants and comparison to Control #2, Variant No. 5 ([H145R]CelA) (SEQ ID NO: 5, FIG. 3). Assay conditions: 3.3 g/l cellobiose, 55° C. and pH 6.0.

| Variant No. | Amino Acid Substitutions[1] | Silent Mutations[2] | Fold improvement[3] over Control Variant No. 5 from Table 2A |
|---|---|---|---|
| 202 | N79D + A143M + H145R + V159E + A198S + G570P | t489c | ++ |
| 203 | N79D + A143M + H145R + V159E + A198S + A485P | t489c | ++ |
| 204 | Q26R + N79D + A143M + H145R + V159E + A198S + T604P | t489c | ++ |
| 205 | N79D + A143M + H145R + V159E + A198S + S479A | t489c + a732g | ++ |
| 206 | N79D + A143M + H145R + V159E + A198S + S213P | g93a + t489c | ++ |
| 207 | N79D + A143M + H145R + V159E + A198S + T604P | t489c | ++ |
| 208 | G59R + N79D + A143M + H145R + V159E + A198S | t489c | ++ |
| 209 | N79D + A143M + H145R + V159E + A198S + M331L + A485P | t489c | ++ |
| 210 | N79D + I120V + A143M + H145R + V159E + A198S + Q517L + T604P | t489c | ++ |

[1]Amino acid position determined by optimal alignment with SEQ ID NO: 4.

[2]Nucleotide position determined by optimal alignment with SEQ ID NO: 3.

[3]Fold improvement over Control #2, i.e., Variant No. 2, H145R, (SEQ ID NO: 5, FIG. 3) is represented as follows: ++ = 1.1 to 6 fold improvement over control Variant No. 2 and +++ = 6 to 13 fold improvement over control Variant No. 2.

[4]This sequence had the sequence GAS preceding the N-terminus (instead of GTS) relative to SEQ ID NO: 4.

**Variant used for comparison of the further improved variants described in Table 2C.

TABLE 2C

Improved CelA variants and comparison to Control #3, Variant 94 ([N79D + A143M + H145R + V159E + A198S + F211Y]) (SEQ ID NO: 6, FIG. 4). Assay conditions: 3.3 g/l cellobiose, 55° C. and pH 5.3 (incubation overnight).

| Variant No. | Amino Acid Mutations[1] | Silent Mutations[2] | Fold improvement[3] over Control Variant No. 94 from Table 2B |
|---|---|---|---|
| 94 Control #3 | N79D + A143M + H145R + V159E + A198S + F211Y | t489c | |
| 211 | A12R + N79D + A143M + H145R + V159E + A198S + F211Y | t489c | +++ |
| 212 | A13P + N79D + A143M + H145R + V159E + A198S + F213Y-des[P641-L663] | t489c | ++++ |
| 213 | A10G + N79D + A143M + H145R + V159E + A198S + F211Y-des[P641-L663] | t489c | ++++ |
| 214 | A3L + N79D + A143M + H145R + V159E + A198S + F211Y-des[P641-L663] | t489c | ++++ |
| 215 | A10P + N79D + A143M + H145R + V159E + A198S + F211Y-des[P641-L663] | t489c | ++++ |
| 216 | I14T + N79D + A143M + H145R + V159E + A198S + F211Y-des[P641-L663] | t489c | ++++ |
| 217 | A10S + N79D + A143M + H145R + V159E + A198S + F211Y-des[P641-L663] | t489c | ++++ |
| 218 | A3N + N79D + A143M + H145R + V159E + A198S + F211Y | t489c | +++ |
| 219 | G8P + N79D + A143M + H145R + V159E + A198S + F211Y | t489c | +++ |
| 220 | A10N + N79D + A143M + H145R + V159E + A198S + F211Y | t489c | +++ |
| 221 | A9T + N79D + A143M + H145R + V159E + A198S + F211Y | t489c | +++ |
| 222 | A5T + N79D + A143M + H145R + V159E + A198S + F211Y-des[P641-L663] | t489c | ++++ |

TABLE 2C-continued

Improved CelA variants and comparison to Control #3, Variant 94 ([N79D + A143M + H145R + V159E + A198S + F211Y]) (SEQ ID NO: 6, FIG. 4). Assay conditions: 3.3 g/l cellobiose, 55° C. and pH 5.3 (incubation overnight).

| Variant No. | Amino Acid Mutations[1] | Silent Mutations[2] | Fold improvement[3] over Control Variant No. 94 from Table 2B |
|---|---|---|---|
| 223 | Q6D + N79D + A143M + H145R + V159E + A198S + F211Y-des[P641-L663] | t489c | ++++ |
| 224 | I4P + N79D + A143M + H145R + V159E + A198S + F211Y | t489c | ++++ |
| 225 | G8Y + N79D + A143M + H145R + V159E + A198S + F211Y-des[P641-L663] | t489c | ++++ |
| 226 | E7H + N79D + A143M + H145R + V159E + A198S + F211Y | t489c | +++ |
| 227 | G8S + N79D + A143M + H145R + V159E + A198S + F211Y-des[P641-L663] | t489c | ++++ |
| 228 | G8R + N79D + A143M + H145R + V159E + A198S + F211Y-des[P641-L663] | t489c | ++++ |
| 229 | Q6T + N79D + A143M + H145R + V159E + A198S + F211Y-des[P641-L663] | t489c | ++++ |
| 230 | A12N + N79D + A143M + H145R + V159E + A198S + F211Y-des[P641-L663] | t489c | ++++ |
| 231 | P13E + N79D + A143M + H145R + V159E + A198S + F211Y-des[P641-L663] | t489c | ++++ |
| 232 | A3P + N79D + A143M + H145R + V159E + A198S + F213Y des[P641-L663] | t489c | ++++ |
| 233 | A5N + N79D + A143M + H145R + V159E + A198S + F211Y des[P641-L663] | t489c | ++++ |
| 234 | Q6P + N79D + A143M + H145R + V159E + A198S + F211Y des[P641-L663] | t489c | ++++ |
| 235 | A3R + N79D + A143M + H145R + V159E + A198S + F211Y des[P641-L663] | t489c | ++++ |
| 236 | Q6S + N79D + A143M + H145R + V159E + A198S + F211Y | t489c | +++ |
| 237 | A12Y + N79D + A143M + H145R + V159E + A198S + F211Y des[P641-L663] | t489c | ++++ |
| 238 | Q6G + N79D + A143M + H145R + V159E + A198S + F211Y | t489c | +++ |
| 239 | A9I + N79D + A143M + H145R + V159E + A198S + F213Y des[P641-L663] | t489c | ++++ |
| 240 | G8A + N79D + A143M + H145R + V159E + A198S + F211Y des[P641-L663] | t489c | ++++ |
| 241 | Q6A + N79D + A143M + H145R + V159E + A198S + F211Y des[P641-L663] | t489c | ++++ |
| 242 | E7P + N79D + A143M + H145R + V159E + A198S + F213Y | t489c | +++ |
| 243 | A5L + N79D + A143M + H145R + V159E + A198S + F211Y | t489c | +++ |
| 244 | P11A + N79D + A143M + H145R + V159E + A198S + F211Y des[P641-L663] | t489c | ++++ |
| 245 | I14R + N79D + A143M + H145R + V159E + A198S + F211Y | t489c | +++ |
| 246 | I4R + N79D + A143M + H145R + V159E + A198S + F211Y | t489c | +++ |
| 247 | A9G + N79D + A143M + H145R + V159E + A198S + F211Y | t489c | ++++ |
| 248 | Q6N + N79D + A143M + H145R + V159E + A198S + F211Y des[P641-L663] | t489c | ++++ |
| 249 | A9K + N79D + A143M + H145R + V159E + A198S + F211Y des[P641-L663] | t489c | ++++ |
| 250 | A5Y + N79D + A143M + H145R + V159E + A198S + F211Y des[P641-L663] | t489c | ++++ |

TABLE 2C-continued

Improved CelA variants and comparison to Control #3, Variant 94 ([N79D + A143M + H145R + V159E + A198S + F211Y]) (SEQ ID NO: 6, FIG. 4). Assay conditions: 3.3 g/l cellobiose, 55° C. and pH 5.3 (incubation overnight).

| Variant No. | Amino Acid Mutations[1] | Silent Mutations[2] | Fold improvement[3] over Control Variant No. 94 from Table 2B |
|---|---|---|---|
| 251 | I14M + N79D + K91Q + H145R + G154V + V159E + A198S + A201P + F211Y + S225C + A525T + K627R | a429g + t489c + a555g | +++ |
| 252 | I14M + N79D + K91Q + A143M + H145R + V159E + A198S + F211Y + I222A + Q508R + A525T + K627R-des[S637-L663] | t489c + a555g | +++ |
| 253 | I14M + N79D + K91Q + A143M + H145R + V159E + A198S + F211Y + Q508R-des[A647-L663] | t489c + 528c + a555g | ++++ |
| 254 | N79D + K91Q + H145R + V159E + A198S + A201P + F211Y + I222S + Q508R + A525T-des[S637-L663] | a429g + t489c + a555g | +++ |
| 255 | I14M + N79D + H145R + V159E + A198S + A201P + F211Y + S225C + A525T + K583R + K627R + L663P | a429g+ t489c + a555g | ++++ |
| 256 | T2A + I14M + N79D + K91Q + A143M + H145R + V159E + A198S + A201P + F211Y + S225C + A525T-des[S637-L663] | t489c + a555g + a1473g | +++ |
| 257 | I14M + N79D + K91Q + A143M + H145R + G154V + V159E + A198S + A201P + F211Y + S225C + Q508R + A525T-des[S637-L663] | a96g + t489c + a555g | +++ |
| 258 | T2A + I14M + N79D + K91Q + A143M + H145R + V159E + A198S + A201P + F211Y + I222A + S225C + A525T + Y594H + K627R-des[A647-L663] | t489c + a555g + a1914g | +++ |
| 259 | I14M + N79D + K91Q + H145R + V159E + A198S + F211Y + I222A + S225C + Q508R + K627R | a429g + t489c + a555g | +++ |
| 260 | T2A + I14M + N79D + K91Q + A143M + H145R + V159E + A198S + A201P + F211Y + S225C + L663P | t489c + a555g | +++ |
| 261 | I14M + N79D + A143M + H145R + V159E + A198S + F211Y + K627R + L663P | t498c + a555g | +++ |
| 262 | I14M + N79D + H145R + G154V + V159E + A198S + A201P + F211Y + S225C + Q508R + A525T + K627R-des[S637-L663] | a429g + t489c; +a555g + g654c | +++ |
| 263 | T2A + I14M + N79D + K91Q + H145R + V159E + A162S + A198S + A201P + F211Y + I222S + S225C + Q508R + A525T + K627R + L663P | a429g + t489c + a555g | +++ |
| 264 | ***T2A + I14M + N79D + A143M + H145R + V159E + A198S + F211Y + I222A + S225C + Q508R + A525T-des[A647-L663] | t489c + a555g | +++ |
| 265 | T2A + N79D + K91Q + H145R + V159E + A198S + F211Y + S225C + Q508R + L663P | a429g + t49c + a555g | ++++ |
| 266 | T2A + I14M + N79D + K91Q + H145R + V159E + A198S + A201P + F211Y + I222A + S225C + L514Q + K627R-des[S637-L663] | a429g + t489c + a565g | +++ |
| 267 | T2A + I14M + N79D + A143M + H145R + V159E + A198S + A201P + F211Y + I222A + S225C-des[A647-L663] | t489c + a555g | +++ |
| 268 | I14M + N79D + K91Q + H145R + V159E + A198S + F211Y + S225C + Q508R-des[S637-L663] | a429g + 489c + a555g | ++++ |
| 269 | N79D + A143M + H145R + V159E + A198S + V207Y + F211Y | t489c | +++ |
| 270 | N79D + G127N + A143M + H145R + V159E + A198S + F211Y | t489c | +++ |
| 271 | N79D + A143M + H145R + V159E + A198S + V207F + F211Y | t4898c | +++ |

TABLE 2C-continued

Improved CelA variants and comparison to Control #3, Variant 94 ([N79D + A143M + H145R + V159E + A198S + F211Y]) (SEQ ID NO: 6, FIG. 4). Assay conditions: 3.3 g/l cellobiose, 55° C. and pH 5.3 (incubation overnight).

| Variant No. | Amino Acid Mutations[1] | Silent Mutations[2] | Fold improvement[3] over Control Variant No. 94 from Table 2B |
|---|---|---|---|
| 272 | N79D + A143M + H145R + V159E + A198S + V207L + F211Y | t489c | +++ |
| 273 | N79D + P109D + A143M + H145R + V159E + A198S + F211Y | t489c | +++ |
| 274 | N79D + A143M + H145R + V159E + M161T + A198S + F211Y | t489c | +++ |
| 275 | I14M + N79D + K91Q + H145R + V159E + A198S + F211Y + I223S + S225C + Q509R + A525T + L663P | a419g + t489c + a555g | ++++ |
| 276 | T2A + I14M + N79D + H145R + V159E + A198S + A201P + V207I + F213Y + S225C + Q508R + K627R + L663P | a419g + t489c + a564g | ++++ |
| 277 | I14M + N79D + K91Q + N128K + H145R + V159E + A198S + F211Y + I222A + Q508R | a429g + t489c + a55g | ++++ |
| 278 | I14M + N79D + A143M + H145R + V159E + A198S + A201P + F211Y + Q508R + A525T + K627R-des[A647-L663] | t489c + a555g + a1812g | ++++ |
| 279 | I14M + N79D + K91Q + A143M + H145R + V159E + A198S + F211Y + A525T + K627R-des[S637-L663] | t489c + a555g | +++ |
| 280 | T2A + N79D + K91Q + H145R + V159E + A198S + A201P + F211Y + S225C + D236G + K627R-des[A647-L663] | a429g + t489c + a555g | ++++ |
| 281 | N79D + K91Q + H145R + V159E + A198S + F211Y + S225C + Q508R + A525T | a429g + t489c + a555g | ++++ |
| 282 | N79D + A143M + H145R + V159E + A198S + F211Y + I246C | t489c | ++++ |
| 283 | N79D + A143M + H145R + V159E + A198S + F211Y + V371M-des[P641-L663] | t489c | ++++ |
| 284 | N79D + A143M + H145R + V159E + A198S + F211Y + G298R + D311E | t489c | ++++ |
| 285 | N79D + A143M + H145R + V159E + A198S + F211Y + G386E-des[P641-L663] | t489c | ++++ |
| 286 | N79D + A143M + H145R + V159E + A198S + F211Y + A357S | t489c | +++ |
| 287 | N79D + A143M + H145R + V159E + A198S + F211Y + D311G | t489c | ++++ |
| 288 | N79D + A143M + H145R + V159E + A198S + F211Y + L372W | t489c | +++ |
| 289 | N79D + A143M + H145R + V159E + A198S + F211Y + P379G | t489c | +++ |

[1]Amino acid position determined by optimal alignment with SEQ ID NO: 4.

[2]Nucleotide position determined by optimal alignment with SEQ ID NO: 3.

[3]Fold improvement over Control #3, Variant No. 94, N79D + A143M + H145R + V159E + A198S + F211Y (SEQ ID NO: 6), is depicted as follows: ++++ = 1.1 to 1.5 fold improvement over Control No. 3, Variant No. 94 and +++++ = 1.6 to 3.0 fold improvement over Control No. 3, Variant No. 94.

***Variant used for comparison of the further improved variants described in Table 2D.

TABLE 2D

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| 264 Control #4 | T2A + I14M + N79D + A143M + H145R + V159E + A198S + F211Y + I222A + S225C + | t489c + a555g | |

TABLE 2D-continued

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| | Q508R + A525T-des[A647-L663] | | |
| 290 | T2A + I14M + N79D + A143M + H145R + P147K + V159E + A198S + F211Y + I222A + S225C + Q508R + A525T-des-[A647-L663] | t489c + a555g | ++++ |
| 291 | T2A + I14M + N79D + A143M + H145R + V159E + A198S + F211Y + I222A + S225C + E377D + Q508R + A525T-des-[A647-L663] | t489c + a555g | ++++ |
| 292 | T2A + I14M + N79D + A143M + H145R + P147T + V159E + A198S + F211Y + I222A + S225C + Q508R + A525T-des-[A647-L663] | t489c + a555g | ++++ |
| 293 | T2A + I14M + N79D + A143M + H145R + V159E + A198S + F211Y + M217L + I222A + S225C + Q508R + A525T-des-[A647-L663] | t489c + a555g | ++++ |
| 294 | T2A + I14M + N79D + A99K + A143M + H145R + V159E + A198S + F211Y + I222A + S225C + Q508R + A525T-des-[A647-L663] | t489c + a555g | ++++ |
| 295 | T2A + I14M + N79D + A99R + A143M + H145R + V159E + A198S + F211Y + I222A + S225C + Q508R + A525T-des-[A647-L663] + | t489c + a555g | ++++ |
| 296 | T2A + I14M + D30E + N79D + A143M + H145R + V159E + A198S + F211Y + I222A + S225C + Q508R + A525T-des-[A647-L663] | g99a + t489c + a5554g | ++++ |
| 297 | T2A + I14M + N79D + A143M + H145R + P147L + V159E + A198S + F211Y + I222A + S225C + Q508R + A525T-des-[A647-L663] | t489c + a555g | ++++ |
| 298 | T2A + I14M + N79D + A143M + H145R + V159E + A198S + F211Y + I222A + S225C + A347K + Q508R + A525T-des-[A647-L663] | t489c + a555g | ++++ |
| 299 | T2A + I14M + N79D + N83H + A143M + H145R + V159E + A198S + F211Y + I223A + S225C + Q508R + A525T-des-[A647-L663] | t489c + a555g | ++++ |
| 300 | T2A + I14M + N79D + A143M + H145R + V159E + A198S + F211Y + I223A + S225C + R455T + Q508R + A525T-des-[A647-L663] | t489c + a555g | ++++ |
| 301 | T2A + I14M + N79D + A143M + H145R + V159E + A198S + F211Y + I222A + S225C + E502N + Q508R + A525T-des-[A647-L663] | t489c + a555g | ++++ |
| 302 | T2A + I14M + N79D + N128H + A143M + H145R + V159E + A198S + F213Y + I222A + S225C + Q508R + A525T-des-[A647-L663] | t489c + a555g | +++++ |
| 303 | T2A + I14M + S73A + N79D + A143M + H145R + V159E + | t489c + a555g | ++++ |

TABLE 2D-continued

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| | A198S + F211Y + I222A + S225C + Q508R + A525T-des-[A647-L663] | | |
| 304 | T2A + I14M + N79D + A143M + H145R + V159E + A298S + I203Y + F211Y + I223A + S225C + Q508R + A525T-des-[A647-L663] | t489c + a555g + a606g | ++++ |
| 305 | T2A + I14M + N79D + A143M + H145R + V159E + A198S + I203H + F211Y + I222A + S225C + Q508R + A525T-des-[A647-L663] | t489c + a555g + a60tg + a62t | ++++ |
| 306 | T2A + I14M + N79D + A143M + H145R + V159E + A198S + V204I + F211Y + I222A + S225C + Q508R + A525T-des-[A647-L663] | t498c + a564g | ++++ |
| 307 | T2A + I14M + N79D + A143M + H145R + V159E + A198S + I203F + F211Y + I222A + S225C + Q508R + A525T-des-[A647-L663] | t489c + a555g + a606g + | ++++ |
| 308 | T2A + I14M + N79D + A143M + H145R + V159E + V177P + A198S + F211Y + I222A + S225C + Q508R + A525T-des-[A647-L663] | t489c + a555g | ++++ |
| 309 | T2A + I14M + N79D + A143M + H145R + V159E + A198S + F211Y + I222A + S225C + Q508R + A525T + T603F-des-[A647-L663] | t489c + a555g | ++++ |
| 310 | T2A + I14M + N79D + A143M + H145R + V159E + A198S + F211Y + I222A + S225C + Q508R + A525T + T603Y-des-[A647-L663] | t489c + a555g | ++++ |
| 311 | T2A + I14M + N79D + A143M + H145R + V159E + A198S + F211Y + I222A + S225C + Q508R + A525T + L553M-des-[A647-L663] | t489c + a555g | ++++ |
| 312 | T2A + E7P + A9G + A10N + I14M + N79D + N128K + A143M + H145R + V159E + A198S + F211Y + I223A + S225C + Q508R + A525T-des-[A647-L663] | t135c + t417c + t489c + a555g | +++++ |
| 313 | T2A + A9G + A10N + I14M + N79D + N128K + A143M + H145R + V159E + A198S + F211Y + I222A + S225C + Q508R + A525T-des-[A647-L663] | t489c + a555g | +++++ |
| 314 | T2A + Q6P + E7P + A9G + I14M + N79D + N128K + A143M + H145R + V159E + A198S + F211Y + I222A + S225C + Q508R + A525T-des-[A647-L663] | t30c + t222c + t489c + a555g + t585c | +++++ |
| 315 | T2A + Q6P + A9K + A10N + I14M + N79D + N128K + A143M + H145R + V159E + A198S + F211Y + I222A + S225C + Q508R + A525T-des-[A647-L663] | t489c + a555g | +++++ |
| 316 | T2A + Q6P + A10N + I14M + N79D + N128K + A143M + | a27t + t489c + a555g | +++++ |

TABLE 2D-continued

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| | H145R + V159E + A198S + F211Y + I222A + S225C + Q508R + A525T-des-[A647-L663] | | |
| 317 | T2A + Q6P + I14M + N79D + N128K + A143M + H145R + V159E + A198S + F211Y + I223A + S225C + Q508R + A525T-des-[A647-L663] | a27t + t30c + t489c + a555g + a1353g | ++++ |
| 318 | T2A + Q6P + E7P + I14M + N79D + N128K + A143M + H145R + V159E + A198S + F211Y + I222A + S225C + Q508R + A525T-des-[A647-L663] | a30t + t328c + t489c + a555g + a1506g | ++++ |
| 319 | T2A + E7P + A9K + A10N + I14M + N79D + N128K + A143M + H145R + R152S + V159E + A198S + F211Y + I222A + S225C + Q508R + A525T-des-[A647-L663] | t489c + a555g | ++++ |
| 320 | T2A + A9G + I14M + N79D + N128K + A143M + H145R + V159E + A198S + F211Y + I222A + S225C + Q508R + A525T-des-[A647-L663] | t30c + t489c + a555g + a702g | ++++ |
| 321 | T2A + I14M + N79D + N128K + A143M + H145R + V159E + A198S + F211Y + I222A + S225C + Q508R + A525T-des-[A647-L663] | t489c + a555g | +++++ |
| 322 | T2A + Q6P + I14M + N79D + A143M + H145R + V159E + A198S + F211Y + M217V + I222A + S225C + D311G + Q508R + A525T-des-[A647-L663] | a27t + t33c + t489c + a555g + t951c | ++++ |
| 323 | T2A + I14M + I61V + N79D + G127N + A143M + H145R + V159E + A198T + F211Y + I222A + S225C + Q508R-des-[A647-L663] | t489c + a555g + t1371c + t1575g | +++++ |
| 324 | T2A + A5T + A13P + I14M + N79D + N128K + A143M + H145R + V159E + A198S + F211Y + I222A + S225C + Q508R + A525T-des-[A647-L663] | t489c + a555g + t1575g + t1623c + t1674a | +++++ |
| 325 | T2A + I14M + N79D + N128K + A143M + H145R + V159E + M161V + A198S + V208L + F211Y + S225C + Q508R + A525T + I535V + N646K-des[A647-L663] | t489c + a555g + t575c | +++++ |
| 326 | T2A + A13P + I14M + N79D + A143M + H145R + V159E + A198S + V207F + F211Y + I222A + S225C + Q508R + A525T-des-[A647-L663] | t417c + t489c + a555g + t1062a | +++++ |
| 327 | T2A + I14M + N79D + G128N + A143M + H145R + V159E + A198S + V207I + F211Y + I222A + S225C + Y342C + Q508R + A525T + K583N + P634S-des-[A647-L663] | t489c + a555g | ++++ |
| 328 | T2A + A5T + I14M + N879 + G127N + A143M + H145R + V159E + M161V + A198S + | t489c + a555g + t1821g | +++++ |

TABLE 2D-continued

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| | F211Y + I222A + S225C + Q508R + A525T-des[A647-L663] | | |
| 329 | T2A + I14M + N79D + A143M + H145R + V159E + M161V + A198S + V207Y + F211Y + S225C + I354T + Q508R-des-[A647-L663] | g99a + t489c + a555g + t1575g | +++++ |
| 330 | T2A + I14M + N79D + A143M + H145R + V159E + A198S + V207Y + F211Y + I222A + S225C + Q508R + A525T-des-[A647-L663] | t489c + a555g | +++++ |
| 331 | T2A + A5T + A13P + I14M + N79D + G127N + N128K + A143M + H145R + V159E + M161V + A198S + F211Y + S225C + Q508R + A525T + F577L-des[A647-L663] | t489c + a555g | ++++ |
| 332 | T2A + I4S + I14M + N79D + A143M + H145R + V159E + A198S + V207F + F211Y + I222A + S225C + Q508R + A525T-des[A647-L663] | t489c + a555g + a1431g | +++++ |
| 333 | T2A + I4S + I14M + N79D + A143M + H145R + V159E + A198S + V207F + F211Y + I222A + S225C + Q508R + A525T-des[A647-L663] | t489c + a555g + a1431g | +++++ |
| 334 | T2A + A9E + I14M + L66Q + N79D + A143M + H145R + V159E + M161V + A198S + V207L + F211Y + S225C + Q508R + A525T-des[A647-L663] | t4489c + a555g | ++++ |
| 335 | T2A + A9G + I14M + N79D + P109D + G127N + A143M + H145R + G154V + V159E + A198S + V207F + F211Y + I222A + S225C + A525T-des[A647-L663] | t489c + a555g + t1356c | +++++ |
| 336 | T2A + I14M + N79D + G127N + N128K + A143M + H145R + V159E + M161V + A198S + V207L + F211Y + S225C + Q508R + A525T-des-[A647-L663] | t489c + g513a + a555g | +++++ |
| 337 | T2A + I14M + N79D + A143M + H145R + V159E + A198S + F211Y + I222A + S225C + Q508R-des[A647-L663] | t282c + t489c + a555g + t1575g | ++++ |
| 338 | T2A + A5T + A13P + I14M + N79D + P109D + A143M + H145R + V159E + A198S + V207L + F211Y + I222A + S225C + Q508R-des[A647-L663] | t489c + a555g + t1575g | +++++ |
| 339 | T2A + A3R + I14M + N79D + P109D + G127N + A143M + H145R + V159E + M161V + A198S + V207F + F211Y + I222A + S225C + Q508R-des[A647-L663] | t489c + a555g + t1575g | +++++ |
| 340 | T2A + A9G + I14M + N79D + G127N + N128K + A143M + H145R + V159E + A198S + V207F + F211Y + I222A + S225C + Q508R + A525T + | t489c + a555g + c1419 | +++++ |

TABLE 2D-continued

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| | Q533L + E636D-des[A647-L663] | | |
| 341 | T2A + A5T + I14M + N79D + G127N + A143M + H145R + V159E + A198S + F211Y + I222A + S225C + Q508R + A525T-des[A647-L663] | t69c + g72a + t489c + a555g + t1620c | +++++ |
| 342 | T2A + A3R + A9G + I14M + N79D + A143M + H145R + V159E + M161V + A198S + V207Y + F211Y + S225C + Q508R + A525T-des[A647-L663] | t489c + a555g | +++++ |
| 343 | T2A + I14M + N79D + N128K + A143M + H145R + V159E + A198S + V207Y + F211Y + I222A + S225C + Q508R + A525T + K583N-des[A647-L663] | t417c + t489c + a2g | +++++ |
| 344 | T2A + I14M + N79D + F118S + A143M + H145R + V159E + A198S + F211Y + I222A + S225C + L390P + Q508R + A525T-des[A647-L663] | c303t + t489c + a555g | ++++ |
| 345 | T2A + I14M + N79D + A143M + H145R + V159E + M161V + A198S + V207Y + F211Y + I222A + S225C + A525T + N646K-des[A647-L663] | t489c + a555g | +++++ |
| 346 | T2A + A13P + I14M + N79D + G127N + N128K + A143M + H145R + V1659 + A198S + V207F + F211Y + I222A + S225C + Q508R + A528T-des[A647-L663] | t489c + a555g + a1635g | +++++ |
| 347 | T2A + I14M + N79D + G127N + A143M + H145R + V159E + A198S + F211Y + I222A + S225C + Q508R + A525T-des[A647-L663] | t4c + a555g | +++++ |
| 348 | T2A + I14M + N79D + A143M + H145R + V159E + M161V + A198S + V207L + F211Y + I222A + S225C + Q508R-des[A647-L663] | t489c + a555g + a1398g + t1575g | +++++ |
| 349 | T2A + A5T + A9G + I14M + N79D + P89S + P109D + G127N + A143M + H145R + V159E + A198S + V207Y + F211Y + I222A + S225C + Q508R + A525T-des[A647-L663] | t489c + a555g | +++++ |
| 350 | T2A + A9G + A13P + I14M + N79D + G127N + A143M + H145R + V159E + A198S + F211Y + I222A + S225C + A525S-des[A647-L663] | t489c + a555g | +++++ |
| 351 | T2A + A9G + I14M + N79D + G127N + A143M + H145R + V159E + A198S + V207Y + F211Y + I222A + S225C + Q508R + A525T-des[A647-L663] | t489c + a555g | +++++ |
| 352 | T2A + A5T + A9G + I14M + N79D + G127N + N128K + A143M + H145R + V159E + A198S + V207Y + F211Y + | t417c + t53c + 5666g | +++++ |

TABLE 2D-continued

Improved CelA truncated variants and comparison to Variant 264 (T2A + I14M + N79D + A143M + H145R + V159E + A198S + F211Y + I222A + S225C + Q508R + A525T]CelA-des[A647-L663]) (SEQ ID NO: 7, FIG. 5). All variants in this table were truncated after N646. Assay conditions: 3.3 g/l cellobiose, 55° C. and pH 5.2.

| Variant No. | Amino Acid Mutations[1] | Silent Mutations[2] | Fold improvement[3] over Control Variant No. 264 from Table 1C |
|---|---|---|---|
| | I222A + S225C + Q508R + A525T-des[A647-L663] | | |
| 353 | T2A + I14M + N79D + A143M + H145R + V159E + A198S + V207F + F211Y + I222A + S225C + Q508R + A525T-des[A647-L663] | t489c + a555g + a13433g | +++++ |
| 354 | T2A + A13P + I14M + N79D + A143M + H145R + V159E + A198S + V207F + F211Y + I222A + S225C + Q508R + A525T + N646K-des[A647-L663] | t489c + a555g | +++++ |
| 355 | T2A + I14M + N79D + A143M + H145R + V159E + M161V + A198S + F211Y + S225C + Q508R-des[A647-L663] | a366g + t489c + a555g + c735t + t1575g | +++++ |

[1]Amino acid position determined by optimal alignment with SEQ ID NO: 4.

[2]Nucleotide position determined by optimal alignment with SEQ ID NO: 3.

[3]Fold improvement over Control #4, Variant No. 264, T2A + I14M + N79D + A143M + H145R + V159E + A198S + F211Y + I222A + S225C + Q508R + A525T]CelA-des[A647-L663] (SEQ ID NO: 7, FIG. 5), is depicted as follows: ++++ = 1.1 to 3.0 fold improvement over Control #4, Variant 264 and +++++ = 3.1 to 12.0 fold improvement over Control #4, Variant 264.

Further variants were prepared as described using the method of Example 1, except the polynucleotide encoding the CelA variant was cloned behind a variant of the *Bacillus megaterium* signal peptide. Mutations in the variant signal peptide sequences and the catalytic CelA domain sequences are described below in Table 3 and are indicated relative to FIG. 1B (signal peptide sequence) and SEQ ID NO: 4 (the wildtype CelA catalytic CelA domain), respectively. As with the sequences described in the tables above, the sequences in Table 3 included residues GTS prior to the N-terminus of SEQ ID NO: 4 (prepared as described in Example 1). Fold improvement was determined as described in Example 7 (with assay conditions indicated below), and is reported relative to Variant No. 264, [T2A+I14M+N79D+A143M+H145R+V159E+A198S+F211Y+I222A+S225C+Q508R+A525T] CelA-des[A647-L663] (SEQ ID NO: 7).

TABLE 3

Signal Peptide and CelA Variants. Assay conditions: 3.3 g/l cellobiose, 55° C. and pH 5.2 (incubation overnight).

| CelA Variant No. | Mutations in Signal Peptide | Amino Acid Mutations in CelA[1] | Silent Mutations[2] | Fold Improvement[3] over Control Variant No. 264 from Table 2C |
|---|---|---|---|---|
| 356 | F-8E[4] | T2A + I14M + N79D + A143M + H145R + V159E + A198S + F211Y + I223A + S225C + Q508R + A525T + Q585R-des[A647-L663] | t489c + t501c + a555g | ++++ |
| 357 | L-19Q[4] | T2A + A9K + I14M + N79D + K107R + N128K + A143M + H145R + V159E + A198S + F211Y + I222A + S225C + Q508R + A525T-des[A647-L663] | t30c + t489c + a555g | +++++ |
| 358 | F-8E[4] | T2A + A9K + A10N + I14M + N79D + A143M + H145R + V159E + A198S + F211Y + I222A + S225C + Q508R + A525T-des[A647-L663] | a147g + a471g + t489c + a555g | ++++ |
| 359 | c-46g[5] (silent mutation) | T2A + E7P + A10N + I14M + N79D + A143M + H145R + V159E + A198S + F211Y + I222A + S225C + M356T + | a27t + t489c + a555g | ++++ |

TABLE 3-continued

Signal Peptide and CelA Variants. Assay conditions: 3.3 g/l cellobiose, 55° C. and pH 5.2 (incubation overnight).

| CelA Variant No. | Mutations in Signal Peptide | Amino Acid Mutations in CelA[1] | Silent Mutations[2] | Fold Improvement[3] over Control Variant No. 264 from Table 2C |
|---|---|---|---|---|
| | | Q508R + A525T + H586Y-des[A647-L663] | | |
| 360 | F-8E[4] | T2A + E7P + A9G + A10N + I14M + N79D + A143M + H145R + V159E + A198S + F211Y + I222A + S225C + Q508R + A525T-des[A647-L663] | t489c + a555g + a1173g + g1728a | ++++ |
| 361 | F-8E[4] | T2A + I14M + N79D + A143M + H145R + V159E + A198S + F211Y + I222A + S225C + Q508R + A525T-des[A647-L663] | t32c + t489c + a555g | ++++ |
| 362 | F-8E[4] | T2A + Q6P + E7P + A9G + A10N + I14M + N79D + A143M + H145R + V159E + A198S + F211Y + I222A + S225C + Q508R + A525T-des[A647-L663] | t489c + a555g + a1350g | ++++ |
| 363 | F-10T[4] | T2A + I14M + N79D + G127N + N128K + A143M + H145R + V159E + A198S + V207F + F211Y + I222A + S225C + I366T + Q508R-des[A647-L663] | t489c + a555g + t1575g | +++++ |
| 364 | F-10T[4] | T2A + A3R + A5T + A9G + A13P + I14M + L44S + N79D + G127N + A143M + H145R + V159E + A198S + V207Y + F211Y + I222A + S225C + Q508R + P518Q + D519N + A525T-des[A647-L663] | t489c + a555g + a1899t | +++++ |
| 365 | F-10T[4] | T2A + I14M + N79D + A143M + H145R + V159E + A198S + V207F + F211Y + I222A + S225C + Q508R + A525T + A600V-des[A647-L663] | t489c + a555g | +++++ |
| 366 | F-10T[4] | ****T2A + A5T + I14M + N79D + G127N + A143M + H145R + V159E + A198S + V207F + F211Y + I222A + S225C + Q508R + A525T-des[A647-L663] | t489c + a555g | +++++ |
| 367 | F-10T[4] | T2A + I14M + N79D + G127N + A143M + H145R + G154V + V159E + A198S + V207Y + F211Y + I222A + S225C + Q508R + A525T-des[A647-L663] | t489c + a555g + a114g | +++++ |
| 368 | F-10T[4] | T2A + I14M + N79D + A143M + H145R + V159E A198S + F211Y + I222A + S225C + F274S + Q508R-des[A647-L663] | t489c + t510c + a555g + a741g + t1575g | ++++ |
| 369 | F-10T[4] | T2A + A9G + I14M + N79D + G127S + A143M + H145R + V159E + A198S + F211Y + I222A + S225C + Q508R + A525T-des[A647-L663] | t489c + a555g + a879g + a1566g | +++++ |
| 370 | F-10T[4] | T2A + A9G + A13P + I14M + N79D + P109D + N128K + A143M + H145R + V159E + A198S + V207I + F211Y + S225C + S247P + Q508R + A525S-des[A647-L663] | t489c + a555g + t1218c | ++++ |
| 371 | F-10T[4] | T2A + I14M + N79D + A143M + H145R + V159E + A198S + V207Y + F211Y + I222A + S225C + Q508R + | t489c + a555g + t1653c | +++++ |

TABLE 3-continued

Signal Peptide and CelA Variants. Assay conditions: 3.3 g/l cellobiose, 55° C. and pH 5.2 (incubation overnight).

| CelA Variant No. | Mutations in Signal Peptide | Amino Acid Mutations in CelA[1] | Silent Mutations[2] | Fold Improvement[3] over Control Variant No. 264 from Table 2C |
|---|---|---|---|---|
| | | A525T + D611E-des[A647-L663] | | |
| 372 | F-10T[4] | T2A + I14M + N79D + A143M + H145R + V159E + M161V + A198S + V207Y + F211Y + I222A + S225C + Q508R + A525T-des[A647-L663] | t489c + a555g + a1467g + a1767g | +++++ |
| 373 | F-10T[4] | T2A + A5T + I14M + N79D + P109N + A143M + H145R + V159E + M161V + A198S + V208Y + F211Y + I222A + Q508R + A525T-des[A647-L663] | t489c + a555g + a675c + a1242g | ++++ |
| 376[6] | F-10T[4] | T2A + A9G + I14M + N79D + A143M + H145R + V159E + A198S + V207F + F211Y + I222A + S225C + A525T-des-A647-L663] | t489c + a555g + t1407c | +++++ |

[1]Amino acid position determined by optimal alignment with SEQ ID NO: 4.
[2]Nucleotide position determined by optimal alignment with SEQ ID NO: 3.
[3]Fold improvement over Control #4, Variant No. 264(SEQ ID NO: 7), is depicted as follows: ++++ = 1.1 to 3.0 fold improvement over Control #4, Variant No. 264 and +++++ = 3.1 to 12.0 fold improvement over Control #4, Variant No. 264.
[4]Amino acid position determined by optimal alignment with SEQ ID NO: 2.
[5]Nucleotide position determined by optimal alignment with SEQ ID NO: 1.
[6]This sequence had the sequence GAS (instead of GTS) preceding the N-terminus of SEQ ID NO: 4.

Example 9

Characterization of Enzyme Stability

Four CelA variants and wildtype CelA were characterized to determine their stabilities at high temperature (55° C.) and low pH (pH5.5) using the method of Example 5A. The samples containing various CelA variant enzymes were pre-incubated at pH 5.5, 55° C. for 0-6 hrs. The residual enzyme activity after the thermal challenge was measured using pNPG as substrate at pH 7, 30° C. for 1 hr. Table 4 illustrates the residual activity of improved CelA variants at pH 5, 65° C. after pre-incubations for different lengths of time. The mutations listed in the table are indicated relative to SEQ ID NO: 4, the wildtype CelA. These sequences included residues GTS prior to the N-terminus of SEQ ID NO: 4 (prepared as described in Example 1).

TABLE 4

Half-lives of improved CelA variants

| Amino Acid Mutations[1] | % residual activity after 10 mins @ pH 5.5, 55° C. | % residual activity after 1 hour @ pH 5.5, 55° C. | % residual activity after 6 hours @ pH 5.5, 55° C. |
|---|---|---|---|
| CelA wildtype | 0 | 0 | 0 |
| H145R (Variant No. 5) | 0 | 0 | 0 |
| N79D + A143M + H145R + V159E + A198S + F211Y (Variant No. 94) | 3% | 0 | 0 |
| T2A + I14M + N79D + A143M + H145R + V159E + A198S + F211Y + I222A + S225C + Q508R + A525T-des[A647-L663] (Variant No. 264) | 95% | 78% | 11% |

[1]Amino acid position is determined by optimal alignment with SEQ ID NO: 4

The results indicate that certain variants exhibit greater thermo- and pH-stability relative to wildtype *Azospirillum irakense* CelA.

Example 10

Further Improved 3-Glucosidase Activities of Engineered CelA Variants

The CelA variants in Example 8 were further improved by introducing substitutions into CelA variant No. 366 (the variant catalytic CelA domain is provided as SEQ ID NO: 9). The polynucleotide sequence encoding the catalytic CelA domain of Variant No. 366 is provided as SEQ ID NO: 8. As with the variants described in the above examples, the new variants contained the native *B. megaterium* penicillin G acylase signal sequence, amino acid residues −1 to −24 of SEQ ID NO: 2 (with numbering depicted in FIG. 1B). As explained in Example 1, the signal peptide is cleaved between amino acid residues −1 and +1. The amino acid residue at position +1, glycine, was engineered into the polypeptide to signal peptide processing in the expression host, *B. megaterium*. The amino acid residues at positions 2 and 3, threonine and serine, respectively, (or in some cases, threonine and arginine, as indicated in the table below), are encoded by a nucleotide sequence that corresponds to a SpeI restriction site. Therefore, the residues GTS/R occur between the C-terminus of the *B. megaterium* signal sequence and the N-terminus of the CelA catalytic domain in the expression construct.

Improved CelA variants were identified from the high throughput screening as described in Example 7, using the cellobiose assay of Example 5 with 3.3 g/l cellobiose at a temperature of 65° C. and pH of 5, with incubation overnight. Table 5 provides the improvement in activities of the variants generated by mutating the C-terminally truncated CelA variant, Variant No. 366. All of these variants include all of the substitutions of variant No. 366 (i.e., T2A+A5T+I14M+N79D+G127N+A143M+H145R+V159E+A198S+V207F+F211Y+I222A+S225C+Q508R+A525-des[A647-L663], in addition to the substitutions separately listed for each variant in Table 5, except where indicated by footnote that a reversion back to the wildtype residue occurred. The amino acid mutations in the CelA catalytic domain are indicated relative to SEQ ID NO: 4 (the wildtype CelA catalytic domain) and the silent (nucleotide) mutations are indicated relative to SEQ ID NO: 3, which corresponds to the codon optimized polynucleotide sequence that encodes the wildtype CelA catalytic domain. Amino acid and silent (nucleotide) mutations in the signal sequence are indicated in Table 4 relative to SEQ ID NOs: 2 and 1, respectively. All of the variants in Table 5 contained the mutation F-10T in the signal sequence (where the numbering of the signal peptide is depicted in FIG. 1B, and the sequence corresponds to amino acid residues 1 through 24 of SEQ ID NO: 2).

Fold improvement is reported relative to Variant No. 366 (substitution in signal sequence: F-10T (with reference to the numbering of amino acid position in the signal sequence depicted in FIG. 1B (SEQ ID NO: 2)); substitutions in CelA catalytic domain: T2A+A5T+I14M+N79D+G127N+A143M+H145R+V159E+A198S+V207F+F211Y+I222A+S225C+Q508R+A525T-des[A647-L663] (relative to SEQ ID NO: 4). The variant catalytic CelA domain of Variant No. 366 is provided as SEQ ID NO: 9. Variant No. 366 contains the substitution F-10T in the signal sequence (where the numbering of amino acid positions in the signal sequence is in accordance with that depicted in FIG. 1B).

TABLE 5

Improved CelA truncated variants and comparison to Variant No. 366 (substitution in signal sequence: F-10T (refer to numbering of amino acid position in signal sequence in FIG. 1B (SEQ ID NO: 2)); substitutions in CelA catalytic domain: T2A + A5T + I14M + N79D + G127N + A143M + H145R + V159E + A198S + V207F + F211Y + I222A + S225C + Q508R + A525T-des[A647-L663] (relative to SEQ ID NO: 4). Assay conditions: 3.3 g/l cellobiose, 65° C. and pH 5 (incubation overnight).

| CelA Variant No. | Mutations in Signal Peptide in addition to F-10T: | Amino Acid Mutations in CelA catalytic domain, SEQ ID NO: 4, in addition to: T2A + A5T + I14M + N79D + G127N + A143M + H145R + V159E + A198S + V207F + F211Y + I222A + S225C + Q508R + A525T-des[A647-L663]: | Silent Mutations (with reference to SEQ ID NO: 3, FIG. 2A) | Fold Improvement[3] over Control Variant |
|---|---|---|---|---|
| 375 | | P109D + V177P + Q287R + A600V | | ++ |
| 376 | | I4S + I61V + V177P + I535V | t516c | ++ |
| 377[1] | | A3R + I4S + I61V + V177P + I203Y + I535V | | ++ |
| 378[1] | | I4S + V177P + N320S + K350E | g1791a | ++ |
| 379 | | A3R + V177P + I535V | c12t + a1734g | ++ |
| 380 | | P89S + V177P + D236Y | a1197g | ++ |
| 381 | | I4S + V177P + A600V | a600g + a1044g + a1077g + t1902c | ++ |
| 382 | | I4S + P89S + V177P + I535V + Q585R | | ++ |
| 383[1] | | I4S + I61V + S73A + V177P + N613D + A617V | | ++ |
| 384 | | V177P + I535V | t351c | ++ |
| 385 | | A3R + S73A + V177P + I203Y + A600V | c12t + a732t | ++ |
| 386[1] | | I4S + P89S + V177P + A600V | a1656g | ++ |
| 387 | | P89S + V177P | | ++ |
| 388 | | K35Q + S73A + I203Y | t693c + a1554g | ++ |
| 389 | | I203Y + I535V | c12t + t693c + t873c | ++ |
| 390 | | P89S + V177P + I203Y + Y594F | c12t + a1173g | ++ |
| 391[1] | | A3R + S73A + V177P + I203Y | c12t | +++ |
| 392 | | S73A + I203Y | t1008c + t1233c | ++ |
| 393 | | A3R + I4S + V177P | | ++ |
| 394[1] | | A3R + I4S + S73A + V177P + I535M | t43c + a450g | ++ |
| 395 | | A3R + I61V + V177P | c12t + t585c + t1260c + a1293g | ++ |
| 396 | | I4S + V177P + A601V | t1290c | ++ |
| 397 | | A3R + M161V + I203Y + A222I + D383G | | ++ |
| 398 | | A3R + V177P + S213T | | ++ |

TABLE 5-continued

Improved CelA truncated variants and comparison to Variant No. 366 (substitution in signal sequence: F-10T (refer to numbering of amino acid position in signal sequence in FIG. 1B (SEQ ID NO: 2)); substitutions in CelA catalytic domain: T2A + A5T + I14M + N79D + G127N + A143M + H145R + V159E + A198S + V207F + F211Y + I222A + S225C + Q508R + A525T-des[A647-L663] (relative to SEQ ID NO: 4). Assay conditions: 3.3 g/l cellobiose, 65° C. and pH 5 (incubation overnight).

| CelA Variant No. | Mutations in Signal Peptide in addition to F-10T: | Amino Acid Mutations in CelA catalytic domain, SEQ ID NO: 4, in addition to: T2A + A5T + I14M + N79D + G127N + A143M + H145R + V159E + A198S + V207F + F211Y + I222A + S225C + Q508R + A525T-des[A647-L663]: | Silent Mutations (with reference to SEQ ID NO: 3, FIG. 2A) | Fold Improvement[3] over Control Variant |
|---|---|---|---|---|
| 399 | | A3R + P109D + V177P + M356T | a27g + a1092g | ++ |
| 400 | | I203Y + M356T + N646K | | ++ |
| 401 | | T25A + N128H + V177P + I203Y + T525S | g612t + t1782c + t1794c | ++ |
| 402 | K-21R[2] | A3R + A13P + P147T + V177P + I203Y + T525S + H586Y | g612t + a726g | ++ |
| 403 | | A13P + P109D + V177P | | ++ |
| 404 | | A13P + P109D + N128K + V177P + P597A | | ++ |
| 405 | | A13P + V177P + A400T + H586Y | t1896c | ++ |
| 406 | | A3R + A13P + P147T + E159G[5] + V177P | | ++ |
| 407 | | P109D + P147T + V177P + E502N + H586Y | | +++ |
| 408 | | A13P + P147T + V177P + A226G + H586Y | a741g | +++ |
| 409 | | P109D + P147T + V177P + T525S | | +++ |
| 410 | | V177P + E502N + T525S[5] | a1305g | +++ |
| 411 | | V177P + L372S | | ++ |
| 412 | | V177P + E502N + R508Q[5] | | +++ |
| 413 | | A3R + A13P + P147T + V177P + E502N + H586Y | | +++ |
| 414 | | A3R + I203Y + A400T + E502N + T525S | g612t | ++ |
| 415 | | A13P + N128H + V177P + E502N + R508Q[5] | | ++ |
| 416 | | P109D + V177P + D351E + H586Y | a252g + t1494c | ++ |
| 417 | | V177P + R508Q[4] | | ++ |
| 418 | N-5H[2] | A3R + A13P + I203Y + A400T | a441t + t516c + g612t | ++ |
| 419 | | A3R + P109D + P147T + V177P + H586Y | t609a + g612t | ++ |
| 420[3] | | A13P + N128H + V177P | t849c + t1707c | ++ |
| 421 | | P109D + V177P + A400T + E502N + H586Y | t762a | ++ |
| 422 | | A13P + P147T + V177P + A400T + E502N + R508Q | t3c + g324a + c330t + a468g | +++ |
| 423 | | P109D + V177P + A400T | t849c | ++ |
| 424 | | A13P + V177P + V204I + D291G | t609a | ++ |
| 425 | | A3R + P147T + V177P + A400T + E502N | | +++ |
| 426 | | V177P + A400T | | ++ |
| 427 | | N128H + V177P + E502N + H586Y | | ++ |
| 428 | | V177P + A400T + R508Q[5] | a1176g | ++ |
| 429 | | A13P + P147T + I203Y + H586Y | g612t + t1377c | ++ |
| 430 | | P109D + V177P | t849c | ++ |
| 431 | | A13P + P109D + V177P + T525S | | ++ |
| 432 | I-14V[2] | A3R + P147T + V177P + I203Y + E502N + H586Y | g612t | ++ |
| 433 | | A3R + V177P | | ++ |
| 434 | | A13P + I203Y + A400T + E502N | g612t + t1008c + t1446c | ++ |
| 435 | | A3R + A13P + V177P + A400T + H586Y | c195t + t1053c | ++ |
| 436 | | A3R + V177P + E502N | | ++ |

TABLE 5-continued

Improved CelA truncated variants and comparison to Variant No. 366 (substitution in signal sequence: F-10T (refer to numbering of amino acid position in signal sequence in FIG. 1B (SEQ ID NO: 2)); substitutions in CelA catalytic domain: T2A + A5T + I14M + N79D + G127N + A143M + H145R + V159E + A198S + V207F + F211Y + I222A + S225C + Q508R + A525T-des[A647-L663] (relative to SEQ ID NO: 4). Assay conditions: 3.3 g/l cellobiose, 65° C. and pH 5 (incubation overnight).

| CelA Variant No. | Mutations in Signal Peptide in addition to F-10T: | Amino Acid Mutations in CelA catalytic domain, SEQ ID NO: 4, in addition to: T2A + A5T + I14M + N79D + G127N + A143M + H145R + V159E + A198S + V207F + F211Y + I222A + S225C + Q508R + A525T-des[A647-L663]: | Silent Mutations (with reference to SEQ ID NO: 3, FIG. 2A) | Fold Improvement[3] over Control Variant |
|---|---|---|---|---|
| 437 | N-5S[2] | A3R + P147T + I203Y + E502N | g612t | ++ |
| 438 | | A3R + T25A + V177P + A400T + R508Q[5] | | ++ |
| 439 | | A3R + V177P + A400T | | ++ |
| 440 | | A3R + M14K + N128H + V177P + R508Q[5] | | ++ |
| 441 | | A13P + P147T + E502N | | ++ |
| 442 | | V177P | t99c | ++ |
| 443 | | A3R + N128H + V177P | t819a | ++ |
| 444 | | N128H + P147T + V177P + T603A | t1617c | ++ |
| 445 | | P147T + I203Y + H586Y | g612t | ++ |
| 446 | | T169N | | ++ |
| 447 | | R508E | | ++ |
| 448 | | F274K | | ++ |
| 449 | | F274N | | +++ |
| 450 | | F274S | | ++ |
| 451 | | L41F + A335P | | ++ |
| 452 | | A272L + N300D | | ++ |
| 453 | | A309G | g912t + g915a | ++ |
| 454 | | V304L | g915a + a1683g | ++ |

[1]This sequence had the sequence GTR (instead of GTS) preceding the N-terminus of the catalytic CelA domain (i.e., corresponding to SEQ ID NO: 4).
[2]Amino acid position determined by optimal alignment with SEQ ID NO: 2.
[3]This sequence had the sequence ATR (instead of GTS) preceding the N-terminus of the catalytic CelA domain (i.e., corresponding to SEQ ID NO: 4).
[4]Fold improvement over Control # 5, i.e. Variant No. 366, (SEQ ID NO: 9) is represented as follows: ++ = 1.1 to 2.0 fold improvement over control Variant No. 366 and +++ = 2.1 to 3.0 fold improvement over control Variant No. 366.
[5]Represents reversion to the wildtype residue.

Example 11

Further Improved i-Glucosidase Activities of Engineered CelA Variants

Additional variants were prepared by introducing substitutions into CelA variant No. 391 (the variant catalytic domain of Variant No. 391 is provided as SEQ ID NO: 11). The polynucleotide encoding the catalytic CelA domain of Variant No. 391 is provided as SEQ NO: 10. These variants were screened using the high throughput screen of Example 7, using the cellbiose assay of Example 5 with 3.3 g/l cellbiose at a temperature of 67° C. and pH 5, with incubation overnight. These variants had the same construction as the variants described above with the native *B. megaterium* penicillin G acylase signal sequence, amino acid residues −1 to −24 of SEQ ID NO: 2 (with the numbering of amino acid positions in the signal sequence as depicted in FIG. 1B), glycine at position +1 to facilitate signal peptide processing in the expression host, *B. megaterium*, and in these variants, threonine and arginine at positions +2 and +3, respectively, followed by a variant CelA catalytic domain. Therefore, the residues GTR occur between the C-terminus of the *B. megaterium* signal sequence and the N-terminus of the CelA variant catalytic domain in the expression construct.

Table 6 provides the improvement in activities of the variants generated by mutating the C-terminally truncated CelA variant, Variant No. 391. All of these variants include all of the substitutions of variant No. 391 (i.e., T2A+A5T+I14M+N79D+G127N+A143M+H145R+V159E+A198S+V207F+F211Y+I222A+S225C+Q508R+A525-des[A647-L663], in addition to the substitutions separately listed for each variant in Table 6, except where indicated by footnote that a reversion back to the wildtype residue occurred. The amino acid mutations in the CelA catalytic domain are indicated relative to SEQ ID NO: 4 (the wildtype CelA catalytic domain) and the silent (nucleotide) mutations are indicated relative to SEQ ID NO: 3, which corresponds to the codon optimized polynucleotide sequence that encodes the wildtype CelA catalytic domain. Amino acid and silent (nucleotide) mutations in the signal sequence are indicated in Table 6 relative to SEQ ID NOs: 2 and 1, respectively. All of the variants in Table 6 contained the mutation F-10T in the signal sequence (where the numbering of amino acid position in the signal sequence is in accordance with that depicted in FIG. 1B).

Fold improvement is reported relative to Variant No. 391 (substitution in signal sequence: F-10T (refer to numbering of amino acid position in signal sequence in FIG. 1B (SEQ ID NO: 2)); substitutions in CelA catalytic domain: T2A+A3R+A5T+I14M+S73A+N79D+G127N+A143M+H145R+V159E+V177P+A198S+I203Y+V207F+F211Y+I222A+S225C+Q508R+A525T-des[A647-L663]), where the amino acid substitutions are indicated relative to the wildtype CelA catalytic domain (SEQ ID NO: 4)).

TABLE 6

Improved CelA truncated variants and comparison to Variant No. 391 (substitution in signal sequence: F-10T (refer to numbering of amino acid position in signal sequence in FIG. 1B (SEQ ID NO: 2)); substitutions in CelA catalytic domain: T2A + A3R + A5T + I14M + S73A + N79D + G127N + A143M + H145R + V159E + V177P + A198S + I203Y + V207F + F211Y + I222A + S225C + Q508R + A525T-des[A647-L663]), where amino acid substitutions in the CelA catalytic domain are indicated relative to SEQ ID NO: 4. Assay conditions: 3.3 g/l cellobiose, 67° C. and pH 5.

| CelA Variant No. | Mutations in Signal Peptide in addition to F-10T: | Amino Acid Mutations in CelA catalytic domain, SEQ ID NO: 4, in addition to: T2A + A5T + I14M + S73A + N79D + G127N + A143M + H145R + V159E + V177P + A198S + I203Y + V207F + F211Y + I222A + S225C + Q508R + A525T-des[A647-L663]: | Silent Mutations with reference to SEQ ID NO: 3, FIG. 2A | Fold Improvement[3] over Control Variant |
|---|---|---|---|---|
| 455 | | T60H + H285N | c195t + c199a + t1617c | ++++ |
| 456 | | S198W + T525M | | ++++ |
| 457 | | S198A + T525G | | ++++ |
| 458 | | D311G + D475E | c1413t + a1428t | +++ |
| 459 | | T169N + Q287R + A309G + D311G | a24t + g33a + a543g + g915a + t1864c | +++ |
| 460 | | L41F + A309G + D311G + A335P | a24t + g33a + g915a + c1002t + g1776a + g1791t | +++ |
| 461 | | D311G + K529E | g786a | +++ |
| 462 | | Y211Q | t1425c | +++ |
| 463 | | T169N + A202P + A272L + Q287R + D311G + E512G | t576c + g804t + c828t + g915a | +++ |
| 464 | | T169N + A202P + N300D A309G + D311G + Y594F | g915a g1776a | +++ |
| 465 | g-67a + g-61a + c-57t + c-46t + a-43t + c-39t[1] (silent mutation) | R67H + T169N + A202P + A335P | c933t + a1353g | +++ |
| 466 | | V304L + A335P | g915a | +++ |
| 467 | | A272L + A335P + A357S | c1002t + a1077t + c1086t + t1324a + g1329a | ++ |
| 468 | g-67a + g-61a + c-57t + c-46t + a-43t + c-39t[1] (silent mutation) | A272L | a24t + c828t + g912t + g915a + t1324a + g1329a + g1434t + c1437t + t1629c + g1776a + g1791t | ++ |
| 469 | | L41F + T169N + A272L + N300D + D311G + A335P + D475E + Y594F | t729c + g894t + g915a + a1077g + t1324a + g1329a + g1776a + g1791t | ++ |
| 470 | g-67a + g-61a + c-57t + c-46t + a-43t + c-4739t[1] (silent mutation) | A202P + N300D + A309G + D311G + A335P + K350R + Q487L | t789c + g915a + a1029g | ++ |
| 471 | | T169N + D311G + A335P + V349A + T452A | t501c + a987g + c1002t + c1011a + g1776a | ++ |

TABLE 6-continued

Improved CelA truncated variants and comparison to Variant No. 391 (substitution in signal sequence: F-10T (refer to numbering of amino acid position in signal sequence in FIG. 1B (SEQ ID NO: 2)); substitutions in CelA catalytic domain: T2A + A3R + A5T + I14M + S73A + N79D + G127N + A143M + H145R + V159E + V177P + A198S + I203Y + V207F + F211Y + I222A + S225C + Q508R + A525T-des[A647-L663]), where amino acid substitutions in the CelA catalytic domain are indicated relative to SEQ ID NO: 4. Assay conditions: 3.3 g/l cellobiose, 67° C. and pH 5.

| CelA Variant No. | Mutations in Signal Peptide in addition to F-10T: | Amino Acid Mutations in CelA catalytic domain, SEQ ID NO: 4, in addition to: T2A + A5T + I14M + S73A + N79D + G127N + A143M + H145R + V159E + V177P + A198S + I203Y + V207F + F211Y + I222A + S225C + Q508R + A525T-des[A647-L663]: | Silent Mutations with reference to SEQ ID NO: 3, FIG. 2A | Fold Improvement[3] over Control Variant |
|---|---|---|---|---|
| 472 | | T69N + A335P + Y594F | g912t + g915a + a1545g + g1776a | ++ |
| 473 | | L41F + A309G + D311G + A335P + E343G | g33a + g915a + t1386c | ++ |
| 474 | | D311G | g915a + g1776a | ++ |
| 475 | | A335P | c1011a | ++ |
| 476 | | T169N + A335P | a24t + a678g + g912t + g915a | ++ |
| 477 | | N300D + A309G + A335P | g915a + c933t + c1002t + a1077t + t1324a + g1329a + t1530c + g1776a + c1930a | ++ |
| 478 | | A335P | t216c + t462c + c1002t + c1011a + g1434t + c1437t + a1899g | ++ |
| 479 | | A202P + A335P + Y594F | g912t + g915a + c1011a + g1776a | ++ |
| 480 | | V511L | | ++ |
| 481 | | T169N + A335P | g1776a | ++ |
| 482 | | D264G + A272L + A309G + A335P | g915a + c1011a | ++ |
| 483 | | A202P + N300D + D311G + A335P | g894t + g915a + c1002t + g1329a | ++ |
| 484 | | T169N + D311G + K531R | a24t + g915a + t1324a + g1329a + a1704g | ++ |
| 485 | | L41F + Q287R + A335P | c933t + a969g + a1185g + t1324a + g1329a + g1434t + c1437t | ++ |
| 486 | | T169N + A202P + D215G + A272L + A309G + A335P + Y594F | a24t + g915a + c933t + c1002t + t1137c + a1302t + g1434a + c1437t + c1737t + g1776a + g1791t + | ++ |
| 487 | | A202P + A335P | t1324a + g1329a | ++ |

TABLE 6-continued

Improved CelA truncated variants and comparison to Variant No. 391 (substitution in signal sequence: F-10T (refer to numbering of amino acid position in signal sequence in FIG. 1B (SEQ ID NO: 2)); substitutions in CelA catalytic domain: T2A + A3R + A5T + I14M + S73A + N79D + G127N + A143M + H145R + V159E + V177P + A198S + I203Y + V207F + F211Y + I222A + S225C + Q508R + A525T-des[A647-L663]), where amino acid substitutions in the CelA catalytic domain are indicated relative to SEQ ID NO: 4. Assay conditions: 3.3 g/l cellobiose, 67° C. and pH 5.

| CelA Variant No. | Mutations in Signal Peptide in addition to F-10T: | Amino Acid Mutations in CelA catalytic domain, SEQ ID NO: 4, in addition to: T2A + A5T + I14M + S73A + N79D + G127N + A143M + H145R + V159E + V177P + A198S + I203Y + V207F + F211Y + I222A + S225C + Q508R + A525T-des[A647-L663]: | Silent Mutations with reference to SEQ ID NO: 3, FIG. 2A | Fold Improvement[3] over Control Variant |
|---|---|---|---|---|
| 488 | | L41F + T169N + A202P + A272L + D311G + K339R + Y594F | g120t + a441g + c828t + g915a + t1324a + g1329a + g1776a + t1839c | ++ |
| 489 | | H282N | t924c + t1911c | ++ |
| 490 | | F118L + T169N + A272L + A335P | c1011a + t1254c + t1324a + g1329a | ++ |
| 491 | | P219Q | | ++ |
| 492 | | D519G | | ++ |
| 493 | | Q522K | | ++ |
| 494 | | G59S | | ++ |
| 495 | | P147W + D475E | | ++ |
| 496 | | Q522R | a732g | ++ |
| 497 | | A309G | g915a + c933t + t1324a + g1329a + g1776a | ++ |
| 498 | N-5D[2] g-67a + g-61a + c-57t + c-46t + a-43t + c-39t[1] (silent mutation) | A226G + E502N | c1206t + c1668t | ++ |
| 499 | g-67a + g-61a + c-57t + c-46t + a-43t + c-39t[1] (silent mutation) | E502N + R508Q[4] + N646K | t688c + a1203g + t1324a + g1329a | ++ |
| 500 | | Q520T | | ++ |
| 501 | | Q520G | | ++ |
| 502 | | T5A[4] + A589R | t1569c | ++ |
| 503 | | Q522K | | ++ |
| 504 | | A202P | | ++ |
| 505 | | A485K | t963c | ++ |
| 506 | | D519K | | ++ |
| 507 | | S198D | | ++ |
| 508 | | Q520N | | ++ |
| 509 | | S198N + T525A[4] | t1476c | ++ |
| 510 | | N83H + D457E | t216c + c259a + a1767g | ++ |
| 511 | | E155G | | ++ |
| 512 | I-15V[2] | R3G | | ++ |
| 513 | | S395K + D519G | | ++ |
| 514 | | P147R + E502N + N646K | | ++ |
| 515 | | Q520K | | ++ |
| 516 | | P219E | t1854c | ++ |
| 517 | g-67a + g-61a[1] (silent mutation) | E502N | a24t + g33a + t1296c + t1324a + g1329a | ++ |

TABLE 6-continued

Improved CelA truncated variants and comparison to Variant No. 391 (substitution in signal sequence: F-10T (refer to numbering of amino acid position in signal sequence in FIG. 1B (SEQ ID NO: 2)); substitutions in CelA catalytic domain: T2A + A3R + A5T + I14M + S73A + N79D + G127N + A143M + H145R + V159E + V177P + A198S + I203Y + V207F + F211Y + I222A + S225C + Q508R + A525T-des[A647-L663]), where amino acid substitutions in the CelA catalytic domain are indicated relative to SEQ ID NO: 4. Assay conditions: 3.3 g/l cellobiose, 67° C. and pH 5.

| CelA Variant No. | Mutations in Signal Peptide in addition to F-10T: | Amino Acid Mutations in CelA catalytic domain, SEQ ID NO: 4, in addition to: T2A + A5T + I14M + S73A + N79D + G127N + A143M + H145R + V159E + V177P + A198S + I203Y + V207F + F211Y + I222A + S225C + Q508R + A525T-des[A647-L663]: | Silent Mutations with reference to SEQ ID NO: 3, FIG. 2A | Fold Improvement[3] over Control Variant |
|---|---|---|---|---|
| 518 | | G386W | | ++ |
| 519 | | E502N + N646K | a186t + t1324a + g1329a | ++ |
| 520 | | D532R | a1605t | ++ |
| 521 | c-46t + a-43t + c-39t-[1] (silent mutation) | A226G + T525S | a615g + t783c + g912t + g915a + c1581t | ++ |
| 522 | | K35R + E502N + N646K | a24t + a102g + t1324a + g1329a | ++ |
| 523 | | P147R + E502N + R508Q[4] | | + |
| 524 | | E92D | c259a | + |
| 525 | | P109D + H282D + L372S + E458D + E502N | a24t + g33a + g324a + g912t + g915a + t1324a + g1329a | + |
| 526 | | T60H | c195t + g1017a | + |

[1]Nucleotide position determined by optimal alignment with SEQ ID NO: 1

[2]Amino acid position determined with reference to the numbering of amino acid position in the signal sequence as depicted in FIG. 1B.

[3]Fold improvement over Control #6, i.e. Variant No. 391, (SEQ ID NO: 11) is represented as follows: + = 0.5-1.0 fold improvement over control Variant No. 391; ++ = 1.1 to 2.0 fold improvement over control Variant No. 391; +++ = 2.1 to 3.0 fold improvement over control Variant No. 391; and ++++ = 3.1 to 4.1 fold improvement over control Variant No. 391.

[4]Represents a reversion to the wildtype residue.

Example 12

Further Improved β-Glucosidase Activities of Engineered CelA Variants

Further variants were prepared by introducing mutations into CelA Variant No. 463 (the variant catalytic domain of Variant No. 463 is provided as SEQ ID NO: 13). The polynucleotide sequence encoding the catalytic CelA domain of Variant No. 463 is provided as SEQ ID NO: 12. These variants were screened using the high throughput screen of Example 7, using the cellbiose assay of Example 5 with 3.3 g/l cellbiose at a temperature of 72° C. and pH 5, with incubation overnight These variants had the same construction as the variants described above with the native *B. megaterium* penicillin G acylase signal sequence, amino acid residues −1 to −24 of SEQ ID NO: 2 (with the numbering of amino acid positions in the signal sequence as depicted in FIG. 1B), glycine at position +1 to facilitate signal peptide processing in the *B. megaterium* expression host, and threonine and arginine at positions +2 and +3, respectively, followed by a variant CelA catalytic domain. Therefore, the residues GTR occur between the C-terminus of the *B. megaterium* signal sequence and the N-terminus of the CelA variant catalytic domain in the pre-protein form of each variant.

Table 7 provides the improvement in activities of the variants generated by mutating the C-terminally truncated CelA variant, Variant No. 463. All of these variants include all of the substitutions of Variant No. 463 (i.e., substitution in signal sequence: F-10T (relative to FIG. 1B, SEQ ID NO: 2); substitutions in the CelA catalytic domain: T2A+A3R+A5T+I14M+S73A+N79D+G127N+I143M+H145R+V159E+T169N+V177P+A198S+A202P+I203Y+V207F+F211Y+I222A+S225C+A272L+Q287R+D311G+Q508R+E512G+A525T-des[A647-L663] (relative to SEQ ID NO: 4)), in addition to the substitutions separately listed for each variant in Table 7. The amino acid mutations in the CelA catalytic domain are indicated relative to SEQ ID NO: 4 (the wildtype CelA catalytic domain) and the silent (nucleotide) mutations are indicted relative to SEQ ID NO: 3, which corresponds to the codon optimized polynucleotide sequence that encodes the wildtype CelA catalytic domain. Amino acid and silent (nucleotide) mutations in the signal sequence are indicated in Table 7 relative to SEQ ID NOs: 2 and 1, respectively. All of the variants in Table 7 contained the mutation F-10T in the signal sequence (wherein the numbering of amino acid position in the signal sequence is in accordance with that depicted in FIG. 1B).

Fold improvement is reported relative to Variant No. 463 [substitution in signal sequence: F-10T (with reference to the numbering of amino acid position in the signal sequence as depicted in FIG. 1B (SEQ ID NO: 2)); substitutions in CelA catalytic domain: T2A+A3R+A5T+I14M+S73A+N79D+G127N+I143M+H145R+V159E+T169N+V177P+A198S+A202P+I203Y+V207F+F211Y+I222A+S225C+A272L+Q287R+D311G+Q508R+E512G+A525T-des[A647-L663], where the amino acid substitutions are indicated relative to the wildtype CelA catalytic domain (SEQ ID NO: 4)).

TABLE 7

Improved CelA truncated variants and comparison to Variant No. 463 (S03837072) (substitution in signal sequence: F-10T(refer to numbering of amino acid position in signal sequence in FIG. 1B (SEQ ID NO: 2)); substitutions in CelA catalytic domain: T2A + A3R + A5T + I14M + S73A + N79D + G127N + A143M + H145R + V159E + T169N + V177P + A198S + A202P + I203Y + V207F + F211Y + I222A + S225C + A272L + Q287R + D311G + Q508R + E512G + A525T-des[A647-L663], where amino acid substitutions in the CelA catalytic domain are indicated relative to SEQ ID NO: 4. Assay conditions: 3.3 g/l cellobiose, 72° C. and pH 5.

| CelA Variant No. | Mutations in Signal Peptide in Addition to F-10T: | Amino Acid Mutations in CelA Relative to SEQ ID NO: 4 in addition to [T2A + A3R + A5T + I14M + S73A + N79D + G127N + A143M + H145R + V159E + T169N + V177P + A198S + A202P + I203Y + V207F + F211Y + I222A + S225C + A272L + Q287R + D311G + Q508R + E512G + A525T-des[A647-L663]]: | Silent Mutations (with reference to SEQ ID NO: 3, FIG. 2A) | Fold Improvement[1] over Control Variant |
|---|---|---|---|---|
| 527 | | T60H + A335P + D475E + V511L + Y594F | a24t + t897c + c1002g + g1536t | ++ |
| 528 | | T60H + A309G + D475E + Y594F | a24t + a678g + a903g | ++ |
| 529 | | T60H + A335P + D475E + Y594F | a24t + a678g + c1002g | ++ |
| 530 | | A335P + D475E | g348a + a678g + c1002g | ++ |
| 531 | | A309G + A335P + D475E + Y594F | a24t + g912t + c1002g + a1506g | ++ |
| 532 | | A309G + A335P + T567A | c1002g | ++ |
| 533 | | A309G + A335P + D475E + Y594F | a24t + a678g + g912t + c1002g | ++ |
| 534 | | T60H + H285N + A335P + Y594F | a24t + a678g + c1002g + t1626c | ++ |
| 535 | | T60H + A335P + K529E + Y594F | t789a + g912t + c1002g + c1588t + a1725g | ++ |
| 536 | | T60H + A309G | t591c | ++ |
| 537 | | T60H + A335P + K529E + Y594F | a24t + a147g + g912t + c1002g + c1500t + c1588t | ++ |
| 538 | | T60H + A309G + A335P | a24t + c1002g + t1401a + a1734g | ++ |
| 539 | | T60H + A335P + Y594F | a24t + c1002g | ++ |
| 540 | | K35R + T60H + A335P + Y594F + K627R | a24t + a678g + c1002g + g1536a | ++ |
| 541 | | T60H + A309G + A335P + V511L | a24t + t282c + a495g + c1002g + t1617c | ++ |

[1]Fold improvement over Control #7, i.e., Variant No. 463, (SEQ ID NO: 13) is represented as follows: ++ = 1.0 to 2.0 fold improvement over control Variant No. 463.

Example 13

Characterization of Enzyme Stability

Representative CelA variants from Tables 6 and 7 were characterized to determine their stabilities at high temperatures (55° C. and 65° C.) and low pH (5.0) using the method of Example 5A. The samples containing various CelA variant enzymes were pre-incubated at pH 5.0, 55° C. for 48 hours and at pH 5.0, 65° C. for either 4 or 5 hours. The residual enzyme activity after the thermal challenge was measured using pNPG as substrate at pH 7, 30° C. for approximately 1 hour. The negative control was the *B. megaterium-E. coli* vector described in Example 1, without any CelA sequence. Tables 8A and 8B list the residual activities of the improved CelA variants at pH5.0, 55° C. The mutations listed in the table are indicated relative to SEQ ID NO: 4, the wildtype CelA.

TABLE 8A

Stability of Enzymes from Table 6.

| Variant No. | % residual activity after 48 hours at 55° C., pH 5.0 | % residual activity after 4 hours at 65° C., pH 5.0 |
|---|---|---|
| Negative Control | | N/A |
| 391 (T2A + A5T + I14M + N79D + G127N + A143M + H145R + V159E + A198S + A207F + F211Y + I222A + S225C + Q508R + A3R + S73A + V177P + I2037-des[A647-L663]) | 0.9 | 0.2 |
| 463 (T2A + A5T + I14M + N79D + G127N + A143M + H145R + V159E + A198S + V207F + F211Y + I22A + S225C + Q508R + A525T + T169N + A202P + A272L + Q287R + D311G + E512G-des[A647-L663]) | 74.2 | 26.5 |
| 459 (T2A + A5T + I14M + N79D + G127N + A143M + H145R + V159E + A198S + V207F + F211Y + I22A + S225C + Q508R + A525T + T169N + Q287R + A309G + D311G-des[A647-L662]) | 70.2 | 0.1 |
| 460 (T2A + A5T + I14M + N79D + G127N + A143M + H145R + V159E + A198S + V207F + F211Y + I22A + S225C + Q508R + A525T + L41F + A309G + D311G + A335P-des[A647-L663] | 89.2 | 1.6 |

TABLE 8B

Stability of Enzymes from Table 7.

| Variant No. | % residual activity after 48 hours at 55° C., pH 5.0 | % residual activity after 5 hours at 65° C., pH 5.0 |
|---|---|---|
| Negative Control | | N/A |
| 463 (T2A + A5T + I14M + N79D + G127N + A143M + H145R + V159E + A198S + V207F + F211Y + I22A + S225C + Q508R + A525T + T169N + A202P + A272L + Q287R + D311G + E512G-des[A647-L663]) | 77.4 | 23.1 |
| 533 (T2A + A3R + A5T + I14M + S73A + N79D + G127N + I143M + H145R + V159E + T169N + V177P + A198S + A202P + I203Y + V207F = F211Y + I222A + S225C + A272L + Q287R + D311G + Q508R + E512G + A525T + A309G + A335P + D475E + Y594F-des[A647-L663]) | 94.5 | 71.0 |
| 541 (T2A + A3R + A5T + I14M + S73A + N79D + G127N + I143M + H145R + V159E + T169N + V177P + A198S + A202P + I203Y + V207F = F211Y + I222A + S225C + A272L + Q287R + D311G + Q508R + E512G + A525T + T60H + A309G + A335P + V511L-des[A647-L663]) | 90.9 | 79.9 |
| 538 (T2A + A3R + A5T + I14M + S73A + N79D + G127N + I143M + H145R + V159E + T169N + V177P + A198S + A202P + I203Y + V207F = F211Y + I222A + S225C + A272L + Q287R + D311G + Q508R + E512G + A525T + T60H + A309G + A335P-des[A647-L663]) | 86.4 | 74.3 |
| 539 (T2A + A3R + A5T + I14M + S73A + N79D + G127N + I143M + H145R + V159E + T169N + V177P + A198S + A202P + I203Y + V207F + F211Y + I222A + S225C + A272L + Q287R + D311G + Q508R + E512G + A525T + T60H + A335P + Y594F-des[A647-L663]) | 86.4 | 57.5 |
| 534 (T2A + A3R + A5T + I14M + S73A + N79D + G127N + I143M + H145R + V159E + T169N + V177P + A198S + A202P + I203Y + V207F = F211Y + I222A + S225C + A272L + Q287R + D311G + Q508R + E512G + A525T + T60H + H285N + A335P + Y594F-des{A647-L663]) | 84.8 | 49.9 |
| 529 (T2A + A3R + A5T + I14M + S73A + N79D + G127N + I143M + H145R + V159E + T169N + V177P + A198S + A202P + I203Y + V207F = F211Y + I222A + S225C + A272L + Q287R + D311G + Q508R + E512G + A525T + T60H + A335P + D475E + Y594F-des[A647-L663]) | 81.8 | 59.0 |

Example 14

Evaluation of Optimal CelA Activity for Additional Variants

Figure 7:
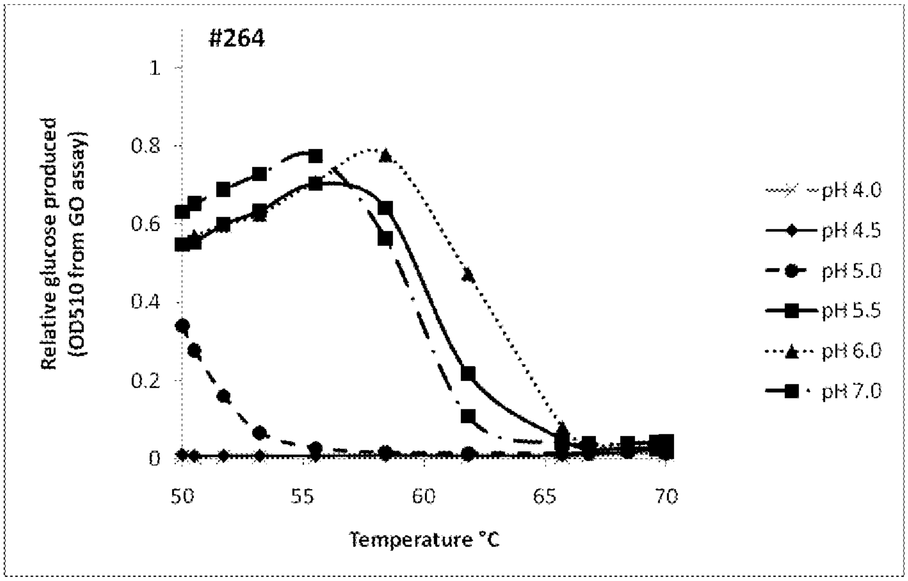
FIG. 7 provides the activity profile for CelA Variant No. 264 (T2A+I14M+N79D+A143M+H145R+V159E+A198S+F211Y+I222A+S225C+Q508R+A525T]CelA-des[A647-L663] (SEQ ID NO: 7, FIG. 5)) at temperatures 50° C.-70° C. and at pH 4.0-7.0 using cellobiose (10 g/L) as a substrate. The experimental procedure is described in Example 14.
Figure 8:
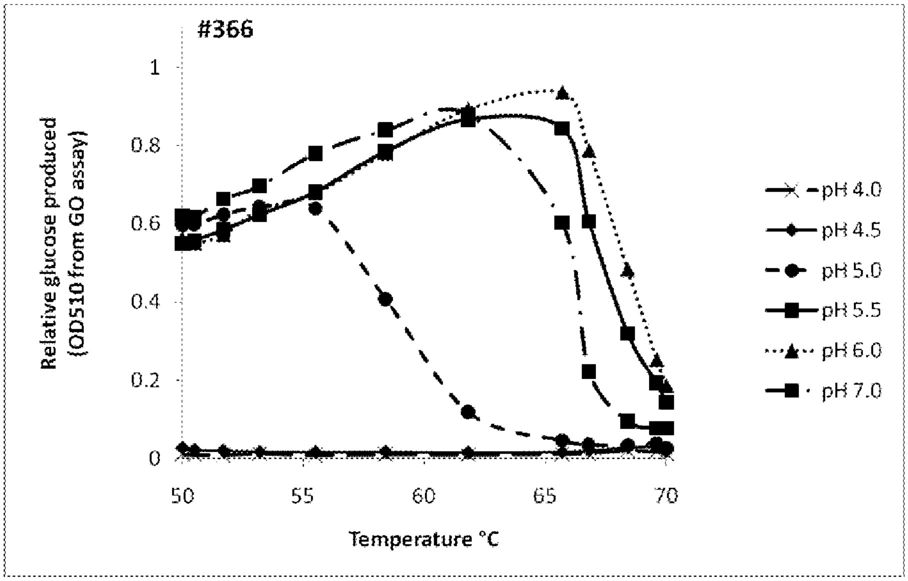
FIG. 8 provides the activity profile for CelA Variant No. 366 (T2A+A5T+I14M+N79D+G127N+A143M+H145R+V159E+A198S+V207F+F211Y+I222A+S225C+Q508R+A525T-des[A647-L663] (SEQ ID NO: 9)) at temperatures 50° C.-70° C. and at pH 4.0-7.0 using cellobiose (10 g/L) as a substrate. The experimental procedure is described in Example 14.
Figure 9:
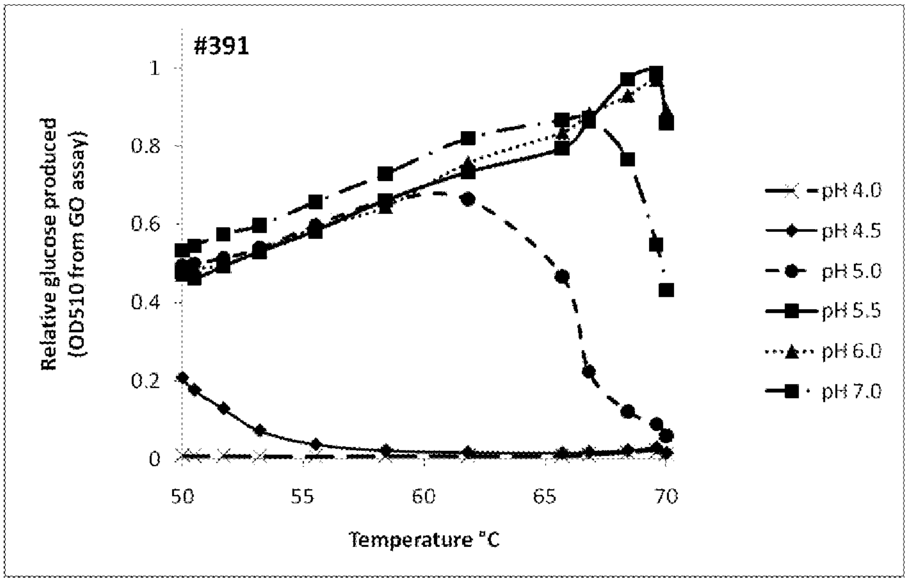
FIG. 9 provides the activity profile for CelA Variant No. 391 (T2A+A5T+I14M+N79D+G127N+A143M+H145R+V159E+A198S+V207F+F211Y+I222A+S225C+Q508R+A525-des[A647-L663] (SEQ ID NO: 11)) at temperatures 50° C.-70° C. and at pH 4.0-7.0 using cellobiose (10 g/L) as a substrate. The experimental procedure is described in Example 14.
Figure 10:
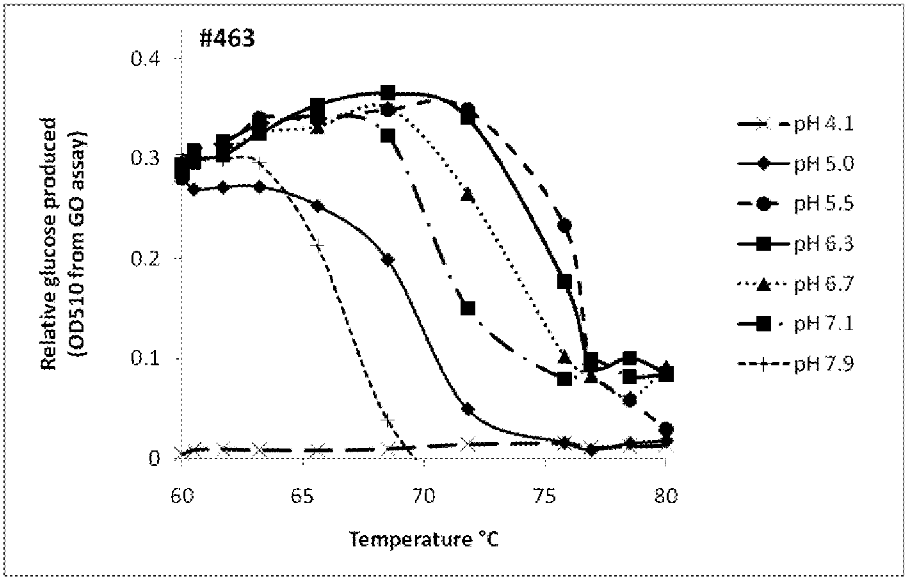
FIG. 10 provides the activity profile for CelA Variant No. 463 (T2A+A3R+A5T+I14M+S73A+N79D+G127N+A143M+H145R+V159E+T169N+V177P+A198S+A202P+I203Y+V207F+F211Y+I222A+S225C+A272L+Q287R+D311G+Q508R+E512G+A525T-des[A647-L663] (SEQ ID NO: 13)) at temperatures 60° C.-80° C. and at pH 4.1-7.9 using cellobiose (10 g/L) as a substrate. The experimental procedure is described in Example 14.
Figure 11:
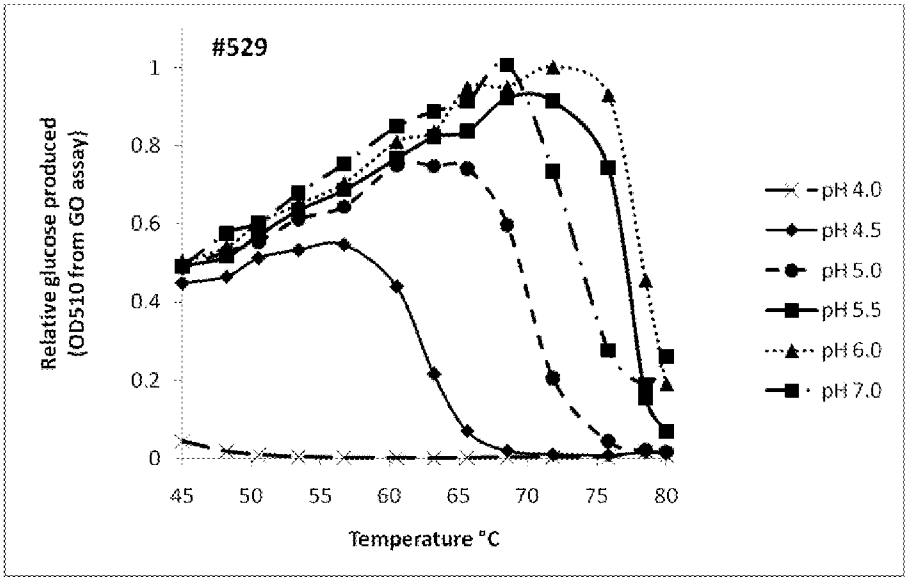
FIG. 11 provides the activity profile for CelA Variant No. 529 (T2A+A3R+A5T+I14M+S73A+N79D+G127N+I143M+H145R+V159E+T169N+V177P+A198S+A202P+I203Y+V207F=F211Y+I222A+S225C+A272L+Q287R+D311G+Q508R+E512G+A525T+T60H+A335P+D475E+Y594F-des[A647-L663])) at temperatures 45° C.-80° C. and at pH 4.0-7.0. The experimental procedure is described in Example 14.
Figure 12:
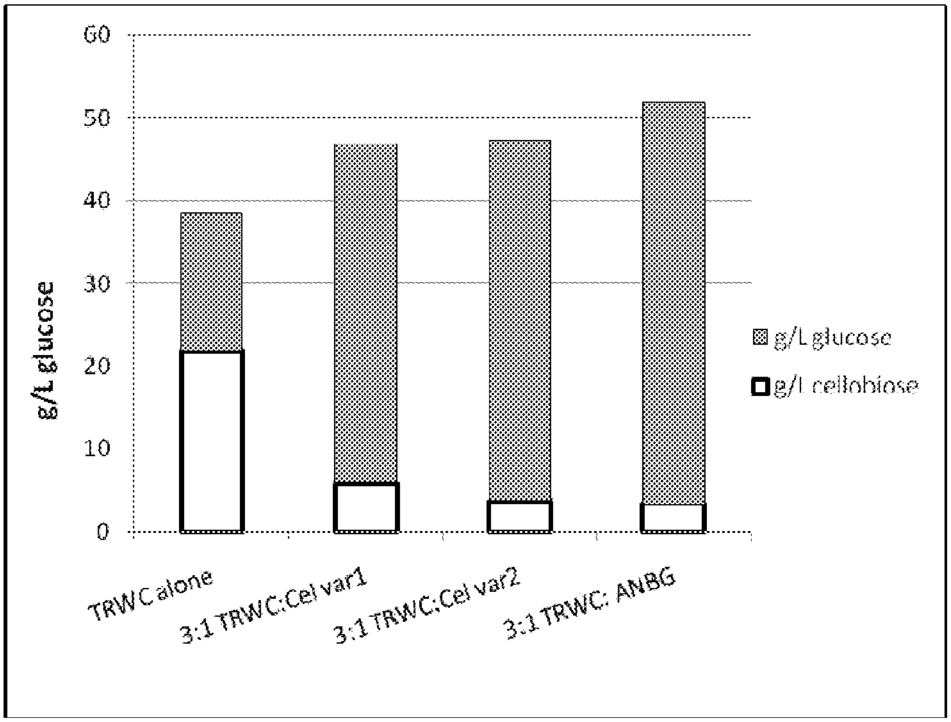
FIG. 12 illustrates the impact of supplementing a commercially available *Trichoderma reesei* whole cellulose ("TRWC") mixture with a CelA variant of the present invention. Compositions containing TRWC were supplemented with β-glucosdiases CelA Variant No. 264 ("Cel var1"), CelA Variant No. 366 ("Cel var2"), and a commercially available *Aspergillus niger* β-glucosidase ("ANBG") in a ratio of 3:1 TRWC to β-glucosidase. The effectiveness of each composition at hydrolyzing microcrystalline cellulose was evaluated as described in Example 15. A plot of glucose and cellobiose concentration (g/L) vs. cellulase composition is depicted. The control composition was TRWC with no added β-glucosidase.

The activity profiles for Variant Nos. 264, 366, 391, 463, and 529 were determined at different temperatures and pH using cellobiose (10 g/L) as a substrate. The experimental and analytical procedures are described in Example 5, incubating the variant with cellobiose at temperatures in the range of 45-80. The results are depicted in FIGS. 7-11. Variant No. 264 exhibited optimum activity at pH 6 and 58° C. The temperature and pH profile for this variant is depicted in FIG. 7. Variant No. 366 exhibited optimum activity at pH 6 and 66° C. The temperature and pH profile for this variant is depicted in FIG. 8. Variant No. 391 exhibited optimum activity at pH 5.5 and 69° C. The temperature and pH profile for this variant is depicted in FIG. 9. Variant No. 463 exhibited optimum activity at pH 6 and 69° C. (with the pH 6 optimum determined by extrapolation). The temperature and pH profile for this variant is depicted in FIG. 10. Variant No. 529 exhibited optimum activity at pH 6 and 69° C. The temperature and pH profile for this variant is depicted in FIG. 11.

Example 15

Evaluation of Addition of CelA Variants to Commercially Available Cellobiase

The impact of adding a CelA variant of the present invention to commercially available cellulose mixtures and microcrystalline cellulose, Avicel™, was evaluated. In the test reactions, 1 g/L *Trichoderma reesei* whole cellulose ("TRWC", Sigma catalog #C85456-10KU (ATCC 26921)) was used to convert 200 g/L of the microcrystalline cellulose Avicel™ (200 mM Sodium acetate; 100 g/L xylose, pH5.5 and 55° C.). The amount of glucose was measured after 48 hours of reaction. As a comparison, 25% of the TRWC was replaced with a β-glucosidase: Variant No. 264 ("Cel var1"), Variant No. 366 ("Cel var2"), or with the commercially available cellobiase, *Aspergillus niger* beta-glucosidase ("ANBG", Sigma catalog #49291-1G).

A plot of the results (glucose production vs. cellulase composition) is, depicted in FIG. 11. The results indicate that 1 g/L of TRWC alone in this saccharification reaction yielded 38 g/L of cellobiose and glucose combined, with about equal amounts of each. Substitution of 25% of the TRWC with ANBG yielded 52 g/L with 94% of the sugar being glucose. Substitution of 25% of TRWC with either Variant No. 264 or Variant 366 gave comparable results.

Example 16

The level of glucose inhibition for variant #391 was determined using the cellobiose assay of Example 5B (except the cellobiose consumption was determined by HPLC) and spiking in glucose as well as varying amounts of glucose under conditions of pH 5, 55° C. in separate reactions. Percent residual activity was calculated relative to the activity computed for the reaction with no glucose. This was used to determine the $IC_{50}$ for glucose (i.e., the concentration of glucose at which enzyme activity is 50% of the activity for the same reaction under conditions of no glucose). The IC50 can be determined from a plot of % residual activity vs. Initial Glucose Concentration of Reaction (g/L) as the glucose concentration where % residual activity is 50%. For variant #391, the IC50 for glucose was greater than 100 g/l.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. An isolated β-glucosidase polypeptide variant having β-glucosidase activity and comprising an amino acid sequence that has at least 85% amino acid sequence identity to the amino acid sequence of SEQ ID NO:4, wherein said SEQ ID NO:4 is the amino acid sequence of wild type *Azospirillum irakense* β-glucosidase and wherein said variant comprises the substitution N79D, wherein the amino acid position is numbered with reference to the amino acid sequence of SEQ ID NO: 4.

2. The β-glucosidase polypeptide variant of claim 1, wherein the variant amino acid sequence comprises at least one substitution selected from the group consisting of T2A, A3L/N/P/R/G, I4P/Q/R/S/T, A5L/N/T/Y, Q6A/D/G/N/P/S/T, E7A/G/H/L/P, G8A/C/D/P/Q/R/S/Y, A9E/G/I/K/T, A10G/N/P/S, P11A/E/L/R/S, A12E/F/N/R/S/Y/-, A13P/V, I14H/L/M/N/R/T/K, L15I/S, P17R, E18F/G/N/R, K19R, W20T, P21I/S, P23L, A24V, T25P, Q26P/R, A24V, T25A, I29V, D30E, E34D/K, K35E/P/Q/R, A39V, L41F, K42R, Q43P, L44S, E47K, V46F, G51P, Q52P, V53T, G56P, G59E/R/S, T60H/Y, I61V, E64S, L66Q, R67C/H, K68E, P70S, S73A, N83H, G84A/E/Q, D85N, R87D, A88T, P89S, K91Q, E92D/G/S/V, A97G/T, A99E/K/R/S, L105Y, K107R, P109D/N, G110S, H111D, T112A/I/N, P113A/K/S/V, I114T/V, F118S/L, I120V, G127A/N/S, N128H/K, I134F/N, F135L, L141I, A143I/M/Q/T, T144S, H145R, D146C/S, P147I/K/L/T/W/R, E148D/G/K, L150M, R151P/W, R152S, I153T, G154V, E155A/D/K/M/P/Q/W/G, A158T, V159E/I/L/A/Q/R, M161T/V, A162S/T/V, A163T, G165E, I166T/V, W168R, T169N, A173S/C, V177P, D180C, G188D, S190Y, I195L, A197D/M/N, A198C/E/L/M/N/Q/S/T/W/D, A201P/S/G, A202F/K/L/N/P/T/Y/S, I203F/H/Y, V204I, E205X G206S, V207A/E/F/I/L/Y, F211C/V/Y/W/Q, G212C/R/V/T, S213C/H/P/V, K214P/Y, D215K/L/N/S/G, F216L, M217L/T/V, A218K/P, P219C/E/I/L/M/T/Q/V, G220S/V, I222A/C/G/I/S/V, S225C/F/N/S/T, A226G, F229I, G233P, D236G/Y, Q237R, G238R, D243G, R245K, I246C/V, S247P, E248K, E250G, R253K/Q, N256L/V, A257P/R, D264G, A272V/L, F274A/K/Q/S/T/Y/N, Q278N/R, I280V, H282N/D, H285D/N, Q287E/L/R, D291G, G295A/Q, M297I, G298R, F299S, N300D, V304L, A309G, D311E/G, Q312L, P314L/S, G315E, F319V, N320E/K/Q/S, T323A/D/G, S324V, I326S, M331L, A335P, K339E/R, Q340R, Y342C, E343A/G, T345S, A347G/K/M/V, V349A, K350F/L/T/Y/E/R, D351E, T353M/N/V/S/Y, I354T, M356K/Q/T, A357E/S/T, R358H, D360G, A362S, I366T, V369A, V371D/E/L/M/Y, L372S/W, A373T, E377D, K378R, P379G/V/Y, P381S, K382R, D383N/G, G386C/E/L/W, L387R, L390I/P, S395G/Q/K, P396N/S, A400K/T, G402S, R403S, K408I, K417R/S, S423D/N, A426S, D433G, Q418D, T419V, R425H, A426Q/S, D436N, G439P, K440N, G444P, T452A, G453R, R455K/P/S/T, D457H/E, E458N/D, A460S, G461K, T463P, G467K/Q, R470K, A474Q, D475K/S/E, A476K, G478P, S479A/H/V, E481G, F482Y, V484D, A485P/K, Q487D/K/N/R/L, Y488N, T490I, K491R, A495T, R501Q, E502G/K/N, F507G/S, Q508R/E, V511L, E512G, L514Q, Q517L, P518Q, D519G/N/K, Q520N/T/G/K, Q522K/R, L524W, A525K/S/T/M/G, K528R, K529R/E, K531E/R, D532G/R, Q533H/L, G534E, I535V/M, A539T/V, W548L, P551R, L553M, S556T, D557G, A562P, W563P, L564P, T567A, G570P, L372S, A573S/V, V575A, F577L, K580N/T, K583N/R/Q, Q585R, H586Y, A589R, G590P, L592F, Y594H/F, S595G, P597A, T599A, A600V, A601V, T603A/F/Y, T604P, D609E, D611C/E, N613D, A617D/P/V, T623S, Y624H, K625Q, K627R, K629C/R, L633D, P634S, E635D/-, E636D/G/-, S637-, G638-, V639-, P640-, A641-, E642A/-, A643P/-, R644-, Q645/-, N646K/-, Q645-, N646-A647-, G648-, I649T/-, Y650-, F651-, R652L/-, A653-, G654-, A655T/-, L656-, R657-, L658-, P659-, G660-, R661-, F662L/-, and L663P/Q/-, wherein amino acid positions are numbered with reference to the amino acid sequence of SEQ ID NO:4.

3. The β-glucosidase polypeptide variant of claim 1, wherein the variant amino acid sequence comprises at least one substitution in a position selected from the group consisting of T2, A3, I4, A5, A9, I14, K35R, L41, S73, P78, A88, , P109, G127, N128, A143, H145, P147, V159, M161, A162, T169, V177, A197, A198, A201, A202, I203, V204, V207, F211, I222, S225, A272, H285, Q287, N300, A309, D311, A335, M356, D475, R501, Q508, V511, E512, A525, K529, T567, Y594, Y594, K625, and N646, wherein amino acid positions are numbered with reference to the amino acid sequence of SEQ ID NO:4.

4. The β-glucosidase polypeptide variant of claim 3, wherein the variant amino acid sequence further comprises one or more substitutions selected from the group consisting of T2A, A3L/N/P/R/G/R, I4P/Q/R/S/T, A5L/N/T/Y, A9E/G/I/K/T, I14H/L/M/N/R/T/K, K35E/P/Q/R, L41F, S73A, P78S, A88T, P109D/N, G127A/N/S, N128H/K, A143I/M/Q/T, H145R, P147I/K/L/T, V158E, V159E/I/L/A/Q/R, M161T/V, A162S/T/V, T169N, V177P, A197D/M/N, A198C/E/L/M/N/Q/S/T/W/D, A201P/S/G, A202F/K/L/N/P/T/Y/S, I203Y/F/H, V204I, V207A/E/F/I/L/Y, F211C/V/Y/W/Q, I222A/C/G/I/S/V, S225C/V/N/S/T, A272V/L, H285D/N, Q287N/R, N300D, A309G, D311E/G, A335P, M356K/Q/T, D475K/S/E, R501Q, Q508R/E, V511L, E512G, A525K/S/T/M/G, K529R/E, T567A, Y594H/F, K625Q, Y594H/F, and N646K, wherein amino acid positions numbered with reference to the amino acid sequence of SEQ ID NO:4.

5. The β-glucosidase polypeptide variant of claim 1, wherein the variant amino acid sequence further comprises one or more substitutions selected from the group consisting of T2A, A3R, I4P/Q/R/S/T, A5T, A9G, I14M, K35E/P/Q/R, L41F, S73A, P78S, A88T, P109D, G127N, N128K, A143M/T, H145R, P147I/K/L/T, V158E, V159E, M161T/V, A162T, T169N, V177P, A197D/M/N, A198S, A201, A202P, I203Y, V204I, V207Y/F, F211Y, I222A/S/V, S225C, A272L, H285D/N, Q287R, N300D, A309G, D311G, A335P, M356K/Q/T, D475E, R501Q, Q508R, V511L, E512G, A525T, K529R/E, T567A, Y594F, K625Q, Y594H/F, and N646K, wherein amino acid positions are numbered with reference to the amino acid sequence of SEQ ID NO:4.

6. The β-glucosidase polypeptide variant of claim 1, wherein the variant amino acid sequence comprises one or more substitutions in a position selected from the group consisting of A5, A9, I14, L41, A88, P89, S109, G127, N128, M143, V159, A162, T169, V177, A198, A201, A202, I203, V207, F211, I222, S225, A272, N300, A309, D311, A335, D475, Q508, A525, Y594, and K625, wherein amino acid positions are numbered with reference to the amino acid sequence of SEQ ID NO:4.

7. The β-glucosidase polypeptide variant of claim 6, wherein the variant amino acid sequence comprises one or more substitutions selected from the group consisting of A5T, A9G, I14M, L41F, A88T, P89S, S109D/N, G127N/S, N128K, M143T, V159E/Q, A162T, T169N, V177P, A198S, A201P, A202P, I203Y, V207Y, F211Y, I222A/S/V, S225C, A272L, N300D, A309G, D311G, A335P, D475E, Q508R, A525T, Y594F, and K625Q, wherein amino acid positions are numbered with reference to the amino acid sequence of SEQ ID NO:4.

8. The β-glucosidase polypeptide variant of claim 2, wherein the variant amino acid sequence comprises 2 or more amino acid substitutions.

9. The β-glucosidase polypeptide variant of claim 8, wherein the variant amino acid sequence comprises 3 or more amino acid substitutions.

10. The β-glucosidase polypeptide variant of claim 9, wherein the variant amino acid sequence comprises 4 or more amino acid substitutions.

11. The β-glucosidase polypeptide variant of claim 10, wherein the variant amino acid sequence comprises 5 or more amino acid substitutions.

12. The β-glucosidase polypeptide variant of claim 1, wherein the variant amino acid sequence further comprises one or more substitutions in a position selected from the group consisting of A143, H145, V159, and F211 wherein amino acid positions are numbered with reference to the amino acid sequence of SEQ ID NO:4.

13. The β-glucosidase polypeptide variant of claim 12, wherein the variant amino acid sequence further comprises one or more substitutions selected from the group consisting of A143M, H145R, V159E, and F211Y wherein amino acid positions are numbered with reference to the amino acid sequence of SEQ ID NO:4.

14. The β-glucosidase polypeptide variant of claim 13, wherein the variant amino acid sequence comprises the substitutions N79D+A143M+H145R+V159E+F211Y wherein amino acid positions are numbered with reference to the amino acid sequence of SEQ ID NO:4.

15. The β-glucosidase polypeptide variant of claim 1, wherein the variant amino acid sequence further comprises one or more substitutions in a position selected from the group consisting of T2, I14, A143, H145, V159, A198, F211, I222, S225, Q508, and A525 wherein amino acid positions are numbered with reference to the amino acid sequence of SEQ ID NO:4.

16. The β-glucosidase polypeptide variant of claim 15, wherein the variant amino acid sequence further comprises one or more substitutions selected from the group consisting of T2A, I14M, A143M, H145R, V159E, A198S , F211Y, I222A, S225C, Q508C, and A525T wherein amino acid positions are numbered with reference to the amino acid sequence of SEQ ID NO:4.

17. The β-glucosidase polypeptide variant of claim 16, wherein the variant amino acid sequence comprises substitutions T2A+I14M+N79D+A143M+H145R+V159E+A198S+F211Y+I222A+S225C+Q508C+A525T wherein amino acid positions are numbered with reference to the amino acid sequence of SEQ ID NO:4.

18. The β-glucosidase polypeptide variant of claim 1, wherein the variant amino acid sequence further comprises one or more substitutions in a position selected from the group consisting of T2, A5, I14, G127, A143, H145, V159, A198, V207, F211, I222, S225, Q508, and A525wherein amino acid positions are numbered with reference to the amino acid sequence of SEQ ID NO:4.

19. The β-glucosidase polypeptide variant of claim 18, wherein the variant amino acid sequence further comprises one or more substitutions selected from the group consisting of T2A, A5T, I14M, G127N, A143M, H145R, V159E, A198S, V207F, F211Y, I222A, S225C, Q508R, and A525T wherein amino acid positions are numbered with reference to the amino acid sequence of SEQ ID NO:4.

20. The β-glucosidase polypeptide variant of claim 19, wherein the variant amino acid sequence comprises substitutions T2A+A5T+I14M+N79D+G127N+A143M+H145R+V159E+A198S+V207F+F211Y+I222A+S225C+Q508R+A525T wherein amino acid positions are numbered with reference to the amino acid sequence of SEQ ID NO:4.

21. The β-glucosidase polypeptide variant of claim 1, wherein the variant amino acid sequence further comprises one or more substitutions in a position selected from the group consisting of T2, A3, A5, I14, S73, G127, A143, H145, V159, V177, A198, I203, F211, I222, S225, Q508, and A525 wherein amino acid positions are numbered with reference to the amino acid sequence of SEQ ID NO:4.

22. The β-glucosidase polypeptide variant of claim 21, wherein the variant amino acid sequence further comprises one or more substitutions selected from the group consisting of T2A, A5, I14M, S73A, G127N, A143M, H145R, V159E, V177P, A198S, I203Y, V207F, F211Y, I222A, S225C, Q508R, and A525T wherein amino acid positions are numbered with reference to the amino acid sequence of SEQ ID NO:4.

23. The β-glucosidase polypeptide variant of claim 21, wherein the variant amino acid sequence comprises substitutions T2A+A5T+I14M+S73A+N79D+G127N+A143M +H145R+V159E+V177P+A198S+I203Y+V207F+F211Y+ I222A+S225C+Q508R+A525T wherein amino acid positions are numbered with reference to the amino acid sequence of SEQ ID NO:4.

24. The β-glucosidase polypeptide variant of claim 1, wherein the variant amino acid sequence further comprises one or more substitutions in a position selected from the group consisting of T2, A3, A5, I14, S73,G127, A143, H145, V159, T169, V177, A198, A202, I203, V207, F211, I222, S225, A272, Q287, D311, Q508, E512, and A525 wherein amino acid positions are numbered with reference to the amino acid sequence of SEQ ID NO:4.

25. The β-glucosidase polypeptide variant of claim 24, wherein the variant amino acid sequence comprises one or more substitutions selected from the group consisting of T2A, A3R, A5T, I*l*4M, S73A, G127N, A143M, H145R, V159E, T169N, V177P, A198S, A202P, I203Y, V207F, F211Y, I222A, S225C, A272L, Q287R, D311G, Q508R, E512G, and A525T wherein amino acid positions are numbered with reference to the amino acid sequence of SEQ ID NO:4.

26. The β-glucosidase polypeptide variant of claim 25, wherein the variant amino acid sequence comprises substitutions T2A+A3R+A5T+I14M+S73A +N79D+G127N+ A143M+H145R+V159E+T169N+V177P+A198S+A202P+ I203Y +V207F +F211Y +I222A +S225C +A272L +Q287R +D311G +Q508R +E512G +A525T wherein amino acid positions are numbered with reference to the amino acid sequence of SEQ ID NO:4.

27. The β-glucosidase polypeptide variant of claim 1, wherein no substitution is made at a position selected from the group consisting of A309 and G509 wherein amino acid positions are numbered with reference to the amino acid sequence of SEQ ID NO:4.

28. The β-glucosidase polypeptide variant of claim 1, wherein the variant amino acid sequence comprises a truncation of from 1 to 40 amino acid residues from the C-terminus.

29. The β-glucosidase polypeptide variant of claim 1, wherein the variant amino acid sequence comprises a truncation of from 1 to 30 amino acid residues from the C-terminus.

30. The β-glucosidase polypeptide variant of claim 1, wherein thevariant amino acid sequence comprises a truncation of from 1 to 20 amino acid residues from the C-terminus.

31. The glucosidase polypeptide of claim 1, wherein the variant amino acid sequence comprises a truncation of 16 amino acid residues from the C-terminus.

32. An enzyme composition comprising the β-glucosidase polypeptide variant of claim 1 and an additional cellulase enzyme.

* * * * *